(12) United States Patent
Wang et al.

(10) Patent No.: US 12,350,268 B2
(45) Date of Patent: Jul. 8, 2025

(54) PHARMACEUTICAL COMPOSITIONS OF PROTAC COMPOUNDS AND USES THEREOF

(71) Applicant: Shenzhen Pharmacin Co., Ltd., Shenzhen (CN)

(72) Inventors: Zeren Wang, Shenzhen (CN); Shun Chen, Shenzhen (CN)

(73) Assignee: SHENZHEN PHARMACIN CO., LTD., Shenzhen (CN)

( * ) Notice: Subject to any disclaimer, the term of this patent is extended or adjusted under 35 U.S.C. 154(b) by 0 days.

(21) Appl. No.: 18/343,324

(22) Filed: Jun. 28, 2023

(65) Prior Publication Data

US 2023/0338371 A1    Oct. 26, 2023

Related U.S. Application Data

(63) Continuation of application No. PCT/CN2023/083796, filed on Mar. 24, 2023.

(30) Foreign Application Priority Data

Mar. 25, 2022   (WO) ................ PCT/CN2022/083105
Mar. 1, 2023    (WO) ................ PCT/CN2023/079057

(51) Int. Cl.
| | |
|---|---|
| *A61K 31/501* | (2006.01) |
| *A61K 9/00* | (2006.01) |
| *A61K 9/16* | (2006.01) |
| *A61K 47/10* | (2017.01) |
| *A61K 47/12* | (2006.01) |
| *A61K 47/24* | (2006.01) |
| *A61K 47/32* | (2006.01) |
| *A61K 47/38* | (2006.01) |

(52) U.S. Cl.
CPC .......... *A61K 31/501* (2013.01); *A61K 9/0053* (2013.01); *A61K 9/16* (2013.01); *A61K 47/10* (2013.01); *A61K 47/12* (2013.01); *A61K 47/24* (2013.01); *A61K 47/32* (2013.01); *A61K 47/38* (2013.01)

(58) Field of Classification Search
CPC .................................................. A61K 31/501
See application file for complete search history.

(56) References Cited

U.S. PATENT DOCUMENTS

| | | | |
|---|---|---|---|
| 9,023,393 B2 | 5/2015 | Babcock et al. | |
| 9,486,410 B2 | 11/2016 | Perlman et al. | |
| 10,357,455 B2 | 7/2019 | Perlman et al. | |
| 10,383,941 B2 | 8/2019 | Beyerinck et al. | |
| 2003/0185893 A1* | 10/2003 | Beyerinck ............... | A61P 43/00 424/489 |
| 2008/0292707 A1 | 11/2008 | Babcock et al. | |
| 2015/0119435 A1 | 4/2015 | Crews et al. | |
| 2017/0281631 A1 | 10/2017 | Wang et al. | |
| 2019/0381050 A1 | 12/2019 | Wang et al. | |
| 2019/0381051 A1 | 12/2019 | Wang et al. | |
| 2020/0222394 A1 | 7/2020 | Jain et al. | |
| 2021/0000835 A1 | 1/2021 | Wang et al. | |
| 2022/0096389 A1 | 3/2022 | Wang et al. | |

FOREIGN PATENT DOCUMENTS

| | | |
|---|---|---|
| CN | 114163444 A | 3/2022 |
| CN | 114181277 A | 3/2022 |
| KR | 20170085629 A | 7/2017 |
| WO | WO-2008016260 A1 | 2/2008 |
| WO | WO-2017166451 A1 | 10/2017 |
| WO | WO-2018071606 A1 | 4/2018 |
| WO | WO-2018102725 A1 | 6/2018 |
| WO | WO-2020121326 A1 | 6/2020 |
| WO | WO-2020225738 A1 | 11/2020 |
| WO | WO-2021219808 A1 | 11/2021 |
| WO | WO-2022049243 A1 | 3/2022 |
| WO | WO-2022068876 A1 | 4/2022 |

OTHER PUBLICATIONS

Anane-Adjei et al., "Amorphous solid dispersions: Utilization and challenges in preclinical drug development within AstraZeneca", 2022, available online Dec. 18, 2021, International Journal of Pharmaceutics, vol. 614, No. 121387, pp. 1-16. (Year: 2021).*
Chaudhari et al., "Evaluating the effect of the porous and non-porous colloidal silicon dioxide as a stabilizer on amorphous solid dispersion", Sep. 15, 2020, Journal of Drug Delivery and Therapeutics, vol. 10, No. 5, pp. 255-263. (Year: 2020).*
Heimbach, T. et al., "Physiologically Based Pharmacokinetic Modeling to Supplement ARV-110 Pharmacokinetics and Confirm Dose Selection in Pediatric Patients," Journal of Pharmaceutical Sciences, 2019, vol. 108, pp. 2191-2198.
International Search Report and Written Opinion issued in PCT/CN2023/083796, mailed Jul. 10, 2023.
Liu, L. et al., "Targeting Oncoproteins for Degradation by Small Molecule-Based Proteolysis Targeting Chimeras (PROTACs) in Sex Hormone-Dependent Cancers," Front Endocrinol, 2022, vol. 13.
Poestges, F. et al., "Solubility Enhanced Formulation Approaches to Overcome Oral Delivery Obstacles of PROTACs, " Pharmaceutics, 2023, vol. 15, No. 1.
Munzenberg, J. et al., Improving the Dissolution of Poorly Soluble APIs with Inorganic Solid Dispersions, Pharmaceutical Technology, vol. 41, 4 (2017).
Zhang, Z. et al., Solid dispersion of berberine-phospholipid complex/TPGS 1000/SiO$_2$: preparation, characterization and in vivo studies. International journal of pharmaceutics, vol. 465, 1-2 (2014):306-316.

(Continued)

*Primary Examiner* — Michael B. Pallay
(74) *Attorney, Agent, or Firm* — WILSON SONSINI GOODRICH & ROSATI

(57) ABSTRACT

Proteolysis Targeting Chimeras (PROTACs) are heterobifunctional degraders that specifically eliminate targeted proteins by hijacking the ubiquitin-proteasome system (UPS). Provided are pharmaceutical compositions which include a mixture of a PROTAC, a hydrophilic polymer, a surfactant, and optionally an acid and an adsorbent. Also described are methods for preparing and using such pharmaceutical compositions. In one aspect, disclosed herein is an amorphous solid dispersion comprising PROTAC.

23 Claims, 10 Drawing Sheets

(56) References Cited

OTHER PUBLICATIONS

Baghel, et al., An investigation into the solid-state properties and dissolution profile of spray dried ternary amorphous solid dispersions: a rational step towards the design and development of multi-component amorphous system, Molecular Pharmaceutics, (2018).

Feng, et al., Polymer-surfactant system based amorphous solid dispersion: precipitation inhibition and bioavailability enhancement of itraconazole, Pharmaceutics, 10(53):1-15, (2018).

Karagianni, et al., Co-amorphous solid dispersions for solubility and absorption improvement of drugs: composition, preparation, characterization and formulations for oral delivery, Pharmaceutics, 10(98):1-26, (2018).

* cited by examiner

PHARMACEUTICAL COMPOSITIONS OF PROTAC COMPOUNDS AND USES THEREOF

CROSS-REFERENCE TO RELATED APPLICATION

This application is a continuation of PCT application No. PCT/CN2023/083796, filed on Mar. 24, 2023, which claims the benefit of patent application Nos. PCT/CN2022/083105, filed on Mar. 25, 2022, and PCT/CN2023/079057, filed on Mar. 1, 2023, each of which is hereby incorporated by reference in its entirety.

TECHNICAL FIELD

The present invention belongs to the pharmaceutical field, and specifically relates to pharmaceutical compositions, and their preparation method and use.

BACKGROUND

Proteolysis Targeting Chimeras (PROTACs) are hetero-bifunctional degraders that specifically eliminate targeted proteins by hijacking the ubiquitin-proteasome system (UPS). This modality has emerged as an orthogonal approach to the use of small-molecule inhibitors for knocking down classic targets and disease-related proteins classified, until now, as "undruggable." However, PROTACs are often affected by poor cellular permeability due to their high molecular weight (MW) and large exposed polar surface area (PSA).

ARV-110, a PROTAC® protein degrader that targets the androgen receptor (AR). ARV-110 is developed by Arvinas for the potential treatment of men with metastatic castration resistant prostate cancer (mCRPC) and who have progressed on existing therapies. Its molecular weight is 812.29 and its calculated log P is about 4.18. It is very hard to dissolve in the aqueous solution and it is reported that it should be taken with food.

ARV-471, a PROTAC® protein degrader that targets the estrogen receptor (ER). ARV-471 is developed by Arvinas for the potential treatment of women with locally advanced or metastatic estrogen receptor (ER) positive/human epidermal growth factor receptor 2 (HER2) negative (ER+/HER2−) breast cancer. Its molecular weight is 723.92 and its calculated log P is about 4-6. It is very hard to dissolve in the aqueous solution and it is reported that it should be taken with food in clinic study.

Poor water solubility and very low oral absorption are the bottlenecks to develop RPOTAC molecules for in vivo applications. Furthermore, the bioavailability of almost all of the PROTAC molecules are subject to food effects. There is a significant need for PROTACs compositions that have improved oral bioavailability, permit administering lower doses, that reduce absorption variations caused by food intake, and that reduce in vivo inter-subject absorption variations.

INCORPORATION BY REFERENCE

All publications and patent applications mentioned in this specification are herein incorporated by reference to the same extent as if each individual publication or patent application was specifically and individually indicated to be incorporated by reference.

BRIEF SUMMARY

Disclosed herein is a pharmaceutical composition, wherein the pharmaceutical composition comprises a) an amorphous solid dispersion (ASD) that comprises: i) a proteolysis targeting chimera (PROTAC) compound or a pharmaceutically acceptable salt thereof; ii) a surfactant; iii) a hydrophilic polymer; iv) optionally an acid; and v) optionally an adsorbent, wherein the PROTAC compound or a pharmaceutically acceptable salt thereof, the surfactant, the hydrophilic polymer, and the optional acid are present in the ADS in an amorphous state; and b) optionally a pharmaceutically acceptable carrier or excipient. In some embodiments, the pharmaceutical composition exhibits a bioavailability of the PROTAC compound or the pharmaceutically acceptable salt thereof that is at least 2-fold compared to a bioavailability of a corresponding composition comprising the PROTAC compound or the pharmaceutically acceptable salt thereof without being a part of an ASD, when said bioavailability is measured as total area under the curve (AUC) or as maximum plasma concentration ($C_{max}$) after oral administration to a subject in a fasted state. In some embodiments, the pharmaceutical composition exhibits a bioavailability of the PROTAC compound or the pharmaceutically acceptable salt thereof that is at least 3, 4, or 5-fold compared to a bioavailability of a corresponding composition comprising the PROTAC compound or the pharmaceutically acceptable salt thereof without being a part of an ASD, when said bioavailability is measured as total area under the curve (AUC) or as maximum plasma concentration ($C_{max}$) after oral administration to a subject in a fasted state. In some embodiments, the pharmaceutical composition exhibits a bioavailability of the PROTAC compound or the pharmaceutically acceptable salt thereof that is at least 1.5-fold compared to a bioavailability of a corresponding composition comprising the PROTAC compound or the pharmaceutically acceptable salt thereof without being a part of an ASD, when said bioavailability is measured as total area under the curve (AUC) or as maximum plasma concentration (Cmax) after oral administration to a subject in a fed state. In some embodiments, the pharmaceutical composition exhibits a bioavailability of the PROTAC compound or the pharmaceutically acceptable salt thereof that is at least 2, 2.5, or 3-fold compared to a bioavailability of a corresponding composition comprising the PROTAC compound or the pharmaceutically acceptable salt thereof without being a part of an ASD, when said bioavailability is measured as total area under the curve (AUC) or as maximum plasma concentration (Cmax) after oral administration to a subject in a fed state. In some embodiments, the bioavailability of the PROTAC compound or the pharmaceutically acceptable salt thereof is at least 5-fold compared to a bioavailability of a corresponding composition comprising the PROTAC compound or the pharmaceutically acceptable salt thereof without being a part of an ASD. In some embodiments, the bioavailability of the PROTAC compound or the pharmaceutically acceptable salt thereof is at least 1.1, 1.5, 2, 3, 4, 5, 6, 7, 8, 9, or 10-fold compared to a bioavailability of a corresponding composition comprising the PROTAC compound or the pharmaceutically acceptable salt thereof without being a part of an ASD. In some embodiments, the corresponding composition comprises the PROTAC compound or the pharmaceutically acceptable salt thereof in an amorphous state. In some embodiments, the corresponding composition comprises the PROTAC compound or the pharmaceutically acceptable salt thereof in a crystalline form. In some embodiments, the pharmaceutical composition exhibits a bioavailability of the PROTAC compound or the pharmaceutically acceptable salt thereof that does not vary more than 100%, 50%, 25%, when orally administered to a subject in a fed state compared to a fasted state, when said bioavailability is measured as total area under the curve (AUC) or as maximum plasma concentration ($C_{max}$) after oral administration to said subject. In some embodiments, the bioavailability is measured in a dog model in a fasted state or in a fed state. In some embodiments, the pharmaceutical composition is in a form of a tablet. In some embodiments, the pharmaceutical composition is in a form of a capsule. In some embodiments, the PROTAC compound is represented by the structure of Formula (I): A-L-B, wherein i) A is an E3 ubiquitin ligase binding moiety; ii) L is a linker; and iii) B is a moiety which binds to a target protein, wherein the target protein is degradable by an E3 ubiquitin ligase. In some embodiments, B is an androgen receptor (AR) binding moiety. In some embodiments, B is an estrogen receptor binding moiety. In some embodiments, the PROTAC compound is an androgen receptor PROTAC degrader. In some embodiments, the androgen receptor PROTAC degrader is ARV-110, or a pharmaceutically acceptable salt or enantiomer thereof. In some embodiments, the androgen receptor PROTAC degrader is represented by the structure of present in the pharmaceutical composition in an amount of about 25 mg to about 250 mg. In some embodiments, the surfactant is present in the pharmaceutical composition in an amount of about 10% to 60% by weight. In some embodiments, the surfactant is present in the pharmaceutical composition in an amount of about 15% to 55% by weight. In some embodiments, the surfactant comprises a non-ionic surfactant, an anionic surfactant, a phospholipid, or any combination thereof. In some embodiments, the surfactant comprises tocopherol polyethylene glycol succinate (TPGS), a block copolymer of polyethylene glycol and polypropylene glycol, polysorbate, lecithin, polyethylene glycol castor oil, hydrogenated castor oil, sorbitan oleate, sodium dodecyl sulfate (SDS), polyvinylcaprolactame-based graft copolymer (PVAc-PVCap-PEG), or a combina-

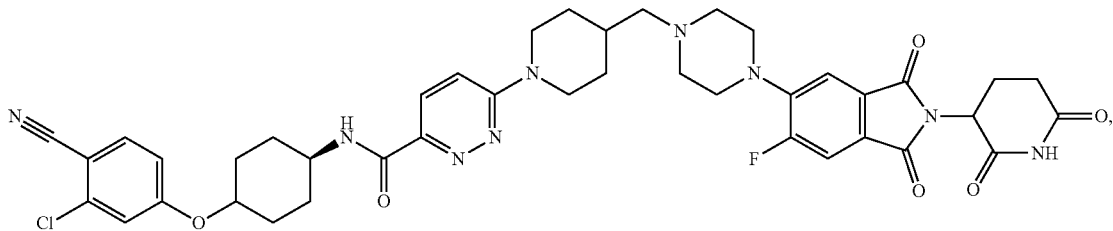

or a pharmaceutically acceptable salt or enantiomer thereof. In some embodiments, the PROTAC compound is an estrogen receptor PROTAC degrader. In some embodiments, the estrogen receptor PROTAC degrader is ARV-471, or a pharmaceutically acceptable salt or enantiomer thereof. In some embodiments, the estrogen receptor PROTAC degrader is represented by the structure of

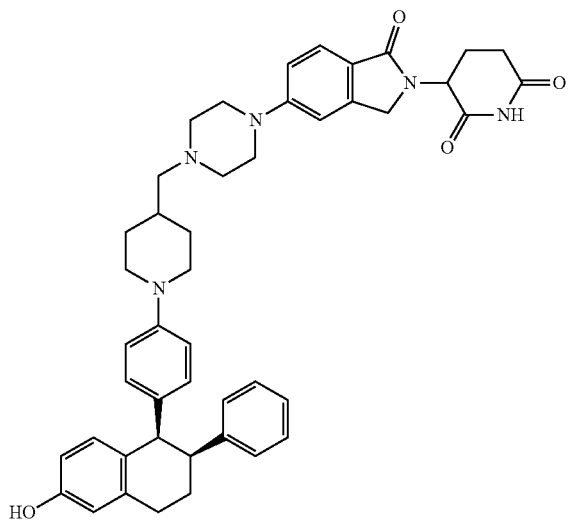 [SMILES: O=C1CCC(N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

or a pharmaceutically acceptable salt or enantiomer thereof. In some embodiments, the PROTAC compound has a log P in octanol-water of at least 2.0. In some embodiments, the PROTAC compound has a log P in octanol-water of at least 2.0, at least 2.5, at least 3, at least 3.5, at least 4, at least 4.5, or at least 5. In some embodiments, the PROTAC compound or a pharmaceutically acceptable salt thereof is present in the pharmaceutical composition in an amount of about 10% to 30% by weight. In some embodiments, the surfactant is tion thereof. In some embodiments, the surfactant comprises tocopherol polyethylene glycol succinate (TPGS) or lecithin or a combination thereof. In some embodiments, the hydrophilic polymer is present in the pharmaceutical composition in an amount of about 10 mg to about 500 mg. In some embodiments, the hydrophilic polymer is present in the amorphous solid dispersion in an amount of about 1% to about 80% by weight. In some embodiments, the hydrophilic polymer is present in the amorphous solid dispersion in an amount of about 15% to about 50% by weight. In some embodiments, the hydrophilic polymer is vinylpyrrolidone-vinyl acetate copolymer, polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), sulfobutylether-β-cyclodextrin, hydropropylmethylcellulose acetate succinate (HPMCAS), polyethylene glycol (PEG), polymethacrylates, hypromellose phthalate (HPMCP), polyvinylcaprolactam, poly vinyl acetate, polyvinyl caprolactam-polyvinyl acetate-polyethylene glycol graft co-polymer, polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, polymethacrylates comprise Eudragit. In some embodiments, the hydrophilic polymer is vinylpyrrolidone-vinyl acetate copolymer, PEG, polymethacrylates (e.g., Eudragit), hypromellose phthalate (HPMCP), polyvinylcaprolactam, polyvinyl acetate, polyvinyl caprolactam-polyvinyl acetate-polyethylene glycol graft co-polymer, or hydropropylmethylcellulose acetate succinate (HPMCAS). In some embodiments, the amorphous solid dispersion comprises an acid. In some embodiments, the acid is an organic acid. In some embodiments, the acid is an inorganic acid. In some embodiments, the acid is selected from the group consisting of tartaric acid, fumaric acid, succinic acid, citric acid, lactic acid, malic acid, methanesulfonic acid, ethanesulfonic acid, isethionic acid, benzenesulfonic acid, p-toluenesulfonic acid, hydrochloric acid, sulfuric acid, and phosphoric acid. In some embodiments, the acid is tartaric acid, citric acid, or succinic acid. In some embodiments, a weight ratio of the PROTAC compound or a pharmaceutically acceptable salt thereof to the hydrophilic polymer is from about 10:1 to about 1:10. In some embodiments, the ASD comprises an adsorbent. In some embodiments, the adsorbent is selected from the group consisting of silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextrin. In some embodiments, the adsorbent is silicon dioxide. In some embodiments, the adsorbent is present in the amorphous solid dispersion in an amount of about 10 to about 35% by weight. In some embodiments, a D50 value of particle diameter of the amorphous solid dispersion is from 1 μm to 1000 μm. In some embodiments, the D50 value is from about 1 μm to about 150 μm (e.g., 10 μm to 15 μm). In some embodiments, the amorphous solid dispersion further comprises an antioxidant (e.g., vitamin E). In some embodiments, the pharmaceutically acceptable carrier or excipient is free of organic acid. In some embodiments, the pharmaceutically acceptable carrier or excipient comprises an external acid that is not present in the amorphous solid dispersion. In some embodiments, the pharmaceutical composition is storage stable for a period of at least 1 month, 2 months, 3 months, 6 months, 9 months, 12 months, or 24 months at 5±3° C., wherein a storage stable pharmaceutical composition retains at least 90 wt % of the PROTAC compound or the pharmaceutically acceptable salt thereof at the end of the period. In some embodiments, the pharmaceutical composition is storage stable for a period of at least 2 weeks, 1 month, 2 months, 3 months, 6 months, 9 months, 12 months, or 24 months at 25±2° C., wherein a storage stable pharmaceutical composition retains at least 90 wt % of the PROTAC compound or the pharmaceutically acceptable salt thereof at the end of the period. In some embodiments, the pharmaceutical composition is storage stable for a period of at least 2 weeks, 1 month, 2 months, 3 months, 6 months, 12 months, or 24 months at 40±2° C., wherein a storage stable pharmaceutical composition retains at least 90 wt % of the PROTAC compound or the pharmaceutically acceptable salt thereof at the end of the period. In some embodiments, the pharmaceutical composition comprises a) an amorphous solid dispersion that comprises: (i) ARV-110, ARV-471, CF17455, AC0682, ARV-766, BGB-16673, DT2216, FHD-609, GT20029, HP518, HSK29116, KT-474, NX-2127, NX-5948, AC0176, BRD4-CHAMP, KT-413, or a pharmaceutically acceptable salt thereof in an amount of about 5% to about 50% by weight of the ASD; (ii) a surfactant in an amount of about 1% to about 60% by weight of the ASD, wherein the surfactant comprises tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof; (iii) a hydrophilic polymer in an amount of about 5% to about 70% by weight of the ASD, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), PEG, polymethacrylates (e.g., Eudragit), hypromellose phthalate (HPMCP), polyvinylcaprolactam, polyvinyl acetate, polyvinyl caprolactam-polyvinyl acetate-polyethylene glycol graft co-polymer, hydropropylmethylcellulose acetate succinate (HPMCAS), hydroxypropyl beta cyclodextrin (HP-β-CD), sulfobutylether-β-cyclodextrin, or a combination thereof; and (iv) optionally an acid in an amount of about 1% to about 50% by weight of the ASD; and b) optionally a pharmaceutically acceptable carrier or excipient. In some embodiments, the pharmaceutical composition comprises a) an amorphous solid dispersion that comprises: (i) an amorphous solid dispersion that comprises: ARV-110, ARV-471, or a pharmaceutically acceptable salt thereof in an amount of about 5% to about 50% by weight of the ASD; (ii) a surfactant in an amount of about 1% to about 50% by weight of the ASD, wherein the surfactant comprises tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof; (iii) a hydrophilic polymer in an amount of about 5% to about 70% by weight of the ASD, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), PEG, polymethacrylates (e.g., Eudragit), hypromellose phthalate (HPMCP), polyvinylcaprolactam, polyvinyl acetate, polyvinyl caprolactam-polyvinyl acetate-polyethylene glycol graft co-polymer, hydropropylmethylcellulose acetate succinate (HPMCAS), or hydroxypropyl beta cyclodextrin (HP-β-CD), sulfobutylether-β-cyclodextrin or a combination thereof; and (iv) optionally an acid in an amount of about 1% to about 50% by weight of the ASD, wherein the acid comprises tartaric acid, fumaric acid, succinic acid, citric acid, lactic acid, malic acid, methanesulfonic acid, ethanesulfonic acid, isethionic acid, benzenesulfonic acid, p-toluenesulfonic acid, hydrochloric acid, sulfuric acid, phosphoric acid, or a combination thereof; and b) optionally a pharmaceutically acceptable carrier or excipient. In some embodiments, a weight ratio of the PROTAC compound or a pharmaceutically acceptable salt thereof to the surfactant is from about 1:0.5 to about 1:6, from about 1:0.8 to about 1:5, or from about 1:1 to about 1:3. In some embodiments, a weight ratio of the PROTAC compound or a pharmaceutically acceptable salt thereof to the hydrophilic polymer is from about 1:0.5 to about 1:6, from about 1:0.8 to about 1:5, or from about 1:1 to about 1:3. In some embodiments, the ASD comprises ARV-110 or a pharmaceutically acceptable salt thereof in an amount of about 10% to about 40% by weight of the ASD; a surfactant in an amount of about 5% to about 60% by weight of the ASD, wherein the surfactant is TPGS or lecithin or a combination thereof; a hydrophilic polymer in an amount of about 10% to about 60% by weight of the ASD, wherein the hydrophilic polymer comprises vinylpyrrolidone-vinyl acetate copolymer, PEG, polymethacrylates (e.g., Eudragit), hypromellose phthalate (HPMCP), polyvinylcaprolactam, polyvinyl acetate, polyvinyl caprolactam-polyvinyl acetate-polyethylene glycol graft co-polymer, or HPMCAS or a combination thereof; and optionally an acid in an amount of about 5% to about 40% by weight of the ASD, wherein the acid is tartaric acid or citric acid. In some embodiments, the ASD comprises ARV-110 or a pharmaceutically acceptable salt thereof in an amount of about 15% to about 35% by weight of the ASD; a surfactant in an amount of about 10% to about 50% by weight of the ASD, wherein the surfactant is TPGS or lecithin; a hydrophilic polymer in an amount of about 10% to about 50% by weight of the ASD, wherein the hydrophilic polymer comprises vinylpyrrolidone-vinyl acetate copolymer, PEG, polymethacrylates (e.g., Eudragit), hypromellose phthalate (HPMCP), polyvinylcaprolactam, polyvinyl acetate, polyvinyl caprolactam-polyvinyl acetate-polyethylene glycol graft co-polymer, or HPMCAS; and optionally an acid in an amount of about 10% to about 35% by weight of the ASD, wherein the acid is tartaric acid or citric acid. In some embodiments, the ARV-471 or a pharmaceutically acceptable salt thereof in an amount of about 10% to about 40% by weight of the ASD; a surfactant in an amount of about 5% to about 60% by weight of the ASD, wherein the surfactant is TPGS or lecithin; a hydrophilic polymer in an amount of about 10% to about 60% by weight of the ASD, wherein the hydrophilic polymer comprises vinylpyrrolidone-vinyl acetate copolymer, PEG, polymethacrylates (e.g., Eudragit), hypromellose phthalate (HPMCP), polyvinylcaprolactam, polyvinyl acetate, polyvinyl caprolactam-polyvinyl acetate-polyethylene glycol graft co-polymer, or HPMCAS; and optionally an acid in an amount of about 5% to about 40% by weight of the ASD, wherein the acid is tartaric acid or succinic acid. In some embodiments, the ASD comprises ARV-471 or a pharmaceutically acceptable salt thereof in an amount of about 15% to about 35% by weight of the ASD; a surfactant in an amount of about 10% to about 50% by weight of the ASD, wherein the surfactant is TPGS or lecithin; a hydrophilic polymer in an amount of about 10% to about 50% by weight of the ASD, wherein the hydrophilic polymer comprises vinylpyrrolidone-vinyl acetate copolymer. PEG, polymethacrylates (e.g., Eudragit), hypromellose phthalate (HPMCP), polyvinylcaprolactam, polyvinyl acetate, polyvinyl caprolactam-polyvinyl acetate-polyethylene glycol graft co-polymer, or HPMCAS; and optionally an acid in an amount of about 10% to about 35% by weight of the ASD, wherein the acid is tartaric acid or succinic acid. In some embodiments, the pharmaceutical composition is formulated in a unit dosage form. In some embodiments, the unit dosage form comprises 30 to 300 mg of the PROTAC compound or a pharmaceutically acceptable salt thereof; 10 to 500 mg of the surfactant; 10 to 500 mg of the hydrophilic polymer; optionally an acid in an amount of 1 to 500 mg; and optionally an adsorbent in an amount of 1 to 500 mg; and optionally a pharmaceutically acceptable carrier or excipient.

Disclosed herein is an amorphous solid dispersion, wherein the amorphous solid dispersion comprises, (i) a proteolysis targeting chimera (PROTAC) compound or a pharmaceutically acceptable salt thereof; (ii) a surfactant; (iii) a hydrophilic polymer; (iv) optionally an acid; and v. optionally an adsorbent, wherein the PROTAC compound or a pharmaceutically acceptable salt thereof, the surfactant, the hydrophilic polymer, and the optional acid are present in the ASD in an amorphous state. In some embodiments, the PROTAC compound is ARV-110 or ARV-471.

Disclosed herein is a method of treating a disease or condition, comprising administering to a subject in need thereof the pharmaceutical composition or the amorphous solid dispersion described herein. In some embodiments, the pharmaceutical composition is administered with or without food. In some embodiments, the subject is in a fasted state. In some embodiments, the subject is in a fed state. In some embodiments, the disease or condition is cancer. In some cases, the cancer is the cancer is prostate cancer or breast cancer.

Disclosed herein is a method of ubiquitinating or degrading a target protein in a cell of a subject, comprising administering to a subject the pharmaceutical composition or the amorphous solid dispersion described herein.

Disclosed herein is a method for preparing an amorphous solid dispersion, comprising the steps: a) combining (i) proteolysis targeting chimera (PROTAC) compound or a pharmaceutically acceptable salt thereof, (ii) a surfactant, (iii) a hydrophilic polymer, (iv) optionally an additive and (v) a solvent, thereby producing a liquid mixture or solution, and b) removing the solvent from said mixture, thereby producing an amorphous solid dispersion.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
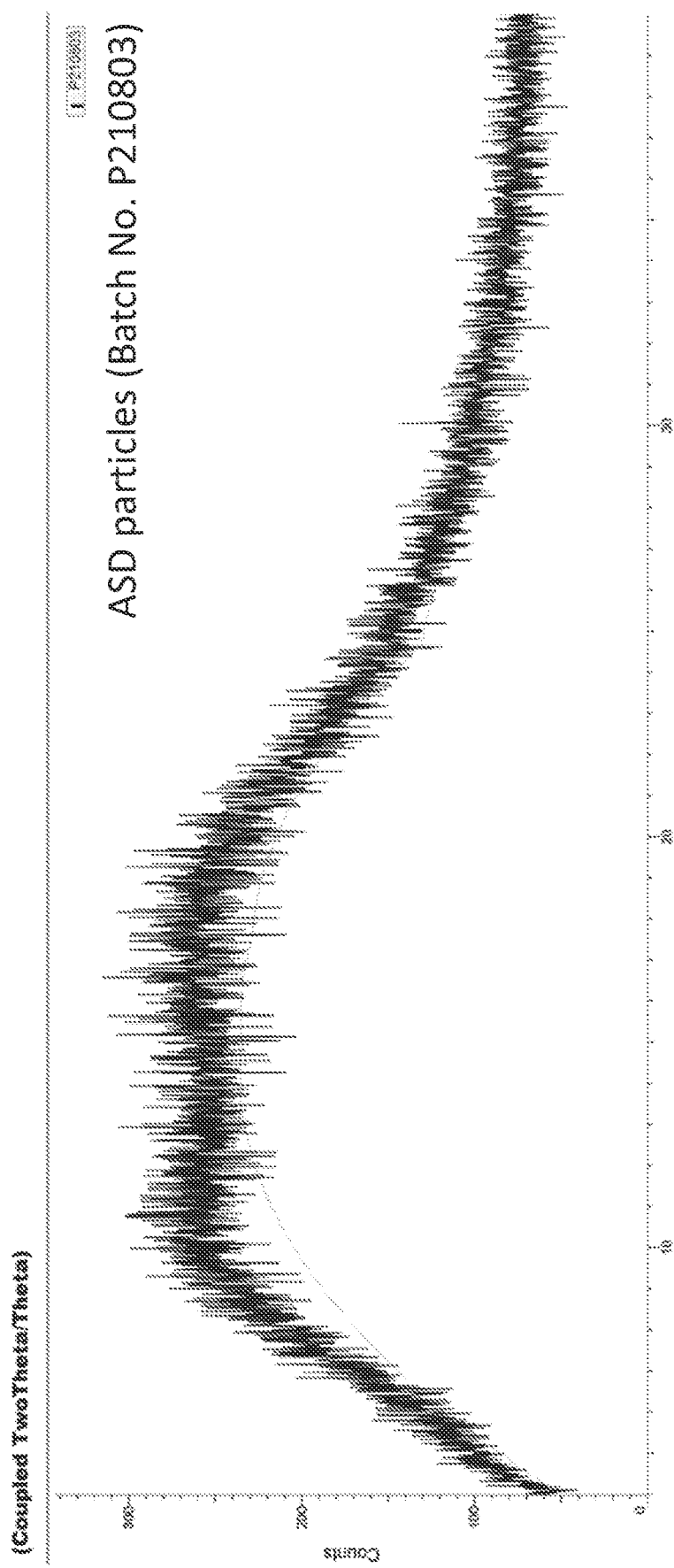
FIG. 1 shows X-ray powder diffraction study for the amorphous solid dispersion (ASD) of ARV-110 formulation batch no. P210803.

The present disclosure is generally directed to compositions comprising pharmaceutically active agents that are useful as therapeutics that alleviate, abate or eliminate one or more conditions in a subject in need thereof, as further described herein. In particular, described herein are pharmaceutical compositions, their manufacturing process and use, where the pharmaceutical compositions comprise a PROTAC, a hydrophilic polymer, and a surfactant in a combination such that the PROTAC has improved bioavailability compared to the PROTAC alone. In some embodiments, the PROTAC, a hydrophilic polymer, one or more surfactant, and optionally an acid, are in an amorphous solid dispersion. The presently disclosed pharmaceutical compositions comprising amorphous solid dispersions that comprise PROTACs and suitable excipients or carriers provide better bioavailability and reduced food-effects than the crystalline form or other conventional dosage forms of such PROTACs. In some embodiments, the conventional dosage forms of PROTACs include dosage forms comprising PROTACs in a crystalline form. In some embodiments, the conventional dosage forms of PROTACs include dosage forms comprising PROTACs in an amorphous state without being a part of an ASD. In some embodiments, the conventional dosage forms comprise the PROTAC in a crystalline form.

In some embodiments, the conventional dosage forms comprise the PROTAC in an amorphous state. In some embodiments, the conventional dosage forms comprise PROTACs compound filled in a capsule. In some embodiments, the conventional dosage forms do not comprise an ASD. In some embodiments, the ASD comprises a PROTAC, a surfactant (e.g., lecithin or TPGS), and a hydrophilic polymer.

Definitions

The general terms used hereinbefore and hereinafter preferably have within the context of this disclosure the following meanings, unless otherwise indicated:

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The singular forms "a." "an," and, "the" include plural referents unless the context clearly dictates otherwise. Thus, for example, reference to "the surfactant" includes reference to one or more specific surfactants, reference to "an antioxidant" includes reference to one or more of such additives.

The term "subject" as used herein refers to a mammal (e.g., a human, mouse, rat, guinea pig, dog, cat, horse, cow, pig, or non-human primate, such as a monkey, chimpanzee or baboon).

"AUC" or "$AUC_{inf}$" as used herein refers to the area under the plasma drug concentration-versus-time curve extrapolated from zero time to infinity. "$AUC_{last}$" as used herein refers to the area under the curve from the time of dosing to the time of the last measurable concentration. "$C_{max}$" as used herein refers to the highest drug concentration observed in plasma following an extravascular dose of drug. "$T_{max}$" as used herein refers to the time after administration of a drug when the maximum plasma concentration is reached. In some cases, the AUC, $AUC_{inf}$, or $C_{max}$ can be used to measure bioavailability of an API described herein (e.g., a PROTAC). In some cases, improvements or differences in bioavailability of the API in various oral compositions (e.g., the ASD compositions described herein) can be evaluated by AUC, $AUC_{inf}$, or $C_{max}$. In some cases, the bioavailability of the API is evaluated in a subject in fed condition or in fasted condition. In some cases, an absolute bioavailability of the API is measured via plasma concentrations of the API achieved by i.v. injection.

"D10," "D50," and "D90" are used herein to describe a particle size distribution. The "D10" as used herein refers to the diameter that has ten percent of the total mass of the particles smaller and ninety percent larger. The "D50" as used herein refers to the median diameter where fifty percent of the total mass of particles are larger and 50% are smaller. The "D90" defines the diameter where ninety percent of the mass distribution has a smaller particle diameter and ten percent has a larger particle diameter.

In some embodiments, an error-band is included. The term "total error band" is used herein to specify all sources of including sampling and sample preparation calculated at a 95% confidence level. An example is: D50 100 μm with a total error band of +/−5% on size. Other statistics are sometimes used to describe a particle size distribution. The most common calculations are standard deviation and variance. The standard deviation (St Dev.). The standard deviation specification defines the diameter where approximately 68.27% of the total population lies within +/−1 St Dev, and 95.45% lies within +/−2 St Dev.

"Effective amount," and "sufficient amount" may be used interchangeably, and refer to an amount of a substance that is sufficient to achieve an intended purpose or objective.

A "therapeutically effective amount" when used in connection with a pharmaceutical composition described herein is an amount of one or more pharmaceutically active agent(s) sufficient to produce a therapeutic result in a subject in need thereof.

"Therapeutically equivalent" when used in connection with a pharmaceutical composition described herein refers to an amount or quantity of a pharmaceutically acceptable salt or ester of a pharmaceutically active agent that is equivalent to the therapeutically effective amount of the free base or alcohol of the pharmaceutically active agent.

The prefix "lower" denotes a radical having up to and including a maximum of 7, especially up to and including a maximum of 4 carbon atoms, the radicals in question being either linear or branched with single or multiple branching.

"Amino" refers to the —$NH_2$ radical.
"Cyano" refers to the —CN radical.
"Nitro" refers to the —$NO_2$ radical.
"Methoxyl" refers to the —O-Me radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Hydroxy" or "hydroxyl" refers to the —OH radical.
"Hydroxyamino" refers to the —NH—OH radical.

"Acyl" refers to a substituted or unsubstituted alkylcarbonyl, substituted or unsubstituted alkenylcarbonyl, substituted or unsubstituted alkynylcarbonyl, substituted or unsubstituted cycloalkylcarbonyl, substituted or unsubstituted heterocycloalkylcarbonyl, substituted or unsubstituted arylcarbonyl, substituted or unsubstituted heteroarylcarbonyl, amide, or ester, wherein the carbonyl atom of the carbonyl group is the point of attachment. Unless stated otherwise specifically in the specification, an alkylcarbonyl group, alkenylcarbonyl group, alkynylcarbonyl group, cycloalkylcarbonyl group, amide group, or ester group is optionally substituted, for example, with oxo, halogen, amino, nitrile, nitro, hydroxyl, haloalkyl, alkoxy, aryl, cycloalkyl, heterocycloalkyl, heteroaryl, and the like.

"Acyl-sulfonamide" refers to a monovalent radical where the carbon atom of a carbonyl is bound to a sulfonamide group. Exemplary acyl-sulfonamides include —C(O)NR$^a$S(O)$_2$R$^a$, —C(O)NR$^a$S(O)$_2$N(R$^a$)$_2$, —NR$^a$S(O)$_2$C(O)R$^a$, —NR$^a$S(O)$_2$C(O)N(R$^a$)$_2$, —C(O)NR$^a$S(O)$_2$C(O)N(R$^a$)$_2$, —NR$^a$S(O)$_2$NR$^a$C(O)N(R$^a$)$_2$, —C(O)NR$^a$S(O)$_2$NR$^a$C(O)N(R$^a$)$_2$, and —C(O)S(O)$_2$N(R$^a$)$_2$, where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkyl" refers to an optionally substituted straight-chain, or optionally substituted branched-chain saturated hydrocarbon monoradical. An alkyl group can have from one to about twenty carbon atoms, from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl, and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, —NO$_2$, or —C≡CH. In some embodiments, the alkyl is optionally substituted with halogen, —CN, —CF$_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds. In some embodiments, an alkenyl group has from two to about ten carbon atoms, or two to about six carbon atoms. The group may be in either the cis or trans configuration about the double bond(s), and should be understood to include both isomers. Examples include, but are not limited to, ethenyl (—CH=CH$_2$), 1-propenyl (—CH$_2$CH=CH$_2$), isopropenyl [—C(CH$_3$)=CH$_2$], butenyl, 1,3-butadienyl, and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms, or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds. In some embodiments, an alkynyl group has from two to about ten carbon atoms, more preferably from two to about six carbon atoms. Examples include, but are not limited to, ethynyl, 2-propynyl, 2-butynyl, 1,3-butadiynyl, and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms, or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —CF$_3$, —OH, —OMe, —NH$_2$, or —NO$_2$. In some embodiments, an alkynyl is optionally substituted with oxo, halogen, —CN, —CF$_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or —OMe. In some embodiments, the alkylene is optionally substituted with halogen. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkylamino" refers to a radical of the formula —N(R$^a$)$_2$ where & is an alkyl radical as defined, or two a, taken together with the nitrogen atom, can form a substituted or unsubstituted C$_2$-C$_7$ heterocyloalkyl ring such as:

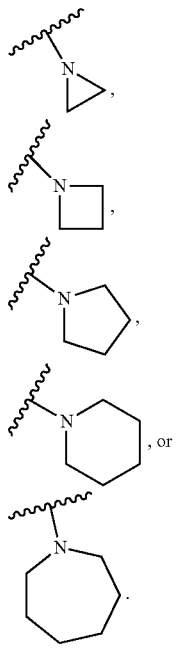

Unless stated otherwise specifically in the specification, an alkylamino group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylamino is optionally substituted with oxo, halogen, —CN, —CF$_3$, —OH, —OMe, —NH$_2$, or —NO$_2$. In some embodiments, an alkylamino is optionally substituted with oxo, halogen, —CN, —CF$_3$, —OH, or —OMe. In some embodiments, the alkylamino is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN. —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Hydroxyalkyl include, for example, aminomethyl, aminoethyl, aminopropyl, aminobutyl, or aminopentyl. In some embodiments, the hydroxyalkyl is aminomethyl.

"Aryl" refers to a radical derived from a hydrocarbon ring system comprising at least one aromatic ring. In some embodiments, an aryl comprises hydrogens and 6 to 30 carbon atoms. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, alkylamino, aminoalkyl, nitrile, nitro, hydroxyl, alkyl, alkenyl, alkynyl, haloalkyl, heteroalkyl, alkoxy, aryl, cycloalkyl, heterocycloalkyl, heteroaryl, —S(O)$_2$NH—C$_1$-C$_6$alkyl, and the like. In some embodiments, an aryl is optionally substituted with halogen, methyl, ethyl, —CN, —CF$_3$, —OH, —OMe, —NH$_2$, —NO$_2$, —S(O)$_2$NH$_2$, —S(O)$_2$NHCH$_3$, —S(O)$_2$NHCH$_2$CH$_3$, —S(O)$_2$NHCH(CH$_3$)$_2$, —S(O)$_2$N(CH$_3$)$_2$, or —S(O)$_2$NHC(CH$_3$)$_2$. In some embodiments, an aryl is optionally substituted with halogen, methyl, ethyl, —CN, —CF$_3$, —OH, or —OMe. In some embodiments, the aryl is optionally substituted with halogen. In some embodiments, the aryl is substituted with alkyl, alkenyl, alkynyl, haloalkyl, or heteroalkyl, wherein each alkyl, alkenyl, alkynyl, haloalkyl, heteroalkyl is independently unsubstituted, or substituted with halogen, methyl, ethyl, —CN, —CF$_3$, —OH, —OMe, —NH$_2$, or —NO$_2$.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom), bridged, or spiro ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example, cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

The term "carbocycle" as used herein refers to a saturated, unsaturated or aromatic ring in which each atom of the ring is carbon atom. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl. The term "unsaturated carbocycle" refers to carbocycles with at least one degree of unsaturation and excluding aromatic carbocycles. Examples of unsaturated carbocycles include cyclohexadiene, cyclohexene, and cyclopentene. The term "saturated cycloalkyl" as used herein refers to a saturated carbocycle. Exemplary saturated cycloalkyl rings include cyclopropyl, cyclohexyl, and norbornane. Carbocycles may be optionally substituted by one or more substituents such as those substituents described herein.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The disclosure relates also to possible tautomers of the compounds of Formula (I).

"Halo" or "halogen" refers to bromo, chloro, fluoro, or iodo. In some embodiments, halogen is fluoro or chloro. In some embodiments, halogen is fluoro.

"Heteroaryl" refers to a ring system radical comprising carbon atom(s) and one or more ring heteroatoms that selected from the group consisting of nitrogen, oxygen, phosphorous, and sulfur, and at least one aromatic ring. In some embodiments, a heteroaryl is a 5- to 14-membered ring system radical comprising one to thirteen carbon atoms, one to six heteroatoms selected from the group consisting of nitrogen, oxygen, phosphorous, and sulfur. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzthiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen "Heterocyclyl," "heterocycle," or "heterocyclic" refers to a stable 3- to 18-membered saturated, unsaturated or aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused, bridged, or spirocyclic ring systems. The heteroatoms in the heterocyclyl radical are optionally oxidized. One or more nitrogen atoms, if present, are optionally quaternized. The heterocyclyl radical can be partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—CN, —R$^b$—O—R$^b$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

Active Pharmaceutical Ingredient (API)

The present disclosure relates to pharmaceutical compositions and methods of administering and uses thereof, compositions comprising an amorphous solid dispersion comprising an API, a hydrophilic polymer, a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, the API is a PROTAC. Proteolysis Targeting Chimeras (PROTACs) generally have poor water solubility and low oral absorption, even when the PROTAC compound is in an amorphous form. Due to these properties, it is very hard to develop PROTAC compositions that have good oral bioavailability at lower doses and reduced absorption variations caused by food intake. The pharmaceutical compositions described herein demonstrate significantly improved PROTACs oral bioavailability as compared to conventional dosage forms. In some embodiments, the pharmaceutical compositions for PROTACs are amorphous solid dispersions (ASD). In some embodiments, the ASD comprises a surfactant. In some embodiments, the surfactant comprises a phospholipid. In some embodiments, the surfactant comprises lecithin. In some embodiments, the PROTAC is one listed in Table 1. In some embodiments, the PROTAC is ARV-110 or a pharmaceutically acceptable salt or enantiomer thereof. In some embodiments, the PROTAC is ARV-110. In some embodiments, the PROTAC is ARV-471 or a pharmaceutically acceptable salt or enantiomer thereof. In some embodiments, the PROTAC is ARV-471. In some embodiments, the conventional dosage forms of PROTACs include dosage forms comprising PROTACs in a crystalline form. In some embodiments, the conventional dosage forms of PROTACs include dosage forms comprising PROTACs in an amorphous state without being a part of an ASD. In some embodiments, the conventional dosage forms do not comprise an ASD. In some embodiments, the ASD comprises a PROTAC, a surfactant (e.g., lecithin or TPGS), and a hydrophilic polymer.

In some embodiments, a solid dispersion is a solid state solution wherein an API (or API salt) and hydrophilic polymer act as solute and solvent, respectively. The solid dispersion can form multiple structures depending on the composition and sample processing history. When the API loading is lower than the equilibrium solubility of API in the hydrophilic polymer, the drug is molecularly dispersed within the polymer matrix and forms a thermodynamically stable, homogeneous solution. A homogenous solution is often attainable only at very low API loading and/or high temperature. For higher loadings, the mixture becomes a supersaturated solution and the drug precipitates out. This can result in a dispersion of crystalline API particles in a hydrophilic polymer matrix, in which the drug concentration corresponds to its equilibrium solubility at that temperature. Alternatively, as API crystallization can be a slow process, an intermediate meta-stable structure may form in which amorphous API aggregates are dispersed in a hydrophilic polymer matrix containing the API in a non-crystalline amorphous state. Such amorphous solid dispersions can provide superior dissolution properties, as compared to the crystalline API.

Amorphous solid dispersions described herein may comprise an API, hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants. In some embodiments, the amorphous solid dispersions described here are homogenous amorphous solid dispersions. In some embodiments, the components of the amorphous dispersion are mixed and heated in a solvent, and the solvent is removed to form the amorphous solid dispersion. In some embodiments, the solvent is water. In some embodiments, the solvent is a polar organic solvent. In some embodiments, the solvent is a non-polar organic solvent. In some embodiments, the solvent is selected from water, n-butanol, n-propanol, isopropanol, formic acid, nitromethane, ethanol, methanol, acetic acid, N-methylpyrrolidone, tetrahydrofuran, ethyl acetate, methyl acetate, dimethylformamide, acetonitrile, dimethyl sulfoxide, dichloromethane (DCM), acetone, tetrahydrofuran (THF), and any combination thereof. In some embodiments, the solvent is selected from water, n-butanol, n-propanol, isopropanol, formic acid, nitromethane, ethanol, methanol, acetic acid, and any combination thereof. In some embodiments, the solvent is selected from water, methanol, ethanol and isopropanol. In some embodiments, the solvent is selected from dichloromethane, methanol, THF, and acetone. In some embodiments, the solvent is selected from a mixture of these solvents.

Amorphous solid dispersions described herein may comprise an API, hydrophilic polymer, a surfactant and optionally, an adsorbent. In some embodiments, the components of the amorphous dispersion, such as API, hydrophilic polymer and surfactant are mixed and solubilized in a solvent, with or without heating to form a solution. In some embodiments, the adsorbent is further added into the solution to form a homogeneous suspension and the solvent is removed to form the amorphous solid dispersion. In some embodiments, the solution is sprayed on to the adsorbent and the solvent is removed to form the amorphous solid dispersion. In some embodiments, the adsorbent is selected from silicon dioxide (also termed silica), magnesium aluminometasilicate (Neusilin), microcrystalline cellulose (MCC), silicified microcrystalline cellulose (SMCC), talc, crosslinked povidone, sodium carboxymethylcellulose, sodium carboxymethylstarch, sugars, and sugar alcohols. In some embodiments, sugars and sugar alcohol comprise sorbitol, mannitol, lactose, cyclodextrin, and maltodextrin. In some embodiments, the adsorbent is silicon dioxide.

PROTAC Compound

Various embodiments described herein are directed to compositions comprising an effective amount of an active pharmaceutical agent (API). "Active pharmaceutical agent," "API," "drug," "pharmaceutically active agent," "bioactive agent," "therapeutic agent." and "active agent" and the like may be used interchangeably and refer to a substance, such as a chemical compound, a complex, or a PROTAC, that has a measurable beneficial physiological effect on the body, such as a therapeutic effect in treatment of a disease or disorder, when administered in an effective amount. Further, when these terms are used, or when a particular active agent is specifically identified by name or category, it is understood that such recitation is intended to include the active agent per se, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, analogs, solvates hydrates, radioisotopes, etc.

The partition-coefficient (P) as referenced herein is a ratio of concentrations of a compound between two immiscible solvent phases at equilibrium. Most commonly, one of the solvents is water and the other is hydrophobic, typically 1-octanol. The logarithm of the ratio is log P, as shown below, (conventionally the lipophilic phase is the numerator and hydrophilic phase is the denominator.)

$$\log P_{octanol/water} = \log\left(\frac{[solute]_{octanol}}{[solute]_{water}}\right)$$

log P is a measure of lipophilicity or hydrophobicity. Hydrophobicity affects drug absorption, bioavailability, hydrophobic drug-receptor interactions, metabolism of molecules, and toxicity. Hydrophilic compounds are soluble in water ("water-loving") and polar solvents. Lipophilic compounds are less soluble in water ("water-fearing" or hydrophobic) and polar solvents, but are more soluble in organic solvents. Thus:

Low hydrophilicity=high lipophilicity=high log P=poor aqueous solubility=poor absorption.

High hydrophilicity=low lipophilicity=low log P=good aqueous solubility=good absorption.

Partition coefficients can be measured experimentally or estimated via calculation. Various methods for calculating (or predicting) log P have been developed, typically by fitting calculated log P values with experimentally measured log P values for training sets of thousands of molecules, mostly drug-like. Log P calculations are considered very robust and accurately process many organic molecules. For example, over 50% of molecules log P is predicted with error of less than 0.25, while over 80% with error of less than 0.5. Less than 3.5% of structures are predicted with an error greater 1.0. To distinguish from a measured log P, a calculated log P is sometimes written as clog P. Unless otherwise indicated, "log P" as used herein refers to an experimental log P value.

In some embodiments, the API is lipophilic. An API is considered lipophilic if its log P or calculated log P is 2.0 or higher. A log P of 2.0 or higher denotes that the solubility of the API is 100-fold or higher in a lipophilic solvent than in water. In some embodiments, the API is insoluble in polar solvents. In some embodiments, the API is insoluble in aqueous media. In some embodiments, the API is insoluble in water.

In some embodiments, the PROTAC has a log P of at least 2.0, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0.

In some embodiments, a PROTAC described herein has a low solubility. In some embodiments, the PROTAC has a solubility of less than 10 mg/mL in water at about 25° C. In some embodiments, the PROTAC has a solubility of at most 1 mg/mL in water at about 25° C. In some embodiments, the PROTAC has a solubility of less than 1 mg/mL in water at about 25° C. In some embodiments, the PROTAC has a solubility of less than 0.5 mg/mL in water at about 25° C. In some embodiments, the PROTAC has a solubility of less than 0.1 mg/mL in water at about 25° C. In some embodiments, the PROTAC has a solubility of less than 0.01 mg/mL in water at about 25° C.

In some embodiments, an API described herein is a heterobifunctional small molecule. In some embodiments, the heterobifunctional small molecule is a PROTAC. In some embodiments, a PROTAC comprises a first active domain. In some embodiments, the heterobifunctional small molecule comprises a second active domain. The heterobifunctional small molecule comprises a linker. In some embodiments, the linker binds the first active domain and the second active domain. In some embodiments, the first active domain and the second active domain are linked covalently. In some embodiments, the first active domain engages an E3 ubiquitin ligase. In some embodiments, the second active domain binds to a target protein. In some embodiments, the target protein is meant for degradation.

In some embodiments, a PROTAC works by inducing selective intracellular proteolysis. In some embodiments, a PROTAC brings together a target protein and an E3 ligase. In some embodiments, a PROTAC recruits the E3 ligase and the target protein. In some embodiments, such recruitment by the PROTAC results in ubiquitination and subsequent degradation of the target protein via the proteasome. In some embodiments, a PROTAC achieves degradation of target protein by "hijacking" the cell's ubiquitin-proteasome system (UPS). In some embodiments, an E1 ligase activates and conjugates the ubiquitin to an E2 ligase. In some embodiments, the E2 ligase then forms a complex with an E3 ligase. In some embodiments, the E3 ligase targets a protein of interest by covalently attaching the ubiquitin to the protein of interest. In some embodiments, after a ubiquitin chain is formed, the protein of interest is recognized and degraded by the 26S proteasome. In some embodiments, a PROTAC takes advantage of the UPS cellular system by putting the target proteins in close proximity to the E3 ligase, which catalyzes the degradation of target proteins. In some embodiments, a PROTAC has a catalytic mechanism, which allows the PROTAC itself to be recycled after the target protein is degraded. As used herein, the terms "PROTAC" and "PROTAC compound" are used interchangeably.

Exemplary PROTACs include, without limitation, those listed in Table 1. In some embodiments the API is ARV-110 or a pharmaceutically acceptable salt thereof. In some embodiments, the API is ARV-110. In some embodiments, the API is a pharmaceutically acceptable salt of ARV-110. In some embodiments, the API is a PROTAC. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

TABLE 1

| Name | IUPAC/Chemical Name/Chemical Structure | Calculated log P |
|---|---|---|
| ARV-110 | | 5.8[1] |
| ARV-471 | | 6.4[2] |
| CFT7455 | — | |
| AC0682 | — | |
| ARV-766 | | |
| BGB-16673 | — | |
| DT2216 | | 12.8[2] |
| FHD-609 | — | |
| GT20029 | — | |
| HP518 | — | |
| HSK29116 | — | |

TABLE 1-continued

| Name | IUPAC/Chemical Name/Chemical Structure | Calculated log P |
|---|---|---|
| KT-474 | — | |
| NX-2127 | — | |
| NX-5948 | — | |
| AC0176 | — | |
| BRD4- CHAMP | — | |
| KT-413 | — | |

[1]Heimbach, T., et al .; *Physiologically Based Pharmacokinetic Modeling to Supplement ARV-110 Pharmacokinetics and Confirm Dose Selection in Pediatric Patients*; Journal of Pharmaceutical Sciences 108 (2019) 2191-2198
[2]Calculation source - Computed by XLogP3 3.0 (PubChem release 2021.05.07) listed onwww.pubchem.ncbi.nlm.nih.gov An acid dissociation constant, Ka, (or acidity constant) is a measure of the strength of an acid or base in solution, typically water. It is the equilibrium constant for the chemical dissociation of acids and bases. In aqueous solution, the equilibrium of acid dissociation is written:

$$HA + H_2O \rightleftharpoons A^- + H_3O^+$$

where HA is an acid that dissociates into $A^-$, (the conjugate base of the acid) and a hydrogen ion (which combines with a water molecule to make a hydronium ion, $H_3O^+$). The dissociation constant can also be written with the $H_2O$ removed:

$$HA \rightleftharpoons A^- + H^+$$

$$K_a = \frac{[A^-][H^+]}{[HA]}$$

The equilibrium of the dissociation of the conjugate acid of a base is written:

$$BH^+ + H_2O \rightleftharpoons B + H_3O^+$$

where $BH^+$ (the conjugate acid of the base) dissociates into B (the free base), and a hydrogen ion, which combines with a water molecule to form a hydronium ion, $H_3O^+$.
The dissociation constant can also be written with the $H_2O$ removed:

$$BH^+ \rightleftharpoons B + H^+$$

$$K_b = \frac{[B][H^+]}{[BH^+]}$$

$pK_a$, the logarithmic value of $K_a$, is more often used to express acid the strength/weakness of acids or the conjugate acid of bases:

$$pK_a = -\log_{10}(K_a)$$

The more positive the value of $pK_a$, the smaller the extent of dissociation, and the weaker the acid.
In general, for acids:
  $pK_a = -2$ to 12→weak acid (little or only partial dissociation in water)
  $pK_a < -2$→strong acid (completely or mostly dissociated in water)
while for bases:
  $pK_a < 12$→weak base (little or only partial dissociation in water)
  $pK_a \geq 12$→strong base (completely or mostly dissociated in water)

In some embodiments, the API is a weak base.
In some embodiments, the API comprises a weak base functional group.
In some embodiments, the API has a pKa of equal or greater than 3.0. In some embodiments, the API has a pKa of equal or greater than 3.5. In some embodiments, the API has a pKa of equal or greater than 4.0. In some embodiments, the API has a pKa of equal or greater than 4.5. In some embodiments, the API has a pKa of equal or greater than 5.0.
In some embodiments, the API is present in the form of a free base. In some embodiments, the API is present in the form of a pharmaceutically acceptable salt. As used herein, a pharmaceutically acceptable salt includes, but is not limited to, metal salts, such as sodium salts, potassium salts, and lithium salts; alkaline earth metals, such as calcium salts, magnesium salts, and the like; organic amine salts, such as triethylamine salts, pyridine salts, picoline salts, ethanolamine salts, triethanolamine salts, dicyclohexylamine salts, N,N'-dibenzylethylenediamine salts, and the like; inorganic acid salts such as hydrochloride salts, hydrobromide salts, sulfate salts, phosphate salts, and the like; organic acid salts such as formate salts, acetate salts, trifluoroacetate salts, maleate salts, tartrate salts, and the like; sulfonate salts such as methanesulfonate salts, benzenesulfonate salts, p-toluenesulfonate salts, and the like; and amino acid salts, such as arginate salts, asparaginate salts, glutamate salts, and the like. In some embodiments the API is a PROTAC. In some embodiments the API is a PROTAC listed in Table 1. In some embodiments the API is ARV-110 or a pharmaceutically acceptable salt or ester thereof. In some embodiments, the API is ARV-110. In some embodiments, the API is a pharmaceutically acceptable salt of ARV-110. In some embodiments, the API is a PROTAC. In some embodiments, the PROTAC is a PROTAC. In some embodiments, a PROTAC is one listed in Table 1, or a pharmaceutically acceptable salt thereof. In some embodiments, the PROTAC, hydrophilic polymer, and the surfactant are formulated as an amorphous solid dispersion. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

Exemplary PROTAC Compounds Including ARV-110 and ARV-471 and Analogs Thereof

Described herein is a pharmaceutical composition that comprises an amorphous solid dispersion comprising an API. In some embodiments, the API is a PROTAC. In some embodiments, the API is ARV-110 or a pharmaceutically acceptable salt thereof. In some embodiments, the API is ARV-110. In some embodiments, the API is ARV-471 or a pharmaceutically acceptable salt thereof. In some embodiments, the API is ARV-471. 100931 In some embodiments, the API is a PROTAC. In some embodiments, the PROTAC is a compound of Formula (I), A-L-B    Formula (I)

wherein
(i) A is an E3 ubiquitin ligase binding moiety;
(ii) L is a linker; and
(iii) B is a moiety which binds to a target protein, wherein the target protein is degradable by an E3 ubiquitin ligase.

In some embodiments, A is an E3 ubiquitin ligase binding moiety. In some embodiments, the E3 ubiquitin ligase binding moiety is a small molecule. In some embodiments, the E3 ubiquitin ligase binding moiety targets an E3 ubiquitin ligase. In some embodiments, the E3 ubiquitin ligase is selected from Von Hippel-Lindau (VLM), cereblon (CLM), mouse double-minute homolog2 (MLM), and IAP (ILM). In some embodiments, the E3 ubiquitin ligase is VLM. In some embodiments, the E3 ubiquitin ligase is CLM. In some embodiments, the E3 ubiquitin ligase is MLM. In some embodiments, the E3 ubiquitin ligase is ILM. In some embodiments, the CLM is selected from the group consisting of a thalidomide, lenalidomide, pomalidomide, analogs thereof, isosteres thereof, or derivatives thereof.

In some embodiments, the CLM has a chemical structure represented by Formula (A):

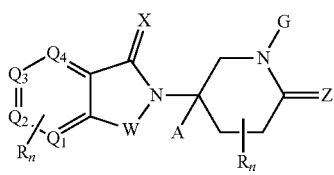

Formula (A)

wherein:
W is selected from the group consisting of $CH_2$, CHR, C=O, $SO_2$, NH, and N-alkyl;
each X is independently selected from the group consisting of O, S, and $H_2$;
Z is selected from the group consisting of O, S, and $H_2$;
G is independently selected from the group consisting of H, $C_1$-$C_6$ alkyl (linear, branched, optionally substituted), OH, R'OCOOR, R'OCONRR", CH, $C_1$-$C_6$ heterocyclyl optionally substituted with R', and benzyl optionally substituted with R';
$Q_1$, $Q_2$, $Q_3$, and $Q_4$ are independently a Carbon atom attached to $R_n$ or a Nitrogen atom;
A is selected from the group H, $C_1$-$C_6$ alkyl (linear, branched, optionally substituted), cycloalkyl, Cl and F;
R comprises —CONR'R", —OR', —NR'R", —SR', —SO, R', —SO, NR'R", —CR'R"—, —CR'NR'R"—, (—CR'OO), R", $C_1$-$C_6$ aryl, —$C_1$-$C_6$ heteroaryl, $C_1$-$C_6$ alkyl (linear, branched, optionally substituted), $C_1$-$C_6$ cycloalkyl, $C_1$-$C_6$ heterocyclyl, —P(O)(OR")R", —P(O)R'R", —OP(O)(OR")R", —OP(O)R'R", —Cl, —F, —Br, —I, —CF, —CN, —NR'SO, NR'R", —NR'CONR'R", —CONR'COR', —NR'C(=N—CN) NR'R", —C(=N—CN)NR'R", —NR'C(=N—CN)R", —NR'C(=C—NO)NR'R", —SO, NR'COR", —$NO_2$, —COR', —C(C=N—OR")R", —CR'=CR'R", —CCR', —S(C=O)(C=N—R")R", —$SF_5$ and —$OCF_3$;

R' and R' are independently selected from the group consisting of a bond, H, $C_1$-$C_6$ alkyl, $C_1$-$C_6$ cycloalkyl, $C_1$-$C_6$ aryl, $C_1$-$C_6$ heteroaryl, halogen, —C(=O)R, and $C_1$-$C_6$ heterocyclyl;

∼∼∼ represents a bond that may be stereospecific ((R) or (S)) or non-stereospecific; and $R_n$ comprises a functional group, a bond, or an atom, wherein n is an integer from 4-10, and wherein one $R_n$ is a bond covalently join one of $Q_1$, $Q_2$, $Q_3$, or $Q_4$ to the linker (L), and any other Rn is optionally selected from the group consisting of H, $C_1$-$C_6$ alkyl, $C_1$-$C_6$ cycloalkyl, $C_1$-$C_6$ aryl, $C_1$-$C_6$ heteroaryl, halogen, and $C_1$-$C_6$ heterocyclyl.

In some embodiments, the CLM has a chemical structure represented by Formula (A), w % herein W is selected from the group consisting of $CH_2$, C=O, and NH:
each X is independently selected from the group consisting of O, and S;
Z is selected from the group consisting of O, and S;
G is independently selected from the group consisting of H, $C_1$-$C_3$ alkyl (linear, branched, optionally substituted), OH.
$Q_1$, $Q_2$, $Q_3$, and $Q_4$ are independently a Carbon atom attached to $R_n$;
A is selected from the group H, $C_1$-$C_3$ alkyl (linear or branched), Cl and F;
∼∼∼ represents a bond that may be stereospecific ((R) or (S)) or non-stereospecific; and
$R_n$ comprises a functional group, a bond, or an atom, wherein n is an integer from 4-10, and wherein one $R_n$ is a bond covalently join one of $Q_1$, $Q_2$, $Q_3$, or $Q_4$ to the linker (L), and any other $R_n$ is optionally selected from the group consisting of H, $C_1$-$C_3$ alkyl, and halogen.

In some embodiments, the CLM has a chemical structure represented by Formula (A), wherein W is selected from the group consisting of $CH_2$ and C=O;
each X is O;
Z is O;
G is H;
$Q_1$, $Q_2$, $Q_3$, and $Q_4$ are independently a Carbon atom attached to $R_n$;
A is H;
∼∼∼ represents a bond that may be stereospecific ((R) or (S)) or non-stereospecific; and
$R_n$ comprises a functional group, a bond, or an atom, wherein n is 4 and each $R_n$ is attached to one of $Q_1$, $Q_2$, $Q_3$, or $Q_4$, wherein one $R_n$ is a bond covalently join $Q_2$ or $Q_3$ to the linker (L), and any other $R_n$ is optionally selected from the group consisting of H and F.

In some embodiments, the CLM has a chemical structure represented by Formula (A), wherein W is C=O; each X is O; Z is O; G is H; $Q_1$, $Q_2$, $Q_3$, and $Q_4$ are independently a Carbon atom attached to $R_n$; A is H;
∼∼∼ represents a bond that may be stereospecific ((R) or (S)) or non-stereospecific; and
$R_n$ comprises a functional group, a bond, or an atom, wherein n is 4 and each $R_n$ is attached to one of $Q_1$, $Q_2$, $Q_3$, or $Q_4$, and wherein one $R_n$ is a bond covalently join $Q_3$ to the linker (L), one $R_n$ is a F attached to $Q_2$, and any other $R_n$ is H.

In some embodiments, the CLM has a chemical structure represented by Formula (A), wherein W is $CH_2$; each X is O; Z is O; G is H; $Q_1$, $Q_2$, $Q_3$, and $Q_4$ are independently a Carbon atom attached to $R_n$; A is H;

represents a bond that may be stereospecific ((R) or (S)) or non-stereospecific; and $R_n$ comprises a functional group, a bond, or an atom, wherein n is 4 and each $R_n$ is attached to one of $Q_1$, $Q_2$, $Q_3$, or $Q_4$, and wherein one $R_n$ is a bond covalently join $Q_2$ to the linker (L), and any other $R_n$ is H.

In some embodiments, the CLM has a chemical structure represented by

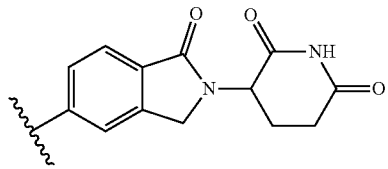 [SMILES: *c1ccc2c(c1)CN(C1CCC(=O)NC1=O)C2=O]

In some embodiments, the CLM has a chemical structure represented by

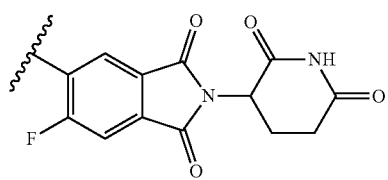 [SMILES: *c1cc2c(cc1F)C(=O)N(C1CCC(=O)NC1=O)C2=O]

In some embodiments, L is a linker. In some embodiments, the linker is a bond. In some embodiments, the linker is a chemical linking moiety connecting A and B.

In some embodiments, L is selected from:

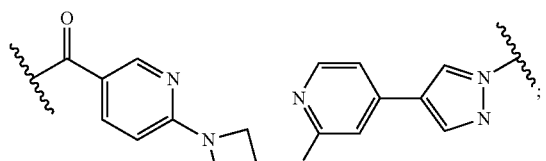

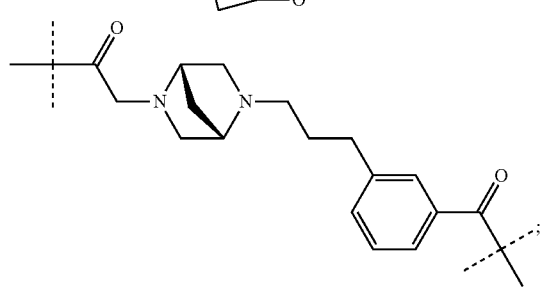

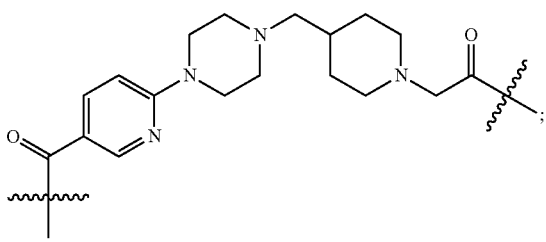

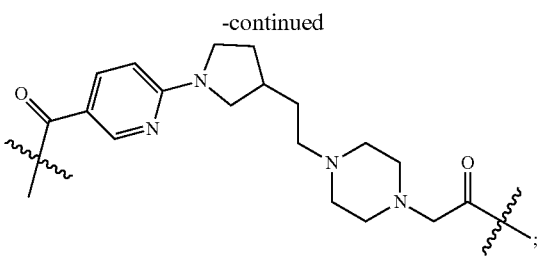

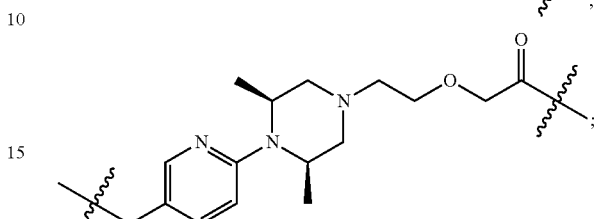

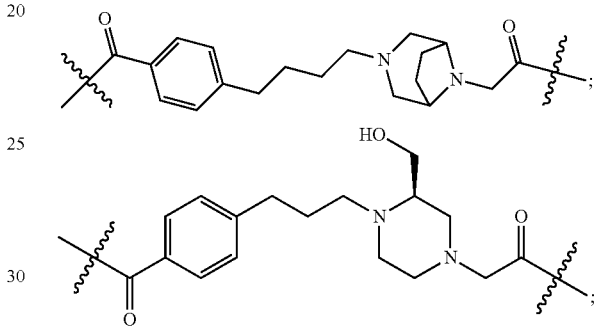

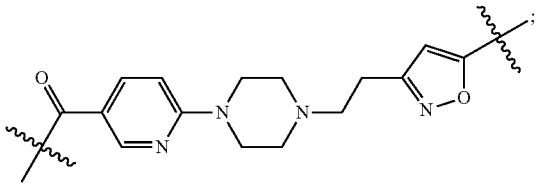

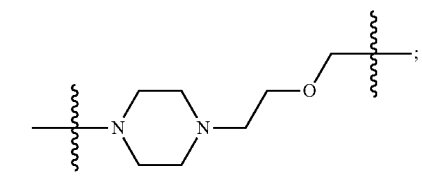

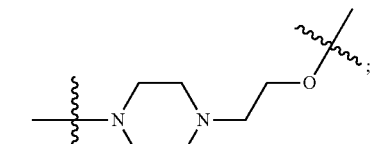

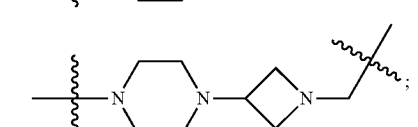

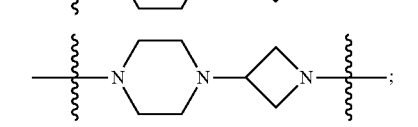

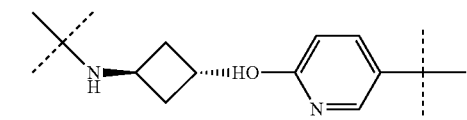

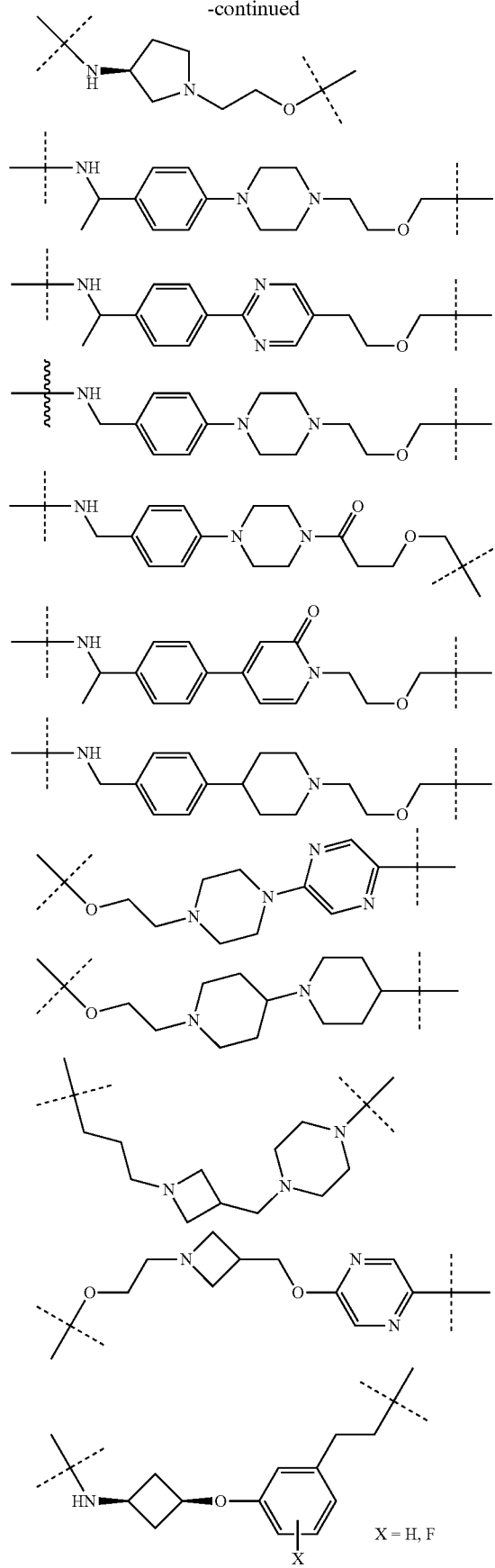
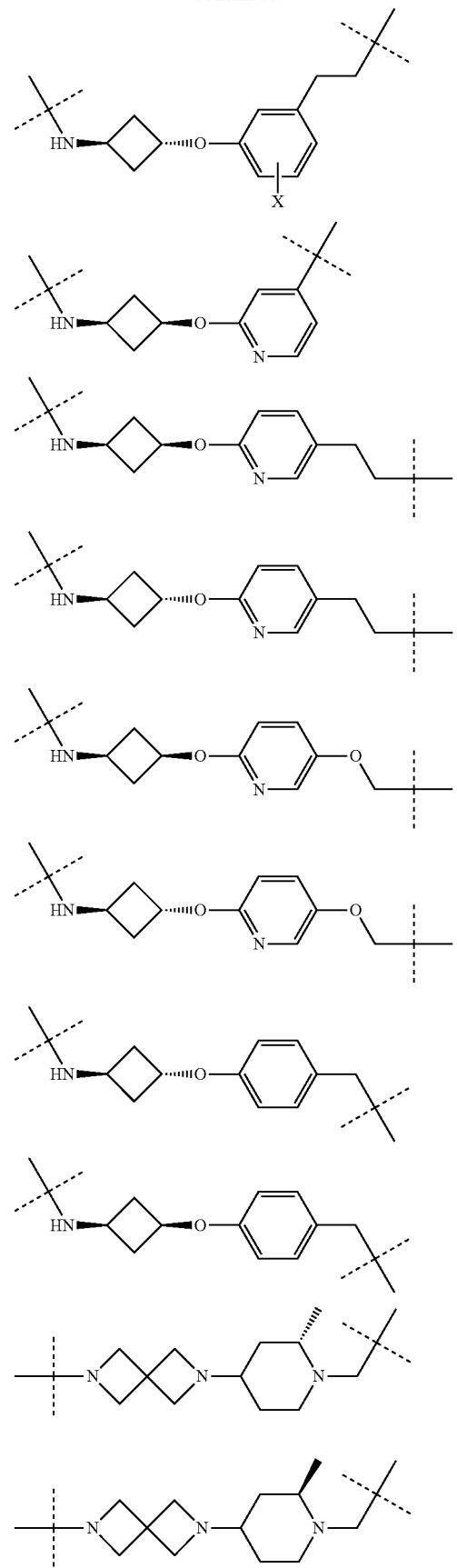

-continued
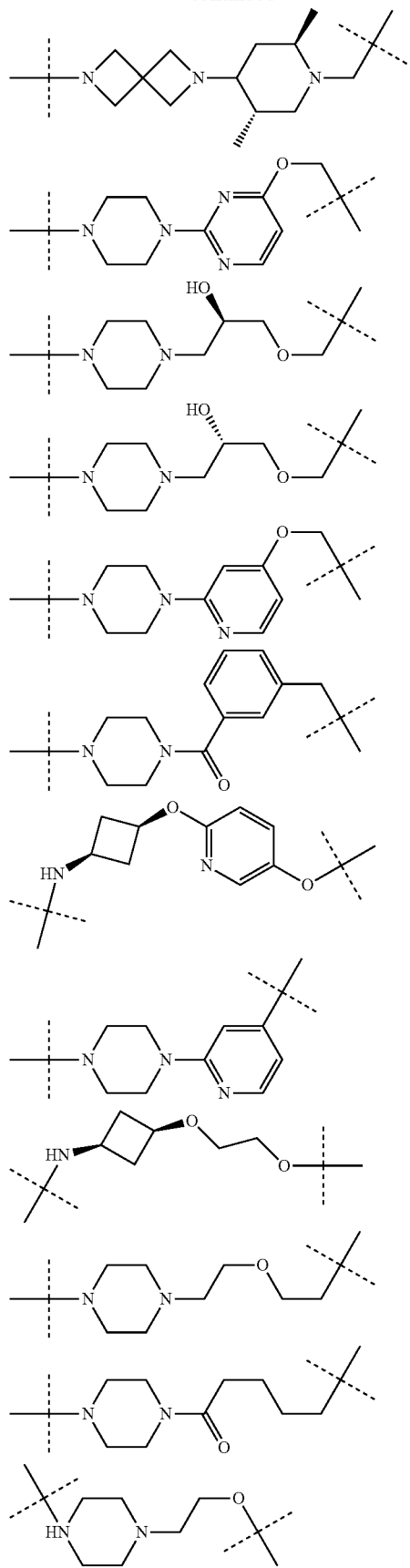
-continued
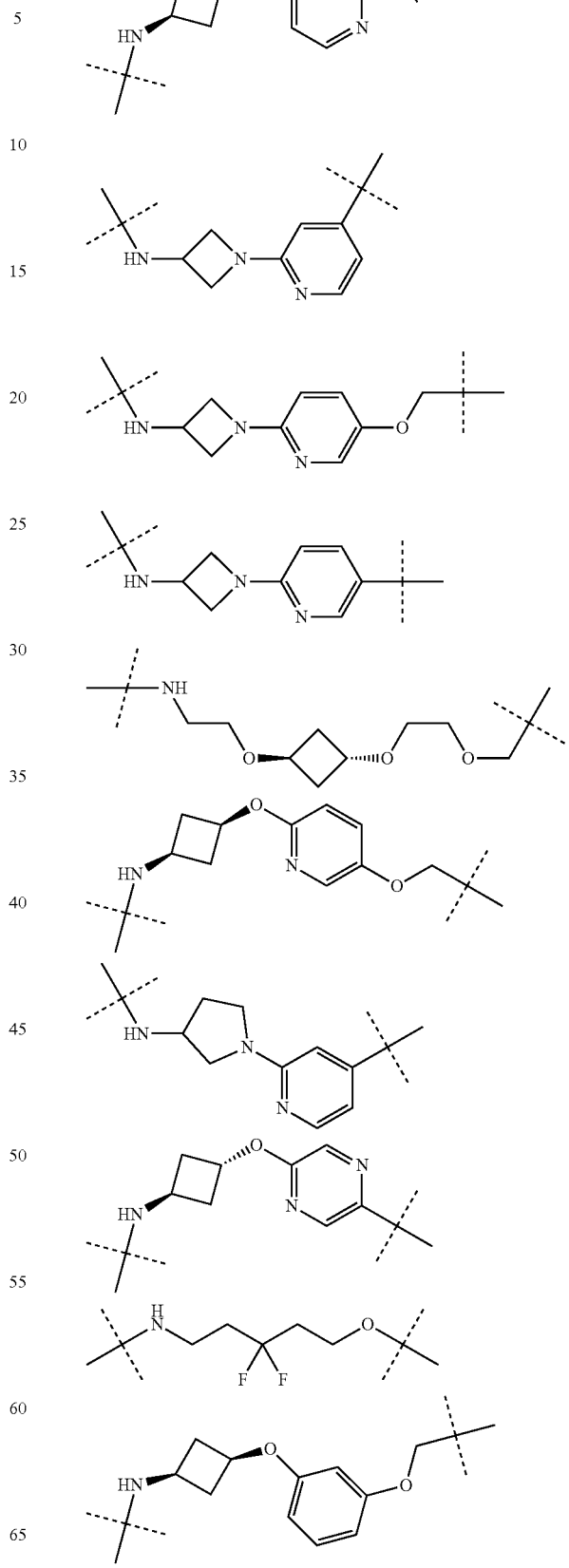

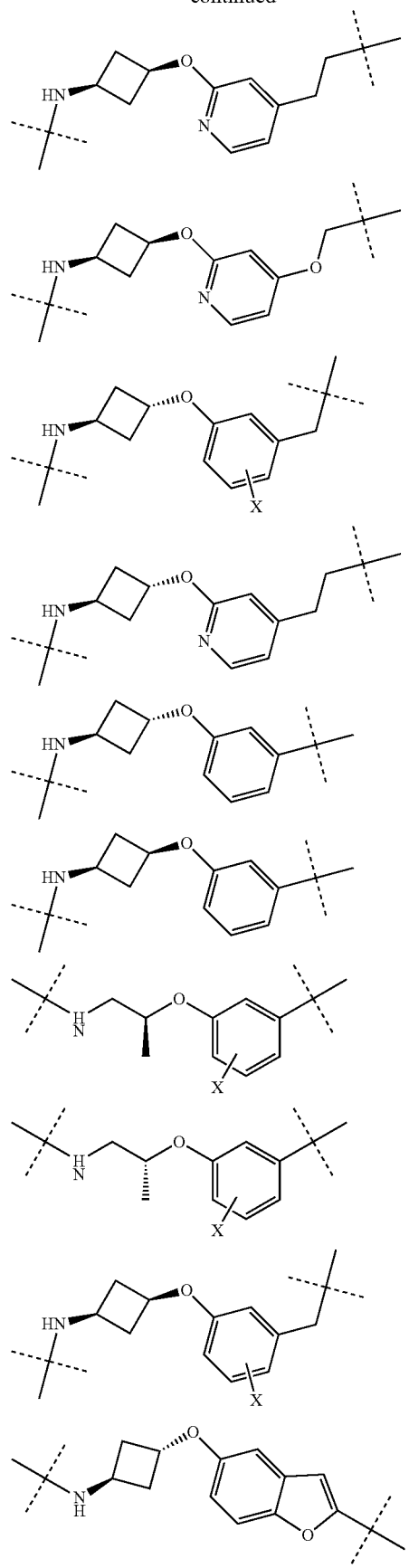
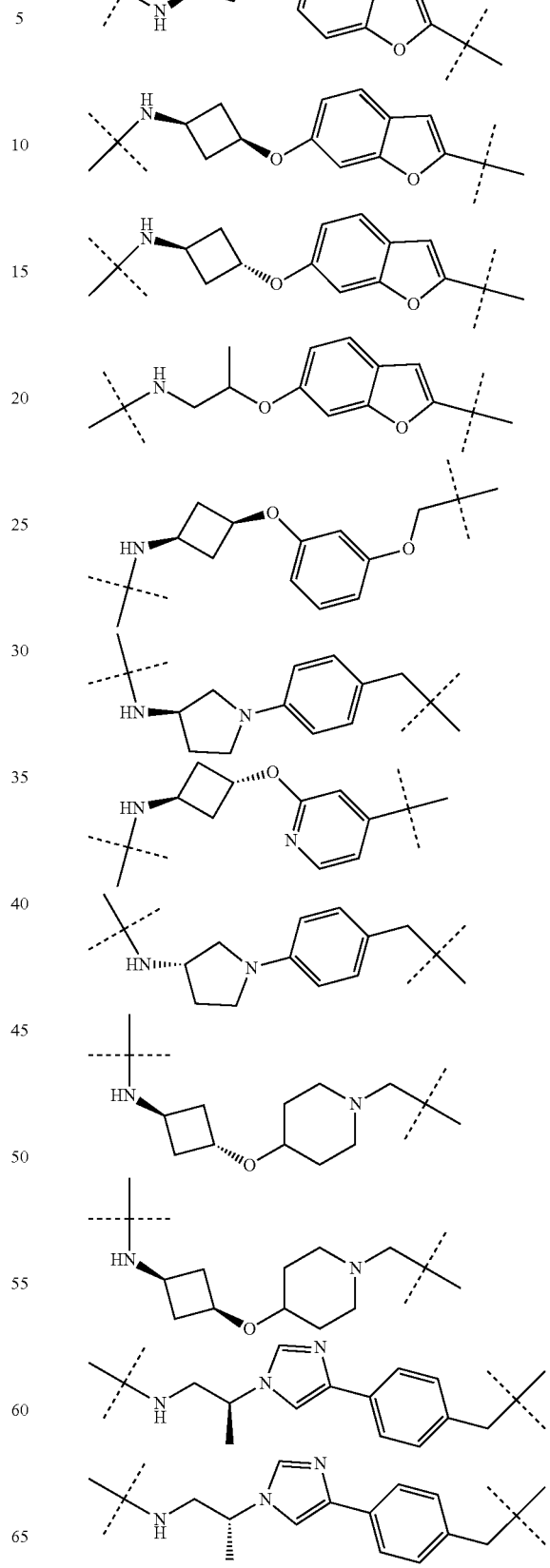

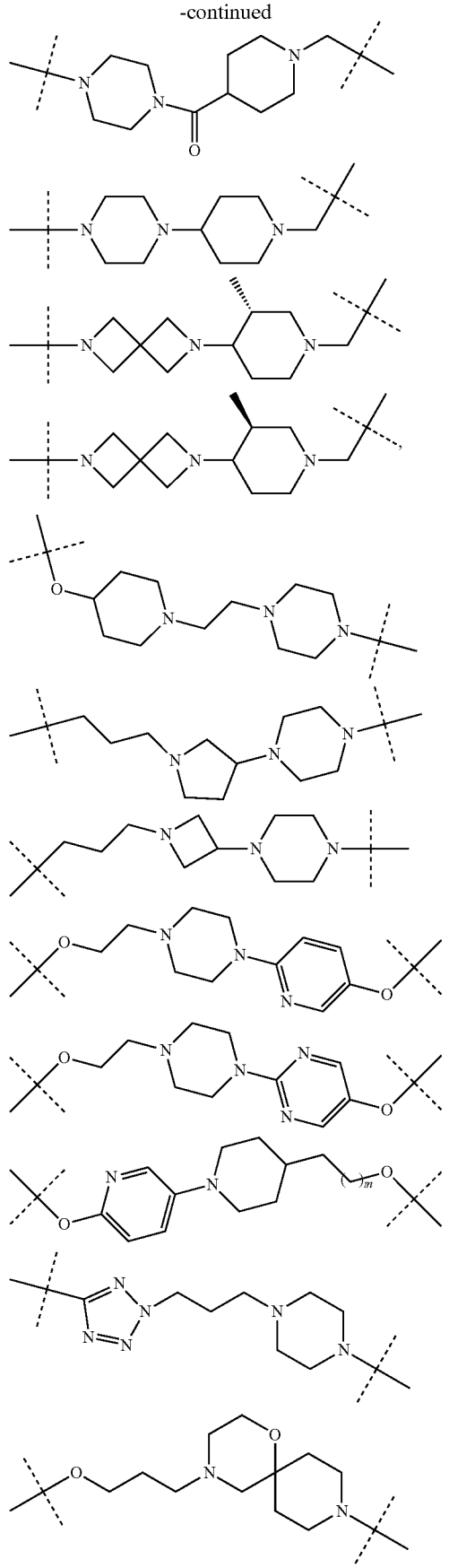
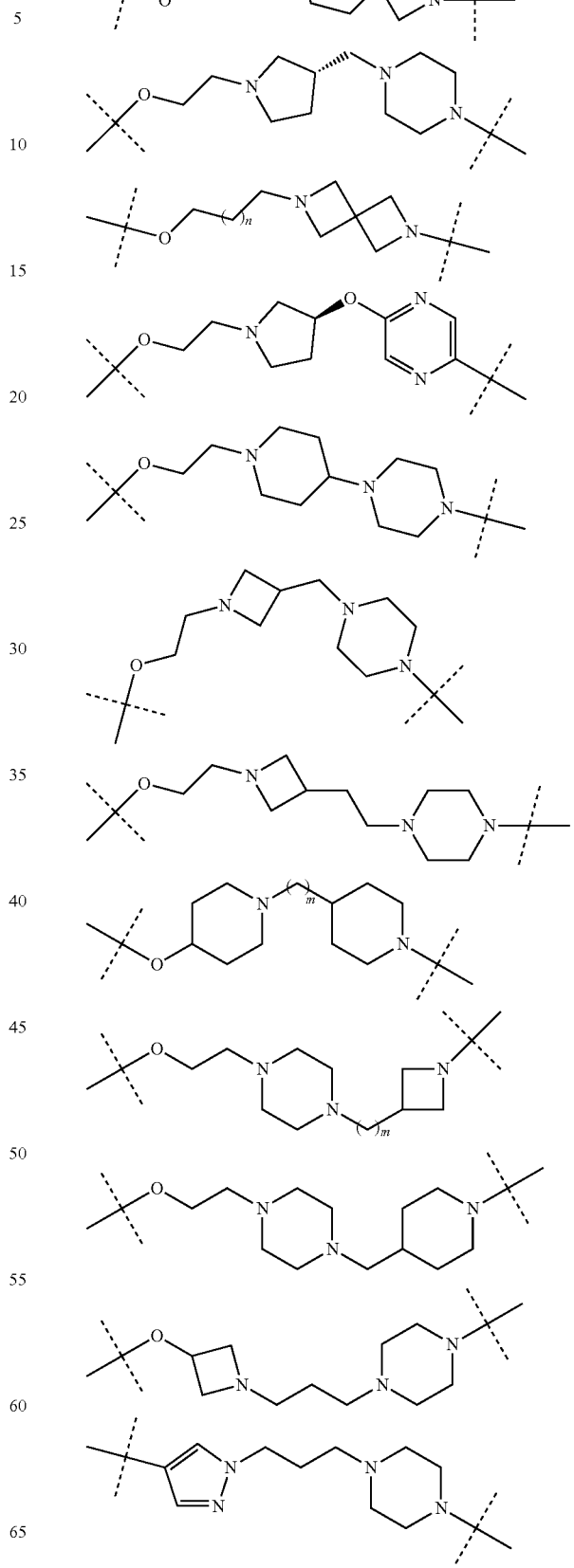

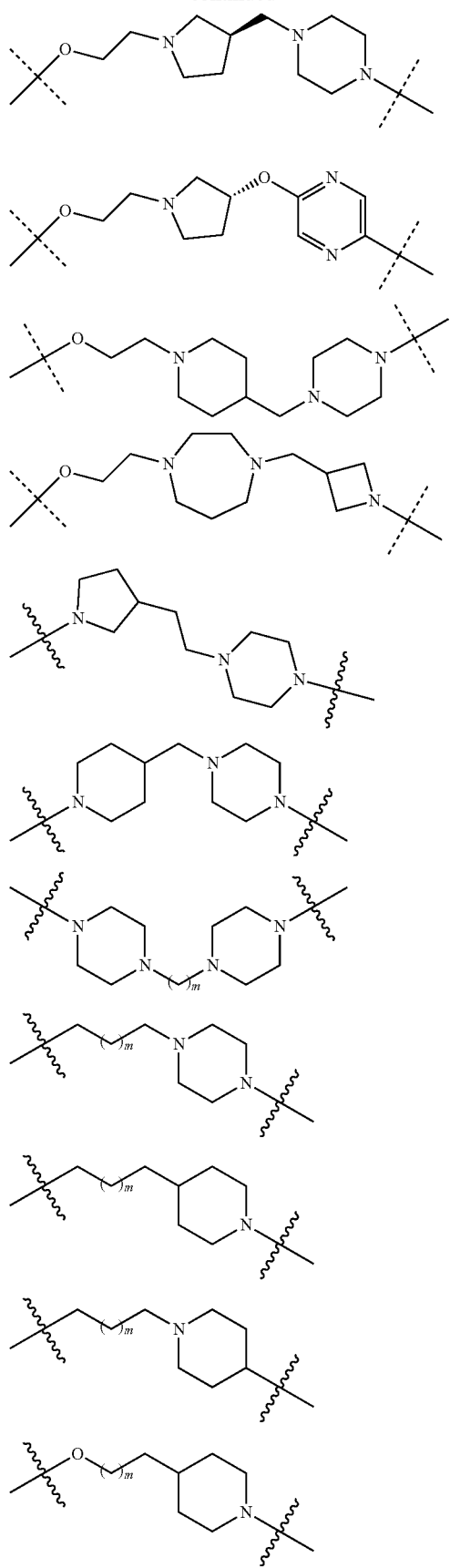
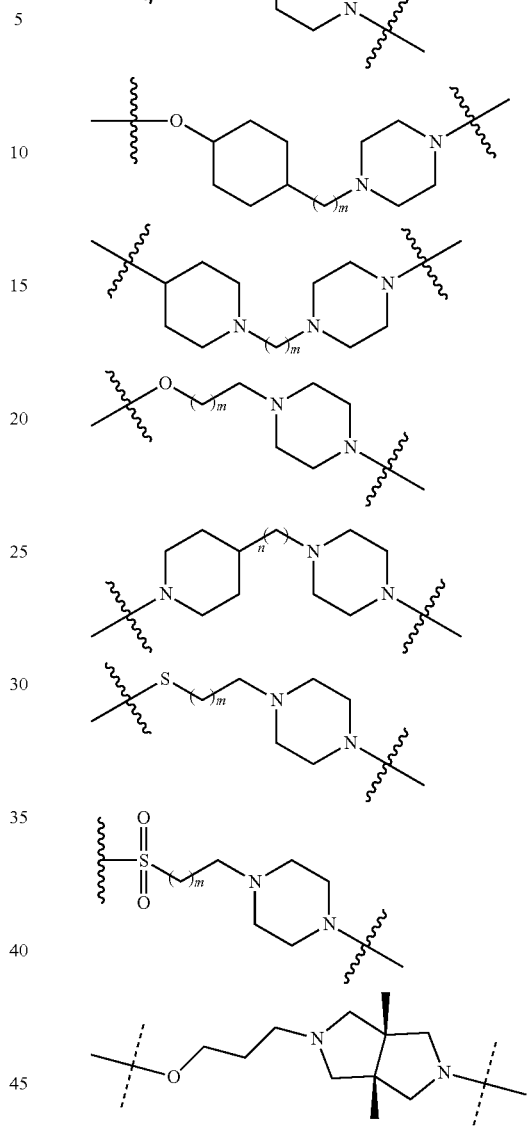
wherein m=1 or 2, n=0, 1;
wherein ⁓ or ⁓ indicates the attachment point to A or B.
In some embodiments, L is selected from:
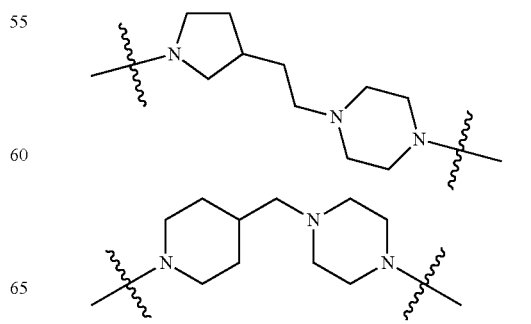

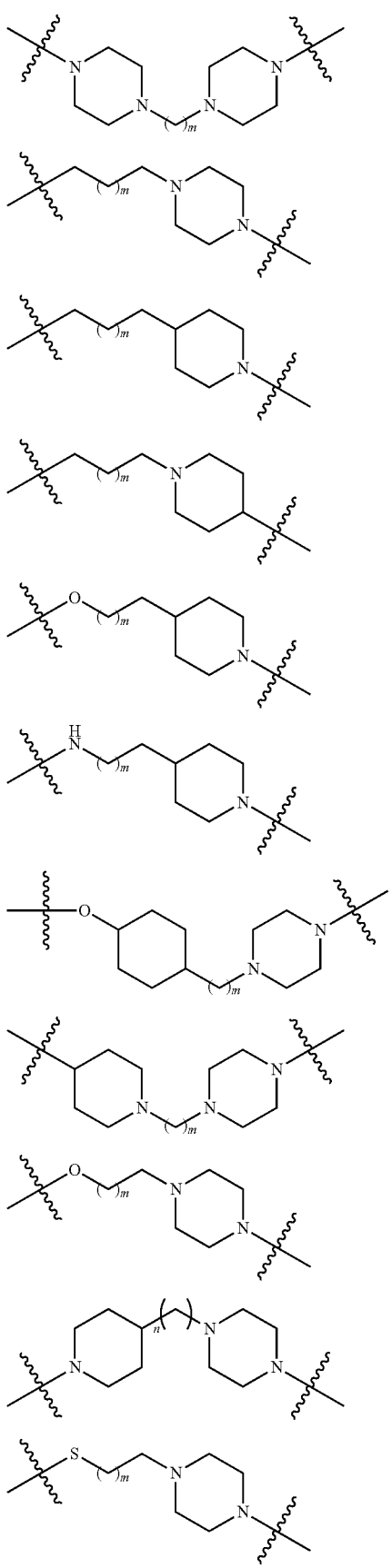
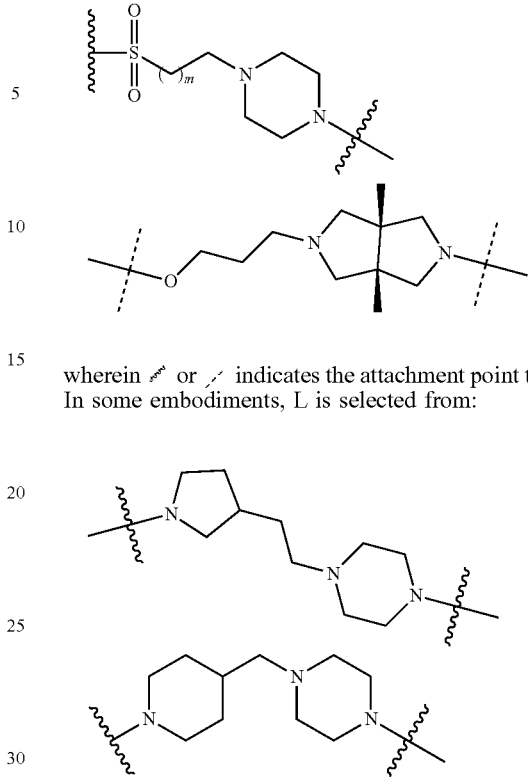

wherein ⁕ or ⁘ indicates the attachment point to A or B.

In some embodiments, L is selected from:

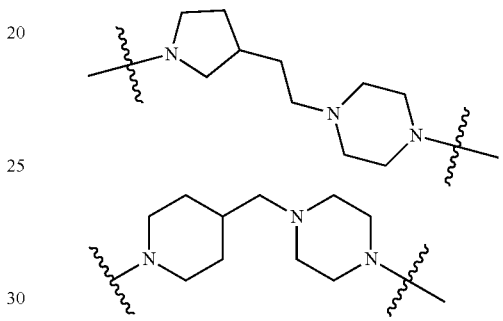

wherein ⁕ indicates the attachment point to A or B.

In some embodiments, L is

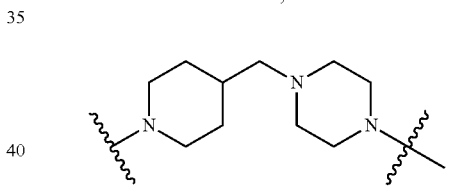

wherein ⁕ indicates the attachment point to A or B.

In some embodiments, L is

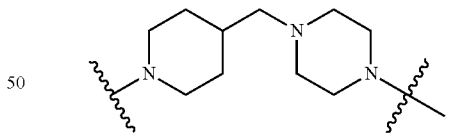

wherein L joins group A and B in formula (I) by the order of

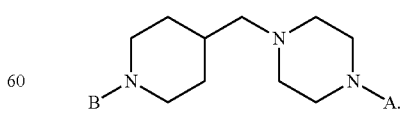

In some embodiments, B is an androgen receptor (AR) binding moiety. In some embodiments, the PROTAC is an AR PROTAC degrader. In some embodiments, B is an estrogen receptor (ER) binding moiety. In some embodiments, the PROTAC is an ER PROTAC degrader.

In some embodiments, the AR binding moiety is represented by the structure of Formula (B1):

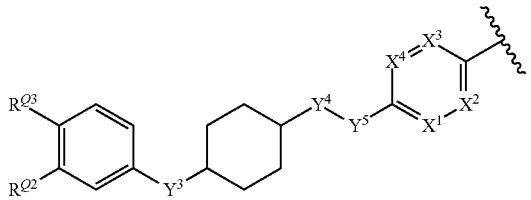

wherein
$Y^3$, $Y^4$, $Y^5$ are each independently a bond, O, C=O, NR, CR', CHR', heteroaryl, or aryl;

⁕ indicates the attachment point to linker group L;

R' is each independently H, or $C_{1-6}$ alkyl (linear, branched, optionally substituted by 1 or more halo, $C_{1-6}$ alkoxyl, $C_{1-6}$ cyclic, or $C_{1-6}$heterocyclyl);

$R^{Q3}$ is a H, halo, hydroxyl, nitro, CN, C=CH, $C_{1-6}$ alkyl (linear, branched, optionally substituted by 1 or more halogen, $C_{1-6}$ alkoxyl), $C_{1-6}$ alkoxyl (linear, branched, optionally substituted by 1 or more halo), $C_{1-6}$ alkenyl, $C_{1-6}$ alkynyl, or $CF_3$;

$R^{Q2}$ is H, halogen, $C_{1-6}$ alkyl (linear, branched, optionally substituted by 1 or more halo, or C4 alkoxyl), or $R^{Q2}$ and $R^{Q3}$ together with the atom they are attached to, form a 3-8 membered ring system containing 0-2 heteroatoms; and each $X^1$, $X^2$, $X^3$ and $X^4$ is independently N or CR'.

In some embodiments, the AR binding moiety is represented by the structure of Formula (B1):
wherein
$R^{Q3}$ is a H, halogen, hydroxyl, nitro, CN, C=CH, $C_{1-3}$ alkyl, $C_{1-3}$ alkenyl, $C_{1-3}$ alkynyl, or $CF_3$;
$Y^3$, $Y^4$, $Y^5$ are each independently O, C=O, NR';

⁕ indicates the attachment point to linker group L;

R' is each independently H, or $C_{1-3}$ alkyl (linear, branched, optionally substituted by 1 or more halogen, $C_{1-3}$ alkoxyl, $C_{1-6}$ cyclic, or $C_{1-6}$heterocyclyl);

$R^{Q2}$ is H or halogen, and each X is independently N or CH.

In some embodiments, the AR binding moiety is represented by the structure of Formula (B1):
wherein
$R^{Q3}$ is a H, halogen, CN, or $CF_3$;
$Y^3$, $Y^4$, $Y^5$ are each independently O, C=O, NH;

⁕ indicates the attachment point to linker group L;

$R^{Q2}$ is halogen;
$X^1$ and $X^2$ is N; and
$X^1$ and $X^2$ is CH.

In some embodiments, the AR binding moiety is represented by the structure of Formula (B1):
wherein
$R^{Q3}$ is CN;
Y is O;
$Y^4$ is NH;
$Y^4$ is C=O;

⁕ indicates the attachment point to linker group L; $R^{Q2}$ is Cl; $X^1$ and $X^2$ is N; and $X^1$ and $X^2$ is CH.

In some embodiments, the AR binding moiety is represented by the structure of

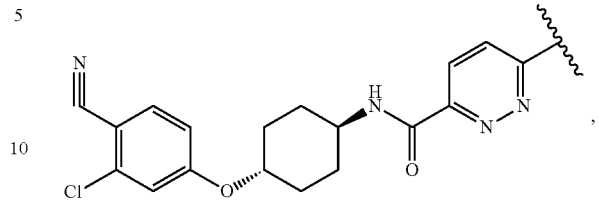

wherein ⁕ indicates the attachment point to linker group L.

In some embodiments, the AR binding moiety is represented by the structure of

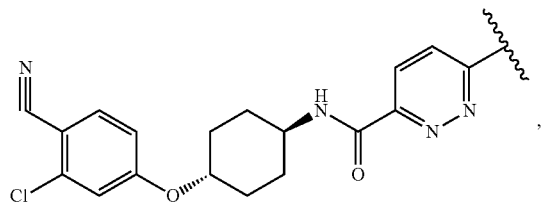 [SMILES: *c1ccc(C(=O)N[C@H]2CC[C@H](Oc3ccc(C#N)c(Cl)c3)CC2)nn1]

wherein ⁕ indicates the attachment point to linker group L, wherein L is

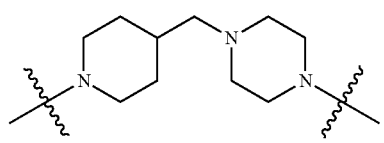

In some embodiments, the ER binding moiety is represented by the structure of Formula (B2):

Formula (B2)

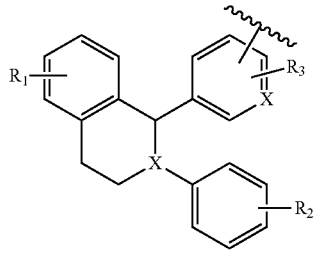

wherein
each X is independently CH or N;

⁕ indicates the attachment point to linker group L;

each $R_1$ is independently H, OH, halogen, alkoxy, methoxy, ethoxy, O(CO)R', wherein the substitution can be a mono-, di- or tri-substitution and the R' is alkyl or cycloalkyl group with 1 to 6 carbons or aryl groups;

each $R_2$, is independently H, halogen, CN, CF, liner or branched alkyl, alkoxy, methoxy, ethoxy, wherein the substitution can be mono- or di-substitution;

each $R^3$ is independently H, halogen, wherein the substitution can be mono- or di-substitution.

In some embodiments, the ER binding moiety is represented by the structure of Formula (B2):
wherein
each X is independently CH;
⌇ indicates the attachment point to linker group L;
each $R_1$ is independently H, OH or halogen;
each $R_2$ is independently H, halogen, CN, or CF;
each $R^3$ is independently H, or halogen.

In some embodiments, the ER binding moiety is represented by the structure of Formula (B2);
wherein
each X is independently CH;
⌇ indicates the attachment point to linker group L;
each $R_1$ is independently H, or OH;
each $R_2$ is H;
each $R^3$ is H.

In some embodiments, the ER binding moiety is represented by the structure of Formula (B2):
wherein
each X is independently CH;
⌇ indicates the attachment point to linker group L;
each $R_1$ is independently H, or OH, wherein one $R_1$ is OH;
each $R_2$ is independently H;
each $R_3$ is independently H.

In some embodiments, the ER binding moiety is represented by the structure of

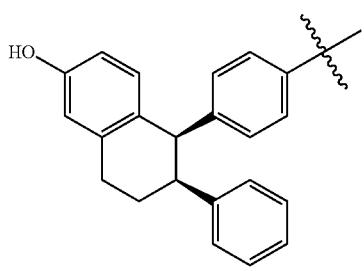 [SMILES: *c1ccc([C@@H]2c3ccc(O)cc3CC[C@@H]2c2ccccc2)cc1]

wherein ⌇ indicates the attachment point to linker group L.

In some embodiments, the ER binding moiety is represented by the structure of

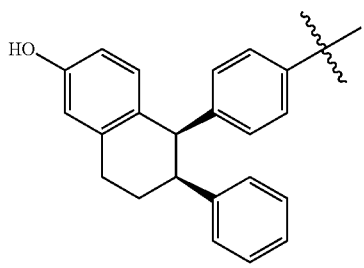 [SMILES: *c1ccc([C@@H]2c3ccc(O)cc3CC[C@@H]2c2ccccc2)cc1]

wherein ⌇ indicates the attachment point to linker group L, wherein L is

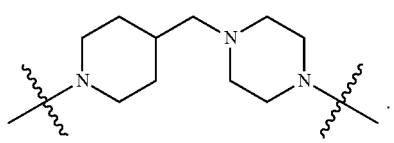 [SMILES: *N1CCC(CN2CCN(*)CC2)CC1]

In some embodiments, salts of compounds of Formula (I) are formed, for example, as acid addition salts (e.g., with organic or inorganic acids), from compounds of formula I with a basic nitrogen atom, e.g., the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N, N´-dimethylpiperazine.

When a basic group and an acid group are present in the same molecule, a compound of Formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In some embodiments, the PROTAC is an AR PROTAC degrader. In some embodiments, the PROTAC has a B group that is an AR binding moiety. In some embodiments, the AR PROTAC degrader is ARV-110 or a pharmaceutically acceptable salt thereof. In some embodiments, the PROTAC is ARV-110. In some embodiments, the ARV-110 compound is N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide.

In some embodiments, the ARV-110 compound is represented by the structure of:

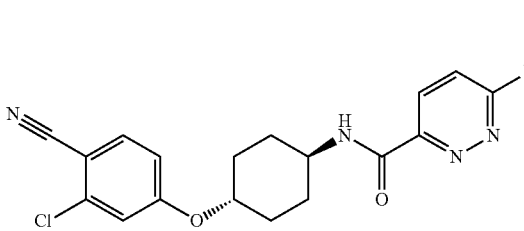

In some embodiments, the PROTAC is an ER PROTAC degrader. In some embodiments, the PROTAC has a B group that is an ER binding moiety. In some embodiments, the ER PROTAC degrader is ARV-471 or a pharmaceutically acceptable salt thereof. In some embodiments, the PROTAC is ARV-471. In some embodiments, the ARV-471 compound is (3S)-3-[5-[4-[[1-[4-[(1R,2S)-6-hydroxy-2-phenyl-tetralin-1-yl]phenyl]-4-piperidyl]methyl]piperazin-1-yl]-1-oxo-isoindolin-2-yl]piperidine-2,6-dione. In some embodiments, the ARV-471 compound is represented by the structure of:

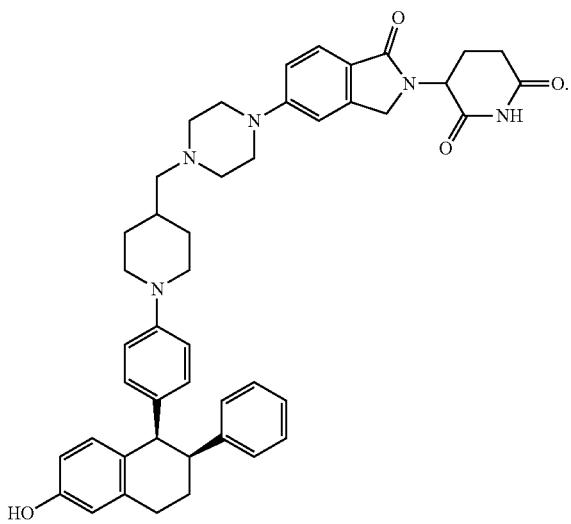 [SMILES: O=C1CCC(N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

In some embodiments, an API is a pharmaceutically acceptable salt of a PROTAC compound described herein. Pharmaceutically acceptable salts include bitartrate, bitartrate hydrate, hydrochloride, p-toluenesulfonate, phosphate, sulfate, trifluoroacetate, bitartrate hemipentahydrate, pentafluoropropionate, hydrobromide, mucate, oleate, phosphate dibasic, phosphate monobasic, acetate trihydrate, bis(heptafluorobutyrate), bis(pentafluoropropionate), bis(pyridine carboxylate), bis(trifluoroacetate), chlorhydrate, and sulfate pentahydrate. Other representative pharmaceutically acceptable salts include, e.g., water-soluble and water-insoluble salts, such as the acetate, amsonate(4,4-diaminostilbene-2,2-disulfonate), benzenesulfonate, benzonate, bicarbonate, bisulfate, bitartrate, borate, butyrate, calcium edetate, camphorsulfonate, camsylate, carbonate, citrate, clavulariate, dihydrochloride, edetate, edisylate, estolate, esylate, fiunarate, fumarate, gluceptate, gluconate, glutamate, glycollylarsanilate, hexafluorophosphate, hexylresorcinate, hydrabamine, hydrobromide, hydrochloride, hydroxynaphthoate, iodide, 49ydroxyapat, lactate, lactobionate, laurate, malate, maleate, mandelate, mesylate, methylbromide, methylnitrate, methylsulfate, mucate, napsylate, nitrate. N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A hydrate is another example of a pharmaceutically acceptable salt.

In some embodiments, the API has a low solubility at a pH of about 6-8. In some embodiments, the API has a solubility of less than 10 mg/ml in a solution with a pH of between about 6-8. In some embodiments, the API has a solubility of less than 1.0 mg/ml in a solution with a pH of between about 6-8. In some embodiments, the API has a solubility of less than 0.5 mg/ml in a solution with a pH of between about 6-8. In some embodiments, the API has a solubility of less than 0.1 mg/ml in a solution with a pH of between about 6-8. In some embodiments, the API has a solubility of less than 0.05 mg/ml in a solution with a pH of between about 6-8. In some embodiments, the API has a solubility of less than 0.04 mg/ml in a solution with a pH of between about 6-8. In some embodiments, the API has a solubility of less than 0.03 mg/ml in a solution with a pH of between about 6-8. In some embodiments, the API has a solubility of less than 0.02 mg/ml in a solution with a pH of between about 6-8. In some embodiments, the API has a solubility of less than 0.01 mg/ml in a solution with a pH of between about 6-8. In some embodiments, the API has a solubility of less than 0.001 mg/ml in a solution with a pH of between about 6-8. In some embodiments, the API has a low solubility at a pH of about 4-8. In some embodiments, the API has a solubility of less than 10 mg/ml in a solution with a pH of between about 4-8. In some embodiments, the API has a solubility of less than 1.0 mg/ml in a solution with a pH of between about 4-8. In some embodiments, the API has a solubility of less than 0.5 mg/ml in a solution with a pH of between about 4-8. In some embodiments, the API has a solubility of less than 0.1 mg/ml in a solution with a pH of between about 4-8. In some embodiments, the API has a solubility of less than 0.05 mg/ml in a solution with a pH of between about 4-8. In some embodiments, the API has a solubility of less than 0.04 mg/ml in a solution with a pH of between about 4-8. In some embodiments, the API has a solubility of less than 0.03 mg/ml in a solution with a pH of between about 4-8. In some embodiments, the API has a solubility of less than 0.02 mg/ml in a solution with a pH of between about 4-8. In some embodiments, the API has a solubility of less than 0.01 mg/ml in a solution with a pH of between about 4-8. In some embodiments, the API has a solubility of less than 0.001 mg/ml in a solution with a pH of between about 4-8. In some embodiments, the API has a low solubility at a pH of about 6-10. In some embodiments, the API has a solubility of less than 10 mg/ml in a solution with a pH of between about 6-10. In some embodiments, the API has a solubility of less than 1.0 mg/ml in a solution with a pH of between about 6-10. In some embodiments, the API has a solubility of less than 0.5 mg/ml in a solution with a pH of between about 6-10. In some embodiments, the API has a solubility of less than 0.1 mg/ml in a solution with a pH of between about 6-10. In some embodiments, the API has a solubility of less than 0.05 mg/ml in a solution with a pH of between about 6-10. In some embodiments, the API has a solubility of less than 0.04 mg/ml in a solution with a pH of between about 6-10. In some embodiments, the API has a solubility of less than 0.03 mg/ml in a solution with a pH of between about 6-10. In some embodiments, the API has a solubility of less than 0.02 mg/ml in a solution with a pH of between about 6-10. In some embodiments, the API has a solubility of less than 0.01 mg/ml in a solution with a pH of between about 6-10. In some embodiments, the API has a solubility of less than 0.001 mg/ml in a solution with a pH of between about 6-10.

In some embodiments, the API is a PROTAC. In some embodiments, the PROTAC is one listed in Table 1, or a pharmaceutically acceptable salt thereof. In some embodiments the API is ARV-110 or ARV-471, or pharmaceutically acceptable salts thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, an amorphous solid dispersion and/or a pharmaceutical composition described herein is free of organic acid. In some embodiments, the amorphous solid dispersion and/or the pharmaceutical composition is free of any acid.

In some embodiments, pharmaceutical compositions comprising ASD that comprises a PROTAC (e.g., ARV-110 or ARV-471) described herein have acceptable storage stability. In some embodiments, the pharmaceutical composition is storage stable for at least 6 months at 40° C./75% RH, wherein a storage stable pharmaceutical composition has less than 0.5% of any impurity at the end of the storage period. In some embodiments, the pharmaceutical composition is storage stable for at least 2 weeks, 1 month, 2 months, 3 months, 6 months, 12 months, or 24 months at 25° C./60% RH, wherein a storage stable pharmaceutical composition has less than 0.5% of any impurity at the end of the storage period.

In some embodiments, a pharmaceutical composition described herein comprises a PROTAC or a salt thereof, such as ARV-110 or ARV-471 or pharmaceutically acceptable salts thereof), a surfactant, and a non-ionic or ionic hydrophilic polymer. In some embodiments, the PROTAC is one listed in Table 1, or a pharmaceutically acceptable salt thereof. In some embodiments, the PROTAC has a log P 2.0 or higher. In some embodiments, the PROTAC (e.g., ARV-110 or ARV-471) or a pharmaceutically acceptable salt thereof is present in the pharmaceutical composition in an amount of about 10 mg to about 500 mg. In some embodiments, the PROTAC (e.g., ARV-110 or ARV-471) or a pharmaceutically acceptable salt thereof is present in the pharmaceutical composition in an amount of about 20 mg to about 200 mg. In some embodiments, the PROTAC (e.g., ARV-110 or ARV-471) or a pharmaceutically acceptable salt thereof is present in the pharmaceutical composition in an amount of about 25 mg, about 50 mg, about 100 mg about 150 mg, or about 200 mg. In some embodiments, the surfactant is present in the pharmaceutical composition in an amount of about 10 mg to about 500 mg. In some embodiments, the surfactant is present in the pharmaceutical composition in an amount of about 20 mg to about 200 mg. In some embodiments, the hydrophilic polymer is present in the pharmaceutical composition in an amount of about 10 mg to about 500 mg. In some embodiments, the hydrophilic polymer is present in the pharmaceutical composition in an amount of about 20 mg to about 200 mg. In some embodiments, the hydrophilic polymer is a non-ionic polymer. In some embodiments, the hydrophilic polymer is an ionic polymer such as sulfobutylether-β-cyclodextrin. In some embodiments, the hydrophilic polymer is copovidone (VA64). In some embodiments, the hydrophilic polymer is an enteric polymer. In some embodiments, the enteric polymer is polymethacrylates (e.g., sold under trade name Eudragit), Hypromellose Phthalate (HPMCP), HPMCAS, cellulose phthalate hydroxypropyl methyl ether, hydroxypropyl methylcellulose benzene-1,2-dicarboxylate, 2-hydroxypropyl methylcellulose phthalate, hypromellosi phthalas, Mantrocel HP-55, methylhydroxypropylcellulose phthalate, or Soluplus. In some embodiments, the hydrophilic polymer comprises PEG, polymethacrylates (e.g., sold under trade name Eudragit), hypromellose phthalate (HPMCP), polyvinylcaprolactam, polyvinyl acetate, polyvinyl caprolactam-polyvinyl acetate-polyethylene glycol graft co-polymer (e.g., sold under trade name Soluplus). In some embodiments, the hydrophilic polymer is hydropropylmethylcellulose acetate succinate (HPMCAS). In some embodiments, the PROTAC is ARV-110. In some embodiments, the PROTAC is ARV-471.

In some embodiments, a weight ratio of the PROTAC (e.g., ARV-110 or ARV-471) or a pharmaceutically acceptable salt thereof to the hydrophilic polymer is from about 1:1 to about 1:10. In some embodiments, a weight ratio of the PROTAC (e.g., ARV-110 or ARV-471) or a pharmaceutically acceptable salt thereof to the hydrophilic polymer is from about 10:1 to about 8:1, about 10:1 to about 6:1, about 10:1 to about 4:1, about 10:1 to about 2:1, about 10:1 to about 1:1, about 10:1 to about 1:2, about 10:1 to about 1:4, about 10:1 to about 1:6, about 10:1 to about 1:8, about 10:1 to about 1:10, about 8:1 to about 6:1, about 8:1 to about 4:1, about 8:1 to about 2:1, about 8:1 to about 1:1, about 8:1 to about 1:2, about 8:1 to about 1:4, about 8:1 to about 1:6, about 8:1 to about 1:8, about 8:1 to about 1:10, about 6:1 to about 4:1, about 6:1 to about 2:1, about 6:1 to about 1:1, about 6:1 to about 1:2, about 6:1 to about 1:4, about 6:1 to about 1:6, about 6:1 to about 1:8, about 6:1 to about 1:10, about 4:1 to about 2:1, about 4:1 to about 1:1, about 4:1 to about 1:2, about 4:1 to about 1:4, about 4:1 to about 1:6, about 4:1 to about 1:8, about 4:1 to about 1:10, about 2:1 to about 1:1, about 2:1 to about 1:2, about 2:1 to about 1:4, about 2:1 to about 1:6, about 2:1 to about 1:8, about 2:1 to about 1:10, about 1:1 to about 1:2, about 1:1 to about 1:4, about 1:1 to about 1:6, about 1:1 to about 1:8, about 1:1 to about 1:10, about 1:2 to about 1:4, about 1:2 to about 1:6, about 1:2 to about 1:8, about 1:2 to about 1:10, about 1:4 to about 1:6, about 1:4 to about 1:8, about 1:4 to about 1:10, about 1:6 to about 1:8, about 1:6 to about 1:10, or about 1:8 to about 1:10. In some embodiments, a weight ratio of the PROTAC (e.g., ARV-110 or ARV-471) or a pharmaceutically acceptable salt thereof to the hydrophilic polymer is from about 10:1, about 8:1, about 6:1, about 4:1, about 2:1, about 1:1, about 1:2, about 1:4, about 1:6, about 1:8, or about 1:10. In some embodiments, a weight ratio of the PROTAC (e.g., ARV-110 or ARV-471) or a pharmaceutically acceptable salt thereof to the hydrophilic polymer is from at least about 10:1, about 8:1, about 6:1, about 4:1, about 2:1, about 1:1, about 1:2, about 1:4, about 1:6, or about 1:8. In some embodiments, a weight ratio of the PROTAC (e.g., ARV-110 or ARV-471) or a pharmaceutically acceptable salt thereof to the hydrophilic polymer is from at most about 8:1, about 6:1, about 4:1, about 2:1, about 1:1, about 1:2, about 1:4, about 1:6, about 1:8, or about 1:10. In some embodiments, the PROTAC is one listed in Table 1, or a pharmaceutically acceptable salt thereof. In some embodiments, the PROTAC has a log P 2.0 or higher. In some embodiments, the PROTAC is ARV-110. In some embodiments, the PROTAC is ARV-471.

In some embodiments, the pharmaceutical compositions described herein have a superior bioavailability than a bioavailability of a corresponding reference composition comprising a crystalline form of PROTAC (e.g., ARV-110 or ARV-471) or an amorphous PROTAC (e.g., ARV-110 or ARV-471) that is not present in an ASD, when measured as AUC, $AUC_{inf}$, or $AUC_{last}$ after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a corresponding composition comprising a crystalline form of PROTAC (e.g., ARV-110 or ARV-471) or an amorphous PROTAC (e.g., ARV-110 or ARV-471) that is not present in an ASD, when measured as the AUC after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a corresponding composition comprising a crystalline form of PROTAC (e.g., ARV-110 or ARV-471) or an amorphous PROTAC (e.g., ARV-110 or ARV-471) that is not present in an ASD, when measured as Cm after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of an amorphous PROTAC (e.g., ARV-110 or ARV-471) that is not present in an ASD capsule comprising the an amorphous PROTAC (e.g., ARV-110 or ARV-471), when measured as AUC after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of an amorphous PROTAC (e.g., ARV-110 or ARV-471) that is not present in an ASD capsule comprising the an amorphous PROTAC (e.g., ARV-110 or ARV-471), when measured as $C_{max}$ after oral administration. In some embodiments, the pharmaceutical composition exhibits a bioavailability that is higher than a bioavailability of an amorphous PROTAC (e.g., ARV-110 or ARV-471) that is not present in an ASD by about 1.1 fold to about 10 fold. In some embodiments, the pharmaceutical composition exhibits a bioavailability that is higher than a bioavailability of an amorphous PROTAC (e.g., ARV-110 or ARV-471) that is not present in an ASD by about 1.1 fold to about 2 fold, about 1.1 fold to about 3 fold, about 1.1 fold to about 4 fold, about 1.1 fold to about 5 fold, about 1.1 fold to about 6 fold, about 1.1 fold to about 7 fold, about 1.1 fold to about 8 fold, about 1.1 fold to about 10 fold, about 1.5 fold to about 2 fold, about 1.5 fold to about 3 fold, about 1.5 fold to about 4 fold, about 1.5 fold to about 5 fold, about 1.5 fold to about 6 fold, about 1.5 fold to about 7 fold, about 1.5 fold to about 8 fold, about 1.5 fold to about 10 fold, about 2 fold to about 4 fold, about 2 fold to about 5 fold, about 2 fold to about 6 fold, about 2 fold to about 7 fold, about 2 fold to about 8 fold, about 2 fold to about 10 fold, about 3 fold to about 4 fold, about 3 fold to about 5 fold, about 3 fold to about 6 fold, about 3 fold to about 7 fold, about 3 fold to about 8 fold, about 3 fold to about 10 fold, about 4 fold to about 5 fold, about 4 fold to about 6 fold, about 4 fold to about 7 fold, about 4 fold to about 8 fold, about 4 fold to about 10 fold, about 5 fold to about 6 fold, about 5 fold to about 7 fold, about 5 fold to about 8 fold, about 5 fold to about 10 fold, about 6 fold to about 7 fold, about 6 fold to about 8 fold, about 6 fold to about 10 fold, about 7 fold to about 8 fold, about 7 fold to about 10 fold, or about 8 fold to about 10 fold. In some embodiments, the PROTAC is one listed in Table 1, or a pharmaceutically acceptable salt thereof. In some embodiments, the PROTAC has a log P 2.0 or higher. In some embodiments, the PROTAC is ARV-110. In some embodiments, the PROTAC is ARV-471.

In some embodiments, the pharmaceutical composition described herein exhibits a bioavailability that is higher than a bioavailability of the an amorphous PROTAC (e.g., ARV-110 or ARV-471) that is not present in the ASD described herein by at least about 1.1 fold, about 1.3 fold, about 1.5 fold, about 1.8 fold, about 2 fold, about 3 fold, about 4 fold, about 5 fold, about 6 fold, about 7 fold, or about 8 fold when measured as AUC or $C_{max}$ after oral administration. In some embodiments, the pharmaceutical composition exhibits a bioavailability that is higher than a bioavailability of an amorphous PROTAC (e.g., ARV-110 or ARV-471) that is not present in the ASD by at least about 2 fold. In some embodiments, the pharmaceutical composition exhibits a bioavailability that is higher than a bioavailability of an amorphous PROTAC (e.g., ARV-110 or ARV-471) that is not present in the ASD by at least about 4 fold. In some embodiments, the pharmaceutical composition exhibits a bioavailability that is higher than a bioavailability of an amorphous PROTAC (e.g., ARV-110 or ARV-471) that is not present in the ASD by at most about 1.3 fold, about 1.5 fold, about 1.8 fold, about 2 fold, about 3 fold, about 4 fold, about 5 fold, about 6 fold, about 7 fold, about 8 fold, or about 10 fold. In some embodiments, the bioavailability is measured in a dog model in a fasted state. In some embodiments, the bioavailability is measured in a dog model in a fed state. In some embodiments, a bioavailability of the pharmaceutical composition does not vary for more than 100% 90%, 80%, 70%, 60%, 50%, 40%, 30%, 20%, 15%, or 10% when orally administered in a fed state compared to administered in a fasted state, when measured AUC after oral administration. In some embodiments, a bioavailability of the pharmaceutical composition does not vary for more than 100% 90%, 80%, 70%, 60%, 50%, 40%, 30%, 20%, 15%, or 10% when orally administered in a fed state compared to administered in a fasted state, when measured as $C_{max}$ after oral administration. In some embodiments, a bioavailability of the pharmaceutical composition does not vary for more than 100% when orally administered in a fed state compared to administered in a fasted state. In some embodiments, a bioavailability of the pharmaceutical composition does not vary for more than 90% when orally administered in a fed state compared to administered in a fasted state. In some embodiments, a bioavailability of the pharmaceutical composition does not vary for more than 80% when orally administered in a fed state compared to administered in a fasted state. In some embodiments, a bioavailability of the pharmaceutical composition does not vary for more than 70% when orally administered in a fed state compared to administered in a fasted state. In some embodiments, a bioavailability of the pharmaceutical composition does not vary for more than 50% when orally administered in a fed state compared to administered in a fasted state. In some embodiments, a bioavailability of the pharmaceutical composition does not vary for more than 50% when orally administered in a fed state compared to administered in a fasted state. In some embodiments, a bioavailability of the pharmaceutical composition does not vary for more than 40% when orally administered in a fed state compared to administered in a fasted state. In some embodiments, a bioavailability of the pharmaceutical composition does not vary for more than 20% when orally administered in a fed state compared to administered in a fasted state. In some embodiments, a bioavailability of the pharmaceutical composition does not vary for more than 10% when orally administered in a fed state compared to administered in a fasted state. In some embodiment, the bioavailability is measured in a dog model. In some embodiment, the dog model is beagle dog. In some embodiments, the PROTAC is one listed in Table 1, or a pharmaceutically acceptable salt thereof. In some embodiments, the PROTAC has a log P 2.0 or higher. In some embodiments, the PROTAC is ARV-110. In some embodiments, the PROTAC is ARV-471.

In some embodiments, the pharmaceutical composition exhibits a bioavailability of the PROTAC (e.g., ARV-110 or ARV-471) or the pharmaceutically acceptable salt thereof that is at least 1.2, 1.5, 2, 3, 4, 5, or 10-fold compared to a bioavailability of a corresponding composition comprising the PROTAC or the pharmaceutically acceptable salt thereof in a dosage form wherein the PROTAC is in a crystalline form. In some embodiments, the pharmaceutical composition exhibits a bioavailability of the PROTAC (e.g., ARV-110 or ARV-471) or the pharmaceutically acceptable salt thereof that is at least 1.2, 1.5, 2, 3, 4, 5, or 10-fold compared to a bioavailability of a corresponding composition comprising the PROTAC or the pharmaceutically acceptable salt thereof in a dosage form, wherein the PROTAC is in an amorphous form without being a part of the ASD. In some embodiments, the pharmaceutical composition exhibits a bioavailability of the PROTAC compound (e.g., ARV-110 or ARV-471) or the pharmaceutically acceptable salt thereof that is at least 2-fold compared to a bioavailability of a corresponding composition comprising the PROTAC compound or the pharmaceutically acceptable salt thereof in a conventional dosage form (such as the PROTAC in a crystalline form or the PROTAC in an amorphous form without being a part of the ASD). In some embodiments, the bioavailability is measured as AUC or as maximum plasma concentration ($C_{max}$) after oral administration to a subject in a fasted state. In some embodiments, the pharmaceutical composition exhibits a bioavailability of the PROTAC (e.g., ARV-110 or ARV-471) or the pharmaceutically acceptable salt thereof that is at least 3, 4, or 5-fold compared to a bioavailability of a corresponding composition comprising the PROTAC or the pharmaceutically acceptable salt thereof in an amorphous form in a conventional dosage form (e.g., without being a part of an ASD). In some embodiments, the bioavailability is measured as AUC or as maximum plasma concentration ($C_{max}$) after oral administration to a subject in a fasted state. In some embodiments, the conventional dosage forms of PROTACs include dosage forms comprising PROTACs in a crystalline form. In some embodiments, the conventional dosage forms of PROTACs include dosage forms comprising PROTACs in an amorphous state without being a part of an ASD. In some embodiments, the conventional dosage forms do not comprise an ASD. In some embodiments, the conventional dosage forms comprise PROTAC compounds filled in a capsule. In some embodiments, the pharmaceutical composition exhibits a bioavailability of the PROTAC (e.g., ARV-110 or ARV-471) or the pharmaceutically acceptable salt thereof that is at least 1.2, 1.5, 2, 3, 4, 5, or 10-fold compared to a bioavailability of a corresponding composition comprising the PROTAC compound or the pharmaceutically acceptable salt thereof in a conventional dosage form (such as the PROTAC in a crystalline form or the PROTAC in an amorphous form without being a part of the ASD). In some embodiments, the pharmaceutical composition exhibits a bioavailability of the PROTAC (e.g., ARV-110 or ARV-471) or the pharmaceutically acceptable salt thereof that is at least 6-fold compared to a bioavailability of a corresponding composition comprising the PROTAC compound or the pharmaceutically acceptable salt thereof in a conventional dosage form (such as the PROTAC in a crystalline form or the PROTAC in an amorphous form without being a part of the ASD). In some embodiments, the bioavailability is measured as maximum plasma concentration ($C_{max}$) after oral administration to a subject in a fasted state. In some embodiments, the subject comprises a dog. In some embodiments, the subject comprises six beagle dogs. In some embodiments, the PROTAC is ARV-110. In some embodiments, the PROTAC is ARV-471.

In some embodiments, the pharmaceutical compositions described herein exhibits a bioavailability that is from about 100% to about 1500%, 120% to about 1000%, 125% to about 500%, about 130% to about 450%, 140% to about 400%, or about 150% to about 300% of a bioavailability of a corresponding reference composition (such as a crystalline form or PROTAC in amorphous form without being a part of the ASD) comprising PROTAC (e.g., ARV-110 or ARV-471) when measured as $AUC_{last}$ or $C_{max}$, after oral administration, wherein the corresponding reference pharmaceutical composition does not comprise an amorphous solid dispersion. In some embodiments, the reference composition is at least about 1.1 times the dosage of the pharmaceutical compositions. In some embodiments, the reference composition is at least about 1.1 times, about 1.5 times, about 2 times, about 2.5 times, about 3 times, about 4 times, about 5 times, about 6 times, about 7 times, about 8 times, about 9 times, or about 10 times the dosage of the pharmaceutical composition. In some embodiments, the pharmaceutical composition comprises an ASD comprising PROTAC or a pharmaceutically acceptable salt thereof. In some embodiments, the reference composition comprises PROTAC (e.g., ARV-110 or ARV-471) free base or a pharmaceutically acceptable salt thereof, wherein the reference composition does not comprise an ASD. In some embodiments, the reference composition comprises PROTAC (e.g., ARV-110 or ARV-471) in amorphous form without being a part of the ASD. In some embodiment, the bioavailability is measured under fasted condition. In some embodiment, the bioavailability is measured under fed condition. In some embodiments, the PROTAC is one listed in Table 1, or a pharmaceutically acceptable salt thereof. In some embodiments, the PROTAC has a log P 2.0 or higher. In some embodiments, the PROTAC is ARV-110. In some embodiments, the PROTAC is ARV-471.

In some embodiments, salts of compounds of PROTAC (e.g., ARV-110 or ARV-471) are formed, for example, as acid addition salts (e.g., with organic or inorganic acids), from compounds of ARV-110 with a basic nitrogen atom, e.g., the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of PROTAC may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

Amorphous Solid Dispersion

The present disclosure relates to pharmaceutical compositions comprising an amorphous solid dispersion, methods of preparing the pharmaceutical composition described thereof, methods of treating a disease or a condition by administering thereof. In some embodiments, the pharmaceutical compositions comprising an amorphous solid dispersion further comprises a PROTAC, a hydrophilic polymer, and a surfactant. In some embodiments, the pharmaceutical composition optionally comprises an adsorbent, an acid, or both.

In one aspect, disclosed herein is an amorphous solid dispersion, wherein the amorphous solid dispersion comprises: a) a PROTAC or a pharmaceutically acceptable salt thereof, wherein the PROTAC has a log P in octanol-water equal or greater than 2.0; b) a surfactant, wherein the surfactant is selected from polymeric surfactants and phospholipids; c) a hydrophilic polymer; d) optionally an adsorbent; and optionally an acid.

In some embodiments, the PROTAC or a pharmaceutically acceptable salt thereof is a PROTAC. In some embodiments, the PROTAC is represented by the structure of Formula (I):

A-L-B      Formula (I)

wherein

A is an E3 ubiquitin ligase binding moiety;

L is a linker; and

B is a moiety which binds to a target protein, wherein the target protein is degradable by an E3 ubiquitin ligase.

In some embodiments, the B is an AR binding moiety. In some embodiments, the B is an ER binding moiety. In some embodiments, the PROTAC compound is an AR PROTAC degrader. In some embodiments, the AR PROTAC degrader is ARV-110, wherein said compound is represented by the structure of

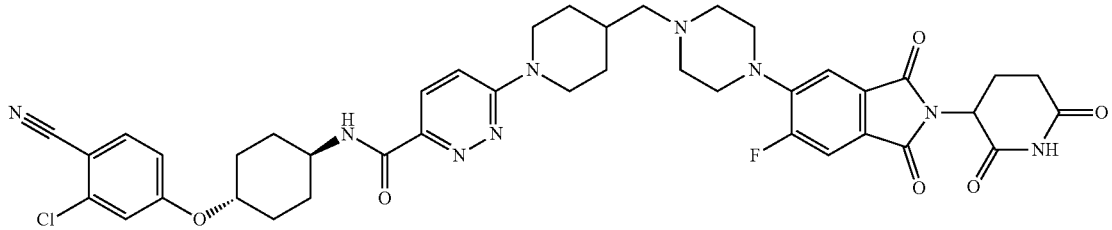 [SMILES: N#Cc1ccc(O[C@H]2CC[C@H](NC(=O)c3ccc(N4CCC(CN5CCN(c6cc7c(cc6F)C(=O)N(C6CCC(=O)NC6=O)C7=O)CC5)CC4)nn3)CC2)cc1Cl]

or a pharmaceutically acceptable salt or enantiomer thereof.

In some embodiments, the PROTAC compound is an ER PROTAC degrader. In some embodiments, the estrogen receptor PROTAC degrader is ARV-471, wherein said compound is represented by the structure of

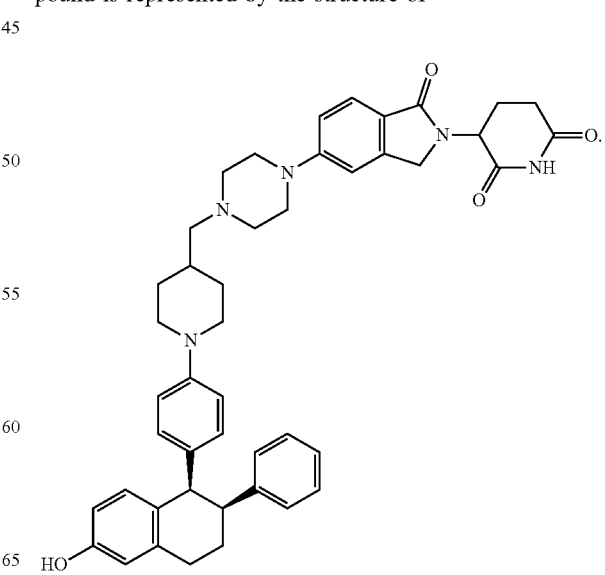

In some embodiment, the PROTAC is selected from ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413, the corresponding free base thereof and pharmaceutically acceptable salts thereof. In some embodiment, the PROTAC is selected from Table 1 or pharmaceutically acceptable salts thereof. In some embodiments, the PROTAC or a pharmaceutically acceptable salt thereof is present in the amorphous solid dispersion in an amount of about 5 wt % to about 70 wt % based on solids. In some embodiments, the surfactant comprises one or more surfactants. In some embodiments, the surfactants are selected from phospholipids, lecithin, polysorbate, TPGS, Kolliphor series (RH40), sorbitan oleate, SDS, Solutol, and Soluplus or a combination thereof. In some embodiments, the surfactant comprises one or more phospholipids. In some embodiments, the surfactant comprises one or more of phosphatidylcholine, phosphatidylethanolamine, phosphatidylinositol, phosphatidylserine, plasmalogen, sphingomyelin, and phosphatidic acid. In some embodiments, the surfactant comprises lecithin. In some embodiments, the surfactant is present in the amorphous solid dispersion in an amount of about 5 wt % to about 70 wt %.

In some embodiments, the PROTAC is present in an amorphous solid dispersion in a weight percent of about 5% to about 60%. In some embodiments, the PROTAC is present in an amorphous solid dispersion in a weight percent of about 15% to about 50%. In some embodiments, the PROTAC is present in an amorphous solid dispersion in a weight percent of about 15% to about 30%. In some embodiments, the PROTAC is present in an amorphous solid dispersion in a weight percent of about 15% to about 25%. In some embodiments, the PROTAC is present in an amorphous solid dispersion in a weight percent of about 20% to about 30%. In some embodiments, the PROTAC is present in an amorphous solid dispersion in a weight percent of about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60%, or about 55% to about 60%. In some embodiments, the PROTAC is present in an amorphous solid dispersion in a weight percent of about 5%, about 10%, about 15%, about 20%, about 25%, about 30%, about 35%, about 40%, about 45%, about 50%, about 55%, or about 60%. In some embodiments, the PROTAC is present in an amorphous solid dispersion in a weight percent of at least about 5%, about 10%, about 15%, about 20%, about 25%, about 30%, about 35%, about 40%, about 45%, about 50%, or about 55%. In some embodiments, the PROTAC is present in an amorphous solid dispersion in a weight percent of at most about 10%, about 15%, about 20%, about 25%, about 30%, about 35%, about 40%, about 45%, about 50%, about 55%, or about 60%. In some embodiments, the PROTAC is present in an amorphous solid dispersion in a weight percent of about 15%. In some embodiments, the PROTAC is present in an amorphous solid dispersion in a weight percent of about 20%. In some embodiments, the PROTAC is present in an amorphous solid dispersion in a weight percent of about 25%. In some embodiments, the PROTAC is present in an amorphous solid dispersion in a weight percent of about 30%. In some embodiments, the PROTAC is one listed in Table 1, or a pharmaceutically acceptable salt thereof. In some embodiments, the PROTAC has a log P 2.0 or higher. In some embodiments, the PROTAC is ARV-110 free base or a pharmaceutically acceptable salt thereof. In some embodiments, the PROTAC is ARV-110. In some embodiments, the PROTAC is ARV-471 free base or a pharmaceutically acceptable salt thereof. In some embodiments, the PROTAC is ARV-471.

In some embodiments, an ASD described herein comprises one or more surfactants. In some embodiments, the one or more surfactants comprise lecithin, a block copolymer of polyethylene glycol and polypropylene glycol, TGPS, polyvinylcaprolactame-based graft copolymer (PVAc-PVCap-PEG), or a combination thereof. In some embodiments, the one or more surfactants comprise lecithin and TPGS. In some embodiments, the one or more surfactants comprise lecithin. In some embodiments, the one or more surfactants comprise TPGS. In some embodiments, the one or more surfactants are present in an amount of about 5% to about 60% by weight of the ASD. In some embodiments, the surfactant is present in an amount of about 15% to about 50% by weight of the ASD. In some embodiments, the surfactant is present in an amount of about 20% to about 40% by weight of the ASD.

In some embodiments, an ASD described herein comprises a hydrophilic polymer. In some embodiments, the hydrophilic polymer is non-ionic. In some embodiments, the hydrophilic polymer is enteric. In some embodiments, the hydrophilic polymer is anionic. In some embodiments, the hydrophilic polymer is cationic. In some embodiments, the pharmaceutical composition described herein comprises an ASD comprising a hydrophilic polymer, wherein the hydrophilic polymer is polymethacrylates (e.g., Eudragit), HPMCP, VA64 or HPMCAS. In some embodiments, the hydrophilic polymer is present in an amount of about 1% to about 80% by weight of the ASD. In some embodiments, the hydrophilic polymer is present in an amount of about 10% to about 70% by weight of the ASD. In some embodiments, the hydrophilic polymer is present in an amount of about 15% to about 60% by weight of the ASD. In some embodiments, the hydrophilic polymer is present in an amount of about 20% to about 50% by weight of the ASD. In some embodiments, the hydrophilic polymer is present in an amount of about 25% to about 45% by weight of the ASD.

In some embodiments, an ASD described herein comprises optionally an adsorbent. In some embodiments, the adsorbent is silicone dioxide. In some embodiments, the adsorbent is present in an amount of about 1% to about 40% by weight of the ASD. In some embodiments, the adsorbent is present in an amount of about 10% to about 30% by weight of the ASD. In some embodiments, the adsorbent is present in an amount of about 15% to about 25% by weight of the ASD.

In some embodiments, an ASD described herein optionally comprises an acid. In some embodiments, the acid is an organic acid. In some embodiments, the organic acid is tartaric acid. In some embodiments, the organic acid is present in an amount of about 1% to about 40% by weight of the ASD. In some embodiments, the organic acid is present in an amount of about 10% to about 30% by weight of the ASD. In some embodiments, the organic acid is present in an amount of about 15% to about 25% by weight of the ASD.

In some embodiments, an ASD described herein comprises an adsorbent. In some embodiments, the adsorbent is selected from silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextrin. In some embodiments, the adsorbent is silicon dioxide. In some embodiments, the adsorbent is present in the amorphous solid dispersion in an amount of about 5 to about 80% wt. In some embodiments, the average particle diameter of the amorphous solid dispersion is from 1 μm to 1000 μm. In some embodiments, an average particle size of the amorphous solid dispersion, in terms of particle diameter, is from about 10 μm to about 150 μm.

In some embodiments, an amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, a solid dispersion is a solid state solution wherein a PROTAC (or PROTAC salt thereof) and hydrophilic polymer act as solute and solvent, respectively. The solid dispersion can form multiple structures depending on the composition and sample processing history. When the PROTAC loading is lower than the equilibrium solubility of PROTAC in the hydrophilic polymer, the drug is molecularly dispersed within the polymer matrix and forms a thermodynamically stable, homogeneous solution. A homogenous solution is often attainable only at very low PROTAC loading and/or high temperature. For higher loadings, the mixture becomes a supersaturated solution and the drug precipitates out. This can result in a dispersion of crystalline PROTAC particles in a hydrophilic polymer matrix, in which the drug concentration corresponds to its equilibrium solubility at that temperature. Alternatively, as PROTAC crystallization can be a slow process, an intermediate meta-stable structure may form in which amorphous PROTAC aggregates are dispersed in a hydrophilic polymer matrix containing the PROTAC in a non-crystalline amorphous state. Such amorphous solid dispersions can provide superior dissolution properties, as compared to the crystalline PROTAC. In some embodiments, the PROTAC is one listed in Table 1, or a pharmaceutically acceptable salt thereof. In some embodiments, the PROTAC has a log P 2.0 or higher. In some embodiments, the PROTAC is ARV-110. In some embodiments, the PROTAC is ARV-471.

In some embodiments, an amorphous solid dispersion described herein comprises a PROTAC, hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants. In some embodiments, the amorphous solid dispersions described here are homogenous amorphous solid dispersions. In some embodiments, the components of the amorphous dispersion are mixed and heated in a solvent, and the solvent is removed to form the amorphous solid dispersion. In some embodiments, the solvent is water. In some embodiments, the solvent is a polar organic solvent. In some embodiments, the solvent is a non-polar organic solvent. In some embodiments, the solvent is selected from water, n-butanol, n-propanol, isopropanol, formic acid, nitromethane, ethanol, methanol, acetic acid, N-methylpyrrolidone, tetrahydrofuran, ethyl acetate, methyl acetate, dimethylformamide, acetonitrile, dimethyl sulfoxide, dichloromethane (DCM), acetone, tetrahydrofuran (THF), and any combination thereof. In some embodiments, the solvent is selected from water, n-butanol, n-propanol, isopropanol, formic acid, nitromethane, ethanol, methanol, acetic acid, and any combination thereof. In some embodiments, the solvent is selected from water, methanol, ethanol and isopropanol. In some embodiments, the solvent is selected from dichloromethane, methanol, THF, and acetone. In some embodiments, the solvent is selected from a mixture of these solvents.

In some embodiments, an amorphous solid dispersion described herein comprises a PROTAC, hydrophilic polymer, a surfactant and optionally, an adsorbent. In some embodiments, the components of the amorphous dispersion, such as PROTAC, hydrophilic polymer and surfactant are mixed and solubilized in a solvent, with or without heating to form a solution. In some embodiments, the adsorbent is further added into the solution to form a homogeneous suspension and the solvent is removed to form the amorphous solid dispersion. In some embodiments, the solution is sprayed on to the adsorbent and the solvent is removed to form the amorphous solid dispersion. In some embodiments, the adsorbent is selected from silicon dioxide (also termed silica), magnesium aluminometasilicate (Neusilin), microcrystalline cellulose (MCC), silicified microcrystalline cellulose (SMCC), talc, crosslinked povidone, sodium carboxymethylcellulose, sodium carboxymethylstarch, sugars, and sugar alcohols. In some embodiments, sugars and sugar alcohol comprise sorbitol, mannitol, lactose, cyclodextrin, and maltodextrin. In some embodiments, the adsorbent is silicon dioxide.

In some embodiments, the ASD exhibits a bioavailability of the PROTAC compound or the pharmaceutically acceptable salt thereof that does not vary more than about 5% to about 60% when orally administered to a subject in a fed state compared to a fasted state. In some embodiments, the ASD exhibits a bioavailability of the PROTAC compound or the pharmaceutically acceptable salt thereof that does not vary more than about 25% to about 100% when orally administered to a subject in a fed state compared to a fasted state. In some embodiments, the ASD exhibits a bioavailability of the PROTAC compound or the pharmaceutically acceptable salt thereof that does not vary more than about 5% to about 10%, about 5% to about 15%, about 5% to about 20%, about 5% to about 25%, about 5% to about 30%, about 5% to about 35%, about 5% to about 40%, about 5% to about 50%, about 5% to about 60%, about 10% to about 15%, about 10% to about 20%, about 10% to about 25%, about 10% to about 30%, about 10% to about 35%, about 10% to about 40%, about 10% to about 50%, about 10% to about 60%, about 15% to about 20%, about 15% to about 25%, about 15% to about 30%, about 15% to about 35%, about 15% to about 40%, about 15% to about 50%, about 15% to about 60%, about 20% to about 25%, about 20% to about 30%, about 20% to about 35%, about 20% to about 40%, about 20% to about 50%, about 20% to about 60%, about 25% to about 30%, about 25% to about 35%, about 25% to about 40%, about 25% to about 50%, about 25% to about 60%, about 30% to about 35%, about 30% to about 40%, about 30% to about 50%, about 30% to about 60%, about 35% to about 40%, about 35% to about 50%, about 35% to about 60%, about 40% to about 50%, about 40% to about 60%, about 50% to about 60%, about 55% to about 65%, about 60% to about 70%, about 65% to about 80%, about 75% to about 90%, about 80% to about 100%, or about 90% to about 100%, when orally administered to a subject in a fed state compared to a fasted state.

In some embodiments, the ASD exhibits a bioavailability of the PROTAC compound or the pharmaceutically acceptable salt thereof that does not vary more than about at most about 10%, about 15%, about 20%, about 25%, about 30%, about 35%, about 40%, about 50%, or about 60% when orally administered to a subject in a fed state compared to a fasted state. In some embodiments, the PROTAC is one selected from Table 1. In some embodiments, the PROTAC is ARV-110. In some embodiments, the PROTAC is ARV-471.

The formation of the amorphous solid dispersion can lead to a certain particle size for the ASD. In some embodiments, the particle size of the ASD is from about 1 nm to 1 mm. In some embodiments, the particle size of the ASD is from about 0.01 to 1000 micrometers. In some embodiments, the particle size of the ASD from about 0.01 micrometers to about 1,000 micrometers. In some embodiments, the particle size of the ASD is at least about 0.01 micrometers. In some embodiments, the particle size of the ASD is at most about 1,000 micrometers. In some embodiments, the particle size of the ASD is from about 1 micrometer to about 50 micrometers. In some embodiments, the particle size of the ASD is at least about 1 micrometer. In some embodiments, the particle size of the ASD is at most about 50 micrometers. In some embodiments, the particle size of the ASD is about 10 micrometer to about 15 micrometers. In some embodiments, the particle size of the ASD is from about 1 micrometer to about 3 micrometers, about 1 micrometer to about 7 micrometers, about 1 micrometer to about 10 micrometers, about 1 micrometer to about 13 micrometers, about 1 micrometer to about 17 micrometers, about 1 micrometer to about 20 micrometers, about 1 micrometer to about 23 micrometers, about 1 micrometer to about 27 micrometers, about 1 micrometer to about 30 micrometers, about 1 micrometer to about 40 micrometers, about 1 micrometer to about 50 micrometers, about 10 micrometers to about 13 micrometers, about 10 micrometers to about 17 micrometers, about 10 micrometers to about 20 micrometers, about 10 micrometers to about 23 micrometers, about 10 micrometers to about 27 micrometers, about 10 micrometers to about 30 micrometers, about 10 micrometers to about 40 micrometers, about 10 micrometers to about 50 micrometers, about 20 micrometers to about 27 micrometers, about 20 micrometers to about 30 micrometers, about 20 micrometers to about 40 micrometers, about 20 micrometers to about 50 micrometers, about 30 micrometers to about 40 micrometers, about 30 micrometers to about 50 micrometers, or about 40 micrometers to about 50 micrometers. In some embodiments, the particle size of the ASD is from about 1 micrometer to about 100 micrometers. In some embodiments, the particle size of the ASD is from at least about 1 micrometer. In some embodiments, the particle size of the ASD is about 0.1, 1, 3, 5, 7, 10, 13, 17, 20, 23, 25, 27, 30, 33, 35, 37, 40, 43, 45, 47, 50, 60, 70, 80, 90, or 100 micrometers or less. In some embodiments, the particle size of the ASD is about 20 micrometers or less.

In some embodiments, a distribution of amorphous solid dispersion particle sizes is obtained. In some embodiments, the terms D10, D50, and/or D90 are used to describe a particle size distribution. In some embodiments, the D90 particle size of the ASD is equal to or less than about 1,000 μm, 950 μm, 900 μm, 800 μm, 700 μm, 600 μm, 500 μm, 400 μm, 30) μm, 200 μm, 100 μm, 75 μm, 65 μm, 50 μm, 25 μm, 20 μm, 15 μm, or 10 μm. In some embodiments, the D50 particle size of the ASD is equal to or less than about 500 μm, 400 μm, 300 μm, 200 μm, 100 μm, 50 μm, 35 μm, 25 μm, 20 μm, 15 μm, 10 μm, or 5 μm. In some embodiments, the D10 particle size of the ASD is equal to or less than about 200 μm, 100 μm, 50 μm, 45 μm, 40 μm, 35 μm, 30 μm, 25 μm, 20 μm, 15 μm, 10 μm, 9 μm, 8 μm, 7 μm, 6 μm, 5 μm, 4 μm, 3 μm, 2 μm, or 1 μm.

In some embodiments, a distribution of amorphous solid dispersion particle sizes is obtained. In some embodiments, the terms D10, D50, and/or D90 are used to describe a particle size distribution. In some embodiments, the D90 particle size of the ASD is about 10 μm to about 1,000 μm. In some embodiments, the D90 particle size of the ASD is about 10 μm to about 20 μm, about 10 μm to about 30 μm, about 10 μm to about 50 μm, about 10 μm to about 100 μm, about 10 μm to about 150 μm, about 10 μm to about 200 μm, about 10 μm to about 500 μm, about 10 μm to about 750 μm, about 10 μm to about 1,000 μm, about 20 μm to about 30 μm, about 20 μm to about 50 μm, about 20 μm to about 100 μm, about 20 μm to about 150 μm, about 20 μm to about 200 μm, about 50 μm to about 100 μm, about 100 μm to about 1,000 μm, about 500 μm to about 1,000 μm, or about 750 μm to about 1,000 μm. In some embodiments, the D90 particle size is at least about 10 μm, about 20 μm, about 30 μm, about 50 μm, about 100 μm, about 150 μm, about 200 μm, about 500 μm, or about 750 μm. In some embodiments, the D90 particle size is at most about 15 μm. In some embodiments, the D90 particle size is at most about 10 μm, 15 μm, 20 μm, about 30 μm, about 50 μm, about 100 μm, about 150 μm, about 200 μm, about 500 μm, or about 1,000 μm.

In some embodiments, a distribution of amorphous solid dispersion particle sizes is obtained. In some embodiments, the terms D10, D50, and/or D90 are used to describe a particle size distribution. In some embodiments, the D50 value of the ASD is about 1 μm to about 100 μm. In some embodiments, the D50 value of the ASD is about 10 μm to about 15 μm. In some embodiments, the D50 particle size is about 5 μm to about 10 μm, about 5 μm to about 15 μm, about 5 μm to about 20 μm, about 5 μm to about 25 μm, about 5 μm to about 30 μm, about 5 μm to about 40 μm, about 5 μm to about 50 μm, about 5 μm to about 60 μm, about 5 μm to about 75 μm, about 5 μm to about 100 μm, about 10 μm to about 15 μm, about 10 μm to about 20 μm, about 10 μm to about 25 μm, about 10 μm to about 30 μm, about 10 μm to about 40 μm, about 10 μm to about 50 μm, about 10 μm to about 60 μm, about 10 μm to about 75 μm, about 10 μm to about 100 μm, about 15 μm to about 20 μm, about 15 μm to about 25 μm, about 15 μm to about 30 μm, about 15 µm to about 40 µm, about 15 µm to about 50 µm, about 15 µm to about 60 µm, about 15 µm to about 75 µm, about 15 µm to about 100 µm, about 20 µm to about 25 µm, about 20 µm to about 30 µm, about 20 µm to about 40 µm, about 20 µm to about 50 µm, about 20 µm to about 60 µm, about 20 µm to about 75 µm, about 20 µm to about 100) µm, about 25 µm to about 30 µm, about 25 µm to about 40 µm, about 25 µm to about 50 µm, about 25 µm to about 60 µm, about 25 µm to about 75 µm, about 25 µm to about 100 µm, about 30 µm to about 40 µm, about 30 µm to about 50 µm, about 30 µm to about 60 µm, about 30 µm to about 75 µm, about 50 µm to about 100 µm, or about 75 µm to about 100 µm. In some embodiments, the D50 particle size is about 5 µm, about 10 µm, about 15 µm, about 20 µm, about 25 µm, about 30 µm, about 40 µm, about 50 µm, about 60 µm, about 75 µm, or about 100 µm. In some embodiments, the D50 particle size is at least about 0.5 µm, 5 µm, about 10 µm, about 15 µm, or about 20 µm. In some embodiments, the D50 particle size is at most about 10 µm, about 15 µm, about 20 µm, about 25 µm, about 30 µm, about 40 µm, about 50 µm, about 60 µm, about 75 µm, or about 100 µm.

In some embodiments, a distribution of amorphous solid dispersion particle sizes is obtained. In some embodiments, the terms D10, D50, and/or D90 are used to describe a particle size distribution. In some embodiments, the D10 value of the ASD is about 0.1 µm to about 50 µm. In some embodiments, the D10 particle size is about 0.1 µm to about 1 µm, about 0.1 µm to about 2 µm about 0.1 µm to about 3 µm, about 0.1 µm to about 4 µm, about 0.1 m to about 5 µm, about 0.1 µm to about 7 µm, about 0.1 µm to about 10 µm, about 0.1 µm to about 20 µm, about 0.1 µm to about 30 µm, about 0.1 µm to about 40 µm, about 0.1 µm to about 50 µm, about 1 µm to about 2 µm, about 1 µm to about 3 µm, about 1 µm to about 4 µm, about 1 µm to about 5 µm, about 1 µm to about 7 µm, about 1 µm to about 10 µm, about 1 µm to about 20 µm, or 1 µm to about 50 µm. In some embodiments, the D10 particle size is about 0.1 µm, about 1 µm, about 2 µm, about 3 µm, about 4 µm, about 5 µm, about 7 µm, about 10 µm, about 20 µm, about 30 µm, about 40 µm, or about 50 µm. In some embodiments, the D10 particle size is at least about 0.1 µm, about 1 µm, about 2 µm, about 3 µm, about 4 µm, about 5 µm, about 7 µm, about 10 µm, about 20 µm, about 30 µm or about 40 µm. In some embodiments, the D10 particle size is at most about 1 µm, about 2 µm, about 3 µm, about 4 µm, about 5 µm, about 7 µm, about 10 µm, about 20 µm, about 30 µm, about 40 µm, or about 50 µm.

In some embodiments, an ASD described herein comprises a PROTAC listed in Table 1, or a pharmaceutically acceptable salt thereof. In some embodiments, the PROTAC has a log P 2.0 or higher. In some embodiments the ASD comprises ARV-110 or ARV-471, or pharmaceutically acceptable salts thereof. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, an amorphous solid dispersion described herein comprises a surfactant. In some embodiments, the surfactant is selected from polymeric non-ionic surfactants and phospholipids. In some embodiments, the surfactant is a polymeric non-ionic surfactant. In some embodiments, the surfactant comprises a block copolymer of polyethylene glycol and polypropylene glycol. In some embodiments, the polymeric non-ionic surfactant has a number average molecular weight of from about 7000 to about 10,000 Da. In some embodiments, an amorphous solid dispersion described herein comprises surfactant TPGS. In some embodiments, an amorphous solid dispersion described herein comprises a surfactant that comprises one or more phospholipids, such as lecithin. In some embodiments, the surfactant comprises one or more of phosphatidylcholine, phosphatidylethanolamine, phosphatidylinositol, phosphatidylserine, plasmalogen, sphingomyelin, and phosphatidic acid. In some embodiments, the one or more phospholipids comprise greater than 50%, 60%, 70%, 80%, or 90% phosphatidylcholine by weight. In some embodiments, the surfactant comprises lecithin. In some embodiments, the surfactant is present in the amorphous solid dispersion in an amount of about 5 wt % to about 70 wt % based on solids. In some embodiments, the surfactant is present in the amorphous solid dispersion in an amount of about 20 wt % to about 60 wt % based on solids. In some embodiments, the surfactant is present in the amorphous solid dispersion in an amount of about 10 wt % to about 30 wt % based on solids.

In some embodiments, the present disclosure discloses an ASD that comprises i) a PROTAC listed in Table 1, or a pharmaceutically acceptable salt thereof, ii) a surfactant, iii) a hydrophilic polymer, and iv) optionally an acid. In some embodiments, the PROTAC is ARV-110. In some embodiments, the PROTAC is ARV-471. In some embodiments, the ASD comprises i) a PROTAC listed in Table 1, or a pharmaceutically acceptable salt thereof, ii) a surfactant, wherein the surfactant comprises tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof, iii) a hydrophilic polymer, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), hydropropylmethylcellulose acetate succinate (HPMCAS), sulfobutylether-β-cyclodextrin, hydroxypropyl beta cyclodextrin (HP-β-CD), or a combination thereof, and iv) optionally an acid. In some embodiments, the PROTAC is ARV-110. In some embodiments, the PROTAC is ARV-471. In some embodiments, the ASD comprises i) a PROTAC listed in Table 1, or a pharmaceutically acceptable salt thereof in an amount of about 5% to about 50% by weight of the ASD, ii) a surfactant in an amount of about 1% to about 60% by weight of the ASD, wherein the surfactant comprises tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof, iii) a hydrophilic polymer in an amount of about 5% to about 70% by weight of the ASD, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), hydropropylmethylcellulose acetate succinate (HPMCAS), sulfobutylether-β-cyclodextrin, hydroxypropyl beta cyclodextrin (HP-β-CD), or a combination thereof, and iv) optionally an acid in an amount of about 1% to about 50% by weight of the ASD. In some embodiments, the PROTAC is ARV-110. In some embodiments, the PROTAC is ARV-471.

In some embodiments, an ASD of the present disclosure comprises i) ARV-110, ARV-471, CFT7455, AC0682. ARV-766, BGB-16673, DT2216, FHD-609, GT20029, HP518, HSK29116, KT-474, NX-2127. NX-5948, AC0176. BRD4-CHAMP, or KT-413, or a pharmaceutically acceptable salt thereof in an amount of about 5% to about 50% by weight of the ASD, ii) a surfactant in an amount of about 1% to about 60% by weight of the ASD, wherein the surfactant comprises tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof, iii) a hydrophilic polymer in an amount of about 5% to about 70% by weight of the ASD, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), hydropropylmethylcellulose acetate succinate (HPMCAS), hydroxypropyl beta cyclodextrin (HP-β-CD), sulfobutylether-β-cyclodextrin, or a combination thereof, and iv) optionally an acid in an amount of about 1% to about 50% by weight of the ASD.

In some embodiments, an ASD of the present disclosure comprises i) ARV-110, or ARV-471, or a pharmaceutically acceptable salt thereof in an amount of about 5% to about 50% by weight of the ASD, ii) a surfactant in an amount of about 1% to about 60% by weight of the ASD, wherein the surfactant comprises tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof, iii) a hydrophilic polymer in an amount of about 5% to about 70% by weight of the ASD, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), hydropropylmethylcellulose acetate succinate (HPMCAS), sulfobutylether-β-cyclodextrin, or hydroxypropyl beta cyclodextrin (HP-β-CD), and iv) optionally an acid in an amount of about 1% to about 50% by weight of the ASD, wherein the acid comprises tartaric acid, fumaric acid, succinic acid, citric acid, lactic acid, malic acid, methanesulfonic acid, ethanesulfonic acid, isethionic acid, benzenesulfonic acid, p-toluenesulfonic acid, hydrochloric acid, sulfuric acid, phosphoric acid, or a combination thereof.

In some embodiments, the present disclosure discloses an ASD comprising PROTAC (e.g., ARV-110 and ARV-471) or a pharmaceutically acceptable salt thereof, a surfactant, a hydrophilic polymer, optionally an adsorbent, and optionally an organic acid. In some embodiments, the present disclosure discloses an ASD comprising PROTAC (e.g., ARV-110 and ARV-471) or a pharmaceutically acceptable salt thereof. In some embodiments, the ASD comprises a surfactant. In some embodiments, the ASD comprises a hydrophilic polymer. In some embodiments, the ASD comprises an adsorbent. In some embodiments, the ASD comprises an acid. In some embodiments, the surfactant comprises lecithin or TPGS or a combination thereof. In some embodiments, the hydrophilic polymer comprises vinylpyrrolidone-vinyl acetate copolymer or HPMCAS or a combination thereof. In some embodiments, the adsorbent is silicone dioxide. In some embodiments, the acid is tartaric acid or citric acid or a combination thereof. In some embodiments, the present disclosure discloses an ASD comprising PROTAC (e.g., ARV-110 and ARV-471) in an amount of about 10% to about 40% by weight of the ASD. In some embodiments, the ASD comprises a surfactant in an amount of about 5% to about 60% by weight of the ASD. In some embodiments, the surfactant is TPGS or lecithin or a combination thereof. In some embodiments, the ASD comprises a hydrophilic polymer in an amount of about 10% to about 60% by weight of the ASD. In some embodiments, the hydrophilic polymer comprises vinylpyrrolidone-vinyl acetate copolymer or HPMCAS or a combination thereof. In some embodiments, the ASD comprises an acid in an amount of about 5% to 40% by weight of the ASD. In some embodiments, the acid is tartaric acid or citric acid or a combination thereof. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof.

In some embodiments, the present disclosure discloses an ASD comprising PROTAC (e.g., ARV-110 and ARV-471) in an amount of about 15% to about 35% by weight of the ASD. In some embodiments, the ASD comprises a surfactant in an amount of about 10% to about 55% by weight of the ASD. In some embodiments, the surfactant is TPGS or lecithin or a combination thereof. In some embodiments, the ASD comprises a hydrophilic polymer in an amount of about 10% to about 50% by weight of the ASD. In some embodiments, the hydrophilic polymer comprises vinylpyrrolidone-vinyl acetate copolymer or HPMCAS or a combination thereof. In some embodiments, the ASD comprises an acid in an amount of about 10% to 35% by weight of the ASD. In some embodiments, the acid is tartaric acid or citric acid or a combination thereof. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof.

In some embodiments, the present disclosure discloses an ASD comprising PROTAC (e.g., ARV-110 and ARV-471) in an amount of about 25% by weight of the ASD. In some embodiments, the ASD comprises a surfactant in an amount of about 25% by weight of the ASD. In some embodiments, the surfactant is TPGS or lecithin or a combination thereof. In some embodiments, the ASD comprises a hydrophilic polymer in an amount of about 25% by weight of the ASD. In some embodiments, the hydrophilic polymer is VA64 or HPMCAS. In some embodiments, the ASD comprises an acid in an amount of about 25% by weight of the ASD. In some embodiments, the acid is tartaric acid. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof.

In some embodiments, the present disclosure discloses an ASD comprises PROTAC (e.g., ARV-110 and ARV-471) in an amount of about 20% by weight of the ASD. In some embodiments, the ASD comprises a surfactant in an amount of about 40% by weight of the ASD. In some embodiments, the surfactant is lecithin or a phospholipid. In some embodiments, the ASD comprises a hydrophilic polymer in an amount of about 40% by weight of the ASD. In some embodiments, the hydrophilic polymer is hydropropylmethylcellulose acetate succinate (HPMCAS) or vinylpyrrolidone-vinyl acetate copolymer. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof.

In some embodiments, an ASD described herein have a superior bioavailability than a bioavailability of a corresponding reference composition comprising a crystalline PROTAC (e.g., ARV-110 and ARV-471) or an amorphous PROTAC that is not present in an ASD, when measured as AUC, $AUC_{inf}$, or $AUC_{last}$ after oral administration. In some embodiments, the ASD exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a corresponding composition comprising a crystalline PROTAC (e.g., ARV-110 and ARV-471) or an amorphous PROTAC that is not present in an ASD, when measured as the AUC after oral administration. In some embodiments, the ASD exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a corresponding composition comprising a crystalline PROTAC (e.g., ARV-110 and ARV-471) or an amorphous PROTAC that is not present in an ASD, when measured as $C_{max}$ after oral administration. In some embodiments, the ASD exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of crystalline PROTAC (e.g., ARV-110 and ARV-471) or an amorphous PROTAC that is not present in an ASD capsule comprising ARV-110, when measured as AUC after oral administration. In some embodiments, the ASD exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of an ARV-110 that is not present in an ASD capsule comprising ARV-110, when measured as Cm after oral administration. In some embodiments, the ASD exhibits a bioavailability that is higher than a crystalline PROTAC (e.g., ARV-110 and ARV-471) or an amorphous PROTAC that is not present in an ASD by about 1.1 fold to about 10 fold. In some embodiments, the ASD exhibits a bioavailability that is higher than a bioavailability of a crystalline PROTAC (e.g., ARV-110 and ARV-471) or an amorphous PROTAC that is not present in an ASD by about 1.1 fold to about 2 fold, about 1.1 fold to about 3 fold, about 1.1 fold to about 4 fold, about 1.1 fold to about 5 fold, about 1.1 fold to about 6 fold, about 1.1 fold to about 7 fold, about 1.1 fold to about 8 fold, about 1.1 fold to about 10 fold, about 1.5 fold to about 2 fold, about 1.5 fold to about 3 fold, about 1.5 fold to about 4 fold, about 1.5 fold to about 5 fold, about 1.5 fold to about 6 fold, about 1.5 fold to about 7 fold, about 1.5 fold to about 8 fold, about 1.5 fold to about 10 fold, about 2 fold to about 4 fold, about 2 fold to about 5 fold, about 2 fold to about 6 fold, about 2 fold to about 7 fold, about 2 fold to about 8 fold, about 2 fold to about 10 fold, about 5 fold to about 10 fold, or about 8 fold to about 10 fold. In some cases, PROTAC (e.g., ARV-110 and ARV-471) that is not present in an ASD capsule comprising PROTAC is in amorphous state. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof.

In some embodiments, the ASD exhibits a bioavailability of the PROTAC (e.g., ARV-110 and ARV-471) compound or the pharmaceutically acceptable salt thereof that is at least 2-fold compared to a bioavailability of a corresponding composition comprising the PROTAC (e.g., ARV-110 and ARV-471) compound or the pharmaceutically acceptable salt thereof in a conventional dosage form (e.g., in crystalline form or in amorphous state without being part of an ASD). In some embodiments, the bioavailability is measured as AUC or as maximum plasma concentration ($C_{max}$) after oral administration to a subject in a fasted state. In some embodiments, the ASD exhibits a bioavailability of the PROTAC (e.g., ARV-110 and ARV-471) compound or the pharmaceutically acceptable salt thereof that is at least 3, 4, or 5-fold compared to a bioavailability of a corresponding composition comprising the PROTAC (e.g., ARV-110 and ARV-471) compound or the pharmaceutically acceptable salt thereof in a conventional dosage form (e.g., in crystalline form or in amorphous state without being part of an ASD). In some embodiments, the bioavailability is measured as AUC or as maximum plasma concentration ($C_{max}$) after oral administration to a subject in a fasted state. In some embodiments, the ASD exhibits a bioavailability of the PROTAC (e.g., ARV-110 and ARV-471) or the pharmaceutically acceptable salt thereof is at least 6-fold compared to a bioavailability of a corresponding composition comprising the PROTAC (e.g., ARV-110 and ARV-471) compound or the pharmaceutically acceptable salt thereof in a conventional dosage form (e.g., in crystalline form or in amorphous state without being part of an ASD). In some embodiments, the bioavailability is measured as maximum plasma concentration ($C_{max}$) after oral administration to a subject in a fasted state. In some embodiments, the subject comprises a dog. In some embodiments, the subject comprises six beagle dogs. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof.

In some embodiments, an ASD described herein exhibits a bioavailability that is from about 100% to about 1500%, 120% to about 1000%, 125% to about 500%, about 130% to about 450%, 140% to about 400%, or about 150% to about 300% of a bioavailability of a corresponding reference composition comprising PROTAC (e.g., ARV-110 and ARV-471) when measured as $AUC_{last}$ or $C_{max}$ after oral administration, wherein the corresponding reference pharmaceutical composition does not comprise an amorphous solid dispersion. In some embodiments, the reference composition is about 1.1 times to about 10 times the dosage of the pharmaceutical compositions. In some embodiments, the reference composition is at least about 1.1 times to about 2 times, about 1.1 times to about 5 times, about 1.1 times to about 10 times, about 1.5 times to about 2 times, about 2 times to about 5 times, about 2 times to about 10 times, about 2.5 times to about 3 times, or about 5 times to about 10 times the dosage of the pharmaceutical composition. In some embodiments, the reference composition is at least about 1.1 times, about 1.5 times, about 2 times, about 2.5 times, about 3 times, about 4 times, about 5 times, about 6 times, about 7 times, about 8 times, about 9 times, or about 10 times the dosage of the pharmaceutical composition. In some embodiments, the pharmaceutical composition comprises an ASD comprising PROTAC (e.g., ARV-110 and ARV-471) free base or a pharmaceutically acceptable salt thereof. In some embodiments, the reference composition comprises PROTAC (e.g., ARV-110 and ARV-471) free base or a pharmaceutically acceptable salt thereof, wherein the reference composition does not comprise an ASD. In some embodiment, the bioavailability is measured under fasted condition. In some embodiment, the bioavailability is measured under fed condition. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof Surfactants In one aspect, disclosed herein are pharmaceutical compositions comprising an amorphous solid dispersion (ASD) that comprises a PROTAC, a hydrophilic polymer, and a surfactant. In some embodiments, the ASD comprises a PROTAC, a hydrophilic polymer, and a surfactant. The surfactant can be present in the ASD in an amorphous state. In some embodiments, the PROTAC is a PROTAC of Table 1 or a pharmaceutically acceptable salt thereof. In some embodiments, the PROTAC has a log P 2.0 or higher. In some embodiments, the PROTAC is ARV-110. In some embodiments, the PROTAC is ARV-471.

In some embodiments, the surfactants are compounds or mixture of compounds comprising a hydrophobic group (usually a hydrocarbon chain) and a hydrophilic group. They may perform one or more roles including solubility enhancer, bioavailability enhancer, stability enhancer, antioxidant and emulsifying agent. Other terms in the art for surfactants include emulsifier, emulsifying agent, surface-active agent, wetting agent, suspending agent and the like. Examples of surfactants include, but are not limited to phospholipids, lecithin, kolliphor series (rh40), sorbitan oleate, SDS, Solutol, Soluplus, sucrose esters of fatty acids, polyoxyl stearate, polyoxyethylene hydrogenated castor oil, polyoxyl 40 hydrogenated castor, macrogolglycerol hydroxystearate oil, peg-40 castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, sodium dodecyl sulfate, polyvinylcaprolactame-based graft copolymer (PVAc-PVCap-PEG), lauromacrogol arlasolve, poloxamers, labrafil, labrasol, tween 80, tocopheryl polyethylene glycol succinate (TPGS or vitamin E TPGS) and the like. In some embodiments, the surfactant is polyvinylcaprolactame-based graft copolymer (PVAc-PVCap-PEG). In some embodiments, the surfactant is tocopheryl polyethylene glycol 1000 succinate. In some embodiments, the PROTAC is ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC is a pharmaceutically acceptable salt of ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC has a calculated log P or log P of at least 2.0. In some embodiments, the PROTAC is one listed in Table 1, or a pharmaceutically acceptable salt thereof. In some embodiments, the PROTAC, hydrophilic polymer, and the surfactant are formulated as an amorphous solid dispersion. In some embodiments, the PROTAC, hydrophilic polymer, the surfactant, and optionally an acid, are formulated as an amorphous solid dispersion. In some embodiments, the PROTAC, hydrophilic polymer, the surfactant, and an acid are formulated as an amorphous solid dispersion.

The surfactant used in the present disclosure can be one or more non-ionic surfactant, one or more an ionic surfactant, or a mixture thereof. In some embodiments, a non-ionic surfactant has no charged groups in its head. Exemplary nonionic surfactants include, without limitation, fatty alcohols, cetyl alcohol, stearyl alcohol, cetostearyl alcohol, and oleyl alcohol. Exemplary nonionic surfactants include, but are not limited to, polyethylene glycol alkyl ethers (such as octaethylene glycol monododecyl ether, polyoxylglycerides, (such as Caprylocaproyl macrogol-8 glycerides or PEG-8 caprylic/capric glycerides sold under the trade name Labrasol), pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), polyethoxylated tallow amine (POEA), and Tocopheryl polyethylene glycol succinate (i.e., TPGS or Vitamin E TPGS). In some embodiments, the surfactant is tocopheryl polyethylene glycol 1000 succinate. In some embodiments, a non-ionic surfactant comprises one or more of fatty alcohols, cetyl alcohol, stearyl alcohol, cetostearyl alcohol, and oleyl alcohol. Exemplary nonionic surfactants include, but are not limited to, polyethylene glycol alkyl ethers (such as octaethylene glycol monododecyl ether, pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), polyethoxylated tallow amine (POEA), and Tocopheryl polyethylene glycol succinate (TPGS or Vitamin E TPGS). In some embodiments, the surfactant is tocopheryl polyethylene glycol 1000 succinate.

In some embodiments, a non-ionic surfactant comprises Vitamin E TPGS, a block copolymer of polyethylene glycol and polypropylene glycol, or any combination thereof. In some embodiments, the surfactant comprises two more repeating units, such as polyoxyalkylene units. In some embodiments, the surfactant comprises polyoxylglycerides (such as Caprylocaproyl macrogol-8 glycerides or PEG-8 caprylic/capric glycerides). In some embodiments, the surfactant is a non-ionic surfactant that comprises polyethylene glycol. In some embodiments, the surfactant is a block copolymer of polyethylene glycol and polypropylene glycol. In some embodiments, the ASD comprises two surfactants. In some embodiments, the ASD comprises two or more surfactants. In some embodiments, the ASD comprises a surfactant wherein the surfactant is lecithin. In some embodiments, the ASD comprises a surfactant wherein the surfactant is TPGS. In some embodiments, the ASD comprises one or more surfactants wherein the surfactant comprises lecithin and TPGS.

In some embodiments, an ionic surfactant has a charged group in its head. In some embodiments, an ionic surfactant has an anionic head group or a cationic head group. In some embodiments, exemplary ionic surfactants include sodium lauryl sulfate (SLS), sodium dodecyl sulfate, calcium oleate, triethanolamine oleate, docusate sodium, benzalkonium chloride, and cetylpyridinium chloride. In some embodiments, the pharmaceutical composition or the amorphous solid dispersion comprises SLS. In some embodiments, the surfactant is a mixture of one or more non-ionic surfactants and one or more ionic surfactant. In some embodiments, the surfactant comprises SLS and TPGS.

In some embodiments, the non-ionic surfactant has a number average molecular weight of from about from about 1000 to about 100,000 Da, 2000 to about 20,000 Da, from about 4000 to about 15,000 Da, from about 6000 to about 12,000 Da, or from about 7000 to about 10,000 Da. In some embodiments, the non-ionic surfactant has a number average molecular weight of from about 7000 to about 10,000 Da. In some embodiments, the non-ionic surfactant has an ethylene glycol content of from about 30 wt % to about 99 wt %, from about 50 wt % to about 95 wt %, from about 60 wt % to about 95 wt %, from about 75 wt % to about 90 wt %, or from about 80 wt % to about 85 wt %. In some embodiments, the non-ionic surfactant has an ethylene glycol content of from about 80 wt % to about 85 wt %.

In some embodiments, the surfactants are selected from fatty acids, phospholipids, sphingolipids, saccharolipids, polyketides, sterol lipids, prenol lipids and the like. In some embodiments, phospholipids are made up of glycerol to which is attached a phosphate group and two fatty acids. Other terms in the art for phospholipids include glycerophospholipids, phosphoglycerides, diacylglycerides and the like. The phosphate group can be unmodified (i.e. in the structure below R=H) or modified by attachment (i.e. in the structure below R≠H) to simple organic molecules such as, but not limited to choline, ethanolamine or serine. Phospholipids may be further modified by substitution onto one or more for the hydrocarbon chains.

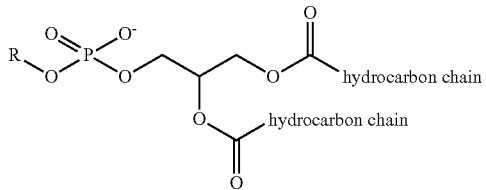

Phospholipids

In one aspect, pharmaceutical compositions described herein comprise an ASD that comprises a surfactant that is a phospholipid. In some embodiments, phospholipids are selected from glycerophospholipid, sphingolipid, and/or phospholipid derivatives. In some embodiments, glycerophospholipids include, but are not limited to phosphatidylcholine, phosphatidyl ethanolamine, phosphatidyl ethanolamine, phosphatidyl serine, phosphatidyl glycerol, diphosphatidylglycerol, phosphatidylinositol, and mixtures thereof. Phospholipid derivatives according to the present disclosure include, but are not limited to dioleoylphosphatidylcholine, dimyristoylphosphatidylcholine, dipentadeanoylphosphatidylcholine, dilauroylphosphatidylchoine, dipalmitoylphosphatidylcholine (DPPC), distearoylphosphatidylcholine (DSPC), diarachidonyiphosphatidylcholine (DAPC), dioleoylphosphatidylethanolamine, dipalmitoylphosphatidylethanolamine (DPPE), and distearoylphosphatidylethanolamine (DSPE), disteraoylphosphatidylglycerol (DSPG), phosphatidylinositol, dipalmitoylphosphatidic acid (DPPA), distearoylphosphatidic acid (DSPA), and the like, and mixtures thereof. In some embodiments, the phospholipids comprise at least 40%, 50%, 60%, 70%, 80%, 90%, or 95% phosphatidylcholine by weight. In some embodiments, the phospholipids comprise greater than 80% phosphatidylcholine.

In some embodiments, the phospholipid is present in the pharmaceutical composition in an amount of about 25 mg to about 200 mg. In some embodiments, the phospholipid is present in an amount of about 50 mg to 150 mg. In some embodiments, the phospholipids comprise 2.5%-20% of the total weight of the pharmaceutical composition. In some embodiments, the phospholipids comprise 5%-17% of the total weight of the pharmaceutical composition. In some embodiments, the phospholipids comprise greater than 80% phosphatidylcholine.

In some embodiments, phosphatidylcholines are phospholipids wherein a choline group ($Me_3N^+$—$CH_2$—$CH_2$—O—) is attached to the phosphate group.

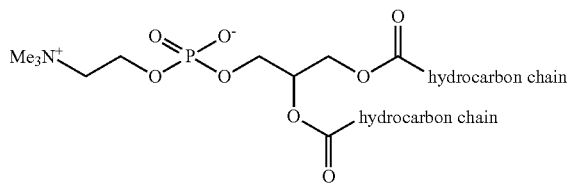

Phosphatidylcholines

In some embodiments, the ASD comprise a phosphatidylcholine. A non-limiting example of a phosphatidylcholine is 1-oleoyl-2-palmitoyl-phosphatidyl choline, as shown below:

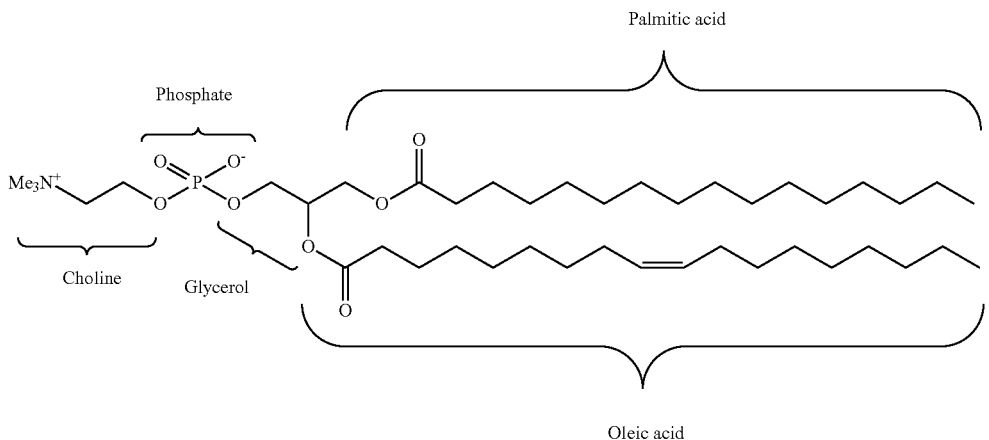

In some embodiments, the surfactant is lecithin. The USP 40 definition of lecithin is "a complex mixture of acetone-insoluble phosphatides, which consist chiefly of phosphatidylcholine, phosphatidylethanolamine, phosphatidylinositol, and phosphatidic acid, present in conjunction with various amounts of other substances such as triglycerides, fatty acids, and carbohydrates, as separated from the crude vegetable oil source." In some embodiments, lecithin is a mixture of phospholipids. In some embodiments, lecithin comprises a mixture of phospholipids, including phosphatidylcholine, phosphatidylethanolamine, phosphatidylinositol, and phosphatidic acid. In some embodiments, lecithin comprises a mixture of phosphatidylcholine, phosphatidylethanolamine, phosphatidylinositol, phosphatidylserine, and phosphatidic acid. Lecithin can be isolated from various sources including, but not limited to eggs, soybeans, milk, marine sources, rapeseed, cottonseed and sunflower. In some embodiments, the lecithin used in the disclosed amorphous solid dispersions and/or pharmaceutical compositions is isolated from egg yolk. Lecithin can be E322. Lecithin can be egg lecithin. Lecithin can be LSC 5050. Lecithin can be LSC 6040. Lecithin can be mixed soybean phosphatides. Lecithin can be ovolecithin. Lecithin can be Phosal 53 MCT. Lecithin can be Phospholipon 100 H. Lecithin can be ProKote LSC. Lecithin can be soybean lecithin. Lecithin can be soybean phospholipids. Lecithin can be Stempur. Lecithin can be vegetable lecithin. Lecithin can be 1,2-diacyl-sn-glycero-3-phosphocholine. In some embodiments, the lecithin contains more than 25% of phosphatidylcholine. In some embodiments, the lecithin contains more than 50% of phosphatidylcholine. In some embodiments, the lecithin contains more than 60% of phosphatidylcholine. In some embodiments, the lecithin contains more than 70% of phosphatidylcholine. In some embodiments, lecithin is from an extract of soybeans (e.g., CAS [8030-76-0]). In some embodiments, lecithin comprises egg yolk lecithin (e.g., CAS 193685-90-61).

In some embodiments, the lecithin contains from about 10% to about 95% of phosphatidylcholine. In some embodiments, the lecithin contains from about 15% to about 80% of phosphatidylcholine In some embodiments, the lecithin contains from about 20% to about 75% of phosphatidylcholine. In some embodiments, the lecithin contains from about 25% to about 70% of phosphatidylcholine. In some embodiments, the lecithin contains from about 30% to about 65% of phosphatidylcholine. In some embodiments, the lecithin contains from about 35% to about 60% of phosphatidylcholine. In some embodiments, the lecithin contains from about 40% to about 55% of phosphatidylcholine. In some embodiments, the lecithin contains about 10%, about 15%, about 20%, about 21%, about 25%, about 30%, about 35%, about 40%, about 45%, about 50%, about 55%, about 60%, about 65%, about 69%, about 70%, about 75%, about 85%, about 90% phosphatidylcholine. In some embodiments, the lecithin contains about 69% phosphatidylcholine. In some embodiments, the lecithin contains about 21% phosphatidylcholine. In some embodiments, the lecithin contains from about 1% to about 55%, about 1% to about 50%, from about 2% to about 40%, from about 3% to about 36%, from about 5% to about 35%, from about 10% to about 30%, from about 15% to about 25% of phosphatidylethanolamine. In some embodiments, the lecithin contains about 1%, about 2%, about 3%, about 4%, about 5%, about 10%, about 15%, about 20%, about 22%, about 24%, about 26%, about 29%, about 30%, about 35%, about 36%, about 40%, about 45%, about 50%, or about 55% phosphatidylethanolamine. In some embodiments, the lecithin contains about 21% phosphatidylcholine, about 22% phosphatidylethanolamine, and about 19% phosphatidylinositol. In some embodiments, the lecithin contains about 69% phosphatidylcholine and about 24% phosphatidylethanolamine. In some embodiments, lecithin is egg yolk lecithin. In some embodiments, In some embodiments, the phosphatidylcholine is from egg origin. In some embodiments, the phosphatidylcholine is from or soybean origin.

In some embodiments, the surfactant is a phospholipid. In some embodiments, the phospholipid is phosphatidylcholine. In some embodiments, the phospholipid is a mixture comprising phosphatidylcholine. In some embodiments, the surfactant is lecithin. In some embodiments, lecithin is a mixture of phospholipids. In some embodiments, the lecithin is comprised of phosphatidylcholine. In some embodiments, the lecithin contains more than 25% of phosphatidylcholine. In some embodiments, the lecithin contains more than 80% of phosphatidylcholine. In some embodiments, the phosphatidylcholine is from egg origin. In some embodiments, the phosphatidylcholine is from or soybean origin.

In some embodiments, the surfactant is present in an ASD described herein in a weight percent of about 10% to about 70%. In some embodiments, the surfactant is present in an amorphous solid dispersion in a weight percent of about 10% to about 60% In some embodiments, the surfactant is present in an amorphous solid dispersion in a weight percent of about 10% to about 50%. In some embodiments, the surfactant is present in the ASD in a weight percent of about 15% to about 45%. In some embodiments, the surfactant is present in the ASD in a weight percent of about 20% to about 40%. In some embodiments, the surfactant is present in the ASD in a weight percent of about 20% to about 30%. In some embodiments, the surfactant is present in the ASD in a weight percent of about 30% to about 40%. In some embodiments, the surfactant is present in an amorphous solid dispersion in a weight percent of about 10% to about 15%, about 10% to about 20%, about 10% to about 25%, about 10% to about 30%, about 10% to about 35%, about 10% to about 40%, about 10% to about 45%, about 10% to about 50%, about 15% to about 20%, about 15% to about 25%, about 15% to about 30%, about 15% to about 35%, about 15% to about 40%, about 15% to about 45%, about 15% to about 50%, about 20% to about 25%, about 20% to about 30%, about 20% to about 35%, about 20% to about 40%, about 20% to about 45%, about 20% to about 50%, about 25% to about 30%, about 25% to about 35%, about 25% to about 40%, about 25% to about 45%, about 25% to about 50%, about 30% to about 35%, about 30% to about 40%, about 30% to about 45%, about 30% to about 50%, about 35% to about 40%, about 35% to about 45%, about 35% to about 50%, about 40% to about 45%, about 40% to about 50%, about 45% to about 50%, about 50% to about 60%, or about 60% to about 70%. In some embodiments, the surfactant is present in an amorphous solid dispersion in a weight percent of about 10%, about 15%, about 20%, about 25%, about 30%, about 35%, about 40%, about 45%, about 50%, about 55%, about 60%, about 65%, or about 70%. In some embodiments, the surfactant is present in an amorphous solid dispersion in a weight percent of at least about 10%, about 15%, about 20%, about 25%, about 30%, about 35%, about 40%, or about 45%. In some embodiments, the surfactant is present in an amorphous solid dispersion in a weight percent of at most about 15%, about 20%, about 25%, about 30%, about 35%, about 40%, about 45%, or about 50%. In some embodiments, the surfactant is present in an amorphous solid dispersion in a weight percent of about 20%. In some embodiments, the surfactant is present in an amorphous solid dispersion in a weight percent of about 25%. In some embodiments, the surfactant is present in an amorphous solid dispersion in a weight percent of about 40%. In some embodiments, the surfactant is TPGS. In some embodiments, the surfactant is lecithin.

In some embodiments, the surfactant is present in an ASD described herein in an amount of about 5 mg to about 5,000 mg. In some embodiments, the surfactant is present in the ASD in an amount of about 5 mg to about 10 mg, about 5 mg to about 20 mg, about 5 mg to about 30 mg, about 5 mg to about 50 mg, about 5 mg to about 80 mg, about 5 mg to about 100 mg, about 5 mg to about 150 mg, about 5 mg to about 200 mg, about 5 mg to about 300 mg, about 5 mg to about 500 mg, about 5 mg to about 5,000 mg, about 10 mg to about 20 mg, about 10 mg to about 30 mg, about 10 mg to about 50 mg, about 10 mg to about 80 mg, about 10 mg to about 100 mg, about 10 mg to about 150 mg, about 10 mg to about 200 mg, about 10 mg to about 300 mg, about 10 mg to about 500 mg, about 10 mg to about 5,000 mg, about 20 mg to about 30 mg, about 20 mg to about 50 mg, about 20 mg to about 80 mg, about 20 mg to about 100 mg, about 20 mg to about 150 mg, about 20 mg to about 200 mg, about 20 mg to about 300 mg, about 20 mg to about 500 mg, about 20 mg to about 5,000 mg, about 30 mg to about 50 mg, about 30 mg to about 80 mg, about 30 mg to about 100 mg, about 30 mg to about 150 mg, about 30 mg to about 200 mg, about 30 mg to about 300 mg, about 30 mg to about 500 mg, about 30 mg to about 5,000 mg, about 50 mg to about 80 mg, about 50 mg to about 100 mg, about 50 mg to about 150 mg, about 50 mg to about 200 mg, about 50 mg to about 300 mg, about 50 mg to about 500 mg, about 50 mg to about 5,000 mg, about 80 mg to about 100 mg, about 80 mg to about 150 mg, about 80 mg to about 200 mg, about 80 mg to about 300 mg, about 80 mg to about 500 mg, about 80 mg to about 5,000 mg, about 100 mg to about 150 mg, about 100 mg to about 200 mg, about 100 mg to about 300 mg, about 100 mg to about 500 mg, about 100 mg to about 5,000 mg, about 150 mg to about 200 mg, about 150 mg to about 300 mg, about 150 mg to about 500 mg, about 150 mg to about 500 mg, about 200 mg to about 300 mg, about 200 mg to about 500 mg, about 200 mg to about 5,000 mg, about 300 mg to about 500 mg, about 300 mg to about 5,000 mg, or about 500 mg to about 5,000 mg. In some embodiments, the surfactant is present in the ASD in an amount of about 5 mg, about 10 mg, about 20 mg, about 30 mg, about 50 mg, about 80 mg, about 100 mg, about 150 mg, about 200 mg, about 300 mg, about 500 mg, or about 5,000 mg. In some embodiments, the surfactant is present in the ASD in an amount of at least about 5 mg, about 10 mg, about 20 mg, about 30 mg, about 50 mg, about 80 mg, about 100 mg, about 150 mg, about 200 mg, about 300 mg, or about 500 mg. In some embodiments, the surfactant is present in the ASD in an amount of at most about 10 mg, about 20 mg, about 30 mg, about 50 mg, about 80 mg, about 100 mg, about 150 mg, about 200 mg, about 300 mg, about 500 mg, or about 5,000 mg. In some embodiments, the surfactant is or comprises a phospholipid. In some embodiments, the phospholipid is or comprises lecithin. In some embodiments, the surfactant is TPGS. In some embodiments, the surfactant is lecithin. In some embodiments, the surfactant is TPGS and lecithin. In some embodiments, the ASD is formulated in a unit dosage form, such as a capsule or a tablet. In some embodiments, the surfactant is present in the pharmaceutical composition in an amount of 10 mg to 500 mg. In some embodiments, the surfactant is present in the pharmaceutical composition in an amount of 20 mg to 300 mg. In some embodiments, the surfactant is present in the pharmaceutical composition in an amount of 30 mg to 100 mg. In some embodiments, the surfactant is present in the pharmaceutical composition in an amount of 40 mg to 80 mg.

In some embodiments, the surfactant, such as TPGS, SLS, lecithin or a combination thereof, is present in an ASD in an amount of no less than 5 mg, 10 mg, 15 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the lecithin is present in an amorphous solid dispersion or in a pharmaceutical composition disclosed herein in an amount of about 5 mg, 10 mg, 15 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the PROTAC is ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC is a pharmaceutically acceptable salt of ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants, such as vitamin E.

In some embodiments, the ratio by weight of the PROTAC to the surfactant is from about 2:1 to about 1:10. In some embodiments, the ratio by weight of the PROTAC to the surfactant is from about 1:0.5 to about 1:6. In some embodiments, the ratio by weight of the PROTAC to the surfactant is from about 1:0.8 to about 1:5. In some embodiments, the ratio by weight of the PROTAC to the surfactant is from about 1:0.8 to about 1:3. In some embodiments, the ratio by weight of the PROTAC to the surfactant is from about 1:1 to about 1:3. In some embodiments, the ratio by weight of the PROTAC to the surfactant is from about 1:0.8 to about 1:2.8. In some embodiments, the ratio by weight of the PROTAC to the surfactant is from about 1:0.8 to about 1:2.5. In some embodiments, the ratio by weight of the PROTAC to the surfactant is from about 1:1 to about 1:2.5. In some embodiments, the ratio by weight of the PROTAC to the surfactant is from about 1:1 to about 1:2. In some embodiments, the ratio by weight of the PROTAC to the surfactant is from about 1:1 to about 1:1.5. In some embodiments, the ratio by weight of the PROTAC to the surfactant is from about 1:1 to about 1:4. In some embodiments, the ratio by weight of the PROTAC to the surfactant is from about 1:1 to about 1:3.5. In some embodiments, the surfactant is TPGS. In some embodiments, the surfactant is lecithin. In some embodiments, the PROTAC is ARV-110. In some embodiments, the PROTAC is ARV-471.

In some embodiments, the surfactant comprises 0.1%-60% of the total weight of a herein described pharmaceutical composition. In some embodiments, the surfactant comprises 0.1%-50% of the total weight of a herein described pharmaceutical composition. In some embodiments, the pharmaceutical composition is an amorphous solid dispersion. In some embodiments, the surfactant comprises 1%-40% of the total weight of the composition. In some embodiments, the surfactant comprises 1%-30% of the total weight of the composition. In some embodiments, the composition is a pharmaceutical composition. In some embodiments, the surfactant comprises 5%-20% of the total weight of the composition. In some embodiments, the surfactant comprises 10%-17% of the total weight of the composition. In some embodiments, the surfactant comprises about 15% of the total weight of the composition. In some embodiments, the surfactant comprises about 16% of the total weight of the composition. In some embodiments, the surfactant comprises about 17% of the total weight of the composition. In some embodiments, the surfactant comprises about 15-30% of the total weight of the composition. In some embodiments, the surfactant comprises about 10-35% of the total weight of the composition. In some embodiments, the surfactant comprises about 20-40% of the total weight of the composition. In some embodiments, the surfactant is TPGS or lecithin or a combination thereof. In some embodiments, the surfactant is a phospholipid. In some embodiments, the ratio by weight of the hydrophilic polymer to the surfactant (e.g., lecithin or TPGS) is greater than 0.75. In some embodiments, the ratio by weight of the hydrophilic polymer to the surfactant (e.g., lecithin or TPGS) is greater than 1.0. In some embodiments, the ratio by weight of the hydrophilic polymer to the surfactant (e.g., lecithin or TPGS) is greater than 1.1. In some embodiments, the ratio by weight of the hydrophilic polymer to the surfactant (e.g., lecithin or TPGS) is greater 1.2. In some embodiments, the ratio by weight of the hydrophilic polymer to the surfactant (e.g., lecithin or TPGS) is greater 1.3. In some embodiments, the ratio by weight of the hydrophilic polymer to the surfactant (e.g., lecithin or TPGS) is greater 1.4. In some embodiments, the ratio by weight of the hydrophilic polymer to the surfactant (e.g., lecithin or TPGS) is greater than 1.5. In some embodiments, pharmaceutical compositions described herein include a PROTAC, a hydrophilic polymer, and a surfactant. In some embodiments, pharmaceutical compositions described herein include a PROTAC, a hydrophilic polymer, and a surfactant or poloxamer. In some embodiments, pharmaceutical compositions described herein include a PROTAC, a hydrophilic polymer, and lecithin. In some embodiments, pharmaceutical compositions described herein include a PROTAC, a hydrophilic polymer, and lecithin. In some embodiments, pharmaceutical compositions described herein include a PROTAC, an ionic hydrophilic polymer, and lecithin. In some embodiments, the PROTAC is ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC is a pharmaceutically acceptable salt of ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC is one listed in Table 1, or a pharmaceutically acceptable salt thereof. In some embodiments, the PROTAC has a log P 2.0 or higher. In some embodiments, the PROTAC is ARV-110. In some embodiments, the PROTAC is ARV-471.

In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants (e.g., vitamin E).

Hydrophilic Polymers

In one aspect, described herein are pharmaceutical compositions comprising an ASD that comprises a PROTAC, a hydrophilic polymer, a surfactant, and optionally an adsorbent. The hydrophilic polymer can be present in the ASD in an amorphous state. In some embodiments, the PROTAC is a PROTAC of Table 1 or a pharmaceutically acceptable salt thereof. In some embodiments, the PROTAC is ARV-110, ARV-471, CFT7455, AC0682, ARV-766, BGB-16673, DT2216, FHD-609, GT20029, HP518. HSK29116, KT-474. NX-2127, NX-5948, AC0176, BRD4-CHAMP, or KT-413. In some embodiments, the PROTAC is a pharmaceutically acceptable salt of ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC is ARV-110 or a pharmaceutically acceptable salt thereof. In some embodiments, the PROTAC is ARV-471 or a pharmaceutically acceptable salt thereof.

In some embodiments, pharmaceutical compositions comprise an ASD that comprises a hydrophilic polymer. In some embodiments, the hydrophilic polymer comprises at least one of polyvinylpyrrolidone (povidone or PVP), vinylpyrrolidone-vinyl acetate copolymer (copovidone), sulfobutylether-β-cyclodextrin, oligosaccharide, polysaccharide, HEC, HPC, PEO, HP-β-CD, PEG, hypromellose phthalate (HPMCP), polymethacrylates (e.g., sold under trade name Eudragit), HPMC, PVP, polyvinylpolypyrrolidone (PVPP), vinylpyrrolidone-vinyl acetate copolymer or Kollidon VA64 (VA64), PVA, hydropropylmethylcellulose acetate succinate (HPMCAS). HPMCP, sulfobutylether-β-cyclodextrin, and polyethylene glycol, polyvinyl acetate and polyvinylcaprolactame-based graft copolymer (PVAc-PVCap-PEG) or polyvinyl caprolactam-polyvinyl acetate-polyethylene glycol (PCL-PVAc-PEG, also termed Soluplus®). In some embodiments, PVP comprises PVP K30. In some embodiments, HMPC comprises HPMC E5 and HMPC E50. In some embodiments, the hydrophilic polymer is sulfobutylether-β-cyclodextrin. In some embodiments, the hydrophilic polymer is a non-ionic polymer. In some embodiments, the hydrophilic polymer is an ionic polymer, e.g., sulfobutylether-β-cyclodextrin. In some embodiments, the hydrophilic polymer comprises copovidone. In some embodiments, the hydrophilic polymer comprises povidone. In some embodiments, the hydrophilic polymer comprises sulfobutylether-β-cyclodextrin. In some embodiments, the HPMCAS is HPMCAS-LF. In some embodiments, the hydrophilic polymer comprises vinylpyrrolidone-vinyl acetate copolymer or Kollidon VA64 (VA64). In some embodiments, the hydrophilic polymer is hydropropylmethylcellulose acetate succinate (HPMCAS), such as HPMCAS-LS. In some embodiments, the hydrophilic polymer is polymethacrylates, such as Eudragit. In some embodiments, the hydrophilic polymer is hypromellose phthalate (HPMCP).

In some embodiments, an amorphous solid dispersion described herein comprises a hydrophilic polymer. In some embodiments, the hydrophilic polymer is a non-ionic polymer. In some embodiments, the hydrophilic polymer is an ionic polymer. In some embodiments, the hydrophilic polymer is a cationic polymer. In some embodiments, the hydrophilic polymer is an anionic polymer. In some embodiments, the hydrophilic polymer comprises polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), hydropropylmethylcellulose acetate succinate (HPMCAS), polyethylene glycol (PEG), polyvinyl acetate and polyvinylcaprolactame-based graft copolymer (PVAc-PVCap-PEG), or polyvinyl caprolactam-polyvinyl acetate-polyethylene glycol (PCL-PVAc-PEG also termed Soluplus®), polyethylene oxide, hydroxypropyl beta cyclodextrin (HP-β-CD), or a combination thereof. In some embodiments, the non-ionic hydrophilic polymer is HPMC, PVP, HP-β-CD, or PVA. In some embodiments, the hydrophilic polymer is a enteric polymer. In some embodiments, an enteric polymer comprises methacrylate copolymers, hydroxypropyl methylcellulose acetate succinates or cellulose acetate phthalate. In some embodiments, the enteric polymer remains unionized at low pH and remain insoluble. In some embodiments, the enteric polymer comprises polymethacrylates (e.g., Eudragit), Hypromellose Phthalate (HPMCP), HPMCAS, or Soluplus. In some embodiments, the polymethacrylates comprises Eudragit. In some embodiments, the polymethacrylates comprises Ammonio Methacrylate Copolymer (Type A). Ammonio Methacrylate Copolymer (Type B). Basic Butylated Methacrylate Copolymer, Methacrylic Acid-Ethyl Acrylate Copolymer (1:1), Methacrylic Acid-Ethyl Acrylate Copolymer (1:1), Dispersion 30 percent, Methacrylic Acid-Methyl Methacrylate Copolymer (1:1), Methacrylic Acid-Methyl Methacrylate Copolymer (1:2), Polyacrylate Dispersion (30 percent), Poly (butyl methacrylate, (2-dimethylaminoethyl) methacrylate, methyl methacrylate) 1:2:1, Poly(ethyl acrylate, methyl methacrylate) 2:1, Poly(methacrylic acid, methyl methacrylate) 1:1, Poly(methacrylic acid, ethyl acrylate) 1:1, Poly (methacrylic acid, methyl methacrylate) 1:2, Poly(methyl acrylate, methyl methacrylate, methacrylic acid) 7:3:1, Poly (ethyl acrylate, methyl methacrylate, trimethylammonioethyl methacrylate chloride) 1:2:0.2, or Poly(ethyl acrylate, methyl methacrylate, trimethylammonioethyl methacrylate chloride) 1:2:0.1. In some cases, the enteric polymer comprises Cellulose phthalate hydroxypropyl methyl ether; HPMCP; hydroxypropyl methylcellulose benzene-1,2-dicarboxylate; 2-hydroxypropyl methylcellulose phthalate; hypromellosi phthalas; Mantrocel HP-55; or methylhydroxypropylcellulose phthalate.

In some embodiments, the hydrophilic polymer is present in an ASD described herein in a weight percent of about 5% to about 90%. In some embodiments, the hydrophilic polymer is present in the amorphous solid dispersion in an amount of about 5% to about 70%. In some embodiments, the hydrophilic polymer is present in the amorphous solid dispersion in an amount of about 15% to about 50%. In some embodiments, the hydrophilic polymer is present in the amorphous solid dispersion in an amount of about 20% to about 30%. In some embodiments, the hydrophilic polymer is present in the amorphous solid dispersion in an amount of about 25% to about 40%. In some embodiments, the hydrophilic polymer is present in an amorphous solid dispersion in a weight percent of about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90%. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone VA64. In some embodiments, the hydrophilic polymer comprises hydropropylmethylcellulose acetate succinate (HPMCAS). In some embodiments, the hydrophilic polymer comprises HPMCP. In some embodiments, the hydrophilic polymer comprises polymethacrylates (e.g., Eudragit). In some embodiments, the hydrophilic polymer comprises polyvinyl caprolactam-polyvinyl acetate-polyethylene glycol. In some embodiments, the ASD comprises two or more hydrophilic polymers. In some embodiments, the two or more hydrophilic polymers are selected from copovidone, HPMCAS, and HPMC.

In some embodiments, a weight ratio of the PROTAC or a pharmaceutically acceptable salt thereof to the hydrophilic polymer is from about 10:1 to about 1:10. In some embodiments, the hydrophilic polymer is selected from PVA, oligosaccharide, polysaccharide, PVP, HPMC, HEC, HPC, PEO, HP-β-CD, HPMCAS, PEG, HPMCP, Eudragit, and Soluplus, or a combination thereof. In some embodiments, the hydrophilic polymer is non-ionic. In some embodiments, the hydrophilic polymer comprises polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), sulfobutylether-β-cyclodextrin, hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the hydrophilic polymer is HPMC, PVP, HP-β-CD, PVA, HPMCAS, or PCL-PVAc-PEG. In some embodiments, the hydrophilic polymer is present in the amorphous solid dispersion in an amount of about 5 wt % to about 70 wt % based on solids. In some embodiments, a weight ratio of the PROTAC or a pharmaceutically acceptable salt thereof to the hydrophilic polymer is from about 10:1 to about 1:10. In some embodiments, the PROTAC is ARV-110. In some embodiments, the PROTAC is ARV-471.

In some embodiments, an ASD is formulated in a unit dosage form, such as a capsule or a tablet. In some embodiments, the hydrophilic polymer is present in the ASD in an amount of about 10 mg to about 6,000 mg. In some embodiments, the hydrophilic polymer is present in the ASD in an amount of about 10 mg to about 500 mg. In some embodiments, the hydrophilic polymer is present in the ASD in an amount of about 20 mg to about 300 mg. In some embodiments, the hydrophilic polymer is present in the ASD in an amount of about 25 mg to about 100 mg. In some embodiments, the hydrophilic polymer is present in the ASD in an amount of about 30 mg to about 80 mg. In some embodiments, the hydrophilic polymer is present in the amorphous solid dispersion in an amount of about 10 mg to about 50 mg, about 10 mg to about 100 mg, about 10 mg to about 150 mg, about 10 mg to about 200 mg, about 10 mg to about 300 mg, about 10 mg to about 500 mg, about 10 mg to about 800 mg, about 10 mg to about 1,000 mg, about 10 mg to about 2,000 mg, about 10 mg to about 4,000 mg, about 10 mg to about 6,000 mg, about 50 mg to about 100 mg, about 50 mg to about 150 mg, about 50 mg to about 200 mg, about 50 mg to about 300 mg, about 50 mg to about 500 mg, about 50 mg to about 800 mg, about 50 mg to about 1,000 mg, about 50 mg to about 2,000 mg, about 50 mg to about 4,000 mg, about 50 mg to about 600 mg, about 100 mg to about 150 mg, about 100 mg to about 200 mg, about 100 mg to about 300 mg, about 100 mg to about 500 mg, about 100 mg to about 800 mg, about 100 mg to about 1,000 mg, about 100 mg to about 2,000 mg, about 100 mg to about 4,000 mg, about 100 mg to about 6,000 mg, about 150 mg to about 200 mg, about 150 mg to about 300 mg, about 150 mg to about 500 mg, about 150 mg to about 800 mg, about 150 mg to about 1,000 mg, about 150 mg to about 2,000 mg, about 150 mg to about 4,000 mg, about 150 mg to about 6,000 mg, about 200 mg to about 300 mg, about 200 mg to about 500 mg, about 200 mg to about 800 mg, about 200 mg to about 1,000 mg, about 200 mg to about 2,000 mg, about 200 mg to about 4,000 mg, about 200 mg to about 6,000 mg, about 300 mg to about 500 mg, about 300 mg to about 800 mg, about 300 mg to about 1,000 mg, about 300 mg to about 2,000 mg, about 300 mg to about 4,000 mg, about 300 mg to about 6,000 mg, about 500 mg to about 800 mg, about 500 mg to about 1,000 mg, about 500 mg to about 2,000 mg, about 500 mg to about 4,000 mg, about 500 mg to about 6,000 mg, about 800 mg to about 1,000 mg, about 800 mg to about 2,000 mg, about 800 mg to about 4,000 mg, about 800 mg to about 6,000 mg, about 1,000 mg to about 200 mg, about 1,000 mg to about 4,000 mg, about 1,000 mg to about 6,000 mg, about 200 mg to about 4,000 mg, about 2,000 mg to about 6,000 mg, or about 4,000 mg to about 6.000 mg. In some embodiments, the hydrophilic polymer is present in the amorphous solid dispersion in an amount of about 10 mg, about 50 mg, about 100 mg, about 150 mg, about 200 mg, about 300 mg, about 500 mg, about 800 mg, about 1,000 mg, about 2,000 mg, about 4,000 mg, or about 6,000 mg. In some embodiments, the hydrophilic polymer is present in the amorphous solid dispersion in an amount of at least about 10 mg, about 50 mg, about 100 mg, about 150 mg, about 200 mg, about 300 mg, about 500 mg, about 800 mg, about 1,000 mg, about 2,000 mg, or about 4,000 mg. In some embodiments, the hydrophilic polymer is present in the amorphous solid dispersion in an amount of at most about 50 mg, about 100 mg, about 150 mg, about 200 mg, about 300 mg, about 500 mg, about 800 mg, about 1,000 mg, about 2,000 mg, about 4,000 mg, or about 6,000 mg. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone K30. In some embodiments, the hydrophilic polymer is polyvinylpyrrolidone (such as VA64). In some embodiments, the hydrophilic polymer comprises hydropropylmethylcellulose acetate succinate (HPMCAS). In some embodiments, the hydrophilic polymer comprises HPMCP. In some embodiments, the hydrophilic polymer comprises polymethacrylates (e.g., Eudragit). In some embodiments, the hydrophilic polymer comprises polyvinyl caprolactam-polyvinyl acetate-polyethylene glycol. In some embodiments, the hydrophilic polymer is polyvinylpyrrolidone HPMC. In some embodiments, the hydrophilic polymer is polyvinylpyrrolidone HPMC E5. In some embodiments, the hydrophilic polymer is polyvinylpyrrolidone HPMC E50.

In some embodiments, a pharmaceutical composition is provided that comprises from about 1 mg to about 500 mg of the hydrophilic polymer. In some embodiments, a pharmaceutical composition is provided that comprises from about 10 mg to about 400 mg of the hydrophilic polymer. In some embodiments, a pharmaceutical composition is provided that comprises from about 25 mg to about 200 mg of the hydrophilic polymer. In some embodiments, a pharmaceutical composition is provided that comprises from about 50 mg to about 150 mg of the hydrophilic polymer. In some embodiments, a pharmaceutical composition is provided that comprises from about 75 mg to about 125 mg of the hydrophilic polymer. In some embodiments, a pharmaceutical composition is provided that comprises from about 75 mg to about 100 mg of the hydrophilic polymer. In some embodiments, a pharmaceutical composition is provided that comprises from about 100 mg to about 125 mg of the hydrophilic polymer. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone such as VA64. In some embodiments, the hydrophilic polymer comprises hydropylmethylcellulose acetate succinate (HPMCAS). In some embodiments, the hydrophilic polymer comprises HPMCP. In some embodiments, the hydrophilic polymer comprises polymethacrylates (e.g., Eudragit). In some embodiments, the hydrophilic polymer comprises polyvinyl caprolactam-polyvinyl acetate-polyethylene glycol. In some embodiments, the ASD comprises two or more hydrophilic polymers. In some embodiments, the two or more hydrophilic polymers are selected from copovidone, HPMCAS, and HPMC.

In some embodiments, a pharmaceutical composition is provided that comprises from about 50 mg to about 150 mg of the hydrophilic polymer. In some embodiments, a pharmaceutical composition is provided that comprises from about 55 mg to about 150 mg of the hydrophilic polymer. In some embodiments, a pharmaceutical composition is provided that comprises from about 60 mg to about 150 mg of the hydrophilic polymer. In some embodiments, a pharmaceutical composition is provided that comprises from about 65 mg to about 150 mg of the hydrophilic polymer. In some embodiments, a pharmaceutical composition is provided that comprises from about 70 mg to about 150 mg of the hydrophilic polymer. In some embodiments, a pharmaceutical composition is provided that comprises from about 75 mg to about 150 mg of the hydrophilic polymer. In some embodiments, a pharmaceutical composition is provided that comprises from about 80 mg to about 150 mg of the hydrophilic polymer. In some embodiments, a pharmaceutical composition is provided that comprises from about 85 mg to about 150 mg of the hydrophilic polymer. In some embodiments, a pharmaceutical composition is provided that comprises from about 90 mg to about 150 mg of the hydrophilic polymer. In some embodiments, a pharmaceutical composition is provided that comprises from about 95 mg to about 150 mg of the hydrophilic polymer. In some embodiments, a pharmaceutical composition is provided that comprises from about 100 mg to about 150 mg of the hydrophilic polymer. In some embodiments, a pharmaceutical composition is provided that comprises from about 105 mg to about 150 mg of the hydrophilic polymer. In some embodiments, a pharmaceutical composition is provided that comprises from about 110 mg to about 150 mg of the hydrophilic polymer. In some embodiments, a pharmaceutical composition is provided that comprises from about 115 mg to about 150 mg of the hydrophilic polymer. In some embodiments, a pharmaceutical composition is provided that comprises from about 120 mg to about 150 mg of the hydrophilic polymer. In some embodiments, a pharmaceutical composition is provided that comprises from about 125 mg to about 150 mg of the hydrophilic polymer. In some embodiments, a pharmaceutical composition is provided that comprises from about 130 mg to about 150 mg of the hydrophilic polymer. In some embodiments, a pharmaceutical composition is provided that comprises from about 135 mg to about 150 mg of the hydrophilic polymer. In some embodiments, a pharmaceutical composition is provided that comprises from about 140 mg to about 150 mg of the hydrophilic polymer. In some embodiments, a pharmaceutical composition is provided that comprises from about 145 mg to about 150 mg of the hydrophilic polymer. In some embodiments, the hydrophilic polymer is poly vinylpyrrolidone (PVP) or hydroxypropyl methylcellulose HMPC. In some embodiments, the hydrophilic polymer is poly vinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone VA64. In some embodiments, the hydrophilic polymer comprises hydropropylmethylcellulose acetate succinate (HPMCAS). In some embodiments, the hydrophilic polymer comprises HPMCP. In some embodiments, the hydrophilic polymer comprises polymethacrylates. In some embodiments, polymethacrylates comprise Eudragit. In some embodiments, the hydrophilic polymer comprises polyvinyl caprolactam-polyvinyl acetate-polyethylene glycol. In some embodiments, the ASD comprises two or more hydrophilic polymers. In some embodiments, the two or more hydrophilic polymers are selected from copovidone, HPMCAS, and HPMC.

In some embodiments, the hydrophilic polymer comprises about 5% of the total weight of the composition. In some embodiments, the hydrophilic polymer comprises about 10% of the total weight of the composition. In some embodiments, the hydrophilic polymer comprises about 15% of the total weight of the composition. In some embodiments, the hydrophilic polymer comprises about 20% of the total weight of the composition. In some embodiments, the hydrophilic polymer comprises about 25% of the total weight of the composition. In some embodiments, the hydrophilic polymer comprises about 30% of the total weight of the composition. In some embodiments, the hydrophilic polymer comprises about 40% of the total weight of the composition. In some embodiments, the hydrophilic polymer comprises about 50% of the total weight of the composition. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone VA64. In some embodiments, the hydrophilic polymer comprises hydropropylmethylcellulose acetate succinate (HPMCAS). In some embodiments, the hydrophilic polymer comprises HPMCP. In some embodiments, the hydrophilic polymer comprises polymethacrylates. In some embodiments, polymethacrylates comprise Eudragit. In some embodiments, the hydrophilic polymer comprises polyvinyl caprolactam-polyvinyl acetate-polyethylene glycol. In some embodiments, the ASD comprises two or more hydrophilic polymers. In some embodiments, the two or more hydrophilic polymers are selected from copovidone, HPMCAS, and HPMC.

In some embodiments, a pharmaceutical composition is provided that comprises from about 0.1% to about 99% by weight of a hydrophilic polymer. In some embodiments, a pharmaceutical composition is provided that comprises from about 0.1% to about 80% by weight of the hydrophilic polymer. In some embodiments, a pharmaceutical composition is provided that comprises from about 0.1% to about 60% by weight of the hydrophilic polymer. In some embodiments, a pharmaceutical composition is provided that comprises from about 0.1% to about 40% by weight of the hydrophilic polymer. In some embodiments, a pharmaceutical composition is provided that comprises from about 0.1% to about 20% by weight of the hydrophilic polymer. In some embodiments, a pharmaceutical composition is provided that comprises from about 0.1% to about 10% by weight of the hydrophilic polymer. In some embodiments, a pharmaceutical composition is provided that comprises from about 0.1% to about 1% by weight of the hydrophilic polymer. In some embodiments, a pharmaceutical composition is provided that comprises from about 20% to about 99% by weight of the hydrophilic polymer. In some embodiments, a pharmaceutical composition is provided that comprises from about 20% to about 80% by weight of the hydrophilic polymer. In some embodiments, a pharmaceutical composition is provided that comprises from about 20% to about 60% by weight of the hydrophilic polymer. In some embodiments, a pharmaceutical composition is provided that comprises from about 20% to about 40% by weight of the hydrophilic polymer. In some embodiments, a pharmaceutical composition is provided that comprises from about 30% to about 99% by weight of the hydrophilic polymer. In some embodiments, a pharmaceutical composition is provided that comprises from about 30% to about 80% by weight of the hydrophilic polymer. In some embodiments, a pharmaceutical composition is provided that comprises from about 30% to about 60% by weight of the hydrophilic polymer. In some embodiments, a pharmaceutical composition is provided that comprises from about 30% to about 40% by weight of the hydrophilic polymer. In some embodiments, a pharmaceutical composition is provided that comprises from about 40% to about 99% by weight of the hydrophilic polymer. In some embodiments, a pharmaceutical composition is provided that comprises from about 40% to about 80% by weight of the hydrophilic polymer. In some embodiments, a pharmaceutical composition is provided that comprises from about 40% to about 60% by weight of the hydrophilic polymer. In some embodiments, the hydrophilic polymer is polyvinylpyrrolidone. In some embodiments, the composition is a herein described amorphous solid dispersion. In some embodiments, the composition is a herein described pharmaceutical composition.

In some embodiments, a pharmaceutical composition comprises an amorphous solid dispersion. In some embodiments, the amorphous solid dispersion comprises a hydrophilic polymer in a weight percent of about 1% to about 90%. In some embodiments, the amorphous solid dispersion comprises a hydrophilic polymer in a weight percent of about 1% to about 80%. In some embodiments, the amorphous solid dispersion comprises a hydrophilic polymer in a weight percent of about 10% to about 60%. In some embodiments, the amorphous solid dispersion comprises a hydrophilic polymer in a weight percent of about 20% to about 50%. In some embodiments, the amorphous solid dispersion comprises a hydrophilic polymer in a weight percent of about 20% to about 40%. In some embodiments, the amorphous solid dispersion comprises a hydrophilic polymer in a weight percent of about 1%, about 10%, about 20%, about 30%, about 35%, about 40%, about 45%, about 50%, about 55%, about 60%, about 80%, or about 90%. In some embodiments, the amorphous solid dispersion comprises a hydrophilic polymer in a weight percent of at least about 1%, about 10%, about 20%, about 30%, about 35%, about 40%, about 45%, about 50%, about 55%, about 60%, or about 80%. In some embodiments, the amorphous solid dispersion comprises a hydrophilic polymer in a weight percent of at most about 10%, about 20%, about 30%, about 35%, about 40%, about 45%, about 50%, about 55%, about 60%, about 80%, or about 90%. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone such as VA64. In some embodiments, the hydrophilic polymer comprises hydropropylmethylcellulose acetate succinate (HPMCAS). In some embodiments, the hydrophilic polymer comprises HPMCP. In some embodiments, the hydrophilic polymer comprises polymethacrylates. In some embodiments, polymethacrylates comprise Eudragit. In some embodiments, the hydrophilic polymer comprises polyvinyl caprolactam-polyvinyl acetate-polyethylene glycol. In some embodiments, the ASD comprises two or more hydrophilic polymers. In some embodiments, the two or more hydrophilic polymers are selected from copovidone, HPMCAS, and HPMC.

Acids

In some embodiments, an amorphous solid dispersion additionally comprises an inorganic acid or organic acid. The inorganic acid or organic acid can be present in the ASD in an amorphous state. In some embodiments, the organic acid is selected from the group consisting of tartaric acid, fumaric acid, succinic acid, citric acid, lactic acid, malic acid, methanesulfonic acid, ethanesulfonic acid, isethionic acid, benzenesulfonic acid, and p-toluenesulfonic acid. In some embodiments, the inorganic acid is selected from the group consisting of hydrochloric acid, sulfuric acid, and phosphoric acid. In some embodiments, the PROTAC is a PROTAC of Table 1 or a pharmaceutically acceptable salt thereof.

In one aspect, described herein is an amorphous solid dispersion comprising an API and one or more acids. Also described herein is a pharmaceutical composition comprising an API and one or more acids. In some embodiments, the amorphous solid dispersion comprises an API, one or more acids, and a hydrophilic high-molecular weight material. In some embodiments, the API is at least partially protonated. In some embodiments, the API is a PROTAC (e.g., PROTAC of Table 1 or a pharmaceutically acceptable salt thereof).

In some embodiments, an amorphous solid dispersion and/or a pharmaceutical composition disclosed herein comprises one or more organic acids. In some embodiments, the one or more organic acids comprise one or more of acetic acid, acrylic acid, adipic acid, alginic acid, amino acids, ascorbic acid, benzoic acid, benzenesulfonic acid, butyric acid, carbonic acid, citric acid, formic acid, fumaric acid, gluconic acid, isoascorbic acid, lactic acid, maleic acid, malic acid, methanesulfonic acid, fluorinated acids, trifluoromethanesulfonic acid, trifluoroacetic acid, oxalic acid, propionic acid, salicylic acid, stearic acid, succinic acid, tannic acid, tartaric acid, thioglycolic acid, aliphatic sulfonic acids (e.g., methanesulfonic acid, methanedisulfonic acid, triflic acid, ethanesulfonic acid, ethanedisulfonic acid, isethionic acid, 2-mercapto-1-ethanesulfonic acid, propanesulfonic acid, butanesulfonic acid), aromatic sulfonic acids (e.g., benzenesulfonic acid, tolylsulfonic acid, or naphthalenesulfonic acid) and uric acid. In some embodiments, the one or more organic acids comprise methanesulfonic acid, tartaric acid, or both. In some embodiments, the one or more organic acids comprise methanesulfonic acid and tartaric acid. In some embodiments, the one or more organic acids excludes acetic acid.

In some embodiments, the organic acid or inorganic acid is present in the ASD by weight of about 1% to about 60%. In some embodiments, the organic acid or inorganic acid is present in the ASD by weight of about 5% to about 50%. In some embodiments, the organic acid or inorganic acid is present in the ASD by weight of about 10% to about 40%. In some embodiments, the organic acid or inorganic acid is present in the ASD by weight of about 15% to about 30%. In some embodiments, the organic acid or inorganic acid is present in the ASD by weight of about 15% to about 25%. In some embodiments, the organic acid or inorganic acid is present in the ASD by weight of about 20% to about 30%. In some embodiments, the organic acid or inorganic acid is present in the ASD by weight of about 1% to about 5%, about 1% to about 10%, about 1% to about 15%, about 1% to about 20%, about 1% to about 25%, about 1% to about 30%, about 1% to about 35%, about 1% to about 40%, about 1% to about 50%, about 1% to about 60%, about 5% to about 10%, about 5% to about 15%, about 5% to about 20%, about 5% to about 25%, about 5% to about 30%, about 5% to about 35%, about 5% to about 40%, about 5% to about 50%, about 5% to about 60%, about 10% to about 15%, about 10% to about 20%, about 10% to about 25%, about 10% to about 30%, about 10% to about 35%, about 10% to about 40%, about 10% to about 50%, about 10% to about 60%, about 15% to about 20%, about 15% to about 25%, about 15% to about 30%, about 15% to about 35%, about 15% to about 40%, about 15% to about 50%, about 15% to about 60%, about 20% to about 25%, about 20% to about 30%, about 20% to about 35%, about 20% to about 40%, about 20% to about 50%, about 20% to about 60%, about 25% to about 30%, about 25% to about 35%, about 25% to about 40%, about 25% to about 50%, about 25% to about 60%, about 30% to about 35%, about 30% to about 40%, about 30% to about 50%, about 30% to about 60%, about 35% to about 40%, about 35% to about 50%, about 35% to about 60%, about 40% to about 50%, about 40% to about 60%, or about 50% to about 60%. In some embodiments, the organic acid or inorganic acid is present in the ASD by weight of about 1%, about 5%, about 10%, about 15%, about 20%, about 25%, about 30%, about 35%, about 40%, about 50%, or about 60%. In some embodiments, the organic acid or inorganic acid is present in the ASD by weight of at least about 1%, about 5%, about 10%, about 15%, about 20%, about 25%, about 30%, about 35%, about 40%, or about 50%. In some embodiments, the organic acid or inorganic acid is present in the ASD by weight of at most about 5%, about 10%, about 15%, about 20%, about 25%, about 30%, about 35%, about 40%, about 50%, or about 60%. In some embodiments, the organic acid or inorganic acid is present in the pharmaceutical compositions and is not present in the ASD. In some embodiments, the organic acid is malic acid. In some embodiments, the organic acid is citric acid. In some embodiments, the organic acid is tartaric acid. In some embodiments, the organic acid is succinic acid.

In some embodiments, the one or more organic acids are present in the amorphous solid dispersion and/or in the pharmaceutical composition in an amount of from about 0.1% to about 99% by weight of the total composition. In some embodiments, the one or more organic acids are present in the amorphous solid dispersion and/or in the pharmaceutical composition in an amount of from about 1% to about 80%, from about 1% to about 60%, from about 1% to about 50%, from about 1% to about 25%, from about 1% to about 10%, from about 1% to about 5%, from about 10% to about 80%, from about 10% to about 60%, from about 10% to about 50%, from about 20% to about 80%, from about 20% to about 60%, from about 20% to about 50%, from about 30% to about 80%, from about 30% to about 60%, from about 30% to about 50%, or from about 30% to about 40% by weight of the total composition. In some embodiments, the one or more organic acids are present in the amorphous solid dispersion and/or in the pharmaceutical composition in an amount of about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, or about 45% by weight of the total composition. In some embodiments, the one or more organic acids comprise tartaric acid. In some embodiments, the one or more organic acids comprise methanesulfonic acid. In some embodiments, the one or more organic acids are present in the amorphous solid dispersion and/or in the pharmaceutical composition in an amount of about 1.0 mg to about 1000 mg, including but not limited to about 5.0 mg, 10.0 mg, 15.0 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, or 350 mg. In some embodiments, the one or more organic acids are present in the amorphous solid dispersion and/or in the pharmaceutical composition in an amount of 1 mg to 500 mg. In some embodiments, the one or more organic acids are present in an amount of from about from about 10 mg to about 400 mg, 20 mg to about 300 mg, from about 25 mg to about 200 mg, from about 50 mg to about 150 mg, from about 75 mg to about 125 mg, from about 75 mg to about 100 mg, from about 100 mg to about 125 mg, from about 1 mg to about 200 mg, or from about 50 mg to about 200 mg. In some embodiments, the one or more organic acids are present in an amount of 25 mg to 250 mg. In some embodiments, the one or more organic acids are present in an amount of 150 mg to 250 mg. In some embodiments, the one or more organic acids are present in an amount of 150 mg to 200 mg. In some embodiments, the one or more organic acids are present in an amount of 50 mg to 200 mg. In some embodiments, the amorphous solid dispersion and/or in the pharmaceutical composition is formulated in a unit dosage form, such as a capsule or a tablet. In some embodiments, the organic acid is present in the pharmaceutical composition in an amount of 1 mg to 500 mg. In some embodiments, the organic acid is present in the pharmaceutical composition in an amount of 10 mg to 300 mg. In some embodiments, the organic acid is present in the pharmaceutical composition in an amount of 30 mg to 100 mg. In some embodiments, the organic acid is present in the pharmaceutical composition in an amount of 30 mg to 80 mg.

In some embodiments, the one or more organic acids are present in a molar ratio to the API of greater than 0.5:1, greater than 1:1, greater than 1.5:1, greater than 2:1, greater than 2.5:1, or greater than 3:1. In some embodiments, the one or more organic acids are present in a molar ratio to the APT of about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1. In some embodiments, the one or more organic acids comprise tartaric acid and methanesulfonic acid.

In some embodiments, an amorphous solid dispersion described herein comprises an API, one or more acids, and a hydrophilic high-molecular weight material. In some embodiments, one or more acids comprises a first acid and a second acid. In some embodiments, the molar ratio of the first acid to API is about 0.1:1 to about 10:1, about 0.5:1 to about 5:1, about 0.5:1 to about 3:1, about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1. In some embodiments, the molar ratio of the second acid to API is present in a molar ratio to the API of about 0.1:1 to about 10:1, about 1:1 to about 8:1, about 2:1 to about 7:1, about 4:1 to about 7:1, about 0.5:1 to about 3:1, about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1. In some embodiments, the mass ratio of the second acid to API is present in a molar ratio to the API of about 0.1:1 to about 10:1, about 0.2:1 to about 5:1, about 0.5:1 to about 3:1, about 0.2:1 to about 1.2:1, about 0.4:1 to about 1:1, about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1. In some embodiments, the molar ratio of the first acid to API is about 0.1:1 to 1.5:1. In some embodiments, the first acid is an inorganic acid. In some embodiments, the first acid is an organic acid.

In some embodiments, the mass ratio of the second acid to API is about 0.05:1 to about 20:1, about 0.5:1 to about 10:1, about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1. In some embodiments, the mass ratio of the second acid to API is about 0.5:1 to about 10:1. In some embodiments, the first acid is an inorganic acid. In some embodiments, the first acid is an organic acid.

In some embodiments, an amorphous solid dispersion and/or a pharmaceutical composition disclosed herein comprises one or more inorganic acids. In some embodiments, the one or more inorganic acids comprise one or more of hydrochloric acid, hydrobromic acid, hydriodic acid, sulfuric acid, nitric acid, boric acid, and phosphoric acid. In some embodiments, the one or more inorganic acids comprise hydrochloric acid. In some embodiments, the inorganic acid is completely ionized. In some embodiments, the inorganic acid is partially ionized. In some embodiments, partial ionization refers to an equilibrium in which 1% or more of the inorganic acid is ionized.

In some embodiments, the one or more inorganic acids are present in the amorphous solid dispersion and/or in the pharmaceutical composition in an amount of from about 0.1% to about 99% by weight of the total composition. In some embodiments, the one or more inorganic acids are present in the amorphous solid dispersion and/or in the pharmaceutical composition in an amount of from about 0.1% to about 80%, 1% to about 80%, from about 1% to about 60%, from about 1% to about 50%, from about 10% to about 80%, from about 10% to about 60%, from about 10% to about 50%, from about 20% to about 80%, from about 20% to about 60%, from about 20% to about 50%, from about 30% to about 80%, from about 30% to about 60%, from about 30% to about 50%, or from about 30% to about 40% by weight of the total composition. In some embodiments, the one or more inorganic acids are present in the amorphous solid dispersion and/or in the pharmaceutical composition in an amount of about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, or about 45% by weight of the total composition. In some embodiments, the one or more inorganic acids comprise hydrochloric acid. In some embodiments, the one or more inorganic acids are present in the amorphous solid dispersion and/or in the pharmaceutical composition in an amount of about 1.0 mg to about 1000 mg, including but not limited to about 1.0 mg, 2.0 mg, 3.0 mg, 4.0 mg, 5.0 mg, 10.0 mg, 15.0 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, or 350 mg. In some embodiments, the one or more inorganic acids are present in an amount of from about 0.1 mg to about 100 mg, from about 1 mg to about 50 mg, from about 2 mg to about 20 mg, from about 5 mg to about 15 mg, from about 7 mg to about 25 mg, from about 7 mg to about 20 mg, or from about 10 mg to about 18 mg. In some embodiments, the amorphous solid dispersion and/or in the pharmaceutical composition is formulated in a unit dosage form, such as a capsule or a tablet. In some embodiments, the inorganic acid is present in the pharmaceutical composition in an amount of 1 mg to 500 mg. In some embodiments, the inorganic acid is present in the pharmaceutical composition in an amount of 10 mg to 300 mg. In some embodiments, the inorganic acid is present in the pharmaceutical composition in an amount of 30 mg to 100 mg. In some embodiments, the inorganic acid is present in the pharmaceutical composition in an amount of 30 mg to 80 mg.

In some embodiments, an amorphous solid dispersion disclosed herein comprises a first acid and a second acid. In some embodiments, a molar ratio of the second acid to the first acid is from about 0.05:1 to about 20:1. In some embodiments, the molar ratio of the second acid to the first acid is from about 0.5:1 to about 10:1. In some embodiments, the molar ratio of the second acid to the first acid is from about 1:1 to about 4:1. In some embodiments, the molar ratio of the second acid to the first acid is about 2:1. In some embodiments, a molar ratio of the API to the first acid is about 0.1:1 to about 10:1. In some embodiments, a molar ratio of the API to the first acid is from about 0.2:1 to about 5:1 or from about 0.5:1 to about 2:1. In some embodiments, a molar ratio of the API to the first acid is about 1:1. In some embodiments, a molar ratio of the API to the second acid is about 0.05:1 to about 20:1. In some embodiments, a molar ratio of the API to the second acid is from about 0.1:1 to about 5:1 or from about 0.2:1 to about 1:1. In some embodiments, a molar ratio of the API to the second acid is about 0.5:1.

Adsorbents

In one aspect, the pharmaceutical compositions disclosed herein comprise an ASD comprising a PROTAC, a hydrophilic polymer, a surfactant and, optionally, an adsorbent. The adsorbent can be present in the ASD in an amorphous state. In some embodiments, the adsorbent is present in the ASD in an amorphous state. In some embodiments, the adsorbent is not present in the ASD in an amorphous state, and the amorphous composition is adsorbed onto the adsorbent. In some embodiments, the PROTAC is a PROTAC of Table 1 or a pharmaceutically acceptable salt thereof. In some embodiments, the ASD optionally comprises an adsorbent. In some embodiments, the ASD optionally comprises one or more adsorbents.

Many adsorbents are solid, porous or super porous adsorption materials. They comprise numerous micro- or nano-pores within their structures, resulting in very large surface areas, for example, greater than 500 m$^2$/g. Exemplary adsorbents include, without limitation, silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextnn. In some embodiments, the adsorbent is silicon dioxide.

In some embodiments, an adsorbent, such as silicon dioxide, is present in the ASD by weight of about 1% to about 70%. In some embodiments, the adsorbent is present in the ASD by weight of about 1% to about 5%, about 1% to about 10%, about 1% to about 20%, about 1% to about 30%, about 1% to about 40%, about 1% to about 50%, about 1% to about 60%, about 1% to about 70%, about 5% to about 10%, about 5% to about 20%, about 5% to about 30%, about 5% to about 40%, about 5% to about 50%, about 5% to about 60%, about 5% to about 70%, about 10% to about 20%, about 10% to about 30%, about 10% to about 40%, about 10% to about 50%, about 10% to about 60%, about 10% to about 70%, about 20% to about 30%, about 20% to about 40%, about 20% to about 50%, about 20% to about 60%, about 20% to about 70%, about 30% to about 40%, about 30% to about 50%, about 30% to about 60%, about 30% to about 70%, about 40% to about 50%, about 40% to about 60%, about 40% to about 70%, about 50% to about 60%, about 50% to about 70%, or about 60% to about 70%. In some embodiments, the adsorbent is present in the ASD by weight of about 5% to about 40%. In some embodiments, the adsorbent is present in the ASD by weight of about 10% to about 35%. In some embodiments, the adsorbent is present in the ASD by weight of about 15% to about 30%. In some embodiments, the adsorbent is present in the ASD by weight of about 1%, about 5%, about 10%, about 20%, about 30%, about 40%, about 50%, about 60%, or about 70%. In some embodiments, the adsorbent is present in the ASD by weight of at least about 1%, about 5%, about 10%, about 20%, about 30%, about 40%, about 50%, or about 60%. In some embodiments, the adsorbent is present in the ASD by weight of at most about 5%, about 10%, about 20%, about 30%, about 40%, about 50%, about 60%, or about 70%. In some embodiments, the adsorbent is SiO$_2$.

In some embodiments, the adsorbent is present in the ASD in an amount of about 1 mg to about 5,000 mg. In some embodiments, the adsorbent is present in the ASD in an amount of about 1 mg to about 5 mg, about 1 mg to about 10 mg, about 1 mg to about 20 mg, about 1 mg to about 30 mg, about 1 mg to about 50 mg, about 1 mg to about 100 mg, about 1 mg to about 200 mg, about 1 mg to about 500 mg, about 1 mg to about 1,000 mg, about 1 mg to about 3,000 mg, about 1 mg to about 5,000 mg, about 5 mg to about 10 mg, about 5 mg to about 20 mg, about 5 mg to about 30 mg, about 5 mg to about 50 mg, about 5 mg to about 100 mg, about 5 mg to about 200 mg, about 5 mg to about 500 mg, about 5 mg to about 1,000 mg, about 5 mg to about 3,000 mg, about 5 mg to about 5,000 mg, about 10 mg to about 20 mg, about 10 mg to about 30 mg, about 10 mg to about 50 mg, about 10 mg to about 100 mg, about 10 mg to about 200 mg, about 10 mg to about 500 mg, about 10 mg to about 1,000 mg, about 10 mg to about 3,000 mg, about 10 mg to about 5,000 mg, about 20 mg to about 30 mg, about 20 mg to about 50 mg, about 20 mg to about 100 mg, about 20 mg to about 200 mg, about 20 mg to about 500 mg, about 20 mg to about 1,000 mg, about 20 mg to about 3,000 mg, about 20 mg to about 5,000 mg, about 30 mg to about 50 mg, about 30 mg to about 100 mg, about 30 mg to about 200 mg, about 30 mg to about 500 mg, about 30 mg to about 1,000 mg, about 30 mg to about 3,000 mg, about 30 mg to about 5,000 mg, about 50 mg to about 100 mg, about 50 mg to about 200 mg, about 50 mg to about 500 mg, about 50 mg to about 1,000 mg, about 50 mg to about 3,000 mg, about 50 mg to about 5,000 mg, about 100 mg to about 200 mg, about 100 mg to about 500 mg, about 100 mg to about 1,000 mg, about 100 mg to about 3,000 mg, about 100 mg to about 5,000 mg, about 200 mg to about 500 mg, about 200 mg to about 1.000 mg, about 200 mg to about 3,000 mg, about 200 mg to about 5,000 mg, about 500 mg to about 1,000 mg, about 500 mg to about 3,000 mg, about 500 mg to about 5,000 mg, about 1,000 mg to about 3,000 mg, about 1,000 mg to about 5,000 mg, or about 3,000 mg to about 5,000 mg. In some embodiments, the adsorbent is present in the ASD in an amount of about 1 mg, about 5 mg, about 10 mg, about 20 mg, about 30 mg, about 50 mg, about 100 mg, about 200 mg, about 500 mg, about 1,000 mg, about 3,000 mg, or about 5,000 mg. In some embodiments, the adsorbent is present in the ASD in an amount of at least about 1 mg, about 5 mg, about 10 mg, about 20 mg, about 30 mg, about 50 mg, about 100 mg, about 200 mg, about 500 mg, about 1,000 mg, or about 3,000 mg. In some embodiments, the adsorbent is present in the ASD in an amount of at most about 5 mg, about 10 mg, about 20 mg, about 30 mg, about 50 mg, about 100 mg, about 200 mg, about 500 mg, about 1,000 mg, about 3,000 mg, or about 5,000 mg. In some embodiments, the ASD is formulated in a unit dosage form, such as a capsule or a tablet. In some embodiments, the adsorbent is present in the pharmaceutical composition in an amount of 1 mg to 500 mg. In some embodiments, the adsorbent is present in the pharmaceutical composition in an amount of 10 mg to 300 mg. In some embodiments, the adsorbent is present in the pharmaceutical composition in an amount of 30 mg to 100 mg. In some embodiments, the adsorbent is present in the pharmaceutical composition in an amount of 30 mg to 80 mg.

In some embodiments, an adsorbent is present in the ASD. In some embodiments, an adsorbent powder described herein has an D50 value of 1-1000 nm. In some embodiments, the D50 value of the adsorbent is from about 0.01 to 1000 nm. In some embodiments, the D50 value of the adsorbent is from about 0.01 nm to about 1,000 nm. In some embodiments, the D50 value of the adsorbent is from at least about 0.01 nm. In some embodiments, the D50 value of the adsorbent is from at most about 1,000 nm. In some embodiments, the D50 value of the adsorbent is from about 1 nm to about 500 nm. In some embodiments, the D50 value of the adsorbent is from at least about 1 nm. In some embodiments, the D50 value of the adsorbent is from at most about 500 nm. In some embodiments, the D50 value of the adsorbent is from about 1 nm to about 300 nm, about 1 nm to about 700 nm, about 1 nm to about 100 nm, about 1 nm to about 130 nm, about 1 nm to about 170 nm, about 1 nm to about 200 nm, about 1 nm to about 230 nm, about 1 nm to about 270 nm, about 1 nm to about 30 nm, about 1 nm to about 400 nm, about 1 nm to about 500 nm, about 10 nm to about 130 nm, about 10 nm to about 170 nm, about 100 nm to about 200 nm, about 100 nm to about 230 nm, about 100 nm to about 270 nm, about 100 nm to about 300 nm, about 100 nm to about 400 nm, about 100 nm to about 500 nm, about 200 nm to about 270 nm, about 200 nm to about 300 nm, about 200 nm to about 400 nm, about 200 nm to about 5000 nm, about 300 nm to about 400 nm, about 300 nm to about 500 nm, or about 400 nm to about 500 nm. In some embodiments, the D50 value of the adsorbent is from about 1 nm to about 100 nm. In some embodiments, the D50 value of the adsorbent is from at least about 1 nm. In some embodiments, the D50 value of the adsorbent is about 0.1, 1, 30, 50, 70, 100, 130, 170, 200, 230, 250, 270, 300, 330, 350, 370, 400, 430, 450, 470, 500, 600, 700, 800, 900, or 1000 nm or less. In some embodiments, the adsorbent is silicon dioxide powder with an average diameter of 1-1000 nm. In some embodiments, the D50 value of the silicon dioxide is from about 0.01 to 1000 nm. In some embodiments, the D50 value of the silicon dioxide is from about 0.01 nm to about 1,000 nm. In some embodiments, the D50 value of the silicon dioxide is from about 1 nm to about 100 nm. In some embodiments, the D50 value of the silicon dioxide is from at least about 1 nm. In some embodiments, the D50 value of the silicon dioxide is about 0.1, 1, 30, 50, 70, 100, 130, 170, 200, 230, 250, 270, 300, 330, 350, 370, 400, 430, 450, 470, 500, 600, 700, 800, 900, or 1000 nm or less.

In some embodiments, the ASD comprises an adsorbent, wherein the adsorbent is silicon dioxide. In some embodiments, the silicon dioxide is present in the amorphous solid dispersion. In some embodiments, the amorphous solid dispersion is granulated and incorporated into a pharmaceutical composition with extra granular additives. In some embodiments, the silicon dioxide is present outside of the amorphous solid dispersion as an extra-granular additive. In some embodiments, silicon dioxide is present in the amorphous solid dispersion as well as being an extra-granular additive.

Prozac Pharmaceutical Compositions

Disclosed herein are pharmaceutical compositions comprising an API. In some embodiments, the API is present in the pharmaceutical composition in an amount of at least 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, or 200 mg. In some embodiments, the API is present in the pharmaceutical composition in an amount of about 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, or 200 mg. In some embodiments, the API is present in the pharmaceutical composition in an amount of no more than 1000 mg, 750 mg, 500 mg, 400 mg, 300 mg, 250 mg, 225 mg, 200 mg, 175 mg, 150 mg, 125 mg, 100 mg, 90 mg, 80 mg, 75 mg, 60 mg, 55 mg, or 50 mg. In some embodiments the API is ARV-110 or a pharmaceutically acceptable salt thereof. In some embodiments the API is ARV-471 or a pharmaceutically acceptable salt thereof. In some embodiments, the API is a PROTAC. In some embodiments the API is ARV-110. In some embodiments the API is ARV-471. In some embodiments, the PROTAC is one listed in Table 1, or a pharmaceutically acceptable salt thereof. In some embodiments, the PROTAC has a log P 2.0 or higher. In some embodiments, the pharmaceutical composition comprises an amorphous solid dispersion that includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

Disclosed herein are pharmaceutical compositions comprising a PROTAC, e.g., a PROTAC compound of Table 1. In some embodiments, the pharmaceutical composition is formulated in a unit dosage form, such as a tablet or a capsule. In some embodiments, the PROTAC is present in the pharmaceutical composition in an amount of 10 mg to 1000 mg. In some embodiments, the PROTAC is present in an amount of 20 mg to 500 mg. In some embodiments, the PROTAC is present in an amount of 20 mg to 400 mg. In some embodiments, the PROTAC is present in the pharmaceutical composition in an amount of 30 mg to 300 mg. In some embodiments, the PROTAC is present in an amount of 20 mg to 300 mg. In some embodiments, the PROTAC is present in an amount of 25 mg to 250 mg. In some embodiments, the PROTAC is present in an amount of 30 mg to 200 mg. In some embodiments, the PROTAC is present in an amount of about 50 mg, about 100 mg or about 150 mg. In some embodiments, the PROTAC is present in an amount of 50 mg, 100 mg or 150 mg. In some embodiments, the PROTAC is present in an amount of 50 mg. In some embodiments, the PROTAC is present in an amount of 60 mg. In some embodiments, the PROTAC is present in an amount of 100 mg. In some embodiments, the PROTAC is present in an amount of 150 mg. In some embodiments the PROTAC is ARV-110 or ARV-471, or pharmaceutically acceptable salts thereof. In some embodiments, the PROTAC is a PROTAC. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments a pharmaceutical composition is provided that comprises a PROTAC that is present at a dose from about 1.0 mg to about 1000 mg. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises ARV-110 or ARV-471, or a pharmaceutically acceptable salt thereof, that is present at a dose from about 1.0 mg to about 1000 mg. In some embodiments, the pharmaceutical composition comprises an amorphous solid dispersion includes an ARV-110 or ARV-471, or a pharmaceutically acceptable salt thereof, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises from about 1 mg to about 500 mg of the PROTAC. In some embodiments, a pharmaceutical composition is provided that comprises from about 10 mg to about 400 mg of the PROTAC. In some embodiments, a pharmaceutical composition is provided that comprises from about 25 mg to about 200 mg of the PROTAC. In some embodiments, a pharmaceutical composition is provided that comprises from about 50 mg to about 150 mg of the PROTAC. In some embodiments, a pharmaceutical composition is provided that comprises about 75 mg to about 125 mg of the PROTAC. In some embodiments, a pharmaceutical composition is provided that comprises from about 75 mg to about 100 mg of the PROTAC. In some embodiments, a pharmaceutical composition is provided that comprises from about 100 mg to about 125 mg of the PROTAC. In some embodiments the PROTAC is ARV-110 or ARV-471, or pharmaceutically acceptable salts thereof. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises from about 50 mg to about 150 mg of the PROTAC. In some embodiments, a pharmaceutical composition is provided that comprises from about 55 mg to about 150 mg of the PROTAC. In some embodiments, a pharmaceutical composition is provided that comprises from about 60 mg to about 150 mg of the PROTAC. In some embodiments, a pharmaceutical composition is provided that comprises from about 65 mg to about 150 mg of the PROTAC. In some embodiments, a pharmaceutical composition is provided that comprises from about 70 mg to about 150 mg of the PROTAC. In some embodiments, a pharmaceutical composition is provided that comprises from about 75 mg to about 150 mg of the PROTAC. In some embodiments, a pharmaceutical composition is provided that comprises from about 80 mg to about 150 mg of the PROTAC. In some embodiments, a pharmaceutical composition is provided that comprises from about 85 mg to about 150 mg of the PROTAC. In some embodiments, a pharmaceutical composition is provided that comprises from about 90 mg to about 150 mg of the PROTAC. In some embodiments, a pharmaceutical composition is provided that comprises from about 95 mg to about 150 mg of the PROTAC. In some embodiments, a pharmaceutical composition is provided that comprises from about 100 mg to about 150 mg of the PROTAC. In some embodiments, a pharmaceutical composition is provided that comprises from about 105 mg to about 150 mg of the PROTAC. In some embodiments, a pharmaceutical composition is provided that comprises from about 110 mg to about 150 mg of the PROTAC. In some embodiments, a pharmaceutical composition is provided that comprises from about 115 mg to about 150 mg of the PROTAC. In some embodiments, a pharmaceutical composition is provided that comprises from about 120 mg to about 150 mg of the PROTAC. In some embodiments, a pharmaceutical composition is provided that comprises from about 125 mg to about 150 mg of the PROTAC. In some embodiments, a pharmaceutical composition is provided that comprises from about 130 mg to about 150 mg of the PROTAC. In some embodiments, a pharmaceutical composition is provided that comprises from about 135 mg to about 150 mg of the PROTAC. In some embodiments, a pharmaceutical composition is provided that comprises from about 140 mg to about 150 mg of the PROTAC. In some embodiments, a pharmaceutical composition is provided that comprises from about 145 mg to about 150 mg of the PROTAC. In some embodiments, a pharmaceutical composition is provided that comprises from about 1 mg to about 50 mg of the PROTAC. In some embodiments, a pharmaceutical composition is provided that comprises from about 5 mg to about 40 mg of the PROTAC. In some embodiments, a pharmaceutical composition is provided that comprises from about 10 mg to about 30 mg of the PROTAC. In some embodiments, a pharmaceutical composition is provided that comprises from about 5 mg to about 25 mg of the PROTAC. In some embodiments, a pharmaceutical composition is provided that comprises from about 25 mg to about 50 mg of the PROTAC. In some embodiments, a pharmaceutical composition is provided that comprises from about 20 mg to about 40 mg of the PROTAC. In some embodiments, a pharmaceutical composition is provided that comprises from about 10 mg to about 25 mg of the PROTAC. In some embodiments, a pharmaceutical composition is provided that comprises from about 5 mg to about 20 mg of the PROTAC. In some embodiments, a pharmaceutical composition is provided that comprises from about 1 mg to about 10 mg of the PROTAC. In some embodiments, a pharmaceutical composition is provided that comprises from about 1 mg to about 20 mg of the PROTAC. In some embodiments the PROTAC is ARV-110 or ARV-471, or pharmaceutically acceptable salts thereof. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises from about 50 mg to about 145 mg of the PROTAC. In some embodiments, a pharmaceutical composition is provided that comprises from about 50 mg to about 140 mg of the PROTAC. In some embodiments, a pharmaceutical composition is provided that comprises from about 50 mg to about 135 mg of the PROTAC. In some embodiments, a pharmaceutical composition is provided that comprises from about 50 mg to about 130 mg of the PROTAC. In some embodiments, a pharmaceutical composition is provided that comprises from about 50 mg to about 125 mg of the PROTAC. In some embodiments, a pharmaceutical composition is provided that comprises from about 50 mg to about 120 mg of the PROTAC. In some embodiments, a pharmaceutical composition is provided that comprises from about 50 mg to about 115 mg of the PROTAC. In some embodiments, a pharmaceutical composition is provided that comprises from about 50 mg to about 110 mg of the PROTAC. In some embodiments, a pharmaceutical composition is provided that comprises from about 50 mg to about 105 mg of the PROTAC. In some embodiments, a pharmaceutical composition is provided that comprises from about 50 mg to about 100 mg of the PROTAC. In some embodiments, a pharmaceutical composition is provided that comprises from about 50 mg to about 95 mg of the PROTAC. In some embodiments, a pharmaceutical composition is provided that comprises from about 50 mg to about 90 mg of the PROTAC. In some embodiments, a pharmaceutical composition is provided that comprises from about 50 mg to about 85 mg of the PROTAC. In some embodiments, a pharmaceutical composition is provided that comprises from about 50 mg to about 80 mg of the PROTAC. In some embodiments, a pharmaceutical composition is provided that comprises from about 50 mg to about 75 mg of the PROTAC. In some embodiments, a pharmaceutical composition is provided that comprises from about 50 mg to about 70 mg of the PROTAC. In some embodiments, a pharmaceutical composition is provided that comprises from about 50 mg to about 65 mg of the PROTAC. In some embodiments, a pharmaceutical composition is provided that comprises from about 50 mg to about 60 mg of the PROTAC. In some embodiments, a pharmaceutical composition is provided that comprises from about 50 mg to about 55 mg of the PROTAC. In some embodiments, a pharmaceutical composition is provided that comprises from about 25 mg to about 50 mg of the PROTAC. In some embodiments, a pharmaceutical composition is provided that comprises from about 40 mg to about 80 mg of the PROTAC. In some embodiments, a pharmaceutical composition is provided that comprises from about 75 mg to about 125 mg of the PROTAC. In some embodiments, a pharmaceutical composition is provided that comprises a PROTAC in an amount of about 25 mg to about 200 mg. In some embodiments the PROTAC is ARV-110 or a pharmaceutically acceptable salt thereof. In some embodiments the PROTAC is ARV-110. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, the PROTAC comprises about 5%, 10%, 15%, 20%, 25%, 30%, 40%, or 50% of the total weight of the composition. In some embodiments the PROTAC is ARV-110 or ARV-471, or pharmaceutically acceptable salts thereof. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises from about 0.1% to about 99% by weight of the PROTAC, or any numbers and ranges therebetween.

In some embodiments, a pharmaceutical composition is provided that comprises from about 0.1% to about 80% by weight of the PROTAC. In some embodiments, a pharmaceutical composition is provided that comprises from about 0.1% to about 60% by weight of the PROTAC. In some embodiments, a pharmaceutical composition is provided that comprises from about 0.1% to about 40% by weight of the PROTAC. In some embodiments, a pharmaceutical composition is provided that comprises from about 0.1% to about 20% by weight of the PROTAC. In some embodiments, a pharmaceutical composition is provided that comprises from about 0.1% to about 10% by weight of the PROTAC. In some embodiments, a pharmaceutical composition is provided that comprises from about 0.10% to about 1% by weight of the PROTAC. In some embodiments, a pharmaceutical composition is provided that comprises from about 20% to about 99% by weight of the PROTAC. In some embodiments, a pharmaceutical composition is provided that comprises from about 20% to about 80% by weight of the PROTAC. In some embodiments, a pharmaceutical composition is provided that comprises from about 20% to about 60% by weight of the PROTAC. In some embodiments, a pharmaceutical composition is provided that comprises from about 20% to about 40% by weight of the PROTAC. In some embodiments, a pharmaceutical composition is provided that comprises from about 30% to about 99% by weight of the PROTAC. In some embodiments, a pharmaceutical composition is provided that comprises from about 30% to about 80% by weight of the PROTAC. In some embodiments, a pharmaceutical composition is provided that comprises from about 30% to about 60% by weight of the PROTAC. In some embodiments, a pharmaceutical composition is provided that comprises from about 30% to about 40% by weight of the PROTAC. In some embodiments, a pharmaceutical composition is provided that comprises from about 40% to about 99% by weight of the PROTAC. In some embodiments, a pharmaceutical composition is provided that comprises from about 40% to about 80% by weight of the PROTAC. In some embodiments, a pharmaceutical composition is provided that comprises from about 40% to about 60% by weight of the PROTAC. In some embodiments, a pharmaceutical composition is provided that comprises from about 5% to about 70% by weight of the PROTAC. In some embodiments, a pharmaceutical composition is provided that comprises a PROTAC in a weight percent from about 5% to about 35%. In some embodiments, a pharmaceutical composition is provided that comprises a PROTAC in a weight percent from about 5% to about 10%, about 5% to about 15%, about 5% to about 18%, about 5% to about 19%, about 5% to about 20%, about 5% to about 21%, about 5% to about 22%, about 5% to about 24%, about 5% to about 25%, about 5% to about 30%, about 5% to about 35%, about 10% to about 15%, about 10% to about 18%, about 10% to about 19%, about 10% to about 20%, about 10% to about 21%, about 10% to about 22%, about 10% to about 24%, about 10% to about 25%, about 10% to about 30%, about 10% to about 35%, about 15% to about 18%, about 15% to about 19%, about 15% to about 20%, about 15% to about 21%, about 15% to about 22%, about 15% to about 24%, about 15% to about 25%, about 15% to about 30%, about 15% to about 35%, about 18% to about 19%, about 18% to about 20%, about 18% to about 21%, about 18% to about 22%, about 18% to about 24%, about 18% to about 25%, about 18% to about 30%, about 18% to about 35%, about 19% to about 20%, about 19% to about 21%, about 19% to about 22%, about 19% to about 24%, about 19% to about 25%, about 19% to about 30%, about 19% to about 35%, about 20% to about 21%, about 20% to about 22%, about 20% to about 24%, about 20% to about 25%, about 20% to about 30%, about 20% to about 35%, about 21% to about 22%, about 21% to about 24%, about 21% to about 25%, about 21% to about 30%, about 21% to about 35%, about 22% to about 24%, about 22% to about 25%, about 22% to about 30%, about 22% to about 35%, about 24% to about 25%, about 24% to about 30%, about 24% to about 35%, about 25% to about 30%, about 25% to about 35%, or about 30% to about 35%. In some embodiments, a pharmaceutical composition is provided that comprises a PROTAC in a weight percent from about 5%, about 10%, about 15%, about 18%, about 19%, about 20%, about 21%, about 22%, about 24%, about 25%, about 30%, or about 35%. In some embodiments, a pharmaceutical composition is provided that comprises a PROTAC in a weight percent from at least about 5%, about 10%, about 15%, about 18%, about 19%, about 20%, about 21%, about 22%, about 24%, about 25%, or about 30%. In some embodiments, a pharmaceutical composition is provided that comprises a PROTAC in a weight percent from at most about 10%, about 15%, about 18%, about 19%, about 20%, about 21%, about 22%, about 24%, about 25%, about 30%, or about 35%. In some embodiments the PROTAC is ARV-110 or ARV-471, or pharmaceutically acceptable salts thereof. In some embodiments, the PROTAC is one listed in Table 1, or a pharmaceutically acceptable salt thereof. In some embodiments, the PROTAC has a log P 2.0 or higher. In some embodiments, an amorphous solid dispersion includes a PROTAC, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In one aspect, disclosed herein are pharmaceutical compositions comprising a pharmaceutically acceptable carrier or excipient and an ASD that comprises i) a PROTAC listed in Table 1, or a pharmaceutically acceptable salt thereof, ii) one or more surfactants, iii) a hydrophilic polymer, and iv) optionally, an acid.

In some embodiments, the ASD comprises i) a PROTAC listed in Table 1, or a pharmaceutically acceptable salt thereof, ii) one or more surfactants, wherein the one or more surfactants comprise tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof, iii) a hydrophilic polymer, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), hydropropylmethylcellulose acetate succinate (HPMCAS), sulfobutylether-β-cyclodextrin, hydroxypropyl beta cyclodextrin (HP-β-CD), or a combination thereof, and iv) an acid.

In some embodiments, the ASD comprises i) a PROTAC listed in Table 1, or a pharmaceutically acceptable salt thereof in an amount of about 5% to about 50% by weight of the ASD, ii) one or more surfactants in an amount of about 1% to about 50% by weight of the ASD, wherein the one or more surfactants comprise tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof, iii) a hydrophilic polymer in an amount of about 5% to about 70% by weight of the ASD, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), sulfobutylether-β-cyclodextrin, hydropropylmethylcellulose acetate succinate (HPMCAS), hydroxypropyl beta cyclodextrin (HP-β-CD), or a combination thereof, and iv) an acid in an amount of about 1% to about 50% by weight of the ASD.

In some embodiments, the ASD comprises i) ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, KT-413, or a pharmaceutically acceptable salt thereof in an amount of about 5% to about 50% by weight of the ASD, ii) one or more surfactants in an amount of about 1% to about 60% by weight of the ASD, wherein the one or more surfactants comprise tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof, iii) a hydrophilic polymer in an amount of about 5% to about 70% by weight of the ASD, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), HPMCAS, hydroxypropyl beta cyclodextrin (HP-β-CD), or a combination thereof, and iv) an acid in an amount of about 1% to about 50% by weight of the ASD.

In some embodiments, the ASD comprises i) ARV-110, ARV-471, or a pharmaceutically acceptable salt thereof in an amount of about 5% to about 50% by weight of the ASD, ii) one or more surfactants in an amount of about 1% to about 50% by weight of the ASD, wherein the one or more surfactants comprise tocopherol polyethylene glycol succinate (TPGS), lecithin, a block copolymer of polyethylene glycol and polypropylene glycol, polyvinylcaprolactame-based graft copolymer (PVAc-PVCap-PEG), or a combination thereof, iii) a hydrophilic polymer in an amount of about 5% to about 70% by weight of the ASD, wherein the hydrophilic polymer comprises vinylpyrrolidone-vinyl acetate copolymer, polyvinyl alcohol (PVA), polyvinylpyrrolidone (PVP), hydroxypropyl methylcellulose (HPMC), HPMCAS, or hydroxypropyl beta cyclodextrin (HP-β-CD), and iv) an acid in an amount of about 1% to about 50% by weight of the ASD, wherein the acid comprises tartaric acid, fumaric acid, succinic acid, citric acid, lactic acid, malic acid, methanesulfonic acid, ethanesulfonic acid, isethionic acid, benzenesulfonic acid, p-toluenesulfonic acid, hydrochloric acid, sulfuric acid, phosphoric acid, or a combination thereof.

In some embodiments, the pharmaceutical compositions described herein have a superior bioavailability than a bioavailability of a corresponding reference composition comprising a crystalline PROTAC or a PROTAC that is not present in an ASD, when measured as AUC, $AUC_{inf}$ or $AUC_{last}$ after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a corresponding composition comprising a crystalline PROTAC or PROTAC that is not present in an ASD, when measured as the AUC after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a corresponding composition comprising a crystalline PROTAC or PROTAC that is not present in an ASD, when measured as $C_{max}$ after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a PROTAC that is not present in an ASD capsule comprising ARV-110, when measured as AUC after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a PROTAC that is not present in an ASD capsule comprising ARV-110, when measured as $C_{max}$ after oral administration. In some embodiments, the pharmaceutical composition exhibits a bioavailability that is higher than a bioavailability of a PROTAC that is not present in an ASD by about 1.1 fold to about 10 fold. In some embodiments, the pharmaceutical composition exhibits a bioavailability that is higher than a bioavailability of a PROTAC that is not present in an ASD by about 1.1 fold to about 2 fold, about 1.1 fold to about 3 fold, about 1.1 fold to about 4 fold, about 1.1 fold to about 5 fold, about 1.1 fold to about 6 fold, about 1.1 fold to about 7 fold, about 1.1 fold to about 8 fold, about 1.1 fold to about 10 fold, about 1.5 fold to about 2 fold, about 1.5 fold to about 3 fold, about 1.5 fold to about 4 fold, about 1.5 fold to about 5 fold, about 1.5 fold to about 6 fold, about 1.5 fold to about 7 fold, about 1.5 fold to about 8 fold, about 1.5 fold to about 10 fold, about 2 fold to about 4 fold, about 2 fold to about 5 fold, about 2 fold to about 6 fold, about 2 fold to about 7 fold, about 2 fold to about 8 fold, about 2 fold to about 10 fold, about 3 fold to about 4 fold, about 3 fold to about 5 fold, about 3 fold to about 6 fold, about 3 fold to about 7 fold, about 3 fold to about 8 fold, about 3 fold to about 10 fold, about 4 fold to about 5 fold, about 4 fold to about 6 fold, about 4 fold to about 7 fold, about 4 fold to about 8 fold, about 4 fold to about 10 fold, about 5 fold to about 6 fold, about 5 fold to about 7 fold, about 5 fold to about 8 fold, about 5 fold to about 10 fold, about 6 fold to about 7 fold, about 6 fold to about 8 fold, about 6 fold to about 10 fold, about 7 fold to about 8 fold, about 7 fold to about 10 fold, or about 8 fold to about 10 fold.

In some embodiments, the pharmaceutical composition described herein exhibits a bioavailability that is higher than a bioavailability of a PROTAC that is not present in an ASD by at least about 1.1 fold, about 1.3 fold, about 1.5 fold, about 1.8 fold, about 2 fold, about 3 fold, about 4 fold, about 5 fold, about 6 fold, about 7 fold, or about 8 fold when measured as AUC or $C_{max}$ after oral administration. In some embodiments, the pharmaceutical composition exhibits a bioavailability that is higher than a bioavailability of a PROTAC that is not present in an ASD by at least about 2 fold. In some embodiments, the pharmaceutical composition exhibits a bioavailability that is higher than a bioavailability of a PROTAC that is not present in an ASD by at least about 4 fold. In some embodiments, the pharmaceutical composition exhibits a bioavailability that is higher than a bioavailability of a PROTAC that is not present in an ASD by at most about 1.3 fold, about 1.5 fold, about 1.8 fold, about 2 fold, about 3 fold, about 4 fold, about 5 fold, about 6 fold, about 7 fold, about 8 fold, or about 10 fold. In some embodiments, the bioavailability is measured in a dog model in a fasted state. In some embodiments, the bioavailability is measured in a dog model in a fed state. In some embodiments, a bioavailability of the pharmaceutical composition does not vary for more than 100% 90%, 80%, 70%, 60%, 50%, 40%, 30%, 20%, 15%, or 10% when orally administered in a fed state compared to administered in a fasted state, when measured AUC after oral administration. In some embodiments, a bioavailability of the pharmaceutical composition does not vary for more than 100% 90%, 80%, 70%, 60%, 50%, 40%, 30%, 20%, 15%, or 10% when orally administered in a fed state compared to administered in a fasted state, when measured as $C_{max}$, after oral administration. In some embodiments, a bioavailability of the pharmaceutical composition does not vary for more than 100% when orally administered in a fed state compared to administered in a fasted state. In some embodiments, a bioavailability of the pharmaceutical composition does not vary for more than 90% when orally administered in a fed state compared to administered in a fasted state. In some embodiments, a bioavailability of the pharmaceutical composition does not vary for more than 80% when orally administered in a fed state compared to administered in a fasted state. In some embodiments, a bioavailability of the pharmaceutical composition does not vary for more than 70% when orally administered in a fed state compared to administered in a fasted state. In some embodiments, a bioavailability of the pharmaceutical composition does not vary for more than 60% when orally administered in a fed state compared to administered in a fasted state. In some embodiments, a bioavailability of the pharmaceutical composition does not vary for more than 50% when orally administered in a fed state compared to administered in a fasted state. In some embodiments, a bioavailability of the pharmaceutical composition does not vary for more than 40% when orally administered in a fed state compared to administered in a fasted state. In some embodiments, a bioavailability of the pharmaceutical composition does not vary for more than 20% when orally administered in a fed state compared to administered in a fasted state. In some embodiment, the bioavailability is measured in a dog model. In some embodiment, the dog model is beagle dog.

In some embodiments, the pharmaceutical composition exhibits a bioavailability of the PROTAC compound or the pharmaceutically acceptable salt thereof that is at least 2-fold compared to a bioavailability of a corresponding composition comprising the PROTAC compound or the pharmaceutically acceptable salt thereof in a conventional dosage form (such as a crystalline form), when said bioavailability is measured as AUC or as maximum plasma concentration ($C_{max}$) after oral administration to a subject in a fasted state. In some embodiments, the pharmaceutical composition exhibits a bioavailability of the PROTAC compound or the pharmaceutically acceptable salt thereof that is at least 3, 4, or 5-fold compared to a bioavailability of a corresponding composition comprising the PROTAC compound or the pharmaceutically acceptable salt thereof in a conventional dosage form (such as a crystalline form), when said bioavailability is measured as AUC or as maximum plasma concentration ($C_{max}$) after oral administration to a subject in a fasted state. In some embodiments, the PROTAC is one listed in Table 1. In some embodiments, the PROTAC is ARV-110. In some embodiments, the PROTAC is ARV-471.

In some embodiments, the pharmaceutical composition exhibits a bioavailability of the PROTAC compound or the pharmaceutically acceptable salt thereof that is at least 1.5-fold compared to a bioavailability of a corresponding composition comprising the PROTAC compound or the pharmaceutically acceptable salt thereof in a conventional dosage form, when said bioavailability is measured as total area under the curve (AUC) or as maximum plasma concentration (Cmax) after oral administration to a subject in a fed state. The pharmaceutical composition of any one of claims 1-3, wherein the pharmaceutical composition exhibits a bioavailability of the PROTAC compound or the pharmaceutically acceptable salt thereof that is at least 2, 2.5, or 3-fold compared to a bioavailability of a corresponding composition comprising the PROTAC compound or the pharmaceutically acceptable salt thereof in a conventional dosage form, when said bioavailability is measured as total area under the curve (AUC) or as maximum plasma concentration (Cmax) after oral administration to a subject in a fed state. In some embodiments, the PROTAC is one listed in Table 1. In some embodiments, the PROTAC is ARV-110. In some embodiments, the PROTAC is ARV-471.

In some embodiments, the pharmaceutical composition exhibits a bioavailability of the PROTAC compound or the pharmaceutically acceptable salt thereof that is at least 5-fold compared to a bioavailability of a corresponding composition comprising the PROTAC compound or the pharmaceutically acceptable salt thereof in a conventional dosage form, when said bioavailability is measured as AUC or as maximum plasma concentration ($C_{max}$) after oral administration to a subject in a fasted state. In some embodiments, the PROTAC is one listed in Table 1. In some embodiments, the PROTAC has a log P 2.0 or higher. In some embodiments, the PROTAC is ARV-110. In some embodiments, the PROTAC is ARV-471.

In some embodiments, the pharmaceutical composition exhibits a bioavailability of the PROTAC compound or the pharmaceutically acceptable salt thereof is at least 5-fold compared to a bioavailability of a corresponding composition comprising the PROTAC compound or the pharmaceutically acceptable salt thereof in a conventional dosage form. In some embodiments, the PROTAC is one listed in Table 1. In some embodiments, the PROTAC has a log P 2.0 or higher. In some embodiments, the PROTAC is ARV-110. In some embodiments, the PROTAC is ARV-471.

In some embodiments, the pharmaceutical composition exhibits a bioavailability of the PROTAC compound or the pharmaceutically acceptable salt thereof is at least 1.1, 1.5, 2, 3, 4, 5, 6, 7, 8, 9, or 10-fold compared to a bioavailability of a corresponding composition comprising the PROTAC compound or the pharmaceutically acceptable salt thereof in a conventional dosage form. In some embodiments, the PROTAC is one listed in Table 1. In some embodiments, the PROTAC has a log P 2.0 or higher. In some embodiments, the PROTAC is ARV-110. In some embodiments, the PROTAC is ARV-471.

In some embodiments, the pharmaceutical composition exhibits a bioavailability of the PROTAC compound or the pharmaceutically acceptable salt thereof that does not vary more than about 5% to about 60% when orally administered to a subject in a fed state compared to a fasted state. In some embodiments, the pharmaceutical composition exhibits a bioavailability of the PROTAC compound or the pharmaceutically acceptable salt thereof that does not vary more than about 25% to about 100% when orally administered to a subject in a fed state compared to a fasted state. In some embodiments, the pharmaceutical composition exhibits a bioavailability of the PROTAC compound or the pharmaceutically acceptable salt thereof that does not vary more than about 5% to about 10%, about 5% to about 15%, about 5% to about 20%, about 5% to about 25%, about 5% to about 30%, about 5% to about 35%, about 5% to about 40%, about 5% to about 50%, about 5% to about 60%, about 10% to about 15%, about 10% to about 20%, about 10% to about 25%, about 10% to about 30%, about 10% to about 35%, about 10% to about 40%, about 10% to about 50%, about 10% to about 60%, about 15% to about 20%, about 15% to about 25%, about 15% to about 30%, about 15% to about 35%, about 15% to about 40%, about 15% to about 50%, about 15% to about 60%, about 20% to about 25%, about 20% to about 30%, about 20% to about 35%, about 20% to about 40%, about 20% to about 50%, about 20% to about 60%, about 25% to about 30%, about 25% to about 35%, about 25% to about 40%, about 25% to about 50%, about 25% to about 60%, about 30% to about 35%, about 30% to about 40%, about 30% to about 50%, about 30% to about 60%, about 35% to about 40%, about 35% to about 50%, about 35% to about 60%, about 40% to about 50%, about 40% to about 60%, about 50% to about 60%, about 55% to about 65%, about 60% to about 70%, about 65% to about 80%, about 75% to about 90%, about 80% to about 100%, or about 90% to about 100%, when orally administered to a subject in a fed state compared to a fasted state. In some embodiments, the pharmaceutical composition exhibits a bioavailability of the PROTAC compound or the pharmaceutically acceptable salt thereof that does not vary more than about at most about 10%, about 15%, about 20%, about 25%, about 30%, about 35%, about 40%, about 50%, or about 60%. In some embodiments, the PROTAC is one selected from Table 1.

In some embodiments, the pharmaceutical composition exhibits a bioavailability of the PROTAC compound or the pharmaceutically acceptable salt thereof that does not vary more than 50% when orally administered to a subject in a fed state compared to a fasted state, when said bioavailability is measured as AUC or as $C_{max}$ after oral administration to said subject. In some embodiments, the PROTAC is one selected from Table 1. In some embodiments, the PROTAC has a log P 2.0 or higher. In some embodiments, the PROTAC is ARV-110. In some embodiments, the PROTAC is ARV-471.

In some embodiments, the pharmaceutical composition exhibits a bioavailability of the PROTAC compound or the pharmaceutically acceptable salt thereof that does not vary more than 25% when orally administered to a subject in a fed state compared to a fasted state, when said bioavailability is measured as AUC or as $C_{max}$ after oral administration to said subject. In some embodiments, the PROTAC is one selected from Table 1. In some embodiments, the PROTAC has a log P 2.0 or higher. In some embodiments, the PROTAC is ARV-110. In some embodiments, the PROTAC is ARV-471.

In some embodiments, the pharmaceutical composition exhibits a bioavailability of the PROTAC compound or the pharmaceutically acceptable salt thereof that does not vary more than 10% when orally administered to a subject in a fed state compared to a fasted state, when said bioavailability is measured as AUC or as $C_{max}$ after oral administration to said subject. In some embodiments, the PROTAC is one selected from Table 1. In some embodiments, the PROTAC has a log P 2.0 or higher. In some embodiments, the PROTAC is ARV-110. In some embodiments, the PROTAC is ARV-471.

In some embodiments, the pharmaceutical compositions described herein exhibits a bioavailability that is from about 100% to about 1500%, 120% to about 1000%, 125% to about 500%, about 130% to about 450%, 140% to about 400%, or about 150% to about 300° % of a bioavailability of a corresponding reference composition comprising PROTAC when measured as $AUC_{last}$, or $C_{max}$ after oral administration, wherein the corresponding reference pharmaceutical composition does not comprise an amorphous solid dispersion. In some embodiments, the reference composition is at least about 1.1 times the dosage of the pharmaceutical compositions. In some embodiments, the reference composition is at least about 1.1 times, about 1.5 times, about 2 times, about 2.5 times, about 3 times, about 4 times, about 5 times, about 6 times, about 7 times, about 8 times, about 9 times, or about 10 times the dosage of the pharmaceutical composition. In some embodiments, the pharmaceutical composition comprises an ASD comprising PROTAC free base or a pharmaceutically acceptable salt thereof. In some embodiments, the reference composition comprises PROTAC free base or a pharmaceutically acceptable salt thereof, wherein the reference composition does not comprise an ASD. In some embodiment, the bioavailability is measured under fasted condition. In some embodiment, the bioavailability is measured under fed condition. In some embodiment, the PROTAC is one listed in Table 1. In some embodiments, the PROTAC has a log P 2.0 or higher. In some embodiments, the PROTAC is ARV-110. In some embodiments, the PROTAC is ARV-471.

In some embodiments, the bioavailability of compositions described herein are determined using a dog model. In some embodiments, the bioavailability of compositions described herein are determined according to conditions described in Example 1. In some embodiments, the bioavailability of compositions described herein are determined in humans.

In some embodiments, a herein described pharmaceutical composition is storage stable for a period of at least 1 month, 2 months, 3 months, 6 months, 9 months, 12 months, or 24 months at 5±3° C., wherein a storage stable pharmaceutical composition retains at least 90 wt % of the PROTAC compound or the pharmaceutically acceptable salt thereof at the end of the period. In some embodiments, a herein described pharmaceutical composition is storage stable for a period of at least 2 weeks, 1 month, 2 months, 3 months, 6 months, 9 months, 12 months, or 24 months at 25±2° C., wherein a storage stable pharmaceutical composition retains at least 90 wt % of the PROTAC compound or the pharmaceutically acceptable salt thereof at the end of the period. In some embodiments, a herein described pharmaceutical composition is storage stable for a period of at least 12 months at 25±2° C., wherein a storage stable pharmaceutical composition retains at least 90 wt % of the PROTAC compound or the pharmaceutically acceptable salt thereof at the end of the period. In some embodiments, a herein described pharmaceutical composition is storage stable for a period of at least 2 weeks, 1 month, 2 months, 3 months, 6 months, 12 months, or 24 months at 40±2° C., wherein a storage stable pharmaceutical composition retains at least 90 wt % of the PROTAC compound or the pharmaceutically acceptable salt thereof at the end of the period. In some embodiments, a herein described pharmaceutical composition is storage stable for a period of at least 1 month, 2 months, 3 months, 6 months, 9 months, 12 months, or 24 months at 5±3° C., wherein a storage stable pharmaceutical composition contains at most 0.5 wt % total impurity at the end of the period. In some embodiments, a herein described pharmaceutical composition is storage stable for a period of at least 2 weeks, 1 month, 2 months, 3 months, 6 months, 9 months, 12 months, or 24 months at 25±2° C., wherein a storage stable pharmaceutical composition contains at most 0.5 wt % total impurity at the end of the period. In some embodiments, a herein described pharmaceutical composition is storage stable for a period of at least 12 months at 25±2° C., wherein a storage stable pharmaceutical composition contains at most 0.5 wt % total impurity at the end of the period. In some embodiments, a herein described pharmaceutical composition is storage stable for a period of at least 2 weeks, 1 month, 2 months, 3 months, 6 months, 12 months, or 24 months at 40±2° C., wherein a storage stable pharmaceutical composition contains at most 0.5 wt % total impurity at the end of the period.

In one aspect, disclosed herein are pharmaceutical compositions comprising a ASD that comprises an API, a surfactant, a hydrophilic polymer, optionally an acid, and optionally an adsorbent. In one aspect, disclosed herein are pharmaceutical compositions comprising an ASD, wherein the ASD comprises an API. In some embodiments, the API is a PROTAC. In some embodiments, the PROTAC is one selected from Table 1. In some embodiments, the PROTAC is ARV-110 free base or a pharmaceutically acceptable salt thereof. In some embodiments, the PROTAC is ARV-110. In some embodiments, the PROTAC is ARV-471 free base or a pharmaceutically acceptable salt thereof. In some embodiments, the PROTAC is ARV-471.

In some embodiments, described herein is an amorphous solid dispersion that comprises a PROTAC such as ARV-110 or a pharmaceutically acceptable salt thereof. In some embodiments, the amorphous solid dispersion is characterized by providing an amorphous powder X-ray diffraction pattern. In some embodiments, the ARV-110 or a pharmaceutically acceptable salt thereof is present in the amorphous solid dispersion in an amount of about 5 wt % to about 70 wt % based on solids. In some embodiments, the ARV-110 or a pharmaceutically acceptable salt thereof is present in the amorphous solid dispersion in an amount of about 10 wt % to about 50 wt % based on solids. In some embodiments, the ARV-110 or a pharmaceutically acceptable salt thereof is present in the amorphous solid dispersion in an amount of about 20 wt % to about 40 wt % based on solids. In some embodiments, the ARV-110 or a pharmaceutically acceptable salt thereof is present in the amorphous solid dispersion in an amount of about 10 wt % to about 30 wt % based on solids.

In some embodiments, a weight ratio of the ARV-110 or a pharmaceutically acceptable salt thereof to the surfactant is from about 10:1 to about 1:10, or any ranges therebetween. In some embodiments, a weight ratio of the ARV-110 or a pharmaceutically acceptable salt thereof to the surfactant is from about 5:1 to about 1:4. In some embodiments, a weight ratio of the ARV-110 or a pharmaceutically acceptable salt thereof to the surfactant is from about 2:1 to about 1:2 In some embodiments, a weight ratio of the ARV-110 or a pharmaceutically acceptable salt thereof to the surfactant is from about 1:1 to about 1:2 In some embodiments, a weight ratio of the ARV-110 or a pharmaceutically acceptable salt thereof to the surfactant is from about 1:1 to about 1:1.5. In some embodiments, a weight ratio of the ARV-110 or a pharmaceutically acceptable salt thereof to the surfactant is from about 0.5:1 to about 1:3 In some embodiments, a weight ratio of the ARV-110 or a pharmaceutically acceptable salt thereof to the surfactant is from about 1:1 to about 1:3.

In some embodiments, described herein is an amorphous solid dispersion that comprises a PROTAC such as ARV-471 or a pharmaceutically acceptable salt thereof. In some embodiments, the amorphous solid dispersion is characterized by providing an amorphous powder X-ray diffraction pattern. In some embodiments, the ARV-471 or a pharmaceutically acceptable salt thereof is present in the amorphous solid dispersion in an amount of about 5 wt % to about 70 wt % based on solids. In some embodiments, the ARV-471 or a pharmaceutically acceptable salt thereof is present in the amorphous solid dispersion in an amount of about 10 wt % to about 50 wt % based on solids. In some embodiments, the ARV-471 or a pharmaceutically acceptable salt thereof is present in the amorphous solid dispersion in an amount of about 20 wt % to about 40 wt % based on solids. In some embodiments, the ARV-471 or a pharmaceutically acceptable salt thereof is present in the amorphous solid dispersion in an amount of about 10 wt % to about 30 wt % based on solids.

In some embodiments, a weight ratio of the ARV-471 or a pharmaceutically acceptable salt thereof to the surfactant is from about 10:1 to about 1:10, or any ranges therebetween. In some embodiments, a weight ratio of the ARV-471 or a pharmaceutically acceptable salt thereof to the surfactant is from about 5:1 to about 1:4. In some embodiments, a weight ratio of the ARV-471 or a pharmaceutically acceptable salt thereof to the surfactant is from about 2:1 to about 1:2 In some embodiments, a weight ratio of the ARV-471 or a pharmaceutically acceptable salt thereof to the surfactant is from about 1:1 to about 1:2 In some embodiments, a weight ratio of the ARV-471 or a pharmaceutically acceptable salt thereof to the surfactant is from about 1:1 to about 1:1.5. In some embodiments, a weight ratio of the ARV-471 or a pharmaceutically acceptable salt thereof to the surfactant is from about 0.5:1 to about 1:3 In some embodiments, a weight ratio of the ARV-471 or a pharmaceutically acceptable salt thereof to the surfactant is from about 1:1 to about 1:3.

In some embodiments, the ASD comprises PROTAC in an amount of about 3% to about 60% by weight of the ASD. In some embodiments, the ASD comprises PROTAC in an amount of about 10% to about 50% by weight of the ASD. In some embodiments, the ASD comprises PROTAC in an amount of about 15% to about 35% by weight of the ASD. In some embodiments, the ASD comprises PROTAC in an amount of about 20% to about 30% by weight of the ASD. In some embodiments, the ASD comprises PROTAC in an amount of about 25% by weight of the ASD. In some embodiments, the PROTAC is ARV-110 free base or a pharmaceutically acceptable salt thereof. In some embodiments, the PROTAC is ARV-110. In some embodiments, the PROTAC is ARV-471 free base or a pharmaceutically acceptable salt thereof. In some embodiments, the PROTAC is ARV-471.

In some embodiments, an ASD described herein comprises ARV-110 in an amount of about 10% to about 40% by weight of the ASD. In some embodiments, the ASD comprises a surfactant in an amount of about 5% to about 40% by weight of the ASD. In some embodiments, the surfactant is TPGS. In some embodiments, the ASD comprises a non-ionic hydrophilic polymer in an amount of about 10% to about 60% by weight of the ASD. In some embodiments, the non-ionic hydrophilic polymer comprises vinylpyrrolidone-vinyl acetate copolymer. In some embodiments, the ASD comprises an acid in an amount of about 5% to 40% by weight of the ASD. In some embodiments, the acid is tartaric acid.

In some embodiments, an ASD described herein comprises ARV-110 in an amount of about 10% to about 40% by weight of the ASD. In some embodiments, the ASD comprises a surfactant in an amount of about 5% to about 60% by weight of the ASD. In some embodiments, the surfactant is tocopherol polyethylene glycol succinate (TPGS) or lecithin or a combination thereof. In some embodiments, the ASD comprises a hydrophilic polymer in an amount of about 10% to about 60% by weight of the ASD. In some embodiments, the hydrophilic polymer comprises vinylpyrrolidone-vinyl acetate copolymer, PEG, polymethacrylates, hypromellose phthalate (HPMCP), polyvinylcaprolactam, polyvinyl acetate, polyvinyl caprolactam-polyvinyl acetate-polyethylene glycol graft co-polymer, or hydropropylmethylcellulose acetate succinate (HPMCAS) or a combination thereof. In some embodiments, polymethacrylates comprise Eudragit. In some embodiments, the ASD comprises an acid in an amount of about 5% to 40% by weight of the ASD. In some embodiments, the acid is tartaric acid or citric acid or a combination thereof.

In some embodiments, an ASD described herein comprises ARV-110 in an amount of about 15% to about 35% by weight of the ASD. In some embodiments, the ASD comprises a surfactant in an amount of about 10% to about 50% by weight of the ASD. In some embodiments, the surfactant is TPGS or lecithin or a combination thereof. In some embodiments, the ASD comprises a hydrophilic polymer in an amount of about 10% to about 50% by weight of the ASD. In some embodiments, the hydrophilic polymer comprises vinylpyrrolidone-vinyl acetate copolymer, PEG, polymethacrylates, hypromellose phthalate (HPMCP), polyvinylcaprolactam, polyvinyl acetate, polyvinyl caprolactam-polyvinyl acetate-polyethylene glycol graft co-polymer, or HPMCAS or a combination thereof. In some embodiments, polymethacrylates comprise Eudragit. In some embodiments, the ASD comprises an acid in an amount of about 10% to 35% by weight of the ASD. In some embodiments, the acid is tartaric acid or citric acid or a combination thereof.

In some embodiments, the ASD comprises ARV-110 in an amount of about 25% by weight of the ASD. In some embodiments, the ASD comprises a surfactant in an amount of about 25% by weight of the ASD. In some embodiments, the surfactant is TPGS, a non-ionic hydrophilic polymer in an amount of about 25% by weight of the ASD. In some embodiments, the non-ionic hydrophilic polymer is copovidone (such as VA64). In some embodiments, the ASD comprises an acid in an amount of about 25% by weight of the ASD. In some embodiments, the acid is tartaric acid.

In some embodiments, an ASD described herein comprises ARV-110 in an amount of about 20% by weight of the ASD. In some embodiments, the ASD comprises a surfactant in an amount of about 40% by weight of the ASD. In some embodiments, the surfactant is lecithin, and a hydrophilic polymer in an amount of about 40% by weight of the ASD. In some embodiments, the hydrophilic polymer is hydropropylmethylcellulose acetate succinate (HPMCAS).

In some embodiments, an ASD described herein comprises ARV-110 in an amount of about 20% by weight of the ASD. In some embodiments, the ASD comprises a surfactant comprising TPGS and lecithin. In some embodiments, TPGS is present in an amount of about 20% by weight of the ASD and lecithin is present in an amount of about 20% by weight of the ASD. In some embodiments, the ASD comprises a hydrophilic polymer in an amount of about 20% by weight of the ASD. In some embodiments, the hydrophilic polymer is copovidone (such as VA64). In some embodiments, the ASD comprises an acid in an amount of about 20% by weight of the ASD. In some embodiments, the acid is citric acid.

In some embodiments, an ASD described herein comprises ARV-110 in an amount of about 25% by weight of the ASD. In some embodiments, the ASD comprises a surfactant comprising TPGS and lecithin. In some embodiments, TPGS is present in an amount of about 25% by weight of the ASD and lecithin is present in an amount of about 25% by weight of the ASD, and a hydrophilic polymer in an amount of about 25% by weight of the ASD. In some embodiments, the hydrophilic polymer is hydropropylmethylcellulose acetate succinate (HPMCAS).

In some embodiments, an ASD described herein comprises ARV-471 in an amount of about 10% to about 40% by weight of the ASD. In some embodiments, the ASD comprises a surfactant in an amount of about 5% to about 60% by weight of the ASD. In some embodiments, the surfactant is TPGS or lecithin or a combination thereof. In some embodiments, the ASD comprises a hydrophilic polymer in an amount of about 10% to about 60% by weight of the ASD. In some embodiments, the hydrophilic polymer comprises vinylpyrrolidone-vinyl acetate copolymer. PEG, polymethacrylates, hypromellose phthalate (HPMCP), polyvinylcaprolactam, polyvinyl acetate, polyvinyl caprolactam-polyvinyl acetate-polyethylene glycol graft co-polymer, or HPMCAS or a combination thereof. In some embodiments, polymethacrylates comprise Eudragit. In some embodiments, the ASD comprises an acid in an amount of about 5% to 40% by weight of the ASD. In some embodiments, the acid is tartaric acid or succinic acid or a combination thereof.

In some embodiments, an ASD described herein comprises ARV-471 in an amount of about 15% to about 45% by weight of the ASD. In some embodiments, the ASD comprises a surfactant in an amount of about 10% to about 50% by weight of the ASD. In some embodiments, the surfactant is TPGS or lecithin or a combination thereof. In some embodiments, the ASD comprises a hydrophilic polymer in an amount of about 10% to about 50% by weight of the ASD. In some embodiments, the hydrophilic polymer comprises vinylpyrrolidone-vinyl acetate copolymer, PEG, polymethacrylates, hypromellose phthalate (HPMCP), polyvinylcaprolactam, polyvinyl acetate, polyvinyl caprolactam-polyvinyl acetate-polyethylene glycol graft co-polymer (such as copovidone), or HPMCAS or a combination thereof. In some embodiments, polymethacrylates comprise Eudragit. In some embodiments, the ASD comprises an acid in an amount of about 10% to 35% by weight of the ASD. In some embodiments, the acid is tartaric acid or succinic acid or a combination thereof.

In some embodiments, an ASD described herein comprises ARV-471 in an amount of about 20 to about 40% by weight of the ASD. In some embodiments, ARV-471 is in an amount of about 25% to about 40% by weight of the ASD. In some embodiments, ARV-471 is in an amount of about 20% to about 30% by weight of the ASD. In some embodiments, the ASD comprises a surfactant in an amount of about 15 to about 45% by weight of the ASD. In some embodiments, the surfactant is in an amount of about 25% to about 40% by weight of the ASD. In some embodiments, the surfactant is in an amount of about 20% to about 30% by weight of the ASD. In some embodiments, the surfactant is TPGS or lecithin or a combination thereof. In some embodiments, the surfactant is lecithin. In some embodiments, the surfactant is a phospholipid. In some embodiments, the ASD comprises a hydrophilic polymer in an amount of about 15 to about 45% by weight of the ASD. In some embodiments, the hydrophilic polymer is in an amount of about 25% to about 40% by weight of the ASD. In some embodiments, the hydrophilic polymer is in an amount of about 20% to about 30% by weight of the ASD. In some embodiments, the hydrophilic polymer is HPMCAS or copovidone (such as VA64) or a combination thereof. In some embodiments, the hydrophilic polymer is HPMCAS. In some embodiments, the ASD comprises an acid in an amount of about 15 to about 45% by weight of the ASD. In some embodiments, the acid is in an amount of about 25% to about 40% by weight of the ASD. In some embodiments, the acid is in an amount of about 20% to about 30% by weight of the ASD. In some embodiments, the acid is tartaric acid, citric acid, or succinic acid or a combination thereof. In some embodiments, the acid is tartaric acid.

In some embodiments, an ASD comprises a PROTAC in an amount of about 40 mg to about 250 mg. In some embodiments, the ASD comprises a surfactant in an amount of about 40 mg to about 250 mg. In some embodiments, the surfactant is TPGS or lecithin or a combination thereof. In some embodiments, the ASD comprises a PROTAC in an amount of about 10% to about 40% by weight of the ASD. In some embodiments, the ASD comprises a surfactant in an amount of about 5% to about 60% by weight of the ASD. In some embodiments, the surfactant is TPGS or lecithin or a combination thereof. In some embodiments, the ASD comprises a hydrophilic polymer in an amount of about 10% to about 60% by weight of the ASD. In some embodiments, the hydrophilic polymer comprises vinylpyrrolidone-vinyl acetate copolymer, PEG, polymethacrylates, hypromellose phthalate (HPMCP), polyvinylcaprolactam, polyvinyl acetate, polyvinyl caprolactam-polyvinyl acetate-polyethylene glycol graft co-polymer, or HPMCAS or a combination thereof. In some embodiments, polymethacrylates comprise Eudragit. In some embodiments, the ASD comprises an acid in an amount of about 5% to 40% by weight of the ASD. In some embodiments, the acid comprises tartaric acid, succinic acid, or citric acid or a combination thereof. In some embodiments, the PROTAC is ARV-110. In some embodiments, the PROTAC is ARV-471.

In some embodiments, an ASD described herein comprises a PROTAC in an amount of about 15% to about 35% by weight of the ASD. In some embodiments, the ASD comprises a surfactant in an amount of about 10% to about 50% by weight of the ASD. In some embodiments, the surfactant is TPGS or lecithin or a combination thereof. In some embodiments, the ASD comprises a hydrophilic polymer in an amount of about 10% to about 50% by weight of the ASD. In some embodiments, the hydrophilic polymer comprises vinylpyrrolidone-vinyl acetate copolymer, PEG, polymethacrylates, hypromellose phthalate (HPMCP), polyvinylcaprolactam, polyvinyl acetate, polyvinyl caprolactam-polyvinyl acetate-polyethylene glycol graft co-polymer, or HPMCAS or a combination thereof. In some embodiments, polymethacrylates comprise Eudragit. In some embodiments, the ASD comprises an acid in an amount of about 10% to 35% by weight of the ASD. In some embodiments, the acid comprises tartaric acid, succinic acid, or citric acid or a combination thereof. In some embodiments, the PROTAC is ARV-110. In some embodiments, the PROTAC is ARV-471.

In some embodiments, an ASD described herein ASD comprises a PROTAC in an amount of about 25% by weight of the ASD, one or more surfactants in an amount of about 25% by weight of the ASD. In some embodiments, the surfactant is TPGS or lecithin or a combination thereof. In some embodiments, the ASD comprises a hydrophilic polymer in an amount of about 25% by weight of the ASD. In some embodiments, the hydrophilic polymer is VA64 or HPMCAS. In some embodiments, the ASD comprises an acid in an amount of about 25% by weight of the ASD. In some embodiments, the acid comprises tartaric acid, succinic acid, or citric acid or a combination thereof. In some embodiments, the PROTAC is ARV-110. In some embodiments, the PROTAC is ARV-471.

In some embodiments, an ASD described herein comprises a hydrophilic polymer in an amount of about 40 mg to about 250 mg. In some embodiments, the hydrophilic polymer comprises vinylpyrrolidone-vinyl acetate copolymer, PEG, polymethacrylates, hypromellose phthalate (HPMCP), polyvinylcaprolactam, polyvinyl acetate, polyvinyl caprolactam-polyvinyl acetate-polyethylene glycol graft co-polymer, or HPMCAS or a combination thereof. In some embodiments, polymethacrylates comprise Eudragit. In some embodiments, the ASD comprises an acid in an amount of about 40 mg to about 250 mg. In some embodiments, the acid comprises tartaric acid, succinic acid, or citric acid or a combination thereof. In some embodiments, the PROTAC is ARV-110. In some embodiments, the PROTAC is ARV-471.

In some embodiments, an ASD described herein ASD comprises a PROTAC, for example, ARV-110 or ARV-471 in an amount of about 60 mg to about 150 mg. In some embodiments, the ASD comprises a surfactant in an amount of about 60 mg to about 150 mg. In some embodiments, the surfactant is TPGS or lecithin or a combination thereof. In some embodiments, the ASD comprises a hydrophilic polymer in an amount of about 60 mg to about 150 mg. In some embodiments, the hydrophilic polymer comprises vinylpyrrolidone-vinyl acetate copolymer, PEG, polymethacrylates, hypromellose phthalate (HPMCP), polyvinylcaprolactam, polyvinyl acetate, polyvinyl caprolactam-polyvinyl acetate-polyethylene glycol graft co-polymer, or HPMCAS or a combination thereof. In some embodiments, polymethacrylates comprise Eudragit. In some embodiments, the ASD comprises an acid in an amount of about 60 mg to about 150 mg. In some embodiments, the acid comprises tartaric acid, succinic acid, or citric acid or a combination thereof.

In some embodiments, an ASD described herein comprises a PROTAC, for example, ARV-110 or ARV-471 in an amount of about 50 mg to 100 mg. In some embodiments, the ASD comprises a surfactant in an amount of about 50 mg to 100 mg. In some embodiments, the surfactant is TPGS or lecithin or a combination thereof. In some embodiments, the ASD comprises a hydrophilic polymer in an amount of about 50 mg to 100 mg. In some embodiments, the hydrophilic polymer comprises vinylpyrrolidone-vinyl acetate copolymer or HPMCAS or a combination thereof. In some embodiments, the ASD comprises an acid in an amount of 50 mg to about 100 mg. In some embodiments, the acid comprises tartaric acid, succinic acid, or citric acid or a combination thereof.

Other Additives

In one aspect, pharmaceutical compositions described herein comprise an amorphous solid dispersion (ASD) comprising a PROTAC, a hydrophilic polymer, a surfactant, optionally an adsorbent, and optionally an additional additive or additives. In some embodiments, the PROTAC is a PROTAC of Table 1 or a pharmaceutically acceptable salt thereof. In some cases, the pharmaceutical compositions described herein comprise an ASD and a pharmaceutically acceptable carrier or excipient. In some cases, the pharmaceutically acceptable carrier or excipient comprises a additive. In some cases, the pharmaceutically acceptable carrier or excipient is free of organic acid. In some cases, the pharmaceutically acceptable carrier or excipient comprises an external acid that is not present in the amorphous solid dispersion.

In some embodiments, a pharmaceutically acceptable organic or inorganic acid or acid is included as an internal additive and thus as part of a solid dispersion. In some embodiments, a pharmaceutically acceptable organic or inorganic acid or acids are included as an external additive that is not part of the ASD. In some embodiments, a pharmaceutically acceptable organic or inorganic acid or acids are included in the pharmaceutical compositions. The pharmaceutically acceptable organic acid is selected from the group consisting of tartaric acid, fumaric acid, succinic acid, citric acid, lactic acid, malic acid, aliphatic sulfonic acids (e.g., methanesulfonic acid, ethanesulfonic acid, isethionic acid, etc.) and aromatic sulfonic acids (e.g., benzenesulfonic acid, p-toluenesulfonic acid, etc.), and the pharmaceutically acceptable inorganic acid is selected from the group consisting of hydrochloric acid, sulfuric acid, phosphoric acid and the like.

In some embodiments, the external acid is a surface modified acid comprising an acid particle and a neutral salt layer. In some embodiments, the neutral salt layer is formed by a reaction between a pharmaceutically acceptable base and a powdered or granulated acid. In some embodiments, the surface modified acid is powdered or granulated. In some embodiments, the external acid is a surface modified organic acid. In some embodiments, the external acid is a surface modified acid selected from the group consisting of tartaric acid, fumaric acid, succinic acid, citric acid, lactic acid, malic acid, maleic acid, benzenesulfonic acid, and p-toluenesulfonic acid. In some embodiments, the external acid is a surface modified acid selected from the group consisting of tartaric acid, fumaric acid, succinic acid, citric acid, lactic acid, malic acid, and maleic acid. In some embodiments, the pharmaceutically acceptable base is selected from sodium carbonate, potassium carbonate, sodium acetate, potassium acetate, sodium stearate, potassium stearate, lysine, arginine and histidine. In some embodiments, the pharmaceutically acceptable base is sodium carbonate.

In some embodiments, the external acid in an amount of from about 1 mg to about 5,000 mg. In some embodiments, the external acid is present in the pharmaceutical composition in an amount of from about 1 mg to about 5 mg, about 1 mg to about 50 mg, about 1 mg to about 100 mg, about 1 mg to about 500 mg, about 1 mg to about 1,000 mg, about 1 mg to about 3,000 mg, about 1 mg to about 5,000 mg, about 10 mg to about 50 mg, about 10 mg to about 100 mg, about 10 mg to about 1,000 mg, about 10 mg to about 3,000 mg, about 10 mg to about 5,000 mg, about 20 mg to about 50 mg, about 20 mg to about 100 mg, about 20 mg to about 200 mg, about 50 mg to about 100 mg, about 50 mg to about 200 mg, about 50 mg to about 500 mg, or about 100 mg to about 200 mg. In some embodiments, the external acid is present in the pharmaceutical compositions and is not present in the ASD. In some embodiments, the external acid is malic acid. In some embodiments, the external acid is citric acid. In some embodiments, the external acid is tartaric acid. In some embodiments, the external acid is succinic acid.

In some embodiments, the external acid is present in a pharmaceutical composition by weight of about 1% to about 60%. In some embodiments, the external acid is present in a pharmaceutical composition by weight of about 5% to about 35%. In some embodiments, the external acid is present in a pharmaceutical composition in amount of about 1% to about 5%, about 1% to about 10%, about 1% to about 15%, about 1% to about 20%, about 1% to about 25%, about 1% to about 30%, about 1% to about 35%, about 1% to about 40%, about 1% to about 50%, about 1% to about 60%, about 5% to about 10%, about 5% to about 15%, about 5% to about 20%, about 5% to about 25%, about 5% to about 30%, about 5% to about 35%, about 5% to about 40%, about 5% to about 50%, about 5% to about 60%, about 10% to about 15%, about 10% to about 20%, about 10% to about 25%, about 10% to about 30%, about 10% to about 35%, about 10% to about 40%, about 10% to about 50%, about 10% to about 60%, about 15% to about 20%, about 15% to about 25%, about 15% to about 30%, about 15% to about 35%, about 15% to about 40%, about 15% to about 50%, about 15% to about 60%, about 20% to about 25%, about 20% to about 30%, about 20% to about 35%, about 20% to about 40%, about 20% to about 50%, about 20% to about 60%, about 25% to about 30%, about 25% to about 35%, about 25% to about 40%, about 25% to about 50%, about 25% to about 60%, about 30% to about 35%, about 30% to about 40%, about 30% to about 50%, about 30% to about 60%, about 35% to about 40%, about 35% to about 50%, about 35% to about 60%, about 40% to about 50%, about 40% to about 60%, or about 50% to about 60% by weight. In some embodiments, the external acid is present in a pharmaceutical composition in an amount of about 1%, about 5%, about 10%, about 15%, about 20%, about 25%, about 30%, about 35%, about 40%, about 50%, or about 60% by weight. In some embodiments, the external acid is present in a pharmaceutical composition in an amount of at least about 1%, about 5%, about 10%, about 15%, about 20%, about 25%, about 30%, about 35%, about 40%, or about 50% by weight. In some embodiments, the external acid is present in a pharmaceutical composition in an amount of at most about 5%, about 10%, about 15%, about 20%, about 25%, about 30%, about 35%, about 40%, about 50%, or about 60% by weight. In some embodiments, the external acid is present in the pharmaceutical compositions and is not present in the ASD. In some embodiments, the external acid is malic acid. In some embodiments, the external acid is citric acid. In some embodiments, the external acid is tartaric acid.

A pharmaceutical composition described herein comprises one or more preservatives. The ASD comprises one or more preservatives. The preservatives can include antimicrobials, antioxidants, and agents that enhance sterility. Exemplary preservatives include ascorbic acid, ascorbyl palmitate, butylatedhydroxyanisole (BHA), Butylatedhydroxytoulene (BHT), propyl gallate, citric acid, EDTA and its salts, erythorbic acid, fumaric acid, malic acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like. In some embodiments, an amorphous solid dispersion composition or a pharmaceutical composition described herein comprises an antioxidant. In some embodiments, the antioxidant comprises a-tocopherol acetate, acetone sodium bisulfite, acetylcysteine, ascorbic acid, vitamin E, ascorbyl palmitate, BHA, BHT, cysteine, cysteine hydrochloride, d-a-tocopherol (natural or synthetic), dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, or tocopherols.

In some embodiments, pharmaceutical compositions described herein comprise an ASD comprising a PROTAC, a hydrophilic polymer, a surfactant, optionally an adsorbent, and optionally an additional additive or additives. In some embodiments, an antioxidant or mixture of antioxidants are included as the internal additive thus as part of a solid dispersion. In some embodiments, an antioxidant or mixture of antioxidants are included as an external additive. The exemplary antioxidants include but are not limited to vitamin E, BHT, BHA, gallic acid, propyl gallate, ascorbic acid, ascorbyl palmitate, 4hydroxymethyl-2,6-di-tert-butyl phenol, and tocopherol.

In some embodiments, the antioxidant is present in the ASD by weight of about 0.0001% to about 15%. In some embodiments, the antioxidant is present in the ASD by weight of about 0.0001% to about 0.1%, about 0.0001% to about 1%, about 0.0001% to about 2%, about 0.01% to about 1%, about 0.01% to about 2%, about 0.01% to about 10%, about 1% to about 2%, about 1% to about 5%, about 1% to about 7%, about 1% to about 10%, about 1% to about 15%, about 2% to about 10%, about 2% to about 15%, about 5% to about 10%, about 5% to about 15%, or about 10% to about 15%. In some embodiments, the antioxidant is present in the ASD by weight of at least about 0.0001%, about 0.001%, about 0.01%, about 0.1%, about 1%, about 2%, about 5%, about 7%, or about 10%. In some embodiments, the antioxidant is present in the ASD by weight of at most about 0.001%, about 0.01%, about 0.1%, about 1%, about 2%, about 5%, about 7%, about 10%, or about 15%.

In some embodiments, the antioxidant is present in a pharmaceutical composition described herein by weight of about 0.0001% to about 15%. In some embodiments, the antioxidant is present in a pharmaceutical composition described herein by weight of about 0.0001% to about 0.1%, about 0.0001% to about 1%, about 0.001% to about 0.1%, about 0.001% to about 1%, about 0.01% to about 10%, about 0.1% to about 1%, about 0.1% to about 2%, about 0.1% to about 5%, about 0.1% to about 10%, about 1% to about 2%, about 1% to about 5%, about 1% to about 10%, about 1% to about 15%, about 2% to about 5%, about 2% to about 10%, about 5% to about 7%, about 5% to about 10%, or about 1% to about 15%. In some embodiments, the antioxidant is present in a pharmaceutical composition described herein in an amount of at least about 0.0001%, about 0.001%, about 0.01%, about 0.1%, about 1%, about 2%, or about 5% by weight. In some embodiments, the antioxidant is present in a pharmaceutical composition described herein in an amount of at most about 0.001%, about 0.01%, about 0.1%, about 1%, about 2%, about 5%, about 7%, about 10%, or about 15% by weight. In some embodiments, the antioxidant is present in the amorphous solid dispersion. In some embodiments, the antioxidant is present in the pharmaceutical composition but not present in the ASD.

The above different additives can be used alone or together.

In some embodiments, a pharmaceutical composition described herein comprises a glidants. In some embodiments, the glidant is silicon dioxide powder. In some embodiments, the silicon dioxide is present in the amorphous solid dispersion. In some embodiments, silicon dioxide is not present in the amorphous solid dispersion, but is included in the pharmaceutical composition. In some embodiments, the silicon dioxide is present in the amorphous solid dispersion as well as being a component of the pharmaceutical composition outside of the amorphous solid dispersion.

In some embodiments, the ASD comprises a PROTAC. In some embodiments, the PROTAC has a calculated log P or log P of at least 2.0. In some embodiments, the PROTAC is ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413, or a pharmaceutically acceptable salt thereof. In some embodiments, the PROTAC is ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC is a pharmaceutically acceptable salt of ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, or KT-413. In some embodiments, the PROTAC is one listed in Table 1, or a pharmaceutically acceptable salt thereof. In some embodiments, other additives conventionally mixed with the ASD is included. In some embodiments, other additives conventionally mixed with pharmaceutical compositions is included but are not present in the ASD. Such additives are well known in the art. The additives include, but are not limited to, anti-adherents (anti-sticking agents, glidants, flow promoters, lubricants) (e.g., talc, magnesium stearate, fumed silica (Carbosil, Aerosil), micronized silica (Syloid No. FP 244. Grace U.S.A.), polyethylene glycols, surfactants, waxes, stearic acid, stearic acid salts, stearic acid derivatives, starch, hydrogenated vegetable oils, sodium benzoate, sodium acetate, silicone dioxide, leucine, PEG-4000 and magnesium lauryl sulfate) anticoagulants (e.g., acetylated monoglycerides), antifoaming agents (e.g., long-chain alcohols and silicone derivatives), antioxidants (e.g., BHT, BHA, gallic acid, propyl gallate, ascorbic acid, ascorbyl palmitate, 4hydroxymethyl-2,6-di-tert-butyl phenol, tocopherol, etc.), binders (adhesives), i.e., agents that impart cohesive properties to powdered materials through particle-particle bonding, (e.g., matrix binders (dry starch, dry sugars), film binders (, starch paste, celluloses, bentonite, sucrose)), chemical binders (e.g., polymeric cellulose derivatives, such as carboxy methyl cellulose, etc., sugar syrups, corn syrup, water soluble polysaccharides (e.g., acacia, tragacanth, guar, alginates, etc.), gelatin, gelatin hydrolysate, agar, sucrose, dextrose, non-cellulosic binders (e.g., PEG, pregelatinized starch, sorbitol, glucose, etc.), bufferants, where the acid is a pharmaceutically acceptable acid, (e.g., hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, etc.) and where the base is a pharmaceutically acceptable base, (e.g., an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a pharmaceutically acceptable salt of acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, parabromophenylsulfonic acid, propionic acid, p-toluenesulfonic acid, salicylic acid, stearic acid, succinic acid, tannic acid, tartaric acid, thioglycolic acid, toluenesulfonic acid, and uric acid, chelating agents (e.g., EDTA and EDTA salts), coagulants (e.g., alginates) colorants or opaquants, (e.g., titanium dioxide, food dyes, lakes, natural vegetable colorants, iron oxides, silicates, sulfates, magnesium hydroxide and aluminum hydroxide), coolants, (e.g. halogenated hydrocarbons (e.g., trichloroethane, trichloroethylene, dichloromethane, fluorotrichloromethane), diethylether and liquid nitrogen) cryoprotectants (e.g., trehalose, phosphates, citric acid, tartaric acid, gelatin, dextran, mannitol, etc.), diluents or fillers, (e.g., lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose disintegrants or super disintegrants (e.g., croscarmellose sodium, starch, starch derivatives, clays, gums, cellulose, cellulose derivatives, alginates, sodium starch glycolate and microcrystalline cellulose), hydrogen bonding agents, (e.g., magnesium oxide), flavorants or desensitizers, (e.g., spray-dried flavors, essential oils and ethyl vanillin), ion-exchange resins (e.g., styrene/divinyl benzene copolymers, and quaternary ammonium compounds), plasticizers (e.g., polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate), preservatives (e.g., ascorbic acid, boric acid, sorbic acid, benzoic acid, and salts thereof, parabens, phenols, benzyl alcohol, and quaternary ammonium compounds), solvents (e.g., alcohols, ketones, esters, chlorinated hydrocarbons and water) sweeteners, including natural sweeteners (e.g., maltose, sucrose, glucose, sorbitol, glycerin and dextrins), and artificial sweeteners (e.g., aspartame, saccharine and saccharine salts) and thickeners (viscosity modifiers, thickening agents), (e.g., sugars, cellulosics, polymers and alginates).

Additives can also be materials such as proteins (e.g., collagen, gelatin, Zein, gluten, mussel protein, lipoprotein), carbohydrates (e.g., alginates, carrageenan, cellulose derivatives, pectin, starch, chitosan), gums (e.g., xanthan gum, gum arabic), spermaceti, natural or synthetic waxes, carnuaba wax, fatty acids (e.g., stearic acid, hydroxystearic acid), fatty alcohols, sugars, shellacs, such as those based on sugars (e.g., lactose, sucrose, dextrose) or starches, polysaccharide-based polymers (e.g., maltodextrin and maltodextrin derivatives, dextrates, cyclodextrin and cyclodextrin derivatives), cellulosic-based polymers (e.g., microcrystalline cellulose, sodium carboxymethyl cellulose, hydroxypropylmethyl cellulose, ethyl cellulose, hydroxypropyl cellulose, cellulose acetate, cellulose nitrate, cellulose acetate butyrate, cellulose acetate, trimellitate, carboxymethylethyl cellulose, hydroxypropylmethyl cellulose phthalate), inorganics, (e.g., dicalcium phosphate, hydroxyapitite, tricalcium phosphate, talc and titania), polyols (e.g., mannitol, xylitol and sorbitol polyethylene glycol esters) and polymers (e.g., alginates, poly(lactide coglycolide), gelatin, crosslinked gelatin and agar-agar). In some embodiments, the proteins comprise amino acids such as glutamic acid, aspartic acid, or acidic salts of glycine, alanine or serine.

In some embodiments, the pharmaceutical compositions described herein comprises a pharmaceutically acceptable carrier or excipient, wherein the pharmaceutically acceptable carrier or excipient is not part of the ASD. In some embodiments, the pharmaceutically acceptable carrier or excipient is free of organic acid. In some embodiments, the pharmaceutically acceptable carrier or excipient is free of inorganic acid. In some embodiments, the pharmaceutically acceptable carrier or excipient is free of acid. In some embodiments, the pharmaceutically acceptable carrier or excipient comprises an external acid that is not present in the amorphous solid dispersion.

In some embodiments, the external acid is a surface modified acid. In some embodiments, a surface modified acid comprises a powdered or granulated acid with a neutral salt layer at least partially coating the exterior of the powdered or granulated acid. In some embodiments, the surface modified acid comprises a powdered or granulated acid selected from tartaric acid, fumaric acid, succinic acid, citric acid, lactic acid, malic acid, maleic acid, benzenesulfonic acid, p-toluenesulfonic acid, glutamic acid, aspartic acid, and acidic salts of glycine, alanine or serine. In some embodiments, the surface modified acid comprises a powdered or granulated acid selected from tartaric acid, fumaric acid, succinic acid, citric acid, lactic acid, and malic acid. In some embodiments, the surface modified acid comprises a powdered or granulated acid selected from tartaric acid.

In some embodiments, the neutral salt layer decreases the reactivity of the acid with other components of the composition, such as the active ingredient. In some embodiments, a PROTAC shows improved solubility in the presence of acids. In some embodiments, pharmaceutical compositions with surface modified acids provide increased solubility while preserving the stability of the active ingredient.

In some embodiments, the surface modified acid is prepared by reacting a basic solution with the acid particle (e.g., powdered or granulated acid to form a neutral salt layer on the surface of the acid. In some embodiments, the neutral salt layer comprises an anion from the acid and a cation from the base. In some embodiments, the basic solution comprises a pharmaceutically acceptable base. In some embodiments, the pharmaceutically acceptable base is selected from sodium carbonate, potassium carbonate, sodium acetate, potassium acetate, sodium stearate, potassium stearate, lysine, arginine and histidine. In some embodiments, the pharmaceutically acceptable base is a carbonate base.

In some embodiments, the surface modified acid is prepared by reacting a basic solution with the powdered or granulated acid to form a neutral salt layer on the surface of the acid. In some embodiments, the concentration of the basic solution in the pharmaceutical composition by weight is about 1% to about 30%. In some embodiments, the concentration of the basic solution by weight in the pharmaceutical composition is about 5% to about 15%. In some embodiments, the concentration of the basic solution in the pharmaceutical composition by weight is about 1% to about 5%, about 1% to about 10%, about 1% to about 12.5%, about 1% to about 15%, about 1% to about 20%, about 1% to about 25%, about 1% to about 30%, about 2.5% to about 10%, about 2.5% to about 15%, about 2.5% to about 20%, about 2.5% to about 30%, about 5% to about 7.5%, about 5% to about 10%, about 5% to about 20%, about 5% to about 25%, about 10% to about 15%, about 10% to about 20%, about 10% to about 25%, about 10% to about 30%, about 12.5% to about 15%, about 12.5% to about 20%, about 12.5% to about 25%, about 12.5% to about 30%, about 15% to about 20%, about 15% to about 25%, about 15% to about 30%, or about 25% to about 30%. In some embodiments, the concentration of the basic solution in the pharmaceutical composition by weight is at most about 2.5%, about 5%, about 7.5%, about 10%, about 12.5%, about 15%, about 20%, about 25%, or about 30%. In some embodiments, the weight ratio of the base to acid is about 1% to about 20%. In some embodiments, the weight ratio of the base to acid is about 1% to about 5%, about 1% to about 10%, about 1% to about 15%, about 1% to about 20%, about 2% to about 20%, about 5% to about 10%, about 5% to about 15%, about 5% to about 20%, about 10% to about 15%, about 10% to about 20%, or about 15% to about 20%. In some embodiments, the weight ratio of the base to acid in the pharmaceutical composition is at least about 1%, about 2%, about 3%, about 4%, about 5%, about 6%, about 7%, about 8%, about 9%, about 10%, or about 15%. In some embodiments, the weight ratio of the base to acid is at most about 2%, about 3%, about 4%, about 5%, about 6%, about 7%, about 8%, about 9%, about 10%, about 15%, or about 20%.

In an exemplary embodiment, surface modified tartaric acid is prepared by reacting a basic solution of sodium carbonate with powdered tartaric acid to form a neutral salt layer on the tartaric acid. In some embodiments, the sodium carbonate aqueous solution is formulated at a concentration of about 5-30%. The amount of sodium carbonate is about 1-10% in a ratio by weight to the tartaric acid Second, the formulated sodium carbonate aqueous solution is added to tartaric acid powder particles having a particle size of about 40 to 60 mesh. After stirring, the tartaric acid powder particles are dried in a drying oven or a fluidized bed to yield the modified tartaric acid powder particles.

Oral Dosage Forms

The present pharmaceutical compositions can take the form of solutions, suspensions, emulsion, tablets, pills, pellets, capsules, capsules containing liquids, powders, suppositories, emulsions, suspensions, or any other form suitable for use. Preferred pharmaceutical compositions are formulated for oral delivery. In some embodiments, the pharmaceutically acceptable vehicle is a capsule. Capsules may be hard capsules or soft capsules, push-fit capsules made of gelatin, as well as soft, sealed capsules made of gelatin and a plasticizer (such as glycerol or sorbitol). In some embodiments, the capsule contains about 1000 mg of the pharmaceutical composition. In some embodiments, the capsule contains less than 1000 mg of the pharmaceutical composition. Capsules can be of any size. Examples of standard sizes include, but are not limited to those listed in Table 2, (#000, #00, #0, #1, #2, #3, #4, and #5). In some embodiments, the pharmaceutical composition is in the dosage form of a liquid filled into a hard capsule. In some embodiments, the pharmaceutical composition is in the dosage form of a liquid filled into a soft capsule. In some embodiments, the pharmaceutical composition is in the dosage form of a tablet. In some embodiments, the pharmaceutical composition comprises an amorphous solid dispersion. In some embodiments, the pharmaceutical composition comprises an amorphous solid dispersion in the dosage form of a tablet. In some embodiments, the pharmaceutical composition is in the dosage form of a multilayer tablet. In some embodiments, the tablet has one, two, three, four or more layers. In some embodiments, the tablet has an inner core and an outer core.

TABLE 2

| Size | Volume (mL) | Locked length (mm) | External diameter (mm) |
|---|---|---|---|
| 000 | 1.37 | 26.1 | 9.9 |
| 00 | 0.91 | 23.3 | 8.5 |
| 0 | 0.68 | 21.7 | 7.6 |
| 1 | 0.50 | 19.4 | 6.9 |
| 2 | 0.37 | 18.0 | 6.3 |
| 3 | 0.30 | 15.9 | 5.8 |
| 4 | 0.21 | 14.3 | 5.3 |

See, e.g., Remington's Pharmaceutical Sciences, page 1658-1659 (Alfonso Gennaro ed., Mack Publishing Company, Easton Pa., 18$^{th}$ ed., 1990), which is incorporated by reference. In some embodiments, the capsules used herein are of size #00 or #0.

Methods of Administration

Pharmaceutical compositions described herein are administered for the treatment or prevention of diseases. When used to treat or prevent diseases or disorders, pharmaceutical compositions are administered or applied singly, or in combination with other agents.

Pharmaceutical compositions may also be administered or applied singly, in combination with other pharmaceutically active agents. Provided herein are methods of treatment and prophylaxis by administration to a subject in need of such treatment of a therapeutically effective amount of a pharmaceutical composition of the disclosure. In some embodiments, the subject is an animal, e.g., a mammal such as a human. In some embodiments, pharmaceutical compositions described herein include an ASD comprising PROTAC, a hydrophilic polymer, a surfactant, optionally an adsorbent and optionally an organic or inorganic acid. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof. In some embodiments, the PROTAC, the hydrophilic polymer, and the surfactant are formulated as an amorphous solid dispersion.

In some embodiments, the pharmaceutical compositions are administered orally. In some embodiments, the pharmaceutical compositions are administered in an oral liquid, semi-liquid or semisolid dosage form. In some embodiments, the pharmaceutical compositions are administered as a solid oral dosage form. In some embodiments, the pharmaceutical compositions are administered as a liquid oral dosage form. In some embodiments, the pharmaceutical compositions are administered as a pill, tablet, chewable tablet, specialty tablet, buccal tablet, sub-lingual tablet, orally-disintegrating tablet, capsule, gel capsule, soft gel capsule, hard gel capsule, specialty capsule, buccal capsule, sub-lingual capsule, orally-disintegrating capsule, powder, granule, crystal or orally dispersible film. In some embodiments, the pharmaceutical compositions are administered as a liquid or a capsule. In some embodiments, the pharmaceutical compositions are administered as a soft gel capsule. In some embodiments, the pharmaceutical compositions are administered as a hard gel capsule.

In some embodiments, the pharmaceutical composition is formulated for oral administration. In some embodiments, the pharmaceutical composition is formulated for once daily dosing. In some embodiments, the pharmaceutical composition is formulated for twice daily dosing.

In some embodiments, the pharmaceutical composition comprising an ASD is formulated with a lower PROTAC dosing than a reference composition comprising the same crystalline PROTAC or PROTAC not in an ASD. In some embodiments, the pharmaceutical composition comprising an ASD is formulated with a PROTAC dosing that is lower than a reference composition comprising the same crystalline PROTAC or PROTAC not in an ASD by at least 5%, 10%, 15%, 20%, 30%, 40%, 50%, 60%, or 70%. In some embodiments, the pharmaceutical composition comprising an ASD is formulated with a PROTAC dosing that is lower than a reference composition comprising the same crystalline PROTAC or PROTAC not in an ASD by about 10% to about 50%. In some embodiments, the pharmaceutical composition comprising an ASD is formulated with a PROTAC dosing that is 25% lower than a reference composition comprising the same crystalline PROTAC or PROTAC not in an ASD. In some embodiments, the pharmaceutical composition comprising an ASD is formulated with a PROTAC dosing that is 50% lower than a reference composition comprising the same crystalline PROTAC or PROTAC not in an ASD. In some embodiments, the pharmaceutical composition comprising an ASD is formulated with a PROTAC dosing that is 90% lower than a reference composition comprising the same crystalline PROTAC or PROTAC not in an ASD. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof.

Conditions

In one aspect, the pharmaceutical compositions or ASDs described herein may be used to treat a disease or condition by administering to a subject in need thereof the pharmaceutical compositions or the ASDs. In some embodiments, the disease or condition is cancer. In some embodiments, the disease or condition is a mental disorder. The pharmaceutical compositions or ASDs described herein can also be used in ubiquitinating or degrading a target protein in a cell of a subject, comprising administering to a subject.

In some embodiments, the pharmaceutical compositions may be used to inhibit one or more tyrosine kinases in a subject in need of inhibiting such tyrosine kinases. In some embodiments, the subject has a disease or condition associated with tyrosine kinase. In some embodiments, pharmaceutical compositions described herein include a PROTAC, a hydrophilic polymer, and a surfactant. In some embodiments, pharmaceutical compositions described herein include a PROTAC, a hydrophilic polymer, and a surfactant. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof. In some embodiments, the PROTAC, hydrophilic polymer, and the surfactant are formulated as an amorphous solid dispersion.

In one aspect, described herein is a method of treating a disease or condition in a subject. The disease or condition can be a cancer. In some embodiments, a pharmaceutical composition described herein may be used to treat or prevent cancer. In some embodiments, the pharmaceutical compositions may be used to treat or prevent prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy, or age-related macular degeneration. In some embodiments, the pharmaceutical compositions may be used to treat or prevent prostate cancer. In some embodiments, the pharmaceutical compositions can be used to treat or prevent one or more of leukemia, Philadelphia chromosome (Ph+)-positive chronic myelogenous leukemia, gastrointestinal stromal tumor, Parkinson's disease, castration-resistant prostate cancer, metastatic castration-resistant prostate cancer, castration-recurrent prostate cancer, high-risk castration-sensitive prostate cancer, metastatic high-risk castration-sensitive prostate cancer, hormone-resistant prostate cancer, hormone-refractory prostate cancer, androgen-independent prostate cancer, androgen deprivation resistant prostate cancer, androgen ablation resistant prostate cancer, androgen depletion-independent prostate cancer, anti-androgen-recurrent prostate cancer, metastatic castration-resistant prostate cancer in patients who have already received prior chemotherapy containing docetaxel, newly diagnosed high risk metastatic hormone sensitive prostate cancer (mHSPC), metastatic castration resistant prostate cancer in patients who are asymptomatic, mildly symptomatic after failure of androgen deprivation therapy in whom chemotherapy is not yet clinically indicated, metastatic castration resistant prostate cancer in patients whose disease has progressed on or after a docetaxel-based chemotherapy regimen. In some embodiments, the pharmaceutical compositions are used to treat newly diagnosed adult patients with Philadelphia chromosome positive chronic myeloid leukemia (Ph+ CML) in chronic phase. In some embodiments, the pharmaceutical compositions are used to treat children with newly diagnosed Philadelphia chromosome-positive (Ph+) chronic myeloid leukemia (CML) in the chronic phase (CP). In some embodiments, the pharmaceutical compositions are used to treat chronic phase (CP) and accelerated phase (AP) Ph+ CML in adult patients resistant to or intolerant to prior therapy that included imatinib. In some embodiments, pharmaceutical compositions described herein include a PROTAC, a hydrophilic polymer, and a surfactant. In some embodiments, pharmaceutical compositions described herein include a PROTAC, a hydrophilic polymer, and a phospholipid or poloxamer.

In some embodiments, pharmaceutical compositions described herein include a PROTAC, a hydrophilic polymer, and lecithin. In some embodiments, pharmaceutical compositions described herein include a PROTAC, a hydrophilic polymer, and lecithin. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof. In some embodiments, the PROTAC, hydrophilic polymer, and the surfactant are formulated as an amorphous solid dispersion.

In some embodiments, the subject is an adult. In some embodiments, the subject is a child. In some embodiments, the subject is at least one year old. In some embodiments, the subject is less than one year old. In some embodiments, the subject is 1 to 12 years old. In some embodiments, the subject is 1 to 18 years old. In some embodiments, the subject is 12 to 18 years old. In some embodiments, the subject is at least 18 years old. In some embodiments, the subject is at least 24 years old. In some embodiments, the subject is 1 to 90 years old. In one aspect, described herein is a method of inhibiting one or more tyrosine kinases.

In some embodiments, the pharmaceutical composition is used to treat a cancer selected from the group consisting of breast cancer, cancer is selected from the group consisting of acute lymphoblastic leukemia, acute myeloid leukemia, adrenocortical carcinoma, AIDS-related cancers. AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor. In some embodiments, the disease or condition is associated with tyrosine kinase.

In some embodiments, pharmaceutical compositions described herein can be used in combination therapy with at least one other therapeutic agent. The pharmaceutical composition and the therapeutic agent can act additively or, more preferably, synergistically. In some embodiments, the pharmaceutical composition is administered concurrently with the administration of another therapeutic agent. In some embodiments, a pharmaceutical composition is administered prior or subsequent to administration of another therapeutic agent. In some embodiments, pharmaceutical compositions described herein include a PROTAC, a hydrophilic polymer, and a surfactant. In some embodiments, pharmaceutical compositions described herein include a PROTAC, a hydrophilic polymer, and a phospholipid or poloxamer. In some embodiments, pharmaceutical compositions described herein include a PROTAC, a hydrophilic polymer, and lecithin. In some embodiments, pharmaceutical compositions described herein include a PROTAC, a hydrophilic polymer, and lecithin. In some embodiments, the PROTAC is one listed in Table 1, or a pharmaceutically acceptable salt thereof. In some embodiments, the PROTAC has a log P 2.0 or higher. In some embodiments, the PROTAC is ARV-110 or a pharmaceutically acceptable salt thereof. In some embodiments, the PROTAC is ARV-471 or a pharmaceutically acceptable salt thereof. In some embodiments, the PROTAC, hydrophilic polymer, and the surfactant are formulated as an amorphous solid dispersion.

ARV-110

In some embodiments, the pharmaceutical compositions or ASD described herein comprising ARV-110 or a pharmaceutically acceptable salt thereof is used to treat cancer. In some embodiments, the cancer comprises a solid tumor. In some embodiments, the solid tumor is prostate cancer. In some embodiments, the prostate cancer is metastatic castration-resistant prostate cancer.

In some embodiments, the pharmaceutical compositions or ASD described herein comprise ARV-110 or a pharmaceutically acceptable salt thereof is used to inhibit AR, comprising administering to a subject in need thereof the pharmaceutical compositions or the ASD.

In some embodiments, the pharmaceutical compositions or ASD described herein comprise ARV-110 or a pharmaceutically acceptable salt thereof is administered to a subject in combination of an immunotherapeutic agent or an chemotherapeutic agent. In some embodiments, the subject has progressed on existing therapies. In some embodiments, the subject is an adult. In some embodiments, the subject is a male.

ARV-471

In some embodiments, the pharmaceutical compositions or ASD described herein comprising ARV-471 or a pharmaceutically acceptable salt thereof is used to treat cancer. In some embodiments, the cancer comprises a solid tumor. In some embodiments, the solid tumor is breast cancer. In some embodiments, the breast cancer is estrogen receptor (ER)+/human epidermal growth factor receptor 2 (HER2)– breast cancer. In some embodiments, the breast cancer is locally advanced or metastatic ER+/HER2– breast cancer.

In some embodiments, the pharmaceutical compositions or ASD described herein comprise ARV-471 or a pharmaceutically acceptable salt thereof is used to inhibit ER, comprising administering to a subject in need thereof the pharmaceutical compositions or the ASD.

In some embodiments, the pharmaceutical compositions or ASD described herein comprise ARV-471 or a pharmaceutically acceptable salt thereof is administered to a subject in combination of an immunotherapeutic agent or an chemotherapeutic agent. In some embodiments, the subject has progressed on existing therapies. In some embodiments, the subject is an adult. In some embodiments, the subject is a female.

Methods of Manufacture

Disclosed herein is a method for preparing an amorphous solid dispersion, comprising the steps of (a) combining (i) an API or a pharmaceutically acceptable salt thereof, wherein the API is a PROTAC, (ii) one or more surfactants (e.g., polymeric non-ionic surfactants and phospholipids), (iii) a hydrophilic polymer (e.g., non-ionic hydrophilic polymer or an ionic hydrophilic polymer), (iv) optionally an adsorbent or adsorbents, (v) optionally other additional additives and (vi) a solvent or solvent mixture, thereby producing a liquid mixture (a solution or suspension), and (b) removing all or a part of the solvent from said mixture, thereby producing an amorphous solid dispersion. In some embodiments, the solvent is selected from an organic solvent and water. In some embodiments, the organic solvent is ethyl acetate, ethanol, isopropanol, or methanol, n-butanol, n-propanol, isopropanol, formic acid, nitromethane, ethanol, acetic acid. N-methylpyrrolidone, tetrahydrofuran (THF), methyl acetate, dimethylformamide, acetonitrile, dimethyl sulfoxide, dichloromethane (DCM), acetone, and any combination thereof. In some embodiments, the solvent is an alcohol. In some embodiments, the alcohol is ethanol. In some embodiments, the solvent is selected from dichloromethane, methanol, tetrahydrofuran, and acetone. In some embodiments, the solvent is selected from a mixture of these solvents. In some embodiments, combining comprises dissolving the PROTAC or a pharmaceutically acceptable salt thereof, the surfactant, the non-ionic or ionic hydrophilic polymer, and optionally an adsorbent and/or additional additives in the solvent. In some embodiments, the adsorbent is suspended in the solvent. In some embodiments, removing of the solvent comprises vacuum-drying, spray-drying or rotary evaporation. In some embodiments, the PROTAC is a PROTAC of Table 1 or a pharmaceutically acceptable salt thereof. In some embodiments, the PROTAC is ARV-110 or a pharmaceutically acceptable salt thereof. In some embodiments, the PROTAC is ARV-471 or a pharmaceutically acceptable salt thereof.

Disclosed herein is a method for preparing an amorphous solid dispersion, comprising the steps of (a) combining (i) an active pharmaceutical ingredient or a pharmaceutically acceptable salt thereof, (ii) one or more surfactants (e.g., polymeric non-ionic surfactants and phospholipids), (iii) a hydrophilic polymer (e.g., non-ionic or ionic hydrophilic polymer), (iv) optionally an adsorbent or adsorbents, and (v) optionally other additional additives such as an acid. In some embodiments, the API, surfactants, and hydrophilic polymer can be combined by any suitable methods in the art. In some embodiments, the API, surfactants, and hydrophilic polymer are combined by melt extrusion (such as hot melt extrusion or HME). In some embodiments, the method for preparing an amorphous solid dispersion, comprises the steps of (a) combining (i) a PROTAC or a pharmaceutically acceptable salt thereof, (ii) one or more surfactants (e.g., polymeric non-ionic surfactants and phospholipids), (iii) a hydrophilic polymer (e.g., non-ionic or ionic hydrophilic polymer), (iv) optionally other additional additives and (v) a solvent or solvent mixture, to produce a liquid mixture or solution; (b) spraying the liquid mixture or solution onto an adsorbent or adsorbents; and (c) removing all or a part of the solvent from the liquid mixture or solution to produce an amorphous solid dispersion. In some embodiments, the solvent is selected from an organic solvent and water. In some embodiments, the organic solvent is ethyl acetate, ethanol, isopropanol, or methanol, n-butanol, n-propanol, isopropanol, formic acid, nitromethane, ethanol, acetic acid, N-methylpyrrolidone, tetrahydrofuran, methyl acetate, dimethylformamide, acetonitrile, dimethyl sulfoxide, dichloromethane (DCM), acetone, and any combination thereof. In some embodiments, the solvent is an alcohol. In some embodiments, the alcohol is ethanol. In some embodiments, the solvent is selected from dichloromethane, tetrahydrofuran, methanol and acetone. In some embodiments, the solvent is dioxane. In some embodiments, the solvent is methyl ethyl ketone. In some embodiments, the solvent is chloroform. In some embodiments, the solvent is selected from a mixture of these solvents. In some embodiments, combining comprises dissolving the PROTAC or a pharmaceutically acceptable salt thereof, the surfactant, the non-ionic or ionic hydrophilic polymer, and optionally additional additives in the solvent. In some embodiments, an amorphous solid dispersion is produced by a fluid-bed spraying and drying process. In some embodiments, an amorphous solid dispersion is produced by rotary evaporation. In some embodiments, the adsorbent is suspended in the solvent. In some embodiments, removing of the solvent comprises vacuum-drying, spray-drying, rotary evaporation or fluid bed drying. In some embodiments, the API is an API of Table 1 or a pharmaceutically acceptable salt thereof. In some embodiments, the solvent or solvent mixture is one selected from Table 6.

TABLE 6

Exemplary solvents or solvent mixture suitable for manufacturing an ASD.

| Solvent or solvent mixture | Ratio, volume by volume (V/V) |
|---|---|
| Methanol | — |
| Water | — |
| DCM | — |
| Ethyl acetate | — |
| Dioxane | — |
| Methyl ethyl ketone | — |
| Tetrahydrofuran | — |
| Chloroform | — |
| Acetonitrile | — |
| Ethanol | — |
| Acetone | — |
| Water/Methanol | 5/5 to 4/6 |
| Methanol/Methyl ethyl ketone | 7/3 to 6/4 |
| Ethanol/Acetonitrile | 3/7 to 4/6 |
| Isopropanol/DCM | 3/7 to 5/5 |
| Dichloromethane (DCM)/Methanol | 7/3 to 5/5 |
| Acetone/Water | 5/5 to 8/2 |
| Methyl ethyl ketone/chloroform | 5/5 to 4/6 |
| Dioxane/Methanol | 7/3 to 5/5 |
| Methanol/Chloroform | 7/3 to 6/4 |
| Acetonitrile/DCM | 3/7 to 4/6 |
| Tetrahydrofuran/Acetonitrile | 2/8 to 3/7 |
| Ethyl acetate/DCM | 5/5 to 4/6 |
| Chloroform/Water | 3/7 to 4/6 |
| Acetonitrile/Methanol | 3/7 to 5/5 |

In an exemplary manufacturing workflow, an amorphous solid dispersion is formed by first adding the PROTAC, hydrophilic polymer, surfactant, and optionally an additive or additives in a solvent (e.g., a solvent or solvent mixture selected from Table 6) or water at a room temperature or heated to form a clear solution. The clear solution is then spray dried or vacuum dried to form an amorphous solid dispersion. Additionally, an amorphous solid dispersion is formed by first a PROTAC, a hydrophilic polymer, a surfactant, and optionally an additive or additives in a solvent (e.g., a solvent or solvent mixture selected from Table 6) or water in a room temperature or heated to form a clear solution. An adsorbent or a mixture of adsorbents is further added at a room temperature or heated to form a homogenous suspension. The homogenous suspension is then spray dried or vacuum dried to form an amorphous solid dispersion. Following the formation of an amorphous solid dispersion, the amorphous solid dispersion is mixed with other additives and excipients used in the formulation. The mixture is then pressed into tablets or loaded into capsules.

In an exemplary manufacturing workflow, an amorphous solid dispersion is formed by first dispersing PROTAC in a solvent (e.g., a solvent or solvent mixture selected from Table 6) or water, optionally with stirring, at a room temperature or heated to form a clear solution. Then, a hydrophilic polymer, a surfactant, and optionally an additive or additives are added in the solution. Optionally, an adsorbent or a mixture of adsorbents is further added to the solution at a room temperature or heated to form a homogenous suspension. The solution or suspension is then spray dried to form an amorphous solid dispersion. The homogenous suspension is then spray dried to form an amorphous solid dispersion. Following the formation of an amorphous solid dispersion, the amorphous solid dispersion is mixed with other additives and excipients used in the formulation. The mixture is then pressed into tablets or loaded into capsules.

A typical spray dryer comprises three chambers, a drying chamber, a cyclone chamber and a sample collection chamber. During the spray drying process, the spray dried dispersion solid is collected in the sample collection chamber. However, the solid may also reside on the surfaces of the drying chamber and cyclone chamber, thus causing a low production yield (a low amount of solid in the sample collection chamber). In some embodiments, the amorphous solid dispersions comprising a PROTAC, a hydrophilic polymer and a surfactant have low production yields. When an adsorbent is incorporated into these amorphous solid dispersions, the production yield can be significantly increased. In some embodiments, the production yield of an amorphous solid dispersion with an adsorbent is increased by at least 10%, in comparison to the solid dispersion without an adsorbent. For clarity, the term of percentage means to be the absolute difference of the yields. For example, if the production yield of an amorphous solid dispersion without an adsorbent is 10% and the production yield of an amorphous solid dispersion with an adsorbent is 20%, the increase of the yield is the difference of these two yields, i.e., 10%. In some embodiments, the production yield of an amorphous solid dispersion with an adsorbent is increased by at least 20%, in comparison to the solid dispersion without an adsorbent. In some embodiments, the production yield of an amorphous solid dispersion with an adsorbent is increased by at least 30%, in comparison to the solid dispersion without an adsorbent. In some embodiments, the production yield of an amorphous solid dispersion with an adsorbent is increased by at least 40%, in comparison to the solid dispersion without an adsorbent. In some embodiments, the production yield of an amorphous solid dispersion with an adsorbent is increased by at least 50%, in comparison to the solid dispersion without an adsorbent. In some embodiments, the production yield of an amorphous solid dispersion with an adsorbent is increased by at least 60%, in comparison to the solid dispersion without an adsorbent. In some embodiments, the production yield of an amorphous solid dispersion with an adsorbent is increased by at least 70%, in comparison to the solid dispersion without an adsorbent. In some embodiments, the production yield of an amorphous solid dispersion with an adsorbent is increased by at least 80%, in comparison to the solid dispersion without an adsorbent. In some embodiments, the production yield of an amorphous solid dispersion with an adsorbent is increased by at least 90%, in comparison to the solid dispersion without an adsorbent.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example 1. PROTAC—ARV-110 Formulations and PK Study in Beagle Dogs

This example illustrates the process of improving the oral absorption of and reducing or removing the food-effect of PROTAC—ARV-110, according to some embodiments of the present disclosure.

Proteolysis Targeting Chimeras (PROTACs) are heterobifunctional degraders that specifically eliminate targeted proteins by hijacking the ubiquitin-proteasome system (UPS). This modality has emerged as an orthogonal approach to the use of small-molecule inhibitors for knocking down classic targets and disease-related proteins classified, until now, as "undruggable." However, PROTACs are often affected by poor cellular permeability due to their high molecular weight (MW) and large exposed polar surface area (PSA). ARV-110, a PROTAC® protein degrader that targets the androgen receptor (AR), is developed by Arvinas for the potential treatment of men with metastatic castration resistant prostate cancer (mCRPC) and who have progressed on existing therapies. Its molecular weight is 812.29 and its log P is about 4.18. It is very hard to dissolve in the aqueous solution and the report shows that it should be taken with food.

One ARV-110 formulation (Batch No. P210803) as described in Table 3A was prepared.

TABLE 3A

ARV-110 ASD formulation batch no. P210803

| Ingredients | Batch No. P210803 | Description |
| --- | --- | --- |
| ARV-110 | 100 mg | PROTAC |
| Tartaric acid | 100 mg | Acid |
| VA64 | 100 mg | Polymer |
| TPGS | 100 mg | Surfactant |

Amorphous solid dispersions were prepared by vacuum drying. Briefly, all ingredients ware dispersed into a mixed organic solvent (e.g., ethanol and acetonitrile (3/7, V/V), methyl ethyl ketone and chloroform (5/5, V/V), dichloromethane and methanol (7/3, V/V), ethyl acetate and DCM (4/6, V/V), tetrahydrofuran and acetonitrile (2/8, V/V) or any mixed organic solvent listed in Table 6) with stirring to form a clear solution. And then the solution was placed to vacuum drying oven. The parameters were set to 40° C., and under 0.05-0.1 mPa. After 1 hour or after the organic solvent was removed, the particles were collected and filled into capsules.

Figure 2:
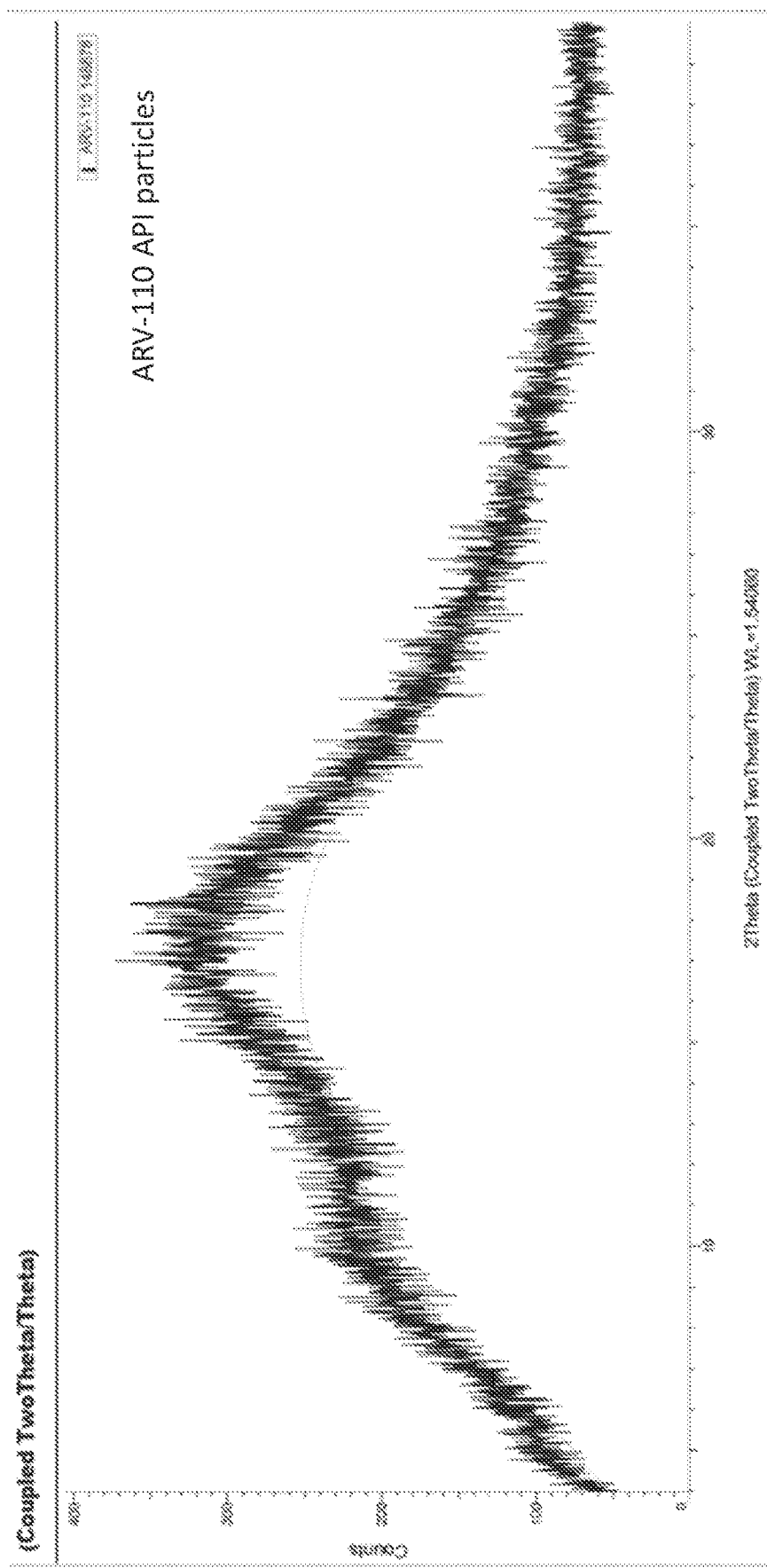
FIG. 2 shows X-ray powder diffraction study for the particles of ARV-110.

The XRPD testing was performed on both API only (ARV-110) and the ASD formulation Batch No. P210803 using D2-Phasher (Bruker) equipment, and with the following parameters: generator, 30.0 kV/10.0 mA; detector, Lynxeye; wavelength, Cu Kal(1.54060); scan mode, continuous PSD fast; scan range, 4-40 degree; step Size, 0.01 degree; time/step, 0.5 s; sample stage rotation, 15 r/min. The results (FIGS. 1 and 2) suggest that both the ARV-110 API and the ASD particles of ARV-110 composition batch no. P210803 were in amorphous state. ARV-110 is still under developing in clinical stage. To measure the absolute oral bioavailability, the capsule filled with ARV-110 API was prepared only for oral administration in fasted condition. API was dissolved in DMA and Solutol mixed solution for injection. Three beagle dogs were tested in two dosing groups, one group was for oral, 50 mg dose per dog, and the other group for injection, 5 mg dose per dog. During the study, the dogs were allowed to drink water freely and were fasted for 12 hours before administration, all dogs were given food 4 hours after drug administration. Each dog was administered together with 50 ml water.

Blood samples were taken from each group of animals at the following time points: 0 h (before test drug administration), and 0.25, 0.5, 1, 1.5, 2, 4, 6, 8, 10, 24 h after the drug administration. ARV-110 plasma concentrations were analyzed by an LC-MS/MS method. The non-compartment model of software WinNonlin was used to calculate the pharmacokinetic parameters of each dog, $C_{max}$, $AUC_{last}$, and $AUC_{inf}$. The geometric averages of each parameters were used for comparisons of the in vivo absorption under different dosing pretreatments.

Figure 3:
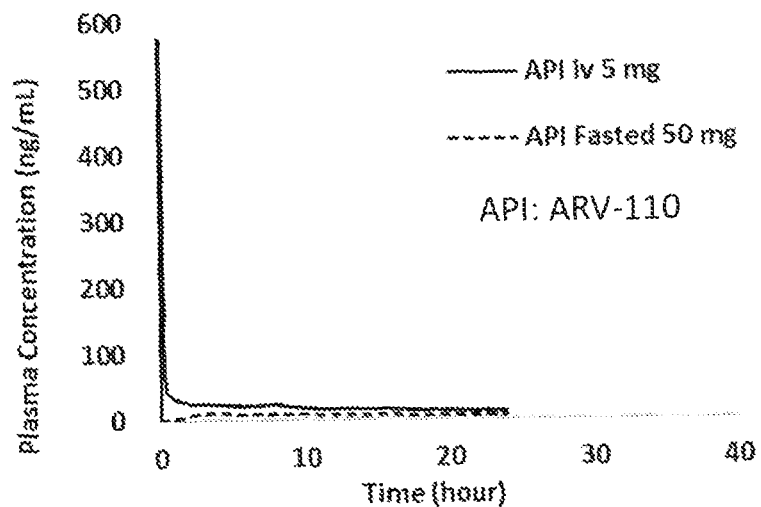
FIG. 3 shows a comparison of plasma concentrations of an active pharmaceutical ingredient (API), ARV-110, in dog model when ARV-110 is delivered intravenously (i.v.) at the dose of 5 mg of API or given orally at the dose of 50 mg of API, all in fasted condition.

The results shown in Table 3B include the geometric mean values as well as coefficient of variation (CV) of the pharmacokinetic parameters of the two dosing groups. FIG. 3 also shows a comparison of plasma concentrations of an active pharmaceutical ingredient (API), ARV-110, in dog model when ARV-110 is delivered intravenously (i.v.) at the dose of 5 mg of API or given orally without being a part of an ASD formulation at the dose of 50 mg of API, all in fasted condition. The results indicated that although ARV-110 API is amorphous, it still has poor absorption in fasted condition. The absolute bioavailability of ARV-110 is about 6.0%.

TABLE 3B

Pharmacokinetic parameters of ARV-110 API delivered via I.V. or orally in dog model

| Study design for ARV-110 API | | $C_{max}$ ng/mL | $AUC_{last}$ h*ng/mL | $AUC_{inf}$ h*ng/mL |
| --- | --- | --- | --- | --- |
| I.V. Injection (5 mg) | Average | 575.0 | 587.7 | 866.3 |
| in fasted condition | CV(%) | 32.7% | 22.3% | 16.8% |
| API oral (50 mg) | Average | 10.7 | 161.8 | 278.8 |
| in fasted condition | CV(%) | 14.8% | 19.2% | 6.0% |

Then, the capsule filled with ARV-110 API was prepared to compare the absorption advantage of our ASD formulation. Each capsule contained 45 mg ARV-110 API. The capsules were tested orally in three beagle dogs under two different dosing pretreatments (with or without high-fat food). During the study, the dogs were allowed to drink water freely and were fasted for 12 hours before administration, for the dosing pretreatment of the fasted condition, all dogs were given food 4 hours after drug administration. Each dog was administered together with 50 ml water. For the dosing pretreatment of the fed condition, all dogs were given a high-fat food 30 minutes prior to dosing.

Blood samples were taken from each group of animals at the following time points: 0 h (before test drug administration), and 0.5, 1, 1.5, 2, 3, 4, 5, 6, 8, 10, 12, 24, 48, 72 h after the drug administration. ARV-110 plasma concentrations were analyzed by an LC-MS/MS method. The non-compartment model of software WinNonlin was used to calculate the pharmacokinetic parameters of each dog, $C_{max}$, $AUC_{last}$ and $AUC_{inf}$. The geometric averages of each parameters were used for comparisons of the in vivo absorption under different doing pretreatments.

Figure 4:
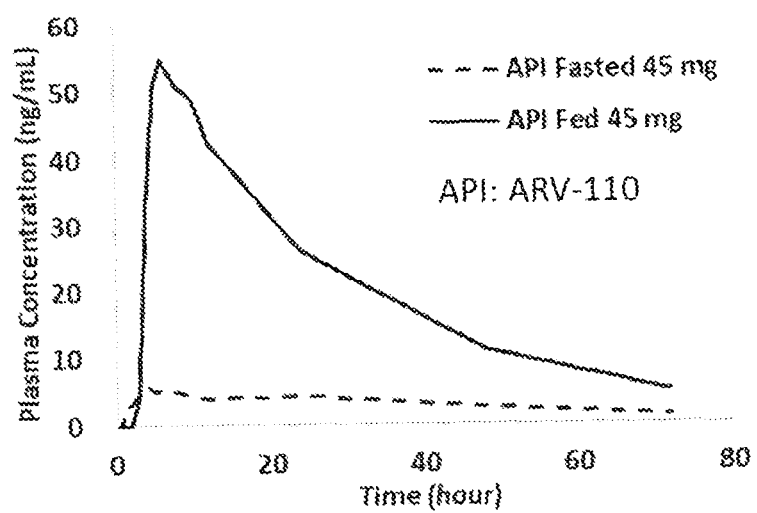
FIG. 4 shows a comparison of plasma concentrations of API (ARV-110) in dog model when ARV-110 is given orally without being a part of an ASD formulation at the dose of 45 mg API in fed and fasted condition.

The results shown in Table 3C include the geometric mean values as well as coefficient of variation (CV) of the pharmacokinetic parameters of two dosing groups. FIG. 4 also shows a comparison of plasma concentrations of API (ARV-110) in dog model when ARV-110 is given orally without being a part of an ASD formulation at the dose of 45 mg API in fed condition and in fasted condition. The results indicated significant food effect. ARV-110 API has poor absorption in fasted condition, and high-fat food could significantly increase oral absorption. The high-fat fed condition can enhance the oral absorption by about 6-folds compared to fasted condition.

TABLE 3C

Pharmacokinetic parameters of ARV-110 API delivered orally in fasted and fed condition in dog model

| Study design for ARV-110 API | | $C_{max}$ ng/mL | $AUC_{last}$ h*ng/mL | $AUC_{inf}$ h*ng/mL |
|---|---|---|---|---|
| API capsules (45 mg) in fasted condition | Average | 7.6 | 218.1 | 278.0 |
| | CV(%) | 30.3% | 58.1% | 57.2% |
| API capsules (45 mg) in fed condition | Average | 56.5 | 1412.9 | 1553.3 |
| | CV(%) | 43.9% | 36.6% | 36.2% |

Finally, the ARV110 ASD capsules (batch No. P210803, with 45 mg ARV-110 for each capsule) were tested orally in three beagle dogs per group under two different dosing pretreatments (with or without high-fat food). During the study, the dogs were allowed to drink water freely and were fasted for 12 hours before administration, for the dosing pretreatment of the fasted condition, all dogs were given food 4 hours after drug administration. Each dog was administered together with 50 ml water. For the dosing pretreatment of the fed condition, all dogs were given a high-fat food 30 minutes prior to dosing.

Blood samples were taken from each group of animals at the following time points: 0 h (before test drug administration), and 0.5, 1, 1.5, 2, 3, 4, 6, 8, 10, 12 and 24 h after the drug administration. ARV-110 concentrations were analyzed by an LC-MS/MS method. The non-compartment model of software WinNonlin was used to calculate the pharmacokinetic parameters of each dog, $C_{max}$, $AUC_{last}$ and $AUC_{inf}$. The geometric averages of each parameters were used for comparisons of the in vivo absorption under different doing pretreatments.

Figure 5:
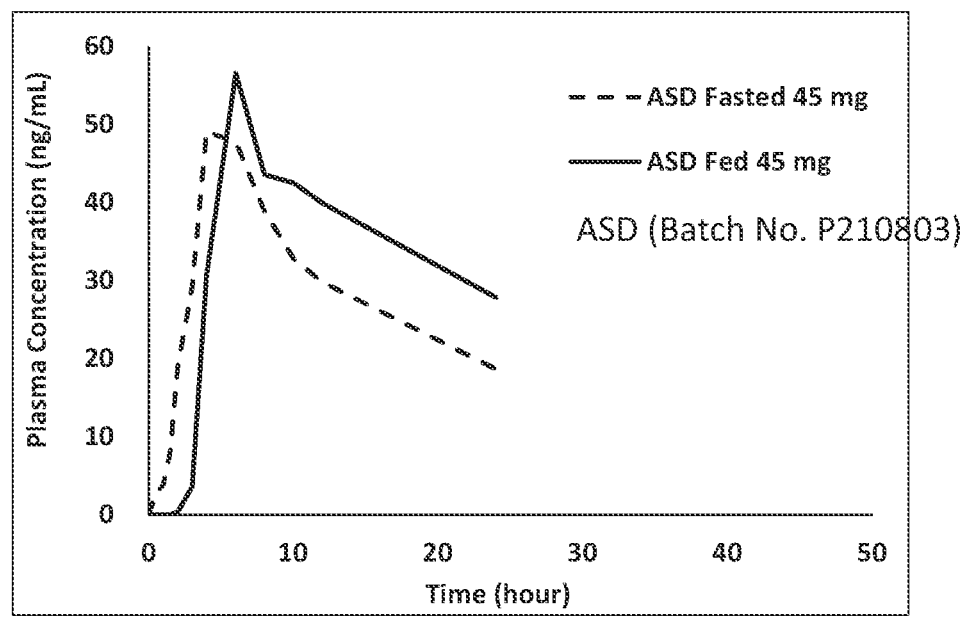
FIG. 5 shows a comparison of plasma concentrations of API (ARV-110) in dog model when an ASD composition of ARV-110 batch no. P210803 is given orally at the dose of 45 mg API in fed and fasted condition.

The results shown in Table 3D include the geometric mean values as well as coefficient of variation (CV) of the pharmacokinetic parameters of two dosing groups. FIG. 5 shows a comparison of plasma concentrations of API (ARV-110) in dog model when an ASD) composition of ARV-110 (Batch No. P210803) is given orally at the dose of 45 mg API in fed condition and in fasted condition. The results indicated that ASD capsule had significantly absorption improvement and the exposure was very close between fasted and fed condition.

TABLE 3D

Pharmacokinetic parameters of ARV-110 ASD composition in fasted and fed condition in dog model

| Study design for ASD capsules batch No. P210803 | | $C_{max}$ ng/mL | $AUC_{last}$ h*ng/mL | $AUC_{inf}$ h*ng/mL |
|---|---|---|---|---|
| ASD capsules (45 mg of API) in fasted condition | Average | 50.9 | 676.3 | 1179.1 |
| | CV(%) | 31.3% | 18.7% | 9.2% |
| ASD capsules (45 mg of API) in fed condition | Average | 56.5 | 773.7 | 2066.5 |
| | CV(%) | 8.2% | 35.8% | 63.6% |

Example 2. Additional ARV-110 Formulations

This example illustrates the process of improving the oral absorption of and reducing or removing the food-effect of PROTAC—ARV-110, according to some embodiments of the present disclosure.

Additional ARV-110 formulations as described in Table 4A were prepared.

TABLE 4A

ARV-110 ASD formulations Batch Nos. P220622-1, P220622-2, P220802-1, 110-A, 110-B

| Description | Ingredients | Batch No. | | | | |
| | | P220622-1 | P220622-2 | P220802-1 | 110-A | 110-B |
|---|---|---|---|---|---|---|
| API | ARV-110 (% wt) | 25 | 20 | 20 | 20 | 25 |
| Acid | Tartaric acid (% wt) | 25 | — | — | — | — |
| | Citric acid (% wt) | — | — | — | 20 | — |
| Polymer | VA64 (% wt) | 25 | — | — | 20 | — |
| | HPMCAS-LF (% wt) | — | 40 | 40 | — | 25 |
| Surfactant | VE-TPGS (% wt) | 25 | — | — | 20 | 25 |
| | Lecithin (% wt) | — | 40 | 40 | 20 | 25 |
| Preparation method | | Spray drying | Spray drying | Spray drying | Spray drying | Spray drying |

Amorphous solid dispersions can be prepared by vacuum drying. Briefly, all ingredients were dispersed into a solvent or mixed solvent (e.g., ethanol and acetonitrile (3/7, V/V), methyl ethyl ketone and chloroform (5/5, V/V), dichloromethane and methanol (7/3, V/V), ethyl acetate and DCM (4/6, V/V), tetrahydrofuran and acetonitrile (2/8, V/V) or any solvent or mixed solvent listed in Table 6) with stirring to form a clear solution. Then the solution was placed to vacuum drying oven. The parameters were set to 40° C., and under 0.05-0.1 mPa. After the organic solvent was removed, the particles were collected and filled into the capsules.

Amorphous solid dispersions can be prepared by spray drying method. Briefly, API was dispersed a solvent or mixed solvent (e.g., ethanol and acetonitrile (3/7, V/V), methyl ethyl ketone and chloroform (5/5, V/V), dichloromethane and methanol (7/3, V/V), ethyl acetate and DCM (4/6, V/V), tetrahydrofuran and acetonitrile (2/8, V/V) or any solvent or mixed organic solvent listed in Table 6) with stirring to form a clear solution. And then the other ingredients were dissolved into the solution completed. The solution was introduced into spray dryer (SD-06AG, Labplant, UK) via flash atomization. The parameters were set to the following: feed rate 4.0-8.0 rpm, inlet temperature 50-100° C., outlet temperature 30-80° C., and atomization pressure 0-4.0 bar. The particles were collected and filled into the capsules.

Example 3. PK Studies Performed on Additional ARV-110 Formulations in Dog Models This example illustrates the process of improving the oral absorption of and reducing or removing the food-effect of PROTAC—ARV-110, according to some embodiments of the present disclosure.

To investigate the oral absorption of ARV-110, two-way crossover or three-way crossover designs were performed. Six Beagle dogs were classified into two or three groups. Each group was administered capsules of different formulations comprising the API or API only at various dose to compare the API absorption in such formulations and also any difference in API absorption in fasted or fed conditions. Each dog was administered with 50 mL water in total. To measure the absolute bioavailability, i.v. injection of a solution comprising API was also performed. The API solution for i.v. injection was prepared by dissolving in DMA and Solutol mixed solution.

In fasted condition, the dogs were allowed to drink water freely and were fasted for 12 hours before administration, and then were given food 4 hours after drug administration.

In fed condition, the dogs were fed with high-fat food 30 mins before administration, according to the FDA guidance entitled "Assessing the effects of food on drug in INDs and NDAs-Clinical pharmacology considerations" published on Feb. 26, 2019.

Blood samples were taken from each group of animals at the different time points after the drug administration. Plasma concentrations were analyzed by an LC-MS/MS method. The non-compartment model of software WinNonlin was used to calculate the pharmacokinetic parameters of each dog, $C_{max}$, $AUC_{last}$ and $AUC_{inf}$. The geometric averages of each parameters were used for comparisons of the in vivo absorption under different doing pretreatments.

Figure 6:
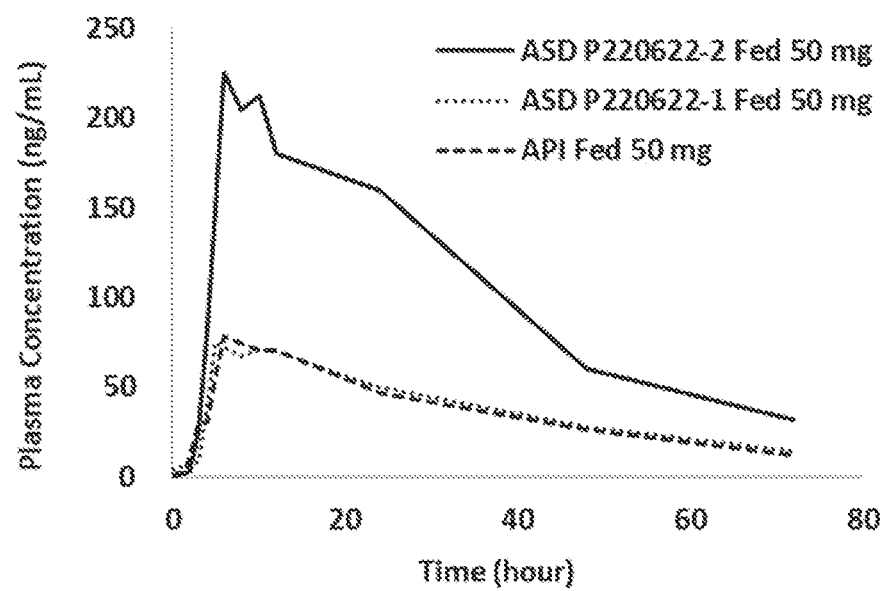
FIG. 6 shows a comparison of plasma concentrations of API (ARV-110) in dog model when two ASD compositions of ARV-110 (Batch Nos. P220622-1 and P220622-2) and API only are given orally at the dose of 50 mg API in fed condition.

A six-dog, three-way crossover study was performed to evaluate oral bioavailability of ARV-110 ASD in beagle dogs in fed condition. There were three study groups, ARV-110 API administered in fed condition, ASD composition batch no. P220622-1 administered in fed condition, and ASD composition batch no. P220622-2 administered in fed condition, each containing 2 dogs. The ARV-110 API powder, ASD composition from batch no. P220622-1, and ASD composition from batch no. P220622-2 were filled in capsules, respectively. The capsules were given at the dose of 50 mg API per dog for oral administration for each group in fed condition. The results shown in Table 4B include the geometric mean values as well as coefficient of variation (CV) of the pharmacokinetic parameters of the three dosing groups. FIG. 6 also shows a comparison of plasma concentrations of API (ARV-110) in dog model after two ASD compositions of ARV-110 (Batch Nos. P220622-1 and P220622-2) and API only are given orally at the dose of 50 mg API in fed condition. The ASD composition batch no. P220622-2 showed significant improvement in absorption as compared to ASD composition batch no. P220622-1 and ARV-110 API in fed condition. The ASD composition batch no. P220622-1 showed no difference than ARV-110 API in fed condition. The results indicated that different surfactants and polymers within the formulation can affect the oral absorption.

TABLE 4B

Pharmacokinetic parameters of ARV-110 API and ASD composition in fed condition in dog model

| PK parameters | | $C_{max}$ (ng/mL) | $AUC_{last}$ (h*ng/mL) | $AUC_{inf}$ (h*ng/mL) |
|---|---|---|---|---|
| API (ARV-110) 50 mg in fed condition | Average | 80.33 | 2571 | 2998 |
| | CV(%) | 21.6 | 45.4 | 47.7 |
| ASD (P220622-1) 50 mg of API in fed condition | Average | 89.64 | 2697 | 3277 |
| | CV(%) | 78 | 87.5 | 85.5 |
| ASD (P220622-2) 50 mg of API in fed condition | Average | 239.1 | 7100 | 8038 |
| | CV(%) | 37.2 | 50.8 | 53.5 |

Figure 7:
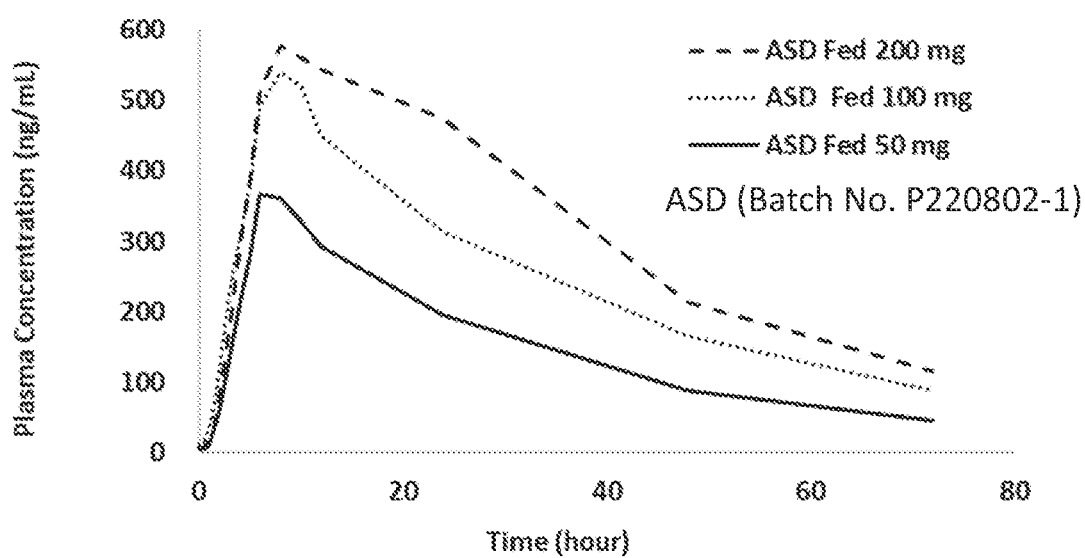
FIG. 7 shows a comparison of plasma concentrations of API (ARV-110) in dog model when an ASD composition of ARV-110 (Batch No. P220802-1) is given orally at the doses of 50 mg of API, 100 mg of API, and 200 mg of API, all in fed condition.

A six-dog, three-way crossover study was performed to evaluate oral bioavailability of ARV-110 ASD dose escalation in beagle dogs in fed condition. There were three study groups, ASD composition batch no. P220802-1 administered in fed condition with a dose of 50 mg API, 100 mg API, and 200 mg API, respectively, each containing 2 dogs. The ASD composition batch no. P220802-1 was filled in capsules. The capsules were given at the dose of 50 mg API, 100 mg API, and 200 mg API per dog for oral administration for each group, respectively. The results shown in Table 4C include the geometric mean values as well as coefficient of variation (CV) of the pharmacokinetic parameters of the three dosing groups. FIG. 7 also shows a comparison of plasma concentrations of API (ARV-110) in dog model when the ASD composition of ARV-110 (Batch No. P220802-1) is given orally at the doses of 50 mg of API, 100 mg of API, and 200 mg of API, all in fed condition. The pharmacokinetic results calculated with AUC showed good linearity with the increased doses of ASD (P220802-1), which means this formulation achieved good enhancement of ARV-110 oral bioavailability.

TABLE 4C

Pharmacokinetic parameters of ARV-110 ASD dose escalation in fed condition in dog model

| PK parameters | | $C_{max}$ (ng/mL) | $AUC_{last}$ (h*ng/mL) | $AUC_{inf}$ (h*ng/mL) |
|---|---|---|---|---|
| ASD (P220802-1) 50 mg of API in fed condition | Average | 397.0 | 10570 | 12100 |
| | CV(%) | 39.4 | 36.6 | 33.7 |
| ASD (P220802-1) 100 mg of API in fed condition | Average | 575.3 | 17450 | 20850 |
| | CV(%) | 33.3 | 32.7 | 34.8 |
| ASD (P220802-1) 200 mg of API in fed condition | Average | 673.7 | 22200 | 26260 |
| | CV(%) | 45.4 | 38.9 | 39.5 |

Example 4. Additional ARV471 Formulations

This example illustrates the process of improving the oral absorption of and reducing or removing the food-effect of PROTAC—ARV471, according to some embodiments of the present disclosure.

ARV-471, a PROTAC®, protein degrader that targets the estrogen receptor (ER). ARV-471 is developed by Arvinas for the potential treatment of women with locally advanced or metastatic estrogen receptor (ER) positive/human epidermal growth factor receptor 2 (HER2) negative (ER+/HER2−) breast cancer. Its molecular weight is 723.92 and its calculated log P is about 4-6. It is very hard to dissolve in the aqueous solution and it is reported that it should be taken with food in clinic study.

ARV-471 formulations as described in Table 5A were prepared.

Amorphous solid dispersions can be prepared by spray drying method. Briefly, API was dispersed a solvent or mixed solvent (e.g., ethanol and acetonitrile (3/7, V/V), methyl ethyl ketone and chloroform (5/5, V/V), dichloromethane and methanol (7/3, V/V), ethyl acetate and DCM (4/6, V/V), tetrahydrofuran and acetonitrile (2/8, V/V) or any solvent or mixed organic solvent listed in Table 6) with stirring to form a clear solution. And then the other ingredients were dissolved into the solution completed. The solution was introduced into spray dryer (SD-06AG, Labplant, UK) via flash atomization. The parameters were set to the following: feed rate 4.0-8.0 rpm, inlet temperature 50-100° C., outlet temperature 30-80° C., and atomization pressure 0-4.0 bar. The particles were collected and filled into the capsules.

Figure 8:
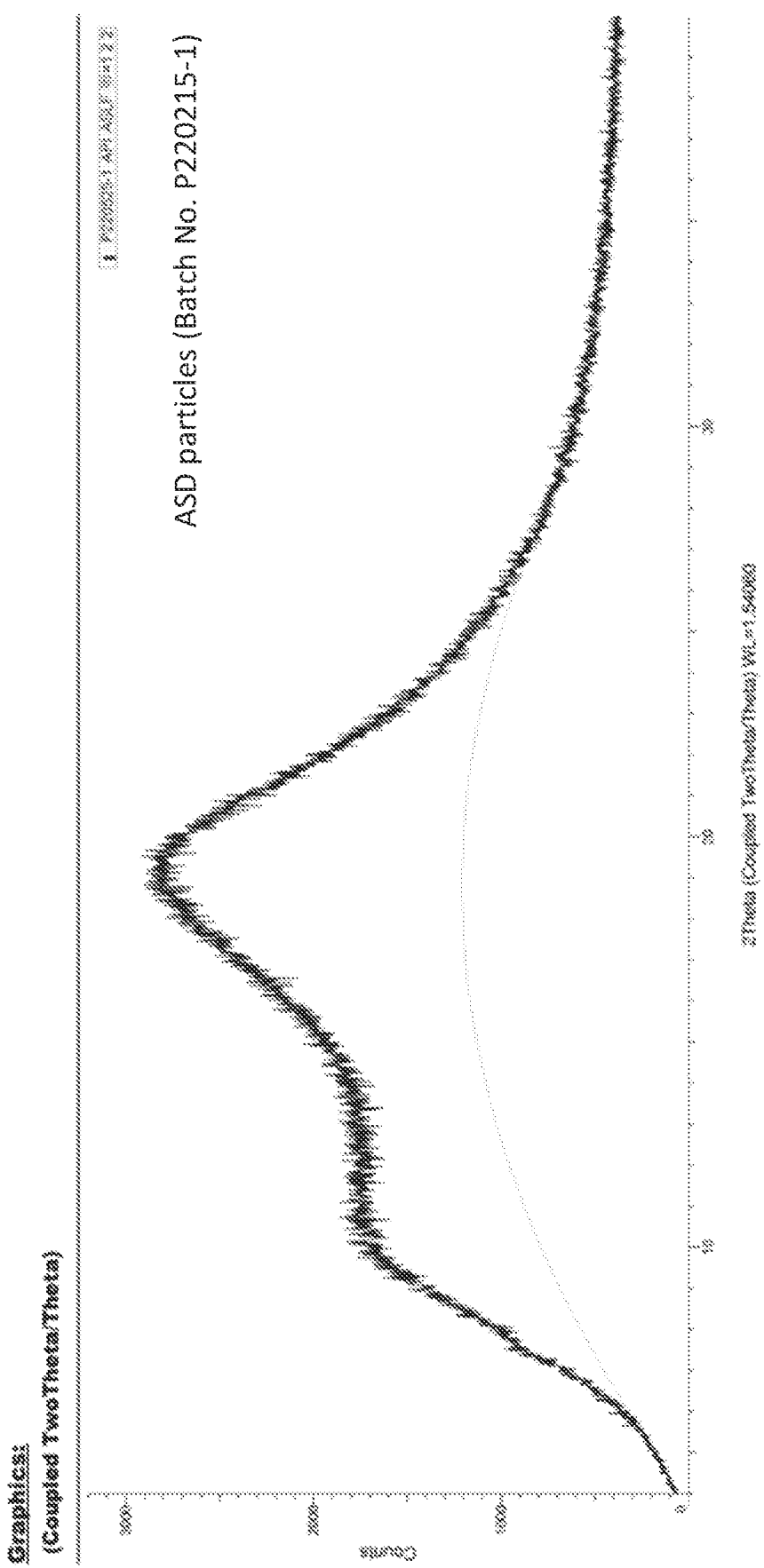
FIG. 8 shows X-ray powder diffraction study for the ASD of ARV-471 composition batch no. P220215-1.
Figure 9:
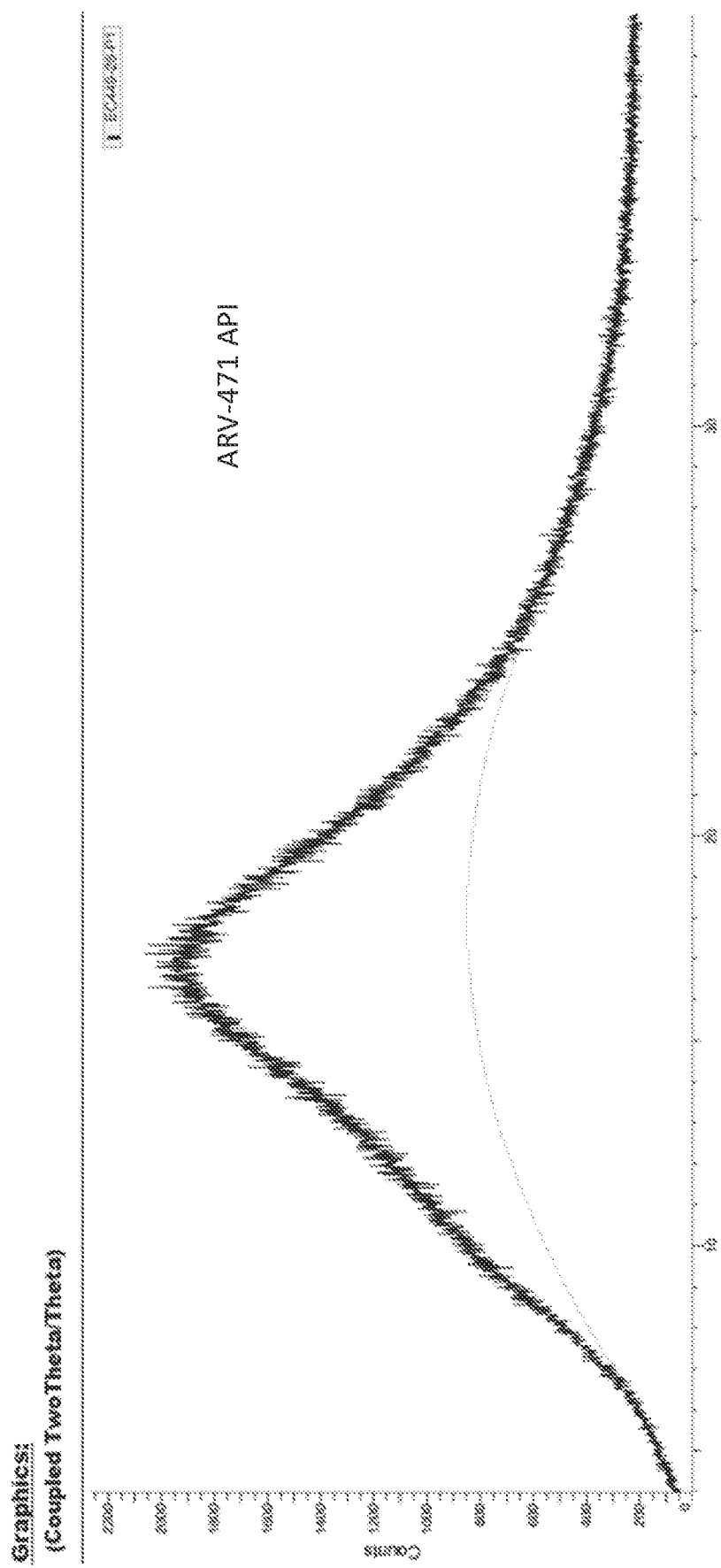
FIG. 9 shows X-ray powder diffraction study for the particles of ARV-471.

The XRPD testing was performed on API only (ARV-471) and/or the ASD composition batch no. P220215-1 prepared using D2-Phasher (Bruker) equipment, and with the following parameters: generator, 30.0 kV/10.0 mA; detector, Lynxeye; wavelength, Cu Kal(1.54060); scan mode, continuous PSD fast; scan range, 4-40 degree; step Size, 0.01 degree; time/step, 0.5 s; sample stage rotation, 15 r/min. The results (FIGS. 8 and 9) suggest that both the ARV-471 API and the ASD particles were in amorphous state.

Example 5. PK Studies Performed on ARV-471 Formulations in Dog Models

This example illustrates the process of improving the oral absorption of and reducing or removing the food-effect of PROTAC—ARV471, according to some embodiments of the present disclosure.

TABLE 5A

ARV-471 ASD formulations Batch Nos. P211222, P220215-1, P220215-2, P220419-1, P220525-1, 471-A, 471-B

| Description | Ingredients | Batch No. | | | | | | |
|---|---|---|---|---|---|---|---|---|
| | | P211222 | P220215-1 | P220215-2 | P220419-1 | P220525-1 | 471-A | 471-B |
| API | ARV-471 (% wt) | 25 | 20 | 20 | 20 | 20 | 25 | 20 |
| Acid | Tartaric acid (% wt) | 25 | — | — | — | — | — | — |
| | Succinic acid (% wt) | — | — | — | — | — | — | 20 |
| Polymer | VA64 (% wt) | — | — | — | — | — | — | 20 |
| | HPMCAS-LF (% wt) | 25 | 40 | 40 | 40 | 40 | 25 | — |
| Surfactant | VE-TPGS (% wt) | 25 | — | 40 | — | — | 25 | 20 |
| | Lecithin (% wt) | — | 40 | — | 40 | 40 | 25 | 20 |
| Preparation method | | Vacuum drying | Spray drying | Spray drying | Spray drying | Spray drying | Spray drying | Spray drying |

Amorphous solid dispersions can be prepared by vacuum drying. Briefly, all ingredients were dispersed into a solvent or mixed solvent (e.g., ethanol and acetonitrile (3/7, V/V), methyl ethyl ketone and chloroform (5/5, V/V), dichloromethane and methanol (7/3, V/V), ethyl acetate and DCM (4/6, V/V), tetrahydrofuran and acetonitrile (2/8, V/V) or any solvent or mixed organic solvent listed in Table 6) with stirring to form a clear solution. Then the solution was placed to vacuum drying oven. The parameters were set to 40° C. and under 0.05-0.1 mPa. After the organic solvent was removed, the particles were collected and filled into the capsules.

To investigate the oral absorption of ARV-471, the same study design and procedures as described in Example 3 were performed.

Figure 10:
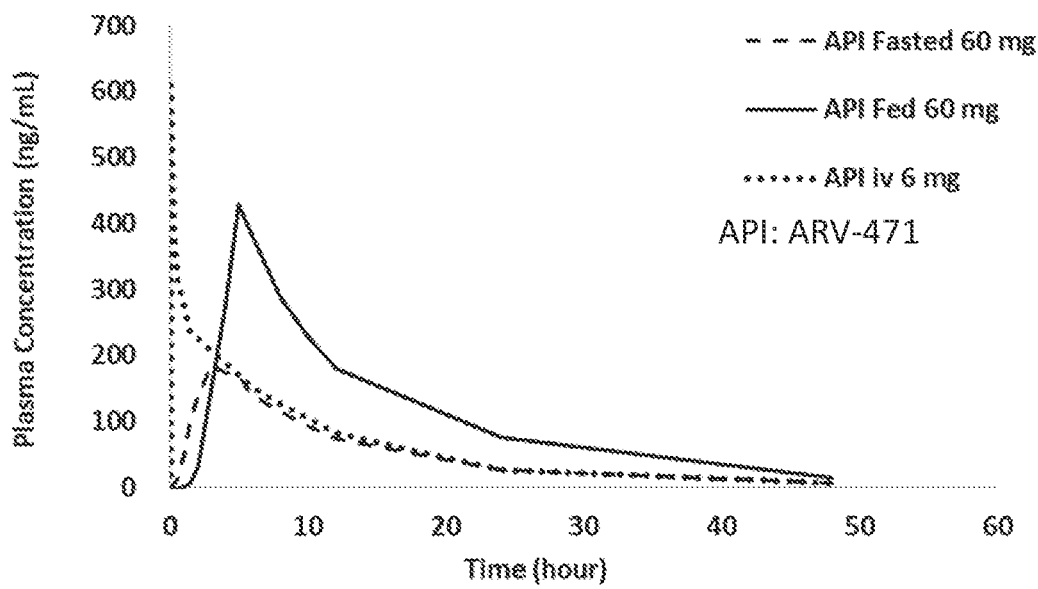
FIG. 10 shows a comparison of plasma concentrations of an active pharmaceutical ingredient (API). ARV-471, in dog model when ARV-471 is delivered intravenously (i.v.) at the dose of 6 mg of API in fasted condition or given orally at the dose of 60 mg of API in both fasted and fed condition.

A three-dog, two-way crossover study was performed to evaluate oral bioavailability of ARV-471 API in beagle dogs in fasted and fed condition. A three-dog study was performed to measure the ARV-471 API bioavailability after i.v. injection in fasted condition. Each capsule was filled with 60 mg of API powder and a 6 mg/vial API solution was prepared. One capsule or one vial of API solution were administered to each dog according to the design of the two studies. The results shown in Table 5B include the geometric mean values as well as coefficient of variation (CV) of the pharmacokinetic parameters of the three dosing groups. FIG. 10 also shows a comparison of plasma concentrations of an active pharmaceutical ingredient (API), ARV-471, in dog model when ARV-471 is delivered intravenously (i.v.) at the dose of 6 mg of API in fasted condition or given orally at the dose of 60 mg of API in both fasted and fed condition. The results indicate that although the ARV-471 API is amorphous, it still has poor absorption in fasted condition. The absolute bioavailability of ARV-471 API is about 7%, and high-fat food can enhance the oral absorption by 2 times.

TABLE 5B

Pharmacokinetic parameters of ARV-471 API oral bioavailability in fasted and fed condition and absolute bioavailability after i.v. in dog model

| PK parameters | | $C_{max}$ (ng/mL) | $AUC_{last}$ (h*ng/mL) | $AUC_{inf}$ (h*ng/mL) |
|---|---|---|---|---|
| ARV-471 i.v. 6 mg in fasted condition | Average CV(%) | 609.0 17.6 | 3121 6.5 | 3215 6.6 |
| ARV-471 oral 60 mg in fasted condition | Average CV(%) | 200 2.9 | 2359 3.0 | 2482 3.1 |
| ARV-471 oral 60 mg in fed condition | Average CV(%) | 427.9 6.6 | 5020 11,4 | 5227 12.1 |

Figure 11:
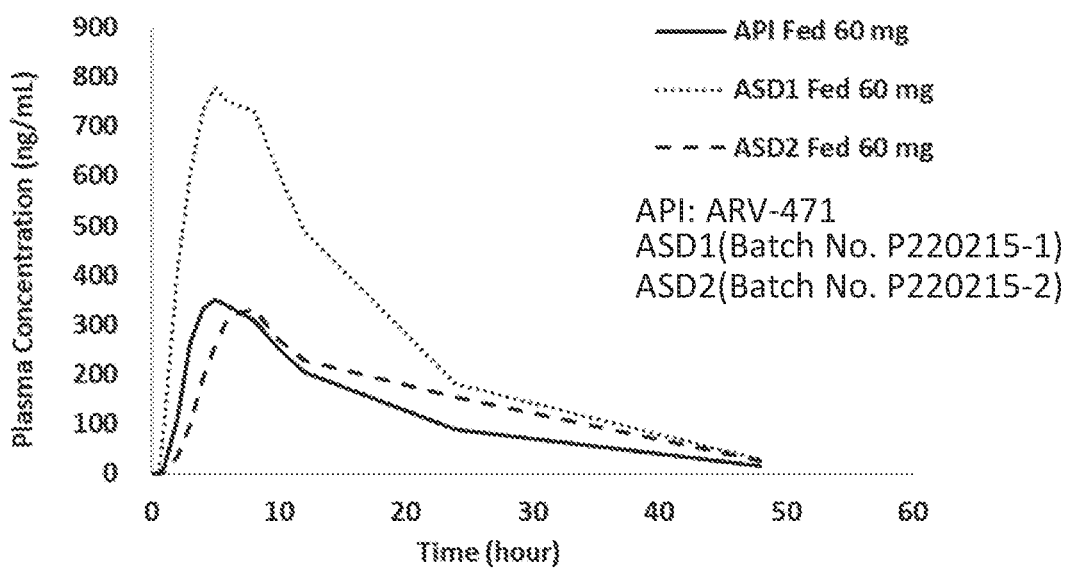
FIG. 11 shows a comparison of plasma concentrations of API (ARV-471) in dog model when two ASD compositions of ARV-471 (Batch Nos. P220215-1 and P220215-2) and API only are given orally at the dose of 60 mg API in fed condition.

A six-dog, three-way crossover study was performed to evaluate oral bioavailability of ARV-471 API and ASD compositions in beagle dogs in fed condition. There were three study groups, ARV471 API administered in fed condition ASD composition batch no. P220215-1 administered in fed condition, and ASD composition batch no. P220215-2 administered in fed condition, each containing 2 dogs. Capsules were filled with API powder, ASD composition from batch no. P220215-1 and ASD composition from batch no. P220215-2, respectively. The capsules were given at the dose of 660 mg of API per dog for oral administration for each group in fed condition. The results shown in Table 5C include the geometric mean values as well as coefficient of variation (CV) of the pharmacokinetic parameters of the three dosing groups. FIG. 11 also shows a comparison of plasma concentrations of API (ARV-471) in dog model after two ASD compositions of ARV-471 (Batch Nos. P220215-1 and P220215-2) and API only are given orally at the dose of 600 mg API in fed condition. The ASD composition P220215-1 showed significant improvement in absorption than ASD composition P220215-2 and API in fed condition. The results indicated that surfactants in the formulations can significantly affect the API oral absorption.

TABLE 5C

Pharmacokinetic parameters of ARV-471 API and ASD compositions in fed condition in dog model

| PK parameters | | $C_{max}$ (ng/mL) | $AUC_{last}$ (h*ng/mL) | $AUC_{inf}$ (h*ng/mL) |
|---|---|---|---|---|
| API 60 mg in fed condition | Average CV(%) | 380.6 22.0 | 5596 23.7 | 5840 23.6 |
| ASD composition P220215-1 60 mg of API in fed condition | Average CV(%) | 902.4 22.4 | 12590 21.2 | 12970 20.8 |

TABLE 5C-continued

Pharmacokinetic parameters of ARV-471 API and ASD compositions in fed condition in dog model

| PK parameters | | $C_{max}$ (ng/mL) | $AUC_{last}$ (h*ng/mL) | $AUC_{inf}$ (h*ng/mL) |
|---|---|---|---|---|
| API composition P220215-2 60 mg of API in fed condition | Average CV(%) | 369.5 22.2 | 6444 6.5 | 6933 8.1 |

Figure 12:
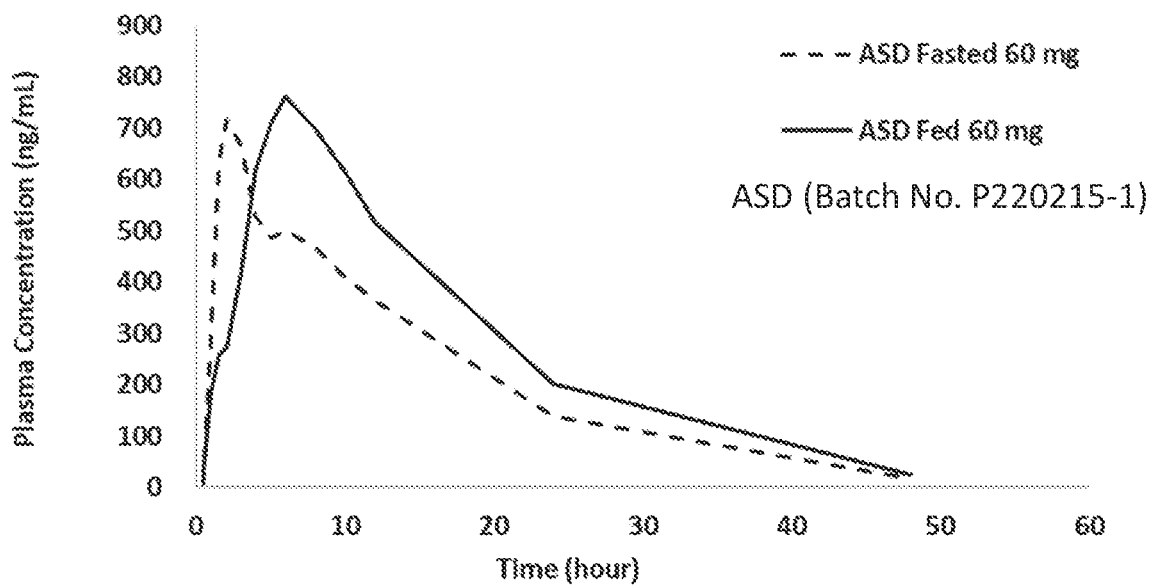
FIG. 12 shows a comparison of plasma concentrations of API (ARV-471) in dog model when an ASD composition of ARV-471 (Batch No. P220215-1) is given orally at the dose of 60 mg API in fed condition and in fasted condition.

A six-dog, two-way crossover study was performed to evaluate oral bioavailability of ARV-471 ASD in beagle dogs in fasted and fed condition. There were two study groups, ASD composition batch no. P220215-1 orally administered in fasted condition and in fed condition, each containing 2 dogs. ASD composition from batch no. P220215-1 was filled in capsules. The capsules were given at the dose of 60 mg API per dog for oral administration for each group. The results shown in Table 5D include the geometric mean values as well as coefficient of variation (CV) of the pharmacokinetic parameters of two dosing groups. FIG. 12 shows a comparison of plasma concentrations of API (ARV-471) in dog model after an ASD composition of ARV-471 (Batch No. P220215-1) is given orally at the dose of 60 mg API in fed condition and in fasted condition. The results indicate that the pharmacokinetic profile was very close between fasted and fed condition, which means ASD composition batch no. P220215-1 had significant improvement of oral absorption in fasted condition.

TABLE 5D

Pharmacokinetic parameters of ARV-471 ASD compositions in fasted and fed condition in dog model

| PK parameters | | $C_{max}$ (ng/mL) | $AUC_{last}$ (h*ng/mL) | $AUC_{inf}$ (h*ng/mL) |
|---|---|---|---|---|
| ASD composition P220215-1 in 60 mg of API fasted condition | Average CV(%) | 894.1 36.0 | 9720 5.3 | 9924 5.3 |
| ASD composition P220215-1 in fed condition 60 mg of API | Average CV(%) | 832.8 5.6 | 12420 18.9 | 12740 17.2 |

Figure 13:
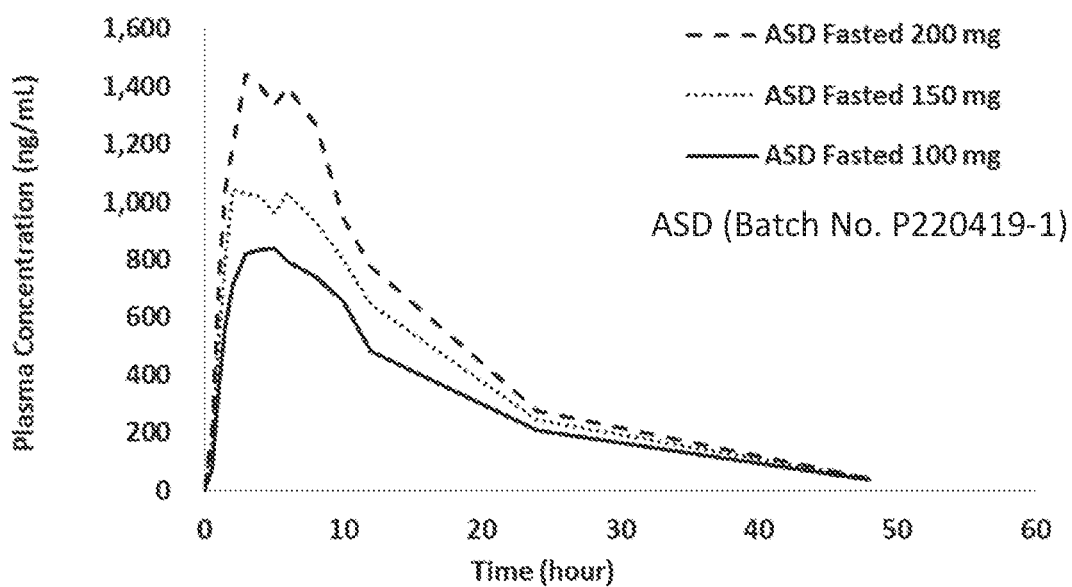
FIG. 13 shows a comparison of plasma concentrations of API (ARV-471) in dog model when an ASD composition of ARV-471 (Batch No. P220419-1) is given orally at the doses of 100 mg API, 150 mg of API, and 200 mg of API, all in fasted condition.

A six-dog, three-way crossover study was performed to evaluate oral bioavailability of ARV-471 ASD dose escalation in beagle dogs in fasted and fed condition. There were three study groups, ASD composition batch no. P220419-1 orally administered at a dose of 100 mg API, 150 mg API, and 200 mg API in fasted condition, each containing 2 dogs. ASD composition from batch no. P220419-1 was filled in capsules, and each capsule contains 50 mg of API. The capsules were given at the dose of 100 mg API, 150 mg API, and 200 mg API per dog for oral administration for each group. The results shown in Table SE include the geometric mean values as well as coefficient of variation (CV) of the pharmacokinetic parameters of the three dosing groups. FIG. 13 shows a comparison of plasma concentrations of API (ARV-471) in dog model when the ASD composition of ARV-471 (Batch No. P220419-1) is given orally at the doses of 100 mg API (2 capsules), 150 mg of API (3 capsules), and 200 mg of API (4 capsules), all in fasted condition. The pharmacokinetics results calculated by AUC showed good linearity of dose-escalation of ASD composition batch no.

P220419-1, which means this formulation has good improvement in oral absorption of ARV-471.

TABLE 5E

Pharmacokinetic parameters of ARV-471 ASD compositions in fasted and fed condition in dog model

| PK parameters | | $C_{max}$ (ng/mL) | $AUC_{last}$ (h*ng/mL) | $AUC_{inf}$ (h*ng/mL) |
|---|---|---|---|---|
| ASD composition P220419-1 in fasted condition 100 mg of API | Average CV(%) | 1045 48.9 | 14210 58.9 | 14720 58.4 |
| ASD composition P220419-1 in fasted condition 150 mg of API | Average CV(%) | 1317 51.2 | 17890 74.8 | 18450 74.7 |
| ASD composition P220419-1 in fasted condition 200 mg of API | Average CV(%) | 1656 58.7 | 22100 71 | 22640 71.1 |

Figure 14:
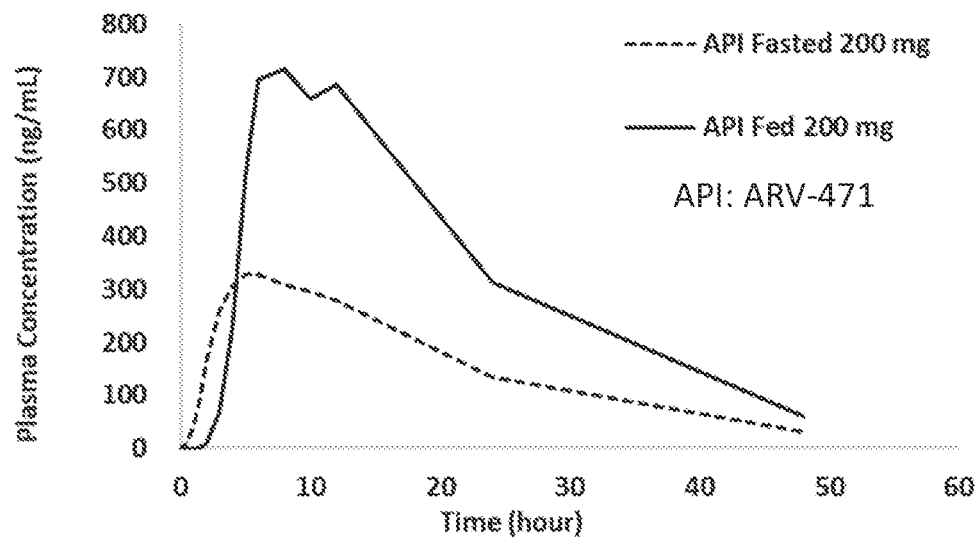
FIG. 14 shows a comparison of plasma concentrations of API (ARV-471) in dog model when only API is given orally at a high dose of 200 mg in fed and fasted condition.

A six-dog, two-way crossover study was performed to evaluate oral bioavailability of ARV-471 API dose escalation in beagle dogs in fasted and fed condition. There were two study groups, ARV-471 API orally administered in fasted condition and in fed condition, 200 mg of ARV-471 API was filled in each capsule. The capsules were given at the dose of 200 mg API per dog for oral administration for each group. The results shown in Table 5F include the geometric mean values as well as coefficient of variation (CV) of the pharmacokinetic parameters of two dosing groups. FIG. 14 shows a comparison of plasma concentrations of API (ARV-471) in dog model when only API is given orally at a high dose of 200 mg in fed and fasted condition. The results indicate that even high dose of ARV-471 API at 200 mg, it still has similar food-effect compared to low dose API, and that high-fat food enhanced the oral absorption by 2-times as compared to the oral absorption in fasted condition.

TABLE 5F

Pharmacokinetic parameters of ARV-471 API high dose in fasted and fed condition in dog model

| PK parameters | | $C_{max}$ (ng/mL) | $AUC_{last}$ (h*ng/mL) | $AUC_{inf}$ (h*ng/mL) |
|---|---|---|---|---|
| API ARV-471 in fasted condition 200 mg | Average CV(%) | 414.7 50.5 | 7138 51.5 | 7649 50.8 |
| API ARV-471 in fed condition 200 mg | Average CV(%) | 860.2 51.5 | 14670 33.7 | 15600 31.2 |

Figure 15:
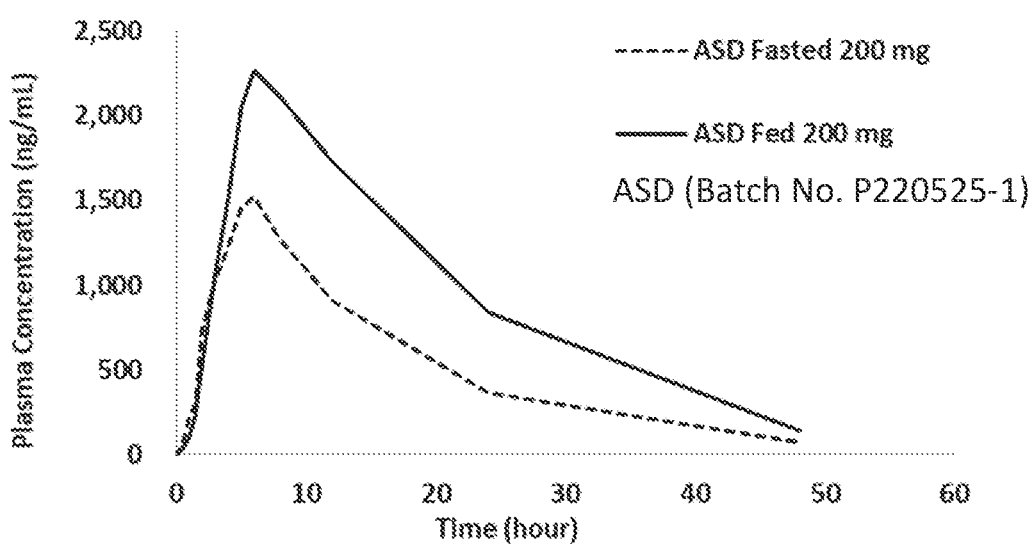
FIG. 15 shows a comparison of plasma concentrations of API (ARV-471) in dog model when an ASD composition of ARV-471 (Batch No. P220525-1) is given orally at a high dose of 200 mg API in fed condition and in fasted condition.

A six-dog, two-way crossover study was performed to evaluate oral bioavailability of ARV-471 ASD in beagle dogs in fasted and fed condition. There were two study groups, ARV-471 ASD composition batch no. P220525-1 orally administered in fasted condition and in fed condition. 200 mg of ASD composition batch no. P220525-1 was filled in each capsule. The capsules were given at the dose of 200 mg API per dog for oral administration for each group. The results shown in Table SG include the geometric mean values as well as coefficient of variation (CV) of the pharmacokinetic parameters of two dosing groups. FIG. 15 shows a comparison of plasma concentrations of API (ARV-471) in dog model when the ASD composition of ARV-471 (Batch No. P220525-1) is given orally at a high dose of 200 mg API in fed condition and in fasted condition. The AUC and $C_{max}$ of ASD composition batch no. P220525-1 were significantly higher than API in both fasted and fed conditions. However, this formulation with 200 mg of API per capsule still showed some food-effects.

TABLE 5G

Pharmacokinetic parameters of ASD composition batch no. P220525-1 in fasted and fed condition in dog model

| PK parameters | | $C_{max}$ (ng/mL) | $AUC_{last}$ (h*ng/mL) | $AUC_{inf}$ (h*ng/mL) |
|---|---|---|---|---|
| ASD composition batch no. P220525-1 in fasted condition 200 mg of API | Average CV(%) | 1717 45.4 | 24030 36.2 | 25050 35.3 |
| ASD composition batch no. P220525-1 in fed condition 200 mg of API | Average CV(%) | 2317 33.4 | 42480 19.6 | 44590 19.4 |

It should be appreciated that there is considerable overlap between the above listed components in common usage, since a given component is often classified differently by different practitioners in the field, or is commonly used for any of several different functions, or may have differing functions depending on the levels in the composition. Thus, the above-listed components should be taken as merely exemplary, and not limiting, of the types of components that can be included in compositions of the present disclosure.

What is claimed is:

1. A pharmaceutical composition, wherein the pharmaceutical composition comprises,
    an amorphous solid dispersion (ASD) that comprises:
        a proteolysis targeting chimera (PROTAC) compound or a pharmaceutically acceptable salt thereof, wherein the PROTAC compound or the pharmaceutically acceptable salt thereof has a log P or calculated log P (clog P) in octanol-water of at least 4.0, and wherein the PROTAC compound or the pharmaceutically acceptable salt thereof is present in the amorphous solid dispersion in a weight percent of from about 10% to about 40%;
        a surfactant, wherein the surfactant comprises a phospholipid and wherein the phospholipid is present in the amorphous solid dispersion in a weight percent of from about 20% to about 40%;
        a hydrophilic polymer, wherein the hydrophilic polymer comprises hydropropylmethylcellulose acetate succinate (HPMCAS), polymethacrylates, hypromellose phthalate (HPMCP), or a combination thereof, and wherein the hydrophilic polymer is present in the amorphous solid dispersion in an amount of from about 20% to about 50% by weight;
    wherein the pharmaceutical composition exhibits a bioavailability of the PROTAC compound or the pharmaceutically acceptable salt thereof that is at least 1.5-fold compared to a bioavailability of a corresponding composition comprising the PROTAC compound or the pharmaceutically acceptable salt thereof without being a part of an ASD, wherein said bioavailability is measured as total area under the curve (AUC) or as maximum plasma concentration ($C_{max}$) after oral administration to a subject;
    wherein the pharmaceutical composition is in an oral dosage form; and
        wherein the PROTAC compound or the pharmaceutically acceptable salt thereof, the surfactant, and the hydrophilic polymer are present in the ASD in an amorphous state.

2. The pharmaceutical composition of claim 1, wherein the pharmaceutical composition exhibits a bioavailability of the PROTAC compound or the pharmaceutically acceptable salt thereof that is at least 2-fold compared to a bioavailability of a corresponding composition comprising the PROTAC compound or the pharmaceutically acceptable salt thereof without being a part of an ASD, when said bioavailability is measured as total area under the curve (AUC) or as maximum plasma concentration ($C_{max}$) after oral administration to a subject in a fasted state.

3. The pharmaceutical composition of claim 1, wherein the pharmaceutical composition exhibits a bioavailability of the PROTAC compound or the pharmaceutically acceptable salt thereof that is at least 1.5-fold compared to a bioavailability of a corresponding composition comprising the PROTAC compound or the pharmaceutically acceptable salt thereof without being a part of an ASD, when said bioavailability is measured as total area under the curve (AUC) or as maximum plasma concentration ($C_{max}$) after oral administration to a subject in a fed state.

4. The pharmaceutical composition of claim 1, wherein the pharmaceutical composition exhibits a bioavailability of the PROTAC compound or the pharmaceutically acceptable salt thereof that does not vary more than 100% when orally administered to a subject in a fed state compared to a fasted state, when said bioavailability is measured as total area under the curve (AUC) or as maximum plasma concentration ($C_{max}$) after oral administration to said subject.

5. The pharmaceutical composition of claim 1, wherein the PROTAC compound is an androgen receptor PROTAC degrader or an estrogen receptor PROTAC degrader.

6. The pharmaceutical composition of claim 1, wherein the pharmaceutical composition further comprises a pharmaceutically acceptable carrier or excipient.

7. The pharmaceutical composition of claim 1, wherein the PROTAC compound or the pharmaceutically acceptable salt thereof is present in the pharmaceutical composition in an amount of from about 10% to 30% by weight.

8. The pharmaceutical composition of claim 1, wherein the surfactant is present in the pharmaceutical composition in an amount of from about 20% to about 30% by weight.

9. The pharmaceutical composition of claim 1, wherein the surfactant further comprises a non-ionic surfactant, an anionic surfactant, or any combination thereof.

10. The pharmaceutical composition of claim 9, wherein the surfactant comprises tocopherol polyethylene glycol succinate (TPGS), a block copolymer of polyethylene glycol and polypropylene glycol, polysorbate, polyethylene glycol castor oil, hydrogenated castor oil, sorbitan oleate, sodium dodecyl sulfate (SDS), polyvinylcaprolactame-based graft copolymer, or a combination thereof.

11. The pharmaceutical composition of claim 1, wherein the amorphous solid dispersion further comprises an adsorbent.

12. The pharmaceutical composition of claim 11, wherein the adsorbent is silicon dioxide, and wherein the adsorbent is present in the amorphous solid dispersion in an amount of from about 1% to about 40% by weight.

13. The pharmaceutical composition of claim 1, wherein the phospholipid comprises lecithin.

14. The pharmaceutical composition of claim 1, wherein the hydrophilic polymer comprises hydropropylmethylcellulose acetate succinate (HPMCAS).

15. The pharmaceutical composition of claim 1, wherein the hydrophilic polymer comprises hypromellose phthalate (HPMCP).

16. The pharmaceutical composition of claim 1, wherein the hydrophilic polymer is present the amorphous solid dispersion in a weight percent of from about 30% to about 50%.

17. The pharmaceutical composition of claim 1, wherein the hydrophilic polymer comprises polymethacrylates.

18. The pharmaceutical composition of claim 1, wherein the amorphous solid dispersion comprises an acid.

19. The pharmaceutical composition of claim 18, wherein the acid is selected from the group consisting of tartaric acid, fumaric acid, succinic acid, citric acid, lactic acid, malic acid, methanesulfonic acid, ethanesulfonic acid, isethionic acid, benzenesulfonic acid, p-toluenesulfonic acid, hydrochloric acid, sulfuric acid, and phosphoric acid.

20. The pharmaceutical composition of claim 1, wherein the pharmaceutical composition comprises:
a) the amorphous solid dispersion that comprises:
the PROTAC compound or the pharmaceutically acceptable salt thereof in an amount of from about 15% to about 25% by weight of the ASD;
lecithin in an amount of from about 20% to about 30% by weight of the ASD;
the hydrophilic polymer in an amount of from about 30% to about 50% by weight of the ASD; and
b) a pharmaceutically acceptable carrier or excipient.

21. The pharmaceutical composition of claim 20, wherein the PROTAC compound is selected from the group consisting of: ARV-110, ARV-471, CFT7455, AC0682, ARV-766, BGB-16673, DT2216, FHD-609, GT20029, HP518, HSK29116, KT-474, NX-2127, NX-5948, AC0176, BRD4-CHAMP, and KT-413.

22. The pharmaceutical composition of claim 1, wherein the pharmaceutical composition is storage stable for at least 3 months at 25° C./60% RH, wherein a storage stable pharmaceutical composition has less than 0.5% of any impurity at the end of the storage period.

23. An amorphous solid dispersion, wherein the amorphous solid dispersion comprises,
a proteolysis targeting chimera (PROTAC) compound or a pharmaceutically acceptable salt thereof, wherein the PROTAC compound or the pharmaceutically acceptable salt thereof has a log P or calculated log P (clog P) in octanol-water of at least 4.0, and wherein the PROTAC compound or the pharmaceutically acceptable salt thereof is present in the amorphous solid dispersion in a weight percent of about 10% to about 40%;
a surfactant, wherein the surfactant comprises a phospholipid and wherein the phospholipid is present in the amorphous solid dispersion in a weight percent of from about 20% to about 40%;
a hydrophilic polymer, wherein the hydrophilic polymer comprises hydropropylmethylcellulose acetate succinate (HPMCAS), polymethacrylates, hypromellose phthalate (HPMCP), or a combination thereof, and wherein the hydrophilic polymer is present in the amorphous solid dispersion in an amount of from about 20% to about 50% by weight;
wherein the amorphous solid dispersion exhibits a bioavailability of the PROTAC compound or the pharmaceutically acceptable salt thereof that is at least 1.5-fold compared to a bioavailability of a corresponding composition comprising the PROTAC compound or the pharmaceutically acceptable salt thereof without being a part of an ASD, wherein said bioavailability is measured as total area under the curve (AUC) or as maximum plasma concentration ($C_{max}$) after oral administration to a subject;
wherein the amorphous solid dispersion is in an oral dosage form; and wherein the PROTAC compound or the pharmaceutically acceptable salt thereof, the surfactant, and the hydrophilic polymer are present in the amorphous solid dispersion in an amorphous state.

* * * * *